US009403816B2

(12) United States Patent
Leonard et al.

(10) Patent No.: US 9,403,816 B2
(45) Date of Patent: *Aug. 2, 2016

(54) PHENYL LINKED QUINOLINYL MODULATORS OF RORγT

(71) Applicant: Janssen Pharmaceutica NV, Beerse (BE)

(72) Inventors: Kristi A. Leonard, Lansdale, PA (US); Kent Barbay, Flourtown, PA (US); James P. Edwards, San Diego, CA (US); Kevin D. Kreutter, Plainsboro, NJ (US); David A. Kummer, San Diego, CA (US); Umar Maharoof, North Wales, PA (US); Rachel Nishimura, San Diego, CA (US); Maud Urbanski, Flemington, NJ (US); Hariharan Venkatesan, San Diego, CA (US); Aihua Wang, Jamison, PA (US); Ronald L. Wolin, San Diego, CA (US); Craig R. Woods, San Diego, CA (US); Maxwell D. Cummings, Ambler, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/053,773

(22) Filed: Oct. 15, 2013

(65) Prior Publication Data
US 2015/0105404 A1 Apr. 16, 2015

(51) Int. Cl.
C07D 417/14 (2006.01)
C07D 401/14 (2006.01)
C07D 409/14 (2006.01)
C07D 401/06 (2006.01)

(52) U.S. Cl.
CPC ............ C07D 417/14 (2013.01); C07D 401/06 (2013.01); C07D 401/14 (2013.01); C07D 409/14 (2013.01)

(58) Field of Classification Search
None
See application file for complete search history.

(56) References Cited

U.S. PATENT DOCUMENTS

| | | | |
|---|---|---|---|
| 3,472,859 A | 10/1969 | Lesher | |
| 4,656,283 A | 4/1987 | Doehner, Jr. | |
| 4,710,507 A | 12/1987 | Campbell et al. | |
| 4,910,327 A | 3/1990 | Doehner, Jr. | |
| 4,927,926 A | 5/1990 | Corominas et al. | |
| 5,409,930 A | 4/1995 | Spada et al. | |
| 5,780,634 A | 7/1998 | Inoue et al. | |
| 6,248,739 B1 | 6/2001 | Turner et al. | |
| 6,451,812 B1 * | 9/2002 | End et al. | 514/312 |
| 6,624,159 B2 | 9/2003 | Anderson et al. | |
| 6,686,356 B2 | 2/2004 | Strohbach et al. | |
| 6,743,805 B2 * | 6/2004 | End et al. | 514/312 |
| 7,053,105 B2 | 5/2006 | Angibaud et al. | |
| 7,652,014 B2 | 1/2010 | Mabire et al. | |
| 7,902,225 B2 | 3/2011 | Guillemont et al. | |
| 8,017,606 B2 | 9/2011 | Andries et al. | |
| 8,389,739 B1 | 3/2013 | Thacher et al. | |
| 2003/0166675 A1 | 9/2003 | Yang | |
| 2005/0131014 A1 | 6/2005 | Collini et al. | |
| 2007/0072844 A1 | 3/2007 | Jones et al. | |
| 2008/0188521 A1 | 8/2008 | Grimm et al. | |
| 2009/0197859 A1 | 8/2009 | Collantes et al. | |
| 2009/0286829 A1 | 11/2009 | Heidelbaugh et al. | |
| 2010/0311760 A1 | 12/2010 | de Vicente Fidalgo et al. | |
| 2011/0124870 A1 | 5/2011 | Guillemont et al. | |
| 2012/0322837 A1 | 12/2012 | Maeba et al. | |

FOREIGN PATENT DOCUMENTS

| | | |
|---|---|---|
| CN | 101143845 | 3/2008 |
| CN | 101899011 | 12/2010 |
| EP | 371564 A2 | 6/1990 |
| EP | 709377 A1 | 5/1996 |
| EP | 1106612 A1 | 6/2001 |
| EP | 2368886 A1 | 9/2011 |

(Continued)

OTHER PUBLICATIONS

Codarri, et al., "RORyt Drives Production of the Cytokine GM-CSF in helper T cells, which is essential for the effector Phase of Autoimmune Neuroinflammation" Nature Immunology, vol. 12(6), Jun. 2011, pp. 560-568.

(Continued)

Primary Examiner — Dennis Heyer
(74) Attorney, Agent, or Firm — Yuriy P. Stercho

(57) ABSTRACT

The present invention comprises compounds of Formula I.

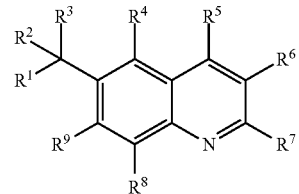

Formula I wherein:
$R^1$, $R^2$, $R^3$, $R^4$, $R^5$, $R^6$, $R^7$, $R^8$, and $R^9$ are defined in the specification.

The invention also comprises a method of treating or ameliorating a syndrome, disorder or disease, wherein said syndrome, disorder or disease is rheumatoid arthritis or psoriasis. The invention also comprises a method of modulating RORγt activity in a mammal by administration of a therapeutically effective amount of at least one compound of claim 1.

5 Claims, No Drawings

(56) References Cited

FOREIGN PATENT DOCUMENTS

| | | |
|---|---|---|
| GB | 2095668 A | 10/1982 |
| JP | 48026772 | 4/1973 |
| JP | 2000169451 A | 6/2000 |
| WO | WO 9718208 A1 | 5/1997 |
| WO | WO 9721701 A1 | 6/1997 |
| WO | WO 9744339 A1 | 11/1997 |
| WO | WO 9855124 A1 | 12/1998 |
| WO | WO 9932450 A1 | 7/1999 |
| WO | WO 9950660 A1 | 10/1999 |
| WO | WO 0001386 A1 | 1/2000 |
| WO | WO 0001411 A1 | 1/2000 |
| WO | WO 0001714 A1 | 1/2000 |
| WO | WO 0039082 A2 | 7/2000 |
| WO | WO 0040561 A1 | 7/2000 |
| WO | WO 0040563 A1 | 7/2000 |
| WO | WO 0047574 A1 | 8/2000 |
| WO | WO 0156552 A1 | 8/2001 |
| WO | WO 0162234 A2 | 8/2001 |
| WO | WO 0164194 A2 | 9/2001 |
| WO | WO 0164195 A2 | 9/2001 |
| WO | WO 0164196 A2 | 9/2001 |
| WO | WO 0164197 A2 | 9/2001 |
| WO | WO 0164198 A2 | 9/2001 |
| WO | WO 0164199 A2 | 9/2001 |
| WO | WO 0164217 A2 | 9/2001 |
| WO | WO 0164218 A2 | 9/2001 |
| WO | WO 0164226 A2 | 9/2001 |
| WO | WO 0164246 A2 | 9/2001 |
| WO | WO 0164252 A2 | 9/2001 |
| WO | WO 0202558 A1 | 1/2002 |
| WO | WO 0204445 A1 | 1/2002 |
| WO | WO 0204462 A1 | 1/2002 |
| WO | WO 0224682 A1 | 3/2002 |
| WO | WO 0224686 A2 | 3/2002 |
| WO | WO 0224687 A1 | 3/2002 |
| WO | WO 0228837 A1 | 4/2002 |
| WO | WO 0243733 A1 | 6/2002 |
| WO | WO 02051835 A1 | 7/2002 |
| WO | WO 02064142 A1 | 8/2002 |
| WO | WO 02070487 A1 | 9/2002 |
| WO | WO 02085364 A1 | 10/2002 |
| WO | WO 03/000705 | 1/2003 |
| WO | WO 03053971 A1 | 7/2003 |
| WO | WO 03053972 A1 | 7/2003 |
| WO | WO 03082350 A2 | 10/2003 |
| WO | WO 2004019932 A1 | 3/2004 |
| WO | WO 2004024693 A1 | 3/2004 |
| WO | WO 2004037792 A2 | 5/2004 |
| WO | WO 2005054201 A1 | 6/2005 |
| WO | WO 2005054210 A1 | 6/2005 |
| WO | WO 2005058843 A1 | 6/2005 |
| WO | WO 2005070430 A1 | 8/2005 |
| WO | WO 2005075428 A1 | 8/2005 |
| WO | WO 2006003146 A1 | 1/2006 |
| WO | WO 2006013896 A1 | 2/2006 |
| WO | WO 2006025683 | 3/2006 |
| WO | WO 2006052718 A2 | 5/2006 |
| WO | WO 2007014940 A2 | 2/2007 |
| WO | WO 2007014941 A2 | 2/2007 |
| WO | WO 2007088978 A1 | 8/2007 |
| WO | WO 2008051805 A2 | 5/2008 |
| WO | WO 2008068267 A1 | 6/2008 |
| WO | WO 2008098104 A8 | 8/2008 |
| WO | WO 2008112525 A2 | 9/2008 |
| WO | WO 2008144767 A1 | 11/2008 |
| WO | WO 2009091735 A1 | 7/2009 |
| WO | WO 2009140138 A1 | 11/2009 |
| WO | WO 2010068296 A1 | 6/2010 |
| WO | WO 2010127208 A1 | 11/2010 |
| WO | WO 2010151740 A4 | 12/2010 |
| WO | WO 2011020861 A1 | 2/2011 |
| WO | WO 2011112264 A1 | 9/2011 |
| WO | WO 2011130707 A2 | 10/2011 |
| WO | WO 2012064744 A2 | 5/2012 |
| WO | WO 2012116137 A2 | 8/2012 |
| WO | WO 2012158784 A2 | 11/2012 |
| WO | WO 2013061074 A1 | 5/2013 |
| WO | WO 2013064231 A1 | 5/2013 |
| WO | WO 2013079223 A1 | 6/2013 |

OTHER PUBLICATIONS

Bink A, (A fungicidal piperazine-1-carboxamidine induces mitochondrial fission-dependent apoptosis in yeast), FEMS Yeast Research (2010), 10(7), 812-818.

Nieman J, (Modifications of C-2 on the pyrroloquinoline template aimed at the development of potent herpes virus antivirals with improved aqueous solubility), Bioorganic & Medicinal Chemistry Letters (2010), 20(10), 3039-3042.

Tanis S, (The design and development of 2-aryl-2-hydroxy ethylamine substituted 1H,7H-pyrido[1,2,3-de]quinoxaline-6-carboxamides as inhibitors of human cytomegalovirus polymerase), Bioorganic & Medicinal Chemistry Letters (2010), 20(6), 1994-2000.

Mao D, (Synthesis and Na+/H+ Exchanger-1 Inhibitory Activity of Substituted (Quinolinecarbonyl)guanidine Derivatives), Chemistry & Biodiversity (2009), 6(10), 1727-1736.

Sato M, (Quinolone Carboxylic Acids as a Novel Monoketo Acid Class of Human Immunodeficiency Virus Type 1 Integrase Inhibitors), Journal of Medicinal Chemistry (2009), 52(15), 4869-4882.

Aghera V, (Synthesis, spectral and microbial studies of some novel quinoline derivatives via Vilsmeier-Haack reagent) Journal; (online computer file) URL: http://www.arkat-usa.org/get-file/25177/.

Inada T, (One-step synthesis of ethyl quinaldates by Lewis acid-catalyzed three-component coupling reaction of aromatic amines, aliphatic aldehydes, and ethyl glyoxylate), Heterocycles (2005), 66, 611-619.

Zelenin A, (Reaction of polyfluoro carbonyl compounds with 1,2,3,4-tetrahydroquinoline), Izvestiya Akademii Nauk SSSR, Seriya Khimicheskaya (1986), (9), 2074-80 Abstract Only.

Hirao I, (Studies on the synthesis of quinoline compounds. I. Syntheses of 3,3'- dicarboxy-1,1'-diethyl-4,4'-dioxo-1,1',4,4'-tetrahydrobiquinolines), Memoirs of the Kyushu Institute of Technology, Engineering (1984), 14, 13-16.

Abdul-Ahad P, (Trends in dehydrogenase inhibitory potencies of some quinolones, using quantum chemical indices), European Journal of Medicinal Chemistry (1982), 17(4), 301-6.

Baker B, (Irreversible enzyme inhibitors. 191. Hydrophobic bonding to some dehydrogenases by 6-, 7-, or 8-substituted-4-hydroxyquinoline-3-carboxylic acids), Journal of Medicinal Chemistry (1972), 15(3), 235-7.

Ramachary D, (A novel and green protocol for two-carbon homologation: a direct amino acid/K2CO3-catalyzed four-component reaction of aldehydes, active methylenes, Hantzsch esters and alkyl halides), Tetrahedron Letters (2006) 47, 651-656.

Dong C, (Diversification of T-helper-cell lineages: finding the family root of IL-17-producing cells), Nat Rev Immunol (2006), 6(4), 329-333.

McKenzie B, (Understanding the IL-23-IL-17 immune pathway), Trends Immunol (2006), 27(1), 17-23.

Ivanov II B, (The orphan nuclear receptor RORgammat directs the differentiation program of proinflammatory IL-17+ T helper cells), Cell (2006), 126(6), 1121-33.

Cua, D (Interleukin-23 rather than interleukin-12 is the critical cytokine for autoimmune inflammation of the brain), Nature (2003), 421(6924), 744-748.

Langrish C, (IL-23 drives a pathogenic T cell population that induces autoimmune inflammation), J Exp Med (2005), 201(2), 233-240.

Tonel G, (Cutting edge: A critical functional role for IL-23 in psoriasis), J Immunol (2010), 185(10), 5688-5691.

Barczyk A, (Interleukin-17 in sputum correlates with airway hyper-responsiveness to methacholine), Respir Med (2003), 97(6), 726-733.

Lock C, (Gene-microarray analysis of multiple sclerosis lesions yields new targets validated in autoimmune encephalomyelitis) Nat Med (2002), 8(5), 500-8.

Papp K, (Brodalumab, an anti-interleukin-17-receptor antibody for psoriasis), N Engl J Med (2012), 366(13), 1181-1189.

(56) References Cited

OTHER PUBLICATIONS

Leonardi C, (Anti-interleukin-17 monoclonal antibody ixekizumab in chronic plaque psoriasis), N Engl J Med (2012), 366(13), 1190-1199.
Hueber W, (Effects of AIN457, a fully human antibody to interleukin-17A, on psoriasis, rheumatoid arthritis, and uveitis), Sci Transl Med (2010), 2, 5272.
Gao W, (Clean and Convienient One-Pot Synthesis of 4-Hydroxycoumarin and 4-Hydroxy-2-Quinolone Derivatives), Synthetic Communications (2010) 40, 732-738.
Moriarty R, Organic Reactions (2001), 57, 327-415.
Pongratz E, et al., (Ylide von Heterocyclen, VIII Reaktionen von Iodonium-Yliden mit Säuren), Monatshefte fur Chemie (1984) 115(2), 231-242.
Osborne A, (Regioselective Al koxydehalogenation of 2,4- Di halogenoquinolines and a Reinvestigation of the Bromination of 2-Methoxyquinoline), J Chem Soc Perkin Trans 1 (1993), 181-184.
Osborne A, (Further studies of regioselective alkoxydehalogenation of 2,4-dichloroquinolines, 2,6-dichloropyridine and 2,4-dichloronitrobenzene), J Chem. Research (S) (2002), 4.
Ramachary D, (Development of Pharmaceutical Drugs, Drug Intermediates and Ingredients by Using Direct Organo-Click Reactions), Eur. J. Org. Chem. (2008), 975-993.
Korn T, (IL-17 and Th17 Cells), Annual Reviews of Immunology (2009), 27, 485-517.
Kolls J, (Interleukin-17 family members and inflammation), Immunity (2004), 21(4), 467-476.
Stamp L, (Interleukin-17: the missing link between T-cell accumulation and effector cell actions in rheumatoid arthritis), Immunol Cell Biol (2004), 82(1), 1-9.
Kamenecka T, (Synthetic modulators of the retinoic acid receptor-related orphan receptors), Med Chem Commun (2013), 4, 764-776.
Yen D, (IL-23 is essential for T cell-mediated colitis and promotes inflammation via IL-17 and IL-6), J Clin Invest (2006), 116(5), 1310-1316.
Fujino S, (Increased expression of interleukin 17 in inflammatory bowel disease) Gut (2003), 52(1), 65-70.
Krueger J, (IL-17A is essential for cell activation and inflammatory gene circuits in subjects with psoriasis) J Allergy Clin Immunol (2012), 130(1), 145-154.
Nunez C, (IL23R: a susceptibility locus for celiac disease and multiple sclerosis?) Genes Immun (2008), 9(4), 289-93.
Bowes J, (The genetics of psoriatic arthritis: lessons from genome-wide association studies), Discov Med (2010), 10(52), 177-83.
Kochi Y, (A regulatory variant in CCR6 is associated with rheumatoid arthritis susceptibility), Nat Genet (2010), 42(6), 515-9.
Garber K, (Psoriasis: from bed to bench and back), Nat Biotech (2011), 29, 563-566.
Madrid P, et al. (Synthesis of ring-substituted 4-aminoquinolines and evaluation of their antimalarial activities), Bioorganic & Medicinal Chemistry Letters (2005), 15, 1015-1018.
Gore T, (Synthesis of substituted 6,6'-biquinolines from ethyl ethoxymethyleneacetoacetate), Indian Journal of Chemistry (1965), 3(2), 90-1.
Gazouli, M, (NOD2/CARD15, ATG16L1 and IL23R gene polymorphisms and childhood-onset of Crohn's disease) World J. Gastroenterol (2010) 16(14), 1753-8.
Knochel P, (Preparation of Polyfunctional Ketones by a Cobalt(II) Mediated Carbonylation of Organozinc Reagents), Tetrahedron Letters (1995), 36(46), 8411-8414.
International Search Report—PCT/US2013/065007, Jan. 7, 2014.
International Search Report—PCT/US2013/065013, Dec. 16, 2013.
International Search Report—PCT/US2013/065031, Dec. 13, 2013.
International Search Report—PCT/US2013/065040, Dec. 16, 2013.
International Search Report—PCT/US2013/065048, Dec. 3, 2013.
International Search Report—PCT/US2013/065053, Jan. 7, 2014.
International Search Report—PCT/US2013/065026, Feb. 21, 2014.
U.S. Appl. No. 14/053,682.
U.S. Appl. No. 14/053,736.
U.S. Appl. No. 14/053,797.
U.S. Appl. No. 14/053,906.
U.S. Appl. No. 14/053,653.
U.S. Appl. No. 14/053,707.
International Search Report—PCT/US2014/60372, Mar. 27, 2015.
International Search Report—PCT/US2014/60375, Mar. 26, 2015.
U.S. Appl. No. 14/053,653, Office Action dated Sep. 15, 2014.
U.S. Appl. No. 14/053,653, Notice of Allowance dated Mar. 30, 2015.
U.S. Appl. No. 14/053,682, Office Action dated Sep. 12, 2014.
U.S. Appl. No. 14/053,682, Notice of Allowance dated Sep. 12, 2014.
U.S. Appl. No. 14/053,707, Office Action dated Sep. 11, 2014.
U.S. Appl. No. 14/053,707, Notice of Allowance dated Sep. 11, 2014.
U.S. Appl. No. 12/053,736, Office action dated Mar. 26, 2015.
U.S. Appl. No. 14/053,736, Office Action dated Oct. 3, 2014.
U.S. Appl. No. 14/053,773, Office Action dated Apr. 6, 2015.
U.S. Appl. No. 14/053,773, Office Action dated Jan. 9, 2015.
U.S. Appl. No. 14/053,797, Office Action dated Sep. 12, 2014.
U.S. Appl. No. 14/053,797, Notice of Allowance Apr. 7, 2015.
U.S. Appl. No. 14/513,426, Office Action dated Apr. 16, 2015.
U.S. Appl. No. 14/513,455, Office Action dated Apr. 28, 2015.
U.S. Appl. No. 14/053,906, Office Action dated Sep. 12, 204.
U.S. Appl. No. 14/053,906, Notice of Allowance dated Mar. 23, 2015.
U.S. Appl. No. 14/513,426.
U.S. Appl. No. 14/513,455.
Dorwald F. A. "Slide Reactions in Organic Synthesis", 2005, Wiley: VCH, Weinheim p. IX of Preface p. 1-15.
Venkatesh, et al. "Role of the Development Scientist in Compound Lead Selection and Optimization", J. Pharm. Sci. vol. 89, No. 2, pp. 145-154 2000.
STN Search Report Mar. 12, 2015, RN 1347913-41-0.

\* cited by examiner

SEQUENCE LISTING

<160> NUMBER OF SEQ ID NOS: 9

<210> SEQ ID NO 1
<211> LENGTH: 3054
<212> TYPE: DNA
<213> ORGANISM: Homo sapiens

```
<400> SEQUENCE: 1
agagagctag gtgcagagct tcaggctgag gcgctgctga gagggcctcg ccccgcctct      60
gccgccagct gcaccccact cctggaccac cccctgctga gaaggacagg gagccaaggc     120
cggcagagcc aaggctcagt catgagaaca caaattgaag tgatcccttg caaaatctgt     180
ggggacaagt cgtctgggat ccactacggg gttatcacct gtgaggggtg caagggcttc     240
ttccgccgga gccagcgctg taacgcggcc tactcctgca cccgtcagca gaactgcccc     300
atcgaccgca ccagccgaaa ccgatgccag cactgccgcc tgcagaaatg cctggcgctg     360
ggcatgtccc gagatgctgt caagttcggc cgcatgtcca gaagcagag ggacagcctg      420
catgcagaag tgcagaaaca gctgcagcag cggcaacagc agcaacagga accagtggtc     480
aagacccctc cagcagggc ccaaggagca gatacccctca cctacacctt ggggctccca     540
gacgggcagc tgcccctggg ctcctcgcct gacctgcctg aggcttctgc ctgtcccccct    600
ggcctcctga aagcctcagg ctctgggccc tcatattcca caacttggc caaggcaggg     660
ctcaatgggg cctcatgcca ccttgaatac agccctgagc ggggcaaggc tgagggcaga     720
gagagcttct atagcacagg cagccagctg accccctgacc gatgtggact tcgttttgag    780
gaacacaggc atcctgggct tggggaactg ggacagggcc cagacagcta cggcagcccc    840
agtttccgca gcacaccgga ggcacccctat gcctccctga cagagataga gcacctggtg    900
cagagcgtct gcaagtccta cagggagaca tgccagctgc ggctggagga cctgctgcgg    960
cagcgctcca acatcttctc ccgggaggaa gtgactggct accagaggaa gtccatgtgg    1020
gagatgtggg aacggtgtgc ccaccacctc accgaggcca ttcagtacgt ggtggagttc    1080
gccaagaggc tctcaggctt tatggagctc tgccagaatg accagattgt gcttctcaaa    1140
gcaggagcaa tggaagtggt gctggttagg atgtgccggg cctacaatgc tgacaaccgc    1200
acggtctttt ttgaaggcaa atacggtggc atggagctgt tccgagcctt gggctgcagc    1260
gagctcatca gctccatctt tgacttctcc cactccctaa gtgccttgca cttttccgag    1320
gatgagattg ccctctacac agcccttgtt ctcatcaatg cccatcggcc agggctccaa    1380
gagaaaagga agtagaaca gctgcagtac aatctggagc tggcctttca tcatcatctc     1440
tgcaagactc atcgccaaag catcctggca aagctgccac ccaaggggaa gcttcggagc    1500
ctgtgtagcc agcatgtgga aaggctgcag atcttccagc acctccaccc catcgtggtc    1560
caagccgctt tccctccact ctacaaggag ctcttcagca ctgaaaccga gtcacctgtg    1620
gggctgtcca agtgacctgg aagagggact ccttgcctct ccctatgcc tgctggccca    1680
cctccctgga ccccgttcca ccctcacccct tttccttccc catgaaccct ggagggtggt    1740
ccccaccagc tctttggaag tgagcagatg ctgcggctgc ctttctgtca gcaggccggc    1800
ctggcagtgg gacaatcgcc agagggtggg gctggcagaa caccatctcc agcctcagct    1860
ttgacctgtc tcatttccca tattccttca cacccagctt ctggaaggca tggggtggct    1920
gggatttaag gacttctggg ggaccaagac atcctcaaga aaacaggggc atccagggct    1980
ccctggatga atagaatgca attcattcag aagctcagaa gctaagaata agcctttgaa    2040
atacctcatt gcatttccct ttgggcttcg gcttggggag atggatcaag ctcagagact    2100
ggcagtgaga gcccagaagg acctgtataa aatgaatctg gagctttaca ttttctgcct    2160
ctgccttcct cccagctcag caaggaagta tttgggcacc ctacccttta cctgggtct     2220
aaccaaaaat ggatgggatg aggatgagag gctggagata attgtttat gggatttggg     2280
```

```
tgtgggacta gggtacaatg aaggccaaga gcatctcaga catagagtta aaactcaaac    2340
ctcttatgtg cactttaaag atagacttta ggggctggca caaatctgat cagagacaca    2400
tatccataca caggtgaaac acatacagac tcaacagcaa tcatgcagtt ccagagacac    2460
atgaacctga cacaatctct cttatccttg aggccacagc ttggaggagc ctagaggcct    2520
caggggaaag tcccaatcct gagggaccct cccaaacatt tccatggtgc tccagtccac    2580
tgatcttggg tctggggtga tccaaatacc accccagctc cagctgtctt ctaccactag    2640
aagacccaag agaagcagaa gtcgctcgca ctggtcagtc ggaaggcaag atcagatcct    2700
ggaggacttt cctggcctgc ccgccagccc tgctcttgtt gtggagaagg aagcagatgt    2760
gatcacatca ccccgtcatt gggcaccgct gactccagca tggaggacac cagggagcag    2820
ggcctgggcc tgtttcccca gctgtgatct tgcccagaac ctctcttggc ttcataaaca    2880
gctgtgaacc ctcccctgag ggattaacag caatgatggg cagtcgtgga gttggggggg    2940 ttggggtgg gattgtgtcc tctaagggga cgggttcatc tgagtaaaca taaaccccaa     3000
cttgtgccat tctttataaa atgattttaa aggcaaaaaa aaaaaaaaaa aaaa           3054

<210> SEQ ID NO 2
<211> LENGTH: 786
<212> TYPE: DNA
<213> ORGANISM: Homo sapiens

<400> SEQUENCE: 2
agcacaccgg aggcacccta tgcctccctg acagagatag agcacctggt gcagagcgtc     60
tgcaagtcct acagggagac atgccagctg cggctggagg acctgctgcg gcagcgctcc    120
aacatcttct cccgggagga agtgactggc taccagagga agtccatgtg ggagatgtgg    180
gaacggtgtg cccaccacct caccgaggcc attcagtacg tggtggagtt cgccaagagg    240
ctctcaggct ttatggagct ctgccagaat gaccagattg tgcttctcaa gcaggagca    300 atggaagtgt gctggttag gatgtgccgg gcctacaatg ctgacaaccg cacggtcttt    360
tttgaaggca aatacggtgg catggagctg ttccgagcct tgggctgcag cgagctcatc    420
agctccatct ttgacttctc ccactcccta agtgccttgc acttttccga ggatgagatt    480
gccctctaca cagcccttgt tctcatcaat gcccatcggc cagggctcca agagaaaagg    540
aaagtagaac agctgcagta caatctggag ctggcctttc atcatcatct ctgcaagact    600
catcgccaaa gcatcctggc aaagctgcca cccaagggga agcttcggag cctgtgtagc    660
cagcatgtgg aaaggctgca gatcttccag cacctccacc ccatcgtggt ccaagccgct    720
ttccctccac tctacaagga gctcttcagc actgaaaccg agtcacctgt ggggctgtcc    780
aagtga                                                                786

<210> SEQ ID NO 3
<211> LENGTH: 7
<212> TYPE: PRT
<213> ORGANISM: Artificial Sequence
<220> FEATURE:
<223> OTHER INFORMATION: TurboTEV protease cleavage site

<400> SEQUENCE: 3

Glu Asn Leu Tyr Phe Gln Gly
1               5

<210> SEQ ID NO 4
<211> LENGTH: 283
<212> TYPE: PRT
```

```
<213> ORGANISM: Artificial Sequence
<220> FEATURE:
<223> OTHER INFORMATION: Construct used in the Thermofluor assay

<400> SEQUENCE: 4

Met Ala His His His His His Ala Gly Gly Ala Glu Asn Leu Tyr
1               5                   10                  15

Phe Gln Gly Ala Met Asp Ser Thr Pro Glu Ala Pro Tyr Ala Ser Leu
            20                  25                  30

Thr Glu Ile Glu His Leu Val Gln Ser Val Cys Lys Ser Tyr Arg Glu
        35                  40                  45

Thr Cys Gln Leu Arg Leu Glu Asp Leu Leu Arg Gln Arg Ser Asn Ile
    50                  55                  60

Phe Ser Arg Glu Glu Val Thr Gly Tyr Gln Arg Lys Ser Met Trp Glu
65                  70                  75                  80

Met Trp Glu Arg Cys Ala His His Leu Thr Glu Ala Ile Gln Tyr Val
                85                  90                  95

Val Glu Phe Ala Lys Arg Leu Ser Gly Phe Met Glu Leu Cys Gln Asn
            100                 105                 110

Asp Gln Ile Val Leu Leu Lys Ala Gly Ala Met Glu Val Val Leu Val
        115                 120                 125

Arg Met Cys Arg Ala Tyr Asn Ala Asp Asn Arg Thr Val Phe Phe Glu
    130                 135                 140

Gly Lys Tyr Gly Gly Met Glu Leu Phe Arg Ala Leu Gly Cys Ser Glu
145                 150                 155                 160

Leu Ile Ser Ser Ile Phe Asp Phe Ser His Ser Leu Ser Ala Leu His
                165                 170                 175

Phe Ser Glu Asp Glu Ile Ala Leu Tyr Thr Ala Leu Val Leu Ile Asn
            180                 185                 190

Ala His Arg Pro Gly Leu Gln Glu Lys Arg Lys Val Glu Gln Leu Gln
        195                 200                 205

Tyr Asn Leu Glu Leu Ala Phe His His Leu Cys Lys Thr His Arg
    210                 215                 220

Gln Ser Ile Leu Ala Lys Leu Pro Pro Lys Gly Lys Leu Arg Ser Leu
225                 230                 235                 240

Cys Ser Gln His Val Glu Arg Leu Gln Ile Phe Gln His Leu His Pro
                245                 250                 255

Ile Val Val Gln Ala Ala Phe Pro Pro Leu Tyr Lys Glu Leu Phe Ser
            260                 265                 270

Thr Glu Thr Glu Ser Pro Val Gly Leu Ser Lys
        275                 280

<210> SEQ ID NO 5
<211> LENGTH: 6
<212> TYPE: PRT
<213> ORGANISM: Homo sapiens

<400> SEQUENCE: 5

Leu Tyr Lys Glu Leu Phe
1               5

<210> SEQ ID NO 6
<211> LENGTH: 6
<212> TYPE: PRT
<213> ORGANISM: Artificial Sequence
<220> FEATURE:
<223> OTHER INFORMATION: mutated AF2 domain
```

<400> SEQUENCE: 6

Leu Phe Lys Glu Leu Phe
1               5

<210> SEQ ID NO 7
<211> LENGTH: 786
<212> TYPE: DNA
<213> ORGANISM: Artificial Sequence
<220> FEATURE:
<223> OTHER INFORMATION: LBD with mutated AF2 domain

<400> SEQUENCE: 7

```
agcacaccgg aggcacccta tgcctccctg acagagatag agcacctggt gcagagcgtc      60
tgcaagtcct acagggagac atgccagctg cggctggagg acctgctgcg gcagcgctcc     120
aacatcttct cccggaggag agtgactggc taccagagga gtccatgtg ggagatgtgg      180
gaacggtgtg cccaccacct caccgaggcc attcagtacg tggtggagtt cgccaagagg     240
ctctcaggct ttatggagct gccagaat gaccagattg tgcttctcaa agcaggagca       300
atggaagtgg tgctggttag gatgtgccgg gcctacaatg ctgacaaccg cacggtcttt     360
tttgaaggca atacggtgg catggagctg ttccgagcct tgggctgcag cgagctcatc      420
agctccatct ttgacttctc ccactcccta agtgccttgc acttttccga ggatgagatt     480
gccctctaca cagcccttgt tctcatcaat gccatcggc cagggctcca agagaaaagg      540
aaagtagaac agctgcagta caatctggag ctggccttc atcatcatct ctgcaagact      600
catcgccaaa gcatcctggc aaagctgcca cccaaggga gcttcggag cctgtgtagc       660
cagcatgtgg aaaggctgca gatcttccag cacctccacc ccatcgtggt ccaagccgct    720
ttccctccac tcttcaagga gctcttcagc actgaaaccg agtcacctgt ggggctgtcc    780
aagtga                                                                786
```

<210> SEQ ID NO 8
<211> LENGTH: 261
<212> TYPE: PRT
<213> ORGANISM: Homo sapiens

<400> SEQUENCE: 8

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
                20                  25                  30

Glu Asp Leu Leu Arg Gln Arg Ser Asn Ile Phe Ser Arg Glu Glu Val
            35                  40                  45

Thr Gly Tyr Gln Arg Lys Ser Met Trp Glu Met Trp Glu Arg Cys Ala
        50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
            100                 105                 110

Asn Ala Asp Asn Arg Thr Val Phe Phe Glu Gly Lys Tyr Gly Gly Met
        115                 120                 125

Glu Leu Phe Arg Ala Leu Gly Cys Ser Glu Leu Ile Ser Ser Ile Phe
    130                 135                 140

Asp Phe Ser His Ser Leu Ser Ala Leu His Phe Ser Glu Asp Glu Ile

```
                145                 150                 155                 160
Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
                180                 185                 190

Phe His His His Leu Cys Lys Thr His Arg Gln Ser Ile Leu Ala Lys
                195                 200                 205

Leu Pro Pro Lys Gly Lys Leu Arg Ser Leu Cys Ser Gln His Val Glu
                210                 215                 220

Arg Leu Gln Ile Phe Gln His Leu His Pro Ile Val Val Gln Ala Ala
225                 230                 235                 240

Phe Pro Pro Leu Tyr Lys Glu Leu Phe Ser Thr Glu Thr Glu Ser Pro
                245                 250                 255

Val Gly Leu Ser Lys
                260

<210> SEQ ID NO 9
<211> LENGTH: 261
<212> TYPE: PRT
<213> ORGANISM: Artificial Sequence
<220> FEATURE:
<223> OTHER INFORMATION: LBD with mutated AF2 domain

<400> SEQUENCE: 9

Ser Thr Pro Glu Ala Pro Tyr Ala Ser Leu Thr Glu Ile Glu His Leu
1               5                   10                  15

Val Gln Ser Val Cys Lys Ser Tyr Arg Glu Thr Cys Gln Leu Arg Leu
                20                  25                  30

Glu Asp Leu Leu Arg Gln Arg Ser Asn Ile Phe Ser Arg Glu Glu Val
                35                  40                  45

Thr Gly Tyr Gln Arg Lys Ser Met Trp Glu Met Trp Glu Arg Cys Ala
            50                  55                  60

His His Leu Thr Glu Ala Ile Gln Tyr Val Val Glu Phe Ala Lys Arg
65                  70                  75                  80

Leu Ser Gly Phe Met Glu Leu Cys Gln Asn Asp Gln Ile Val Leu Leu
                85                  90                  95

Lys Ala Gly Ala Met Glu Val Val Leu Val Arg Met Cys Arg Ala Tyr
                100                 105                 110

Asn Ala Asp Asn Arg Thr Val Phe Phe Glu Gly Lys Tyr Gly Gly Met
                115                 120                 125

Glu Leu Phe Arg Ala Leu Gly Cys Ser Glu Leu Ile Ser Ser Ile Phe
                130                 135                 140

Asp Phe Ser His Ser Leu Ser Ala Leu His Phe Ser Glu Asp Glu Ile
145                 150                 155                 160

Ala Leu Tyr Thr Ala Leu Val Leu Ile Asn Ala His Arg Pro Gly Leu
                165                 170                 175

Gln Glu Lys Arg Lys Val Glu Gln Leu Gln Tyr Asn Leu Glu Leu Ala
                180                 185                 190

Phe His His His Leu Cys Lys Thr His Arg Gln Ser Ile Leu Ala Lys
                195                 200                 205

Leu Pro Pro Lys Gly Lys Leu Arg Ser Leu Cys Ser Gln His Val Glu
                210                 215                 220

Arg Leu Gln Ile Phe Gln His Leu His Pro Ile Val Val Gln Ala Ala
225                 230                 235                 240

Phe Pro Pro Leu Phe Lys Glu Leu Phe Ser Thr Glu Thr Glu Ser Pro
```

245 250 255
Val Gly Leu Ser Lys
260

PHENYL LINKED QUINOLINYL MODULATORS OF RORγT

FIELD OF THE INVENTION

The invention is directed to substituted quinoline compounds, which are modulators of the nuclear receptor RORγt, pharmaceutical compositions, and methods for use thereof. More particularly, the RORγt modulators are useful for preventing, treating or ameliorating an RORγt mediated inflammatory syndrome, disorder or disease.

BACKGROUND OF THE INVENTION

Retinoic acid-related nuclear receptor gamma t (RORγt) is a nuclear receptor, exclusively expressed in cells of the immune system, and a key transcription factor driving Th17 cell differentiation. Th17 cells are a subset of $CD4^+$ T cells, expressing CCR6 on their surface to mediate their migration to sites of inflammation, and dependent on IL-23 stimulation, through the IL-23 receptor, for their maintenance and expansion. Th17 cells produce several proinflammatory cytokines including IL-17A, IL-17F, IL-21, and IL-22 (Korn, T., E. Bettelli, et al. (2009). "IL-17 and Th17 Cells." Annu Rev Immunol 27: 485-517.), which stimulate tissue cells to produce a panel of inflammatory chemokines, cytokines and metalloproteases, and promote recruitment of granulocytes (Kolls, J. K. and A. Linden (2004). "Interleukin-17 family members and inflammation." Immunity 21(4): 467-76; Stamp, L. K., M. J. James, et al. (2004). "Interleukin-17: the missing link between T-cell accumulation and effector cell actions in rheumatoid arthritis" Immunol Cell Biol 82(1): 1-9). Th17 cells have been shown to be the major pathogenic population in several models of autoimmune inflammation, including collagen-induced arthritis (CIA) and experimental autoimmune encephalomyelitis (EAE) (Dong, C. (2006). "Diversification of T-helper-cell lineages: finding the family root of IL-17-producing cells." Nat Rev Immunol 6(4): 329-33; McKenzie, B. S., R. A. Kastelein, et al. (2006). "Understanding the IL-23-IL-17 immune pathway." Trends Immunol 27(1): 17-23.). RORγt-deficient mice are healthy and reproduce normally, but have shown impaired Th17 cell differentiation in vitro, a significantly reduced Th17 cell population in vivo, and decreased susceptibility to EAE (Ivanov, II, B. S. McKenzie, et al. (2006). "The orphan nuclear receptor RORgamma t directs the differentiation program of proinflammatory IL-17+T helper cells." Cell 126(6): 1121-33.). Mice deficient for IL-23, a cytokine required for Th17 cell survival, fail to produce Th17 cells and are resistant to EAE, CIA, and inflammatory bowel disease (IBD) (Cua, D. J., J. Sherlock, et al. (2003). "Interleukin-23 rather than interleukin-12 is the critical cytokine for autoimmune inflammation of the brain." Nature 421(6924): 744-8; Langrish, C. L., Y. Chen, et al. (2005). "IL-23 drives a pathogenic T cell population that induces autoimmune inflammation." J Exp Med 201(2): 233-40; Yen, D., J. Cheung, et al. (2006). "IL-23 is essential for T cell-mediated colitis and promotes inflammation via IL-17 and IL-6." J Clin Invest 116(5): 1310-6.). Consistent with these findings, an anti-IL23-specific monoclonal antibody blocks development of psoriasis-like inflammation in a murine disease model (Tonel, G., C. Conrad, et al. "Cutting edge: A critical functional role for IL-23 in psoriasis." J Immunol 185(10): 5688-91).

In humans, a number of observations support the role of the IL-23/Th17 pathway in the pathogenesis of inflammatory diseases. IL-17, the key cytokine produced by Th17 cells, is expressed at elevated levels in a variety of allergic and autoimmune diseases (Barczyk, A., W. Pierzchala, et al. (2003). "Interleukin-17 in sputum correlates with airway hyperresponsiveness to methacholine." Respir Med 97(6): 726-33; Fujino, S., A. Andoh, et al. (2003). "Increased expression of interleukin 17 in inflammatory bowel disease." Gut 52(1): 65-70; Lock, C., G. Hermans, et al. (2002). "Gene-microarray analysis of multiple sclerosis lesions yields new targets validated in autoimmune encephalomyelitis." Nat Med 8(5): 500-8; Krueger, J. G., S. Fretzin, et al. "IL-17A is essential for cell activation and inflammatory gene circuits in subjects with psoriasis." J Allergy Clin Immunol 130(1): 145-154 e9.). Furthermore, human genetic studies have shown association of polymorphisms in the genes for Th17 cell-surface receptors, IL-23R and CCR6, with susceptibility to IBD, multiple sclerosis (MS), rheumatoid arthritis (RA) and psoriasis (Gazouli, M., I. Pachoula, et al. "NOD2/CARD15, ATG16L1 and IL23R gene polymorphisms and childhood-onset of Crohn's disease." World J Gastroenterol 16(14): 1753-8., Nunez, C., B. Dema, et al. (2008). "IL23R: a susceptibility locus for celiac disease and multiple sclerosis?" Genes Immun 9(4): 289-93; Bowes, J. and A. Barton "The genetics of psoriatic arthritis: lessons from genome-wide association studies." Discov Med 10(52): 177-83; Kochi, Y., Y. Okada, et al. "A regulatory variant in CCR6 is associated with rheumatoid arthritis susceptibility." Nat Genet 42(6): 515-9.).

Ustekinumab (Stelara®), an anti-p40 monoclonal antibody blocking both IL-12 and IL-23, is approved for the treatment of adult patients (18 years or older), with moderate to severe plaque psoriasis, who are candidates for phototherapy or systemic therapy. Currently, monoclonal antibodies specifically targeting only IL-23, to more selectively inhibit the Th17 subset, are also in clinical development for psoriasis (Garber K. (2011). "Psoriasis: from bed to bench and back" Nat Biotech 29, 563-566), further implicating the important role of the IL-23- and RORγt-driven Th17 pathway in this disease. Results from recent phase II clinical studies strongly support this hypothesis, as anti-IL-17 receptor and anti-IL-17 therapeutic antibodies both demonstrated high levels of efficacy in patients with chronic psoriasis (Papp, K. A., "Brodalumab, an anti-interleukin-17-receptor antibody for psoriasis." N Engl J Med 2012 366(13): 1181-9; Leonardi, C., R. Matheson, et al. "Anti-interleukin-17 monoclonal antibody ixekizumab in chronic plaque psoriasis." N Engl J Med 366(13): 1190-9.). Anti-IL-17 antibodies have also demonstrated clinically relevant responses in early trials in RA and uveitis (Hueber, W., Patel, D. D., Dryja, T., Wright, A. M., Koroleva, I., Bruin, G., Antoni, C., Draelos, Z., Gold, M. H., Durez, P., Tak, P. P., Gomez-Reino, J. J., Foster, C. S., Kim, R. Y., Samson, C. M., Falk, N. S., Chu, D. S., Callanan, D., Nguyen, Q. D., Rose, K., Haider, A., Di Padova, F. (2010) Effects of AIN457, a fully human antibody to interleukin-17A, on psoriasis, rheumatoid arthritis, and uveitis. Sci Transl Med 2, 5272.).

All the above evidence supports inhibition of the Th17 pathway by modulating RORγt activity as an effective strategy for the treatment of immune-mediated inflammatory diseases.

SUMMARY OF THE INVENTION

The present invention comprises compounds of Formula I.

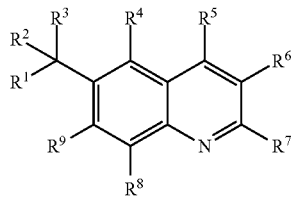

Formula I wherein:
- $R^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups; and wherein said azetidinyl is optionally substituted with $CO_2C(CH_3)_3$, $C(O)NH_2$, $CH_3$, $SO_2CH_3$, or $C(O)CH_3$;
- $R^2$ is 1-methyl-1,2,3-triazolyl, pyridyl, pyridyl-N-oxide, 1-methyl pyrazol-4-yl, pyrimidin-5-yl, pyridazyl, pyrazin-2-yl, oxazolyl, isoxazolyl, N-acetyl-azetidin-3-yl, N-methylsulfonyl-azetidin-3-yl, N-Boc-azetidin-3-yl, N-methyl-azetidin-3-yl, N-acetamidyl-azetidin-3-yl, N-acetyl piperidinyl, 1-H-piperidinyl, N-Boc-piperidinyl, N—$C_{(1-2)}$alkyl-piperidinyl (including N-methyl piperidin-4-yl), thiazol-5-yl, 1-methyl imidazol-2-yl, 1-(3-methoxypropyl)-imidazol-5-yl, or 1-$C_{(1-2)}$alkyl imidazol-5-yl; wherein said 1-$C_{(1-2)}$alkyl imidazol-5-yl is optionally substituted with up to two additional $CH_3$ groups, or one substituent selected from the group consisting of $SCH_3$, and Cl; and said pyridyl, and pyridyl-N-oxide are optionally substituted with up to two substituents independently selected from the group consisting of $C(O)NH_2$, —CN, $OCH_3$, $CF_3$, Cl, and $CH_3$; and said thiazol-5-yl, oxazolyl, and isoxazolyl are optionally substituted with up to two $CH_3$ groups; and said 1-methyl pyrazol-4-yl is optionally substituted with up to two additional $CH_3$ groups;
- $R^3$ is H, OH, $OCH_3$, $NHCH_3$, $N(CH_3)_2$, or $NH_2$;
- $R^4$ is H, or F;
- $R^5$ is H, Cl, —CN, $CF_3$, $SCH_3$, $OC_{(1-3)}$alkyl, OH, $C_{(1-4)}$alkyl, $N(CH_3)OCH_3$, $NH(C_{(1-2)}$alkyl), $N(C_{(1-2)}$alkyl)$_2$, NH-cyclopropyl, $OCHF_2$, 4-hydroxy-piperidinyl, azetidin-1-yl, or fur-2-yl;
- $R^6$ is 2-chloro-thiophen-5-yl, 1-methyl-pyrazol-4-yl, phenyl, pyrimidinyl, or pyridyl, wherein said phenyl, pyrimidinyl, and pyridyl are optionally substituted with $SO_2CH_3$, $NHSO_2CH_3$, $CF_3$, F, Cl, —CN, $OCH_3$, or $OCF_3$;
- $R^7$ is H, Cl, —CN, $C_{(1-4)}$alkyl, $OCH_2CF_3$, $OCH_2CH_2OCH_3$, $CF_3$, $SCH_3$, $SO_2CH_3$, $OCHF_2$, $NA^1A^2$, $C(O)NHCH_3$, $N(CH_3)CH_2CH_2NA^1A^2$, $OCH_2CH_2NA^1A^2$, $OCH_2CH_2NH_2$, $OC_{(1-3)}$alkyl, $OCH_2$-(1-methyl)-imidazol-2-yl, imidazol-2-yl, fur-2-yl, pyrazol-4-yl, pyrid-3-yl, or pyrimidin-5-yl; thiophen-3-yl, 1-methyl-indazol-5-yl, 1-methyl-indazol-6-yl, phenyl, or

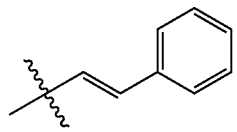 [SMILES: */C=C/c1ccccc1]

wherein said imidazolyl or pyrazolyl can be optionally substituted with a $CH_3$ group;
- $A^1$ is H or $C_{(1-4)}$alkyl (including $CH_3$);
- $A^2$ is $C_{(1-4)}$alkyl (including $CH_3$), cyclopropyl, $C_{(1-4)}$alkylO$C_{(1-4)}$alkyl, $C_{(1-4)}$alkylOH, $C(O)C_{(1-2)}$alkyl, or $OCH_3$; or $A^1$ and $A^2$ may be taken together with their attached nitrogen to form a ring selected from the group consisting of:

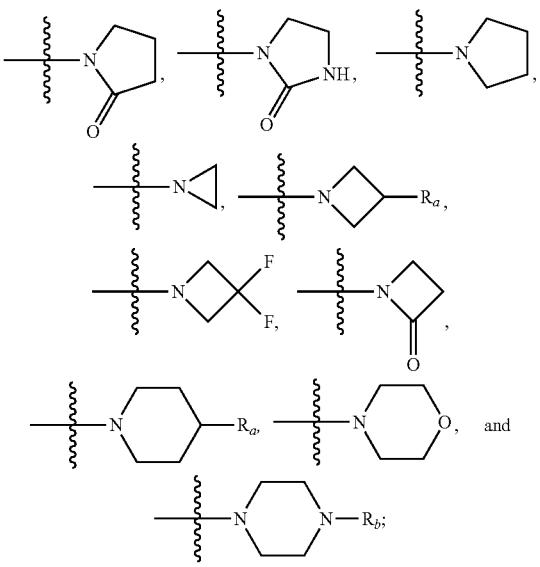

$R_a$ is H, F, $OCH_3$, or OH;
$R_b$ is $CH_3$, or phenyl;
$R^8$ is H, $CH_3$, $OCH_3$, or F;
$R^9$ is H, or F;
and pharmaceutically acceptable salts thereof;
provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, 4-(2-((4-chloro-6-((4-chlorophenyl)(hydroxy)(1-methyl-1H-imidazol-5-yl)methyl)-3-phenylquinolin-2-yl)oxy)ethyl)thiomorpholine 1,1-dioxide, 1-(2-((4-chloro-6-((4-chlorophenyl)(hydroxy)(1-methyl-1H-imidazol-5-yl)methyl)-3-phenylquinolin-2-yl)oxy)ethyl)pyrrolidin-2-one, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl)methanol, (4-chloro-2-(1-methyl-1H-pyrazol-4-yl)-3-phenylquinolin-6-yl)(4-chlorophenyl)(pyridin-3-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-chlorophenyl)(2,4-dichloro-3-(2-chlorophenyl)quinolin-6-yl)(1-methyl-1H-imidazol-5-yl)methanol, (2,4-dichloro-3-phenylquinolin-6-yl)(phenyl)(pyridin-2-yl)methanol, (2,4-dichloro-3-phenylquinolin-6-yl)(oxazol-2-yl)(phenyl)methanol, the second eluting enantiomer of (4-methoxy-3-phenyl-2-(trifluoromethyl)quinolin-6-yl)(1-methyl-1H-imidazol-5-yl)(pyridin-2-yl)methanol, and the second eluting enantiomer of (4-chloro-2-methoxy-3-phenylquinolin-6-yl)(1-methyl-1H-imidazol-5-yl)pyrimidin-2-ylmethanol (when purified on a chiralcel OD column) are excluded from the embodiment.

DETAILED DESCRIPTION OF THE INVENTION

The present invention comprises compounds of Formula I.

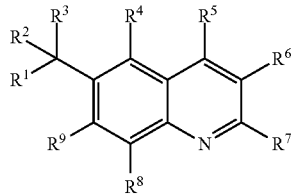

Formula I wherein:
R$^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups; and wherein said azetidinyl is optionally substituted with $CO_2C(CH_3)_3$, $C(O)NH_2$, $CH_3$, $SO_2CH_3$, or $C(O)CH_3$;

R$^2$ is 1-methyl-1,2,3-triazolyl, pyridyl, pyridyl-N-oxide, 1-methyl pyrazol-4-yl, pyrimidin-5-yl, pyridazyl, pyrazin-2-yl, oxazolyl, isoxazolyl, N-acetyl-azetidin-3-yl, N-methylsulfonyl-azetidin-3-yl, N-Boc-azetidin-3-yl, N-methyl-azetidin-3-yl, N-acetamidyl-azetidin-3-yl, N-acetyl piperidinyl, 1-H-piperidinyl, N-Boc-piperidinyl, N—$C_{(1-2)}$alkyl-piperidinyl (including N-methyl piperidin-4-yl), thiazol-5-yl, 1-methyl imidazol-2-yl, 1-(3-methoxypropyl)-imidazol-5-yl, or 1-$C_{(1-2)}$alkyl imidazol-5-yl; wherein said 1-$C_{(1-2)}$alkyl imidazol-5-yl is optionally substituted with up to two additional $CH_3$ groups, or one substituent selected from the group consisting of $SCH_3$, and Cl; and said pyridyl, and pyridyl-N-oxide are optionally substituted with up to two substituents independently selected from the group consisting of $C(O)NH_2$, —CN, $OCH_3$, $CF_3$, Cl, and $CH_3$; and said thiazol-5-yl, oxazolyl, and isoxazolyl are optionally substituted with up to two $CH_3$ groups; and said 1-methyl pyrazol-4-yl is optionally substituted with up to two additional $CH_3$ groups;

R$^3$ is H, OH, $OCH_3$, $NHCH_3$, $N(CH_3)_2$, or $NH_2$;

R$^4$ is H, or F;

R$^5$ is H, Cl, —CN, $CF_3$, $SCH_3$, $OC_{(1-3)}$alkyl, OH, $C_{(1-4)}$alkyl, $N(CH_3)OCH_3$, $NH(C_{(1-2)}$alkyl), $N(C_{(1-2)}$alkyl)$_2$, NH-cyclopropyl, $OCHF_2$, 4-hydroxy-piperidinyl, azetidin-1-yl, or fur-2-yl;

R$^6$ is 2-chloro-thiophen-5-yl, 1-methyl-pyrazol-4-yl, phenyl, pyrimidinyl, or pyridyl, wherein said phenyl, pyrimidinyl, and pyridyl are optionally substituted with $SO_2CH_3$, $NHSO_2CH_3$, $CF_3$, F, Cl, —CN, $OCH_3$, or $OCF_3$;

R$^7$ is H, Cl, —CN, $C_{(1-4)}$alkyl, $OCH_2CF_3$, $OCH_2CH_2OCH_3$, $CF_3$, $SCH_3$, $SO_2CH_3$, $OCHF_2$, $NA^1A^2$, $C(O)NHCH_3$, $N(CH_3)CH_2CH_2NA^1A^2$, $OCH_2CH_2NA^1A^2$, $OCH_2CH_2NH_2$, $OC_{(1-3)}$alkyl, $OCH_2$-(1-methyl)-imidazol-2-yl, imidazol-2-yl, fur-2-yl, pyrazol-4-yl, pyrid-3-yl, or pyrimidin-5-yl; thiophen-3-yl, 1-methyl-indazol-5-yl, 1-methyl-indazol-6-yl, phenyl, or

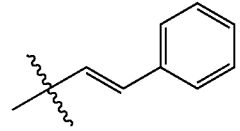 [SMILES: */C=C/c1ccccc1]

wherein said imidazolyl or pyrazolyl can be optionally substituted with a $CH_3$ group;

A$^1$ is H or $C_{(1-4)}$alkyl (including $CH_3$);

A$^2$ is $C_{(1-4)}$alkyl (including $CH_3$), cyclopropyl, $C_{(1-4)}$alkylO$C_{(1-4)}$alkyl, $C_{(1-4)}$alkylOH, $C(O)C_{(1-2)}$alkyl, or $OCH_3$; or A$^1$ and A$^2$ may be taken together with their attached nitrogen to form a ring selected from the group consisting of:

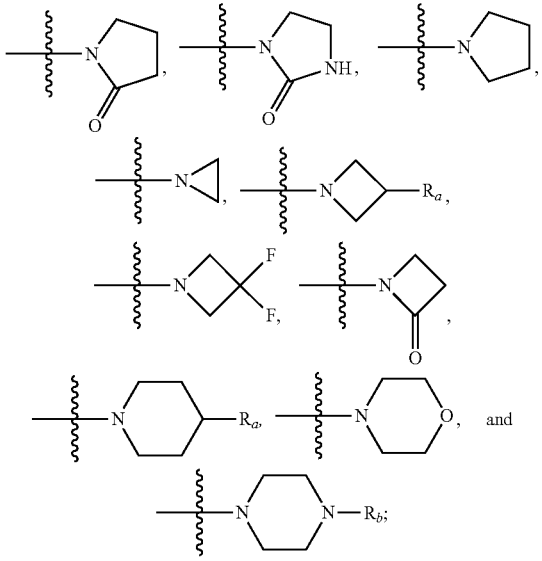

and

R$_a$ is H, F, OCH$_3$, or OH;

R$_b$ is CH$_3$, or phenyl;

R$^8$ is H, CH$_3$, OCH$_3$, or F;

R$^9$ is H, or F;

and pharmaceutically acceptable salts thereof;

provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, 4-(2-((4-chloro-6-((4-chlorophenyl)(hydroxy)(1-methyl-1H-imidazol-5-yl)methyl)-3-phenylquinolin-2-yl)oxy)ethyl)thiomorpholine 1,1-dioxide, 1-(2-((4-chloro-6-((4-chlorophenyl)(hydroxy)(1-methyl-1H-imidazol-5-yl)methyl)-3-phenylquinolin-2-yl)oxy)ethyl)pyrrolidin-2-one, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl)methanol, (4-chloro-2-(1-methyl-1H-pyrazol-4-yl)-3-phenylquinolin-6-yl)(4-chlorophenyl)(pyridin-3-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-chlorophenyl)(2,4-dichloro-3-(2-chlorophenyl)quinolin-6-yl)(1-methyl-1H-imidazol-5-yl)methanol, (2,4-dichloro-3-phenylquinolin-6-yl)(phenyl)(pyridin-2-yl)methanol, (2,4-dichloro-3-phenylquinolin-6-yl)(oxazol-2-yl)(phenyl)methanol, the second eluting enantiomer of (4-methoxy-3-phenyl-2-(trifluoromethyl)quinolin-6-yl)(1-methyl-1H-imidazol-5-yl)(pyridin-2-yl)methanol, and the second eluting enantiomer of (4-chloro-2-methoxy-3-phenylquinolin-6-yl)(1-methyl-1H-imidazol-5-yl)pyrimidin-2-ylmethanol (when purified on a chiralcel OD column) are excluded from the embodiment.

In another embodiment of the invention:

R$^1$ is imidazolyl, thiazolyl, pyridyl, pyrimidinyl, or phenyl; wherein said pyridyl, and said phenyl are optionally substituted with —CN, CF$_3$, F, or Cl; and wherein said imidazolyl, and thiazolyl are optionally substituted with one or two CH$_3$ groups;

R$^2$ is 1-methyl-1,2,3-triazol-5-yl, N-acetyl piperidin-4-yl, N-Boc-piperidin-4-yl, N-methyl piperidin-4-yl 1-H-piperidin-4-yl, oxazol-2-yl, 2,4-dimethyl thiazol-5-yl, 1-methyl imidazol-2-yl, 1-methyl-imidazol-5-yl, or pyridyl; wherein said pyridyl is optionally substituted with CF$_3$;

R$^3$ is H, OH;

R$^4$ is H;

R$^5$ is H, Cl, —CN, C$_{(1-4)}$alkyl, OC$_{(1-2)}$alkyl, SCH$_3$, N(CH$_3$)$_2$, or N(CH$_3$)OCH$_3$;

R$^6$ is 2-chloro-thiophen-5-yl, 1-methyl-pyrazol-4-yl, phenyl, pyrimidinyl, or pyridyl, wherein said phenyl, pyrimidinyl, and pyridyl are optionally substituted with SO$_2$CH$_3$, NHSO$_2$CH$_3$, CF$_3$, Cl, —CN, OCF$_3$, or OCH$_3$;

R$^7$ is Cl, —CN, CF$_3$, SCH$_3$, OCH$_2$CF$_3$, NA$^1$A$^2$, N(CH$_3$)CH$_2$CH$_2$NA$^1$A$^2$, OC$_{(1-3)}$alkyl, OCH$_2$CH$_2$OCH$_3$, OCH$_2$CH$_2$NA$^1$A$^2$, or OCH$_2$CH$_2$NH$_2$;

A$^1$ is H, or CH$_3$;

A$^2$ is OCH$_3$, CH$_3$, CH$_2$CH$_2$OH, C(O)C$_{(1-2)}$alkyl, or CH$_2$CH$_2$OCH$_3$; or A$^1$ and A$^2$ may be taken together with their attached nitrogen to form a ring selected from the group consisting of:

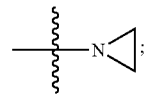

R$^8$ is H, or CH$_3$;

R$^9$ is H;

and pharmaceutically acceptable salts thereof;

provided that (4-chlorophenyl)(2,4-dichloro-3-(2-chlorophenyl)quinolin-6-yl)(1-methyl-1H-imidazol-5-yl)methanol, 6-((3-chlorophenyl)(hydroxy)(2-(trifluoromethyl)pyridin-4-yl)methyl)-3-phenylquinoline-2-carbonitrile, (2,4-dichloro-3-phenylquinolin-6-yl)di(pyridin-2-yl)methanol, (2,4-dichloro-3-phenylquinolin-6-yl)(phenyl)(pyridin-2-yl)methanol, (2-chloro-4-(dimethylamino)-3-phenylquinolin-6-yl)(pyridin-2-yl)(pyridin-4-yl)methanol, (4-chlorophenyl)(2,4-dichloro-3-(2-chlorophenyl)quinolin-6-yl)(1-methyl-1H-imidazol-2-yl)methanol, (2,4-dichloro-3-phenylquinolin-6-yl)(oxazol-2-yl)(phenyl)methanol, the second eluting enantiomer of (4-methoxy-3-phenyl-2-(trifluoromethyl)quinolin-6-yl)(1-methyl-1H-imidazol-5-yl)(pyridin-2-yl)methanol, and the second eluting enantiomer of (4-chloro-2-methoxy-3-phenylquinolin-6-yl)(1-methyl-1H-imidazol-5-yl)pyrimidin-2-ylmethanol (when purified on a chiralcel OD column) are excluded from the embodiment.

Another embodiment of the invention is a compound selected from the group consisting of:

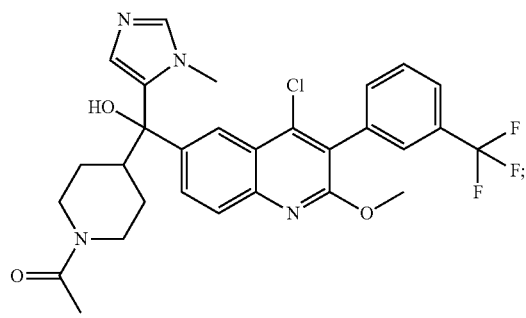

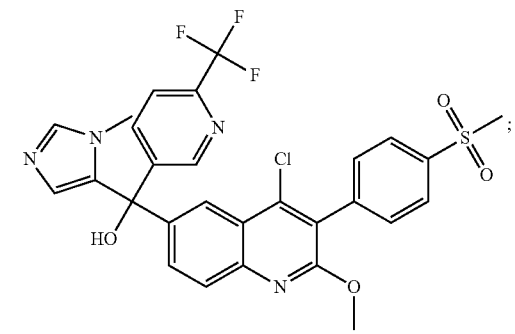

-continued
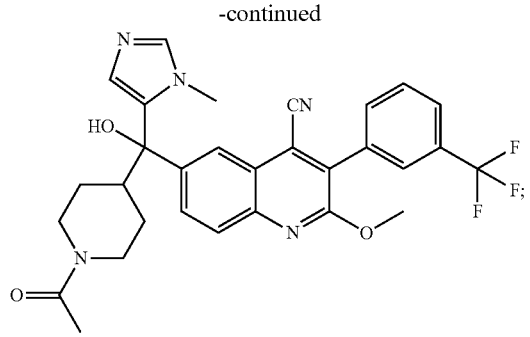
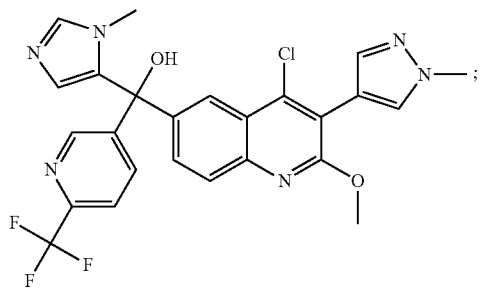
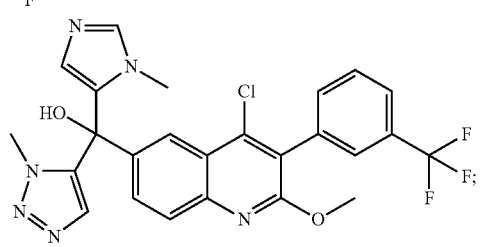
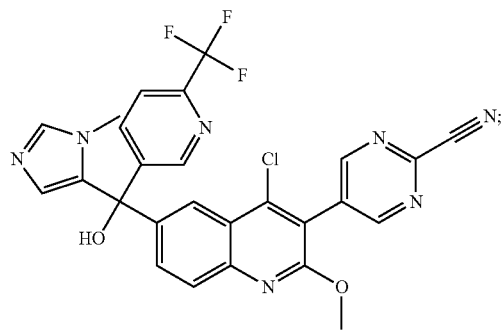
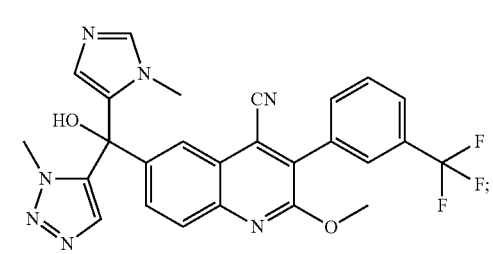
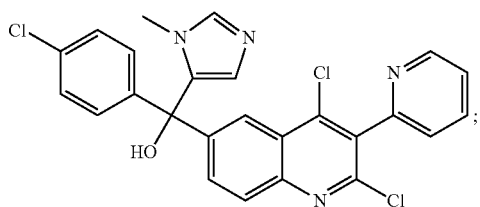
-continued
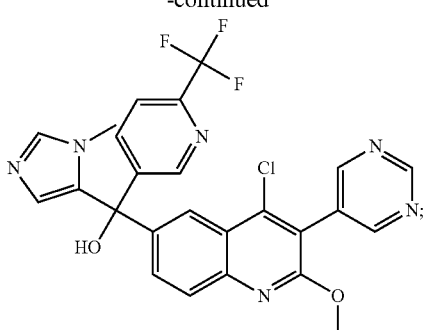
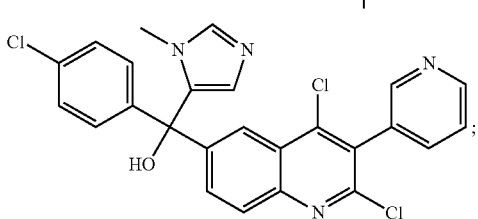
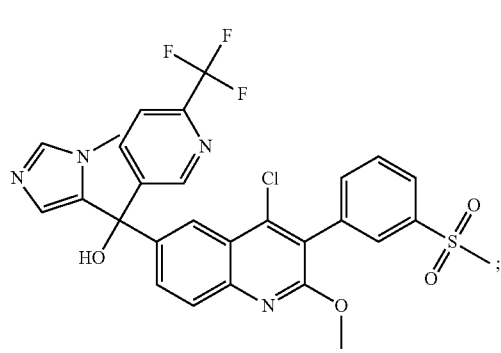
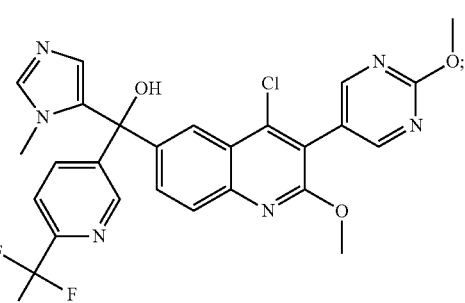
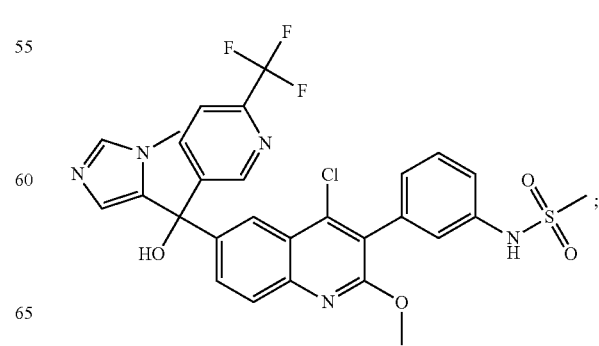

11
-continued
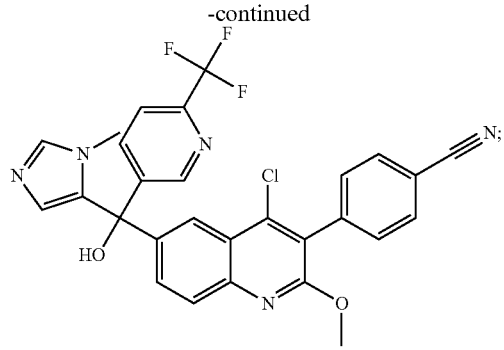
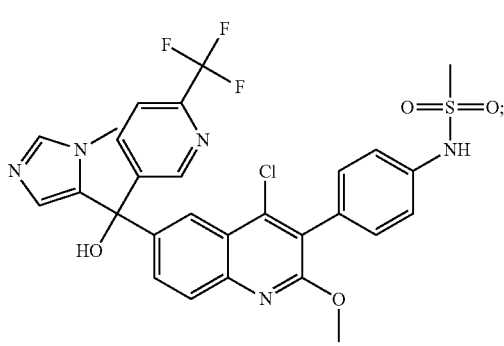
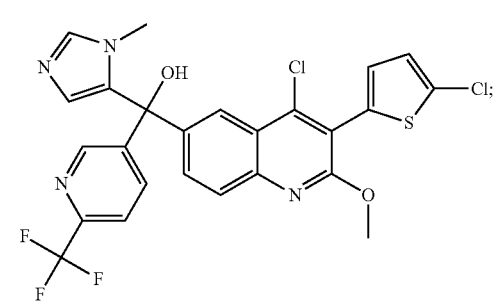
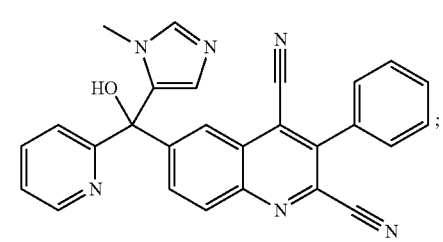
12
-continued
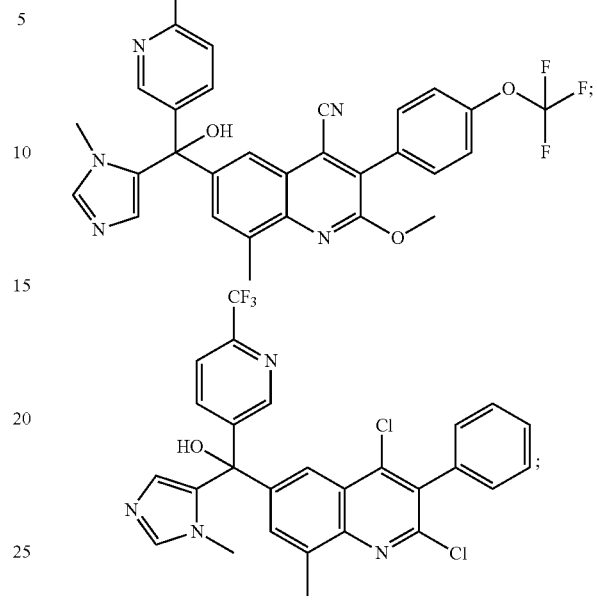

-continued
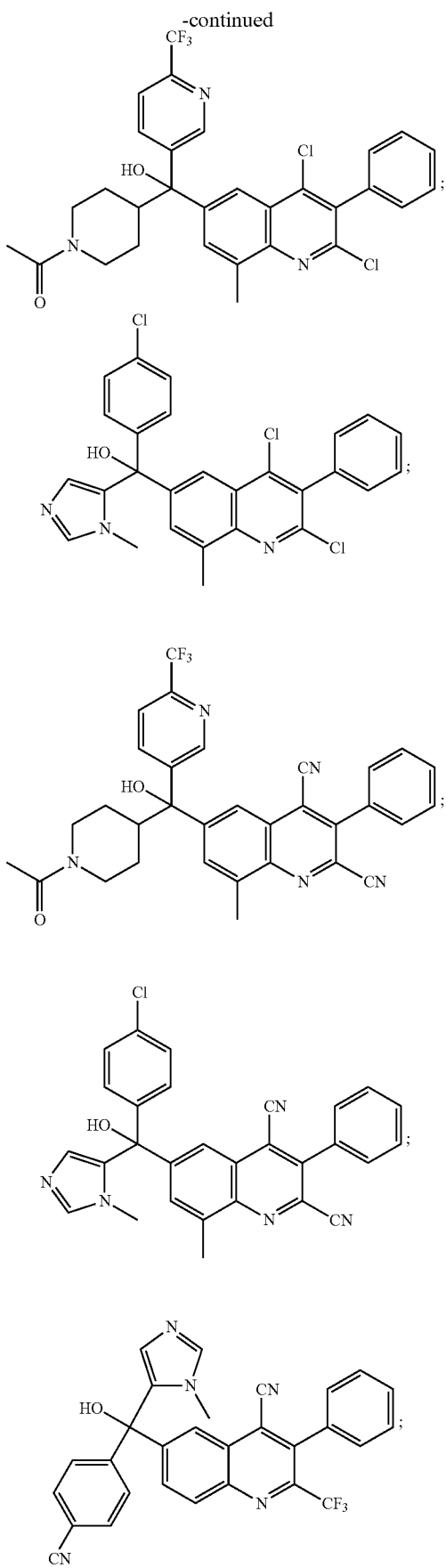
-continued
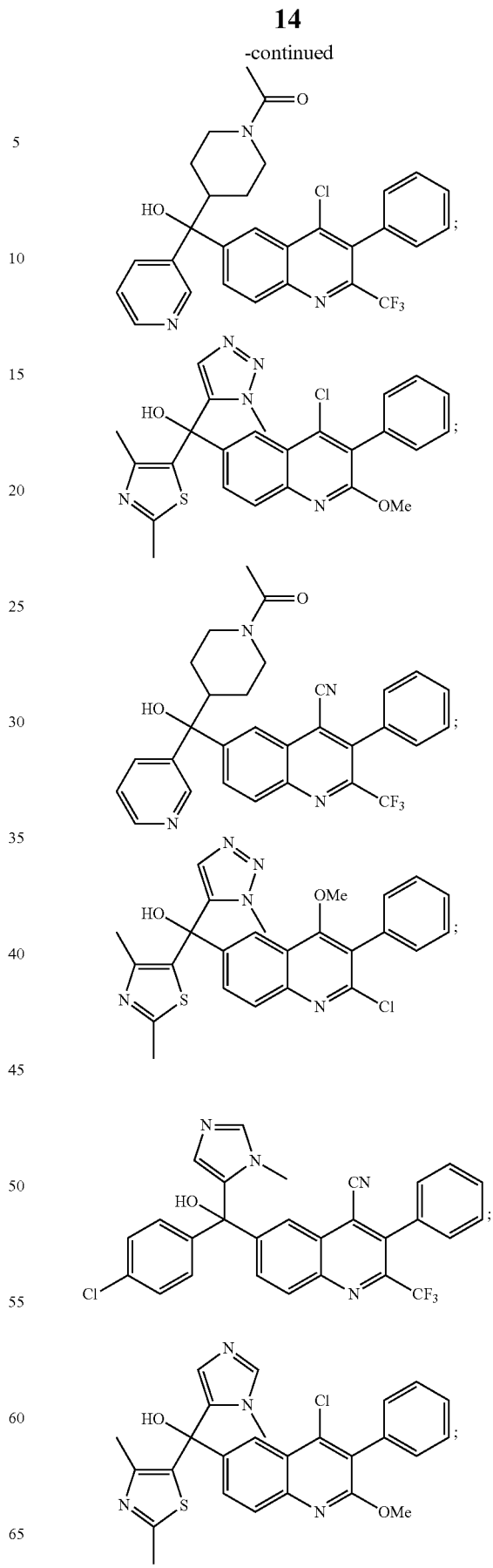

-continued
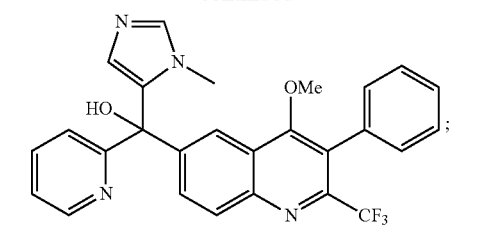
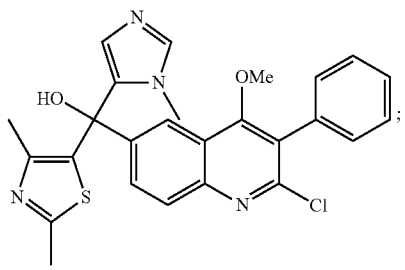
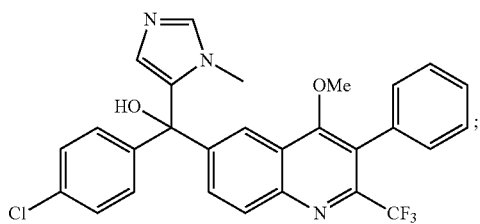
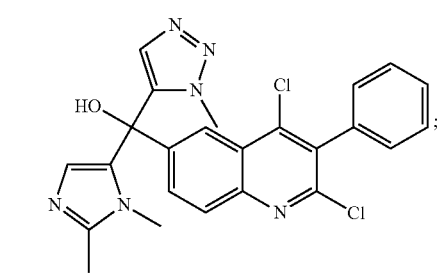
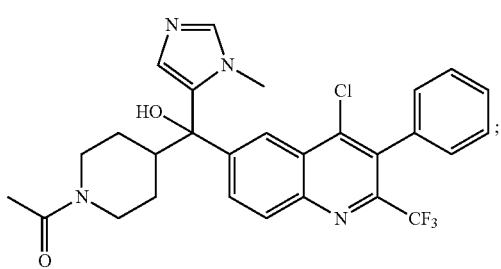
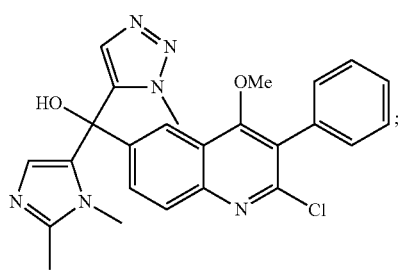
-continued
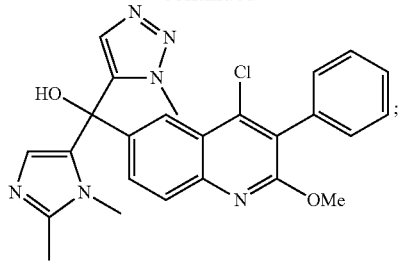
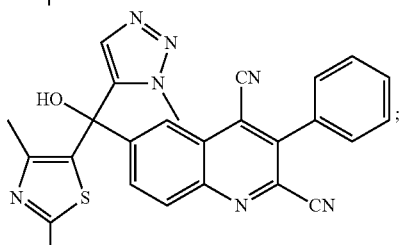
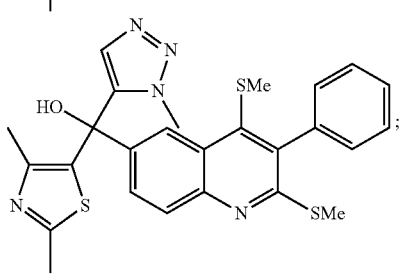
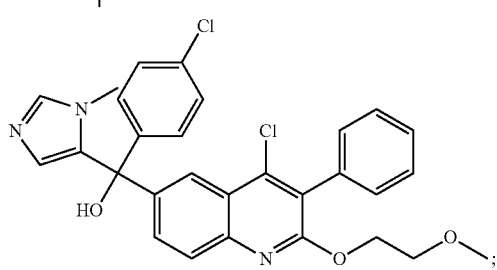
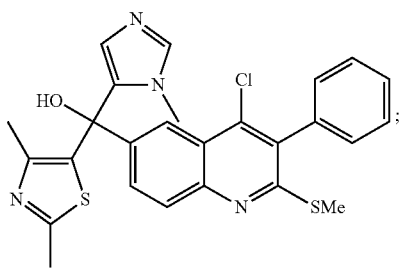
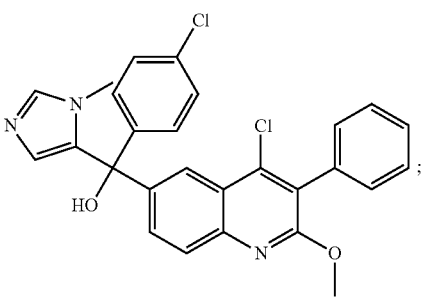

17
-continued
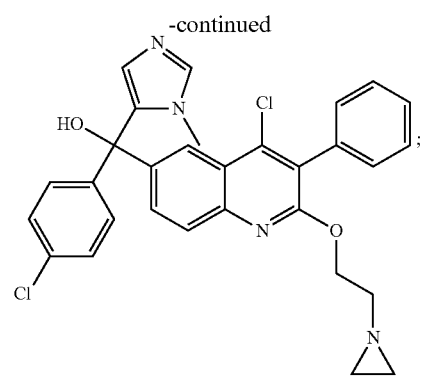
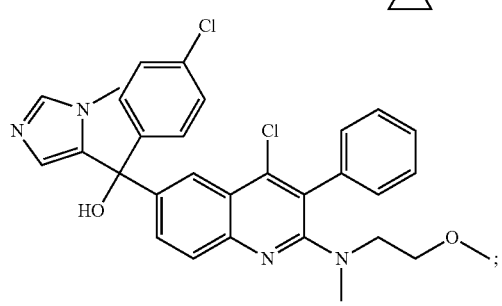
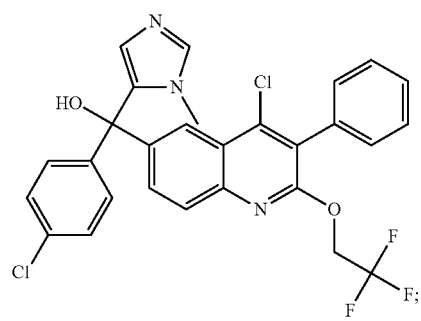
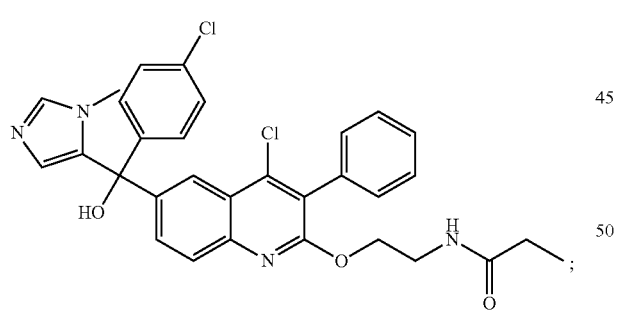
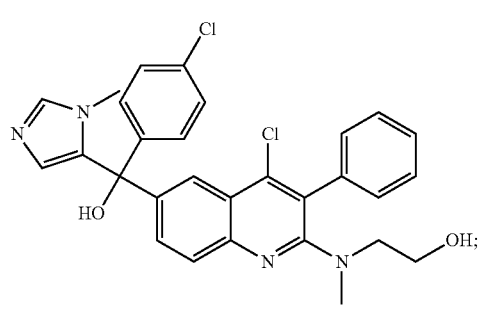
18
-continued
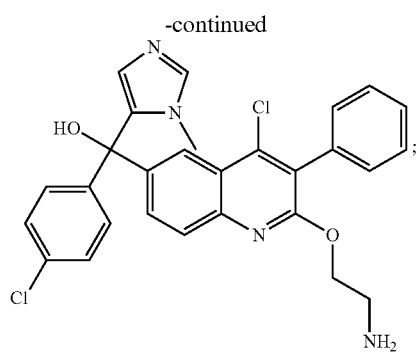
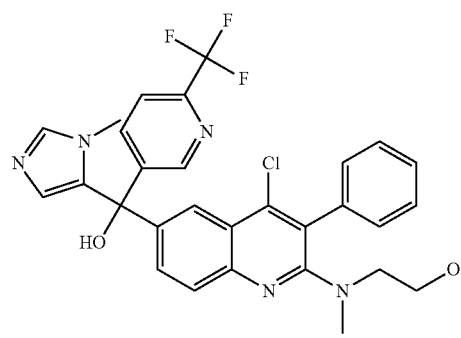
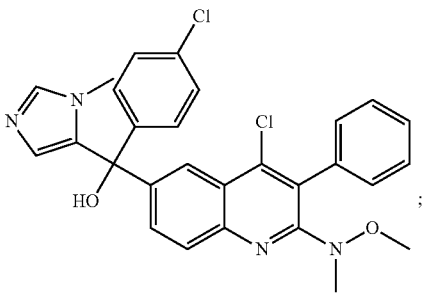
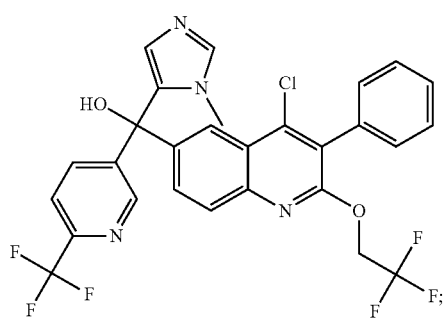
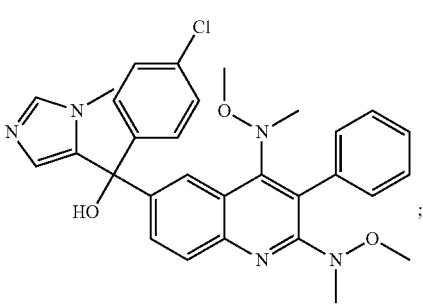

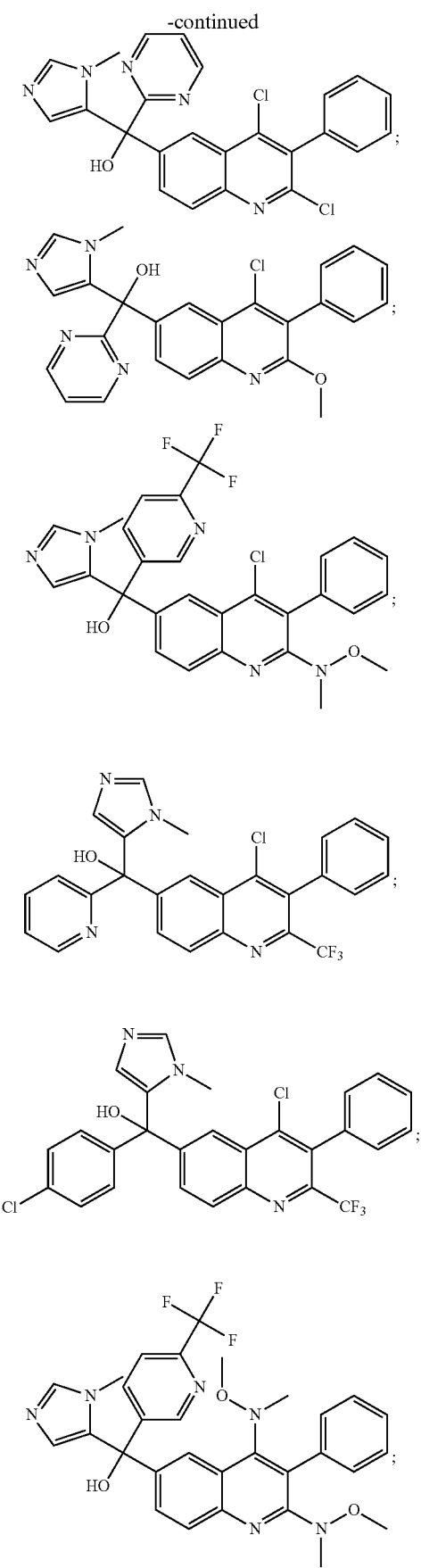
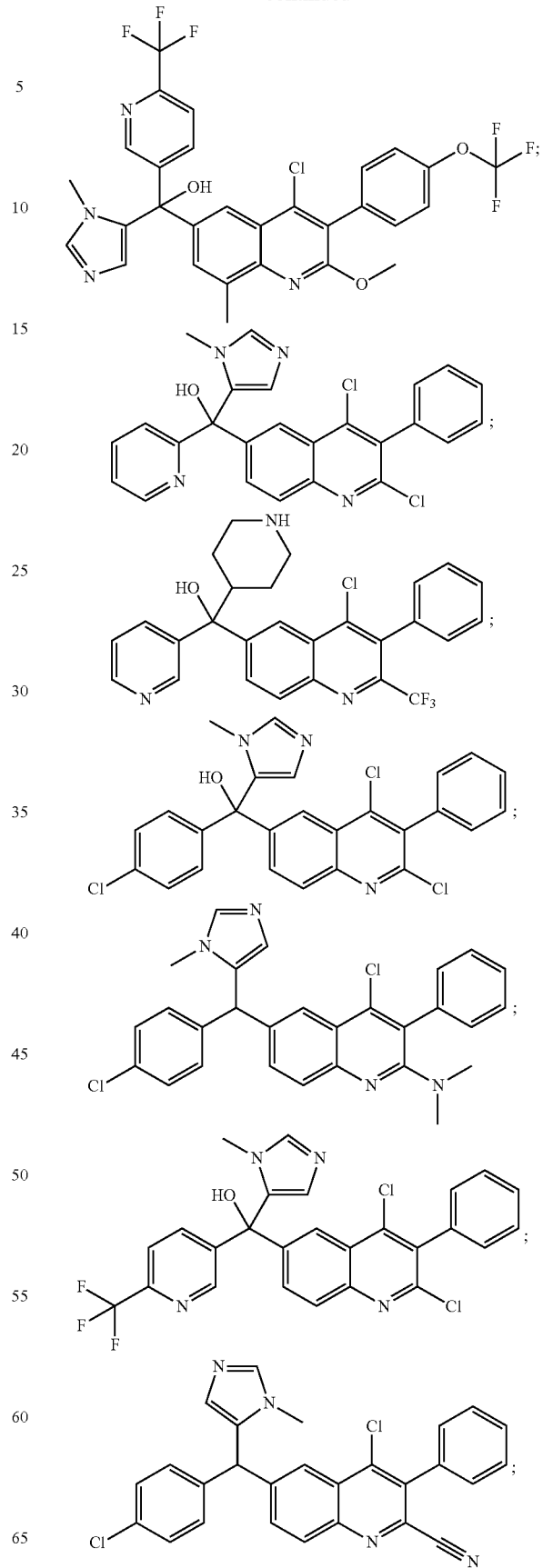

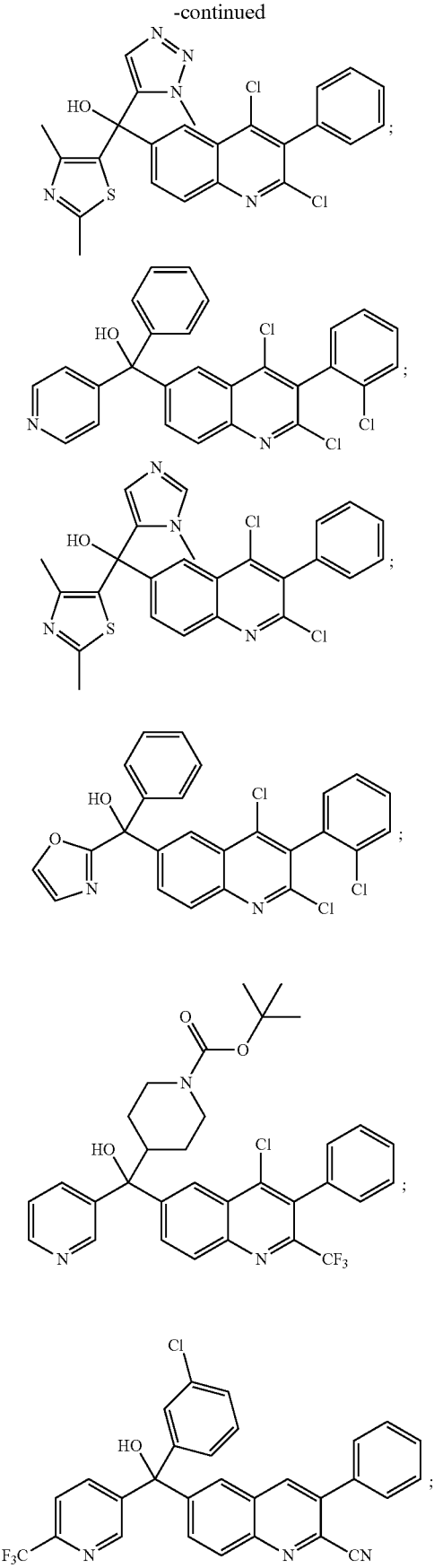
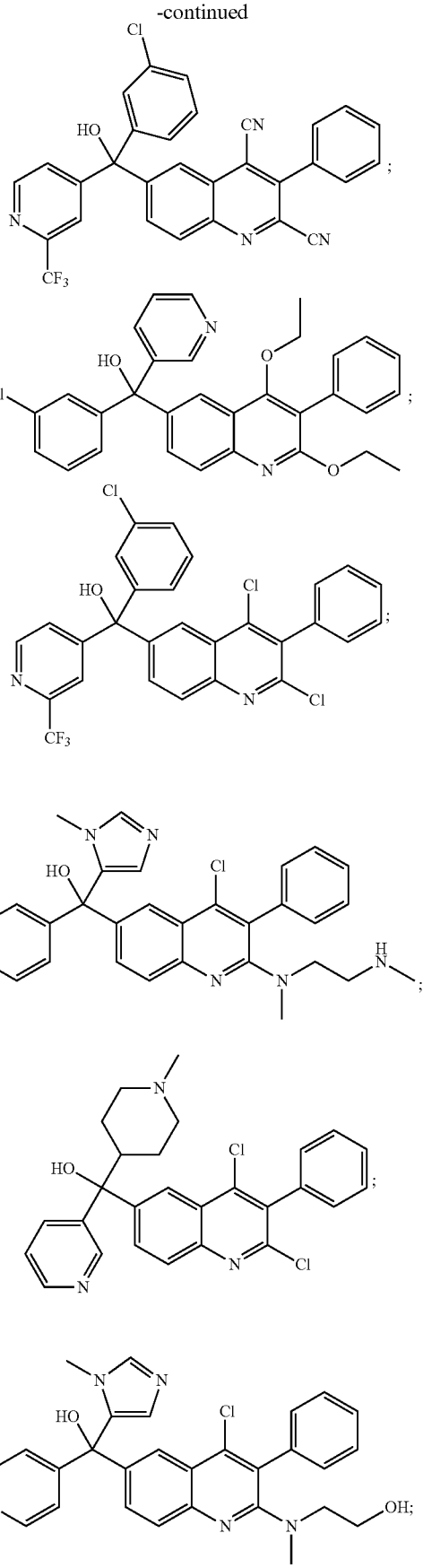

-continued

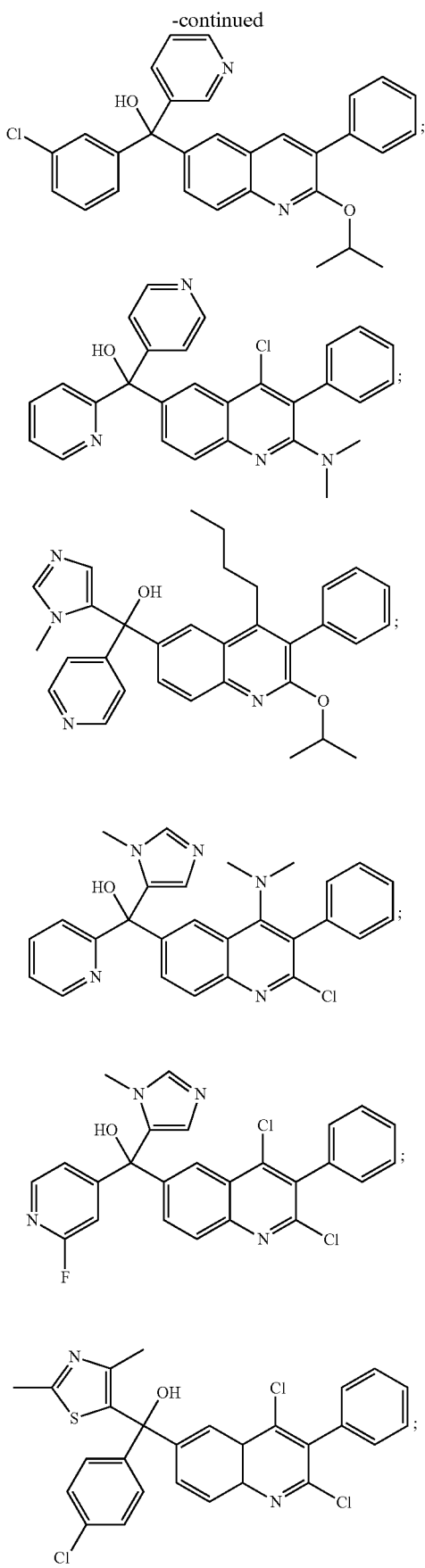

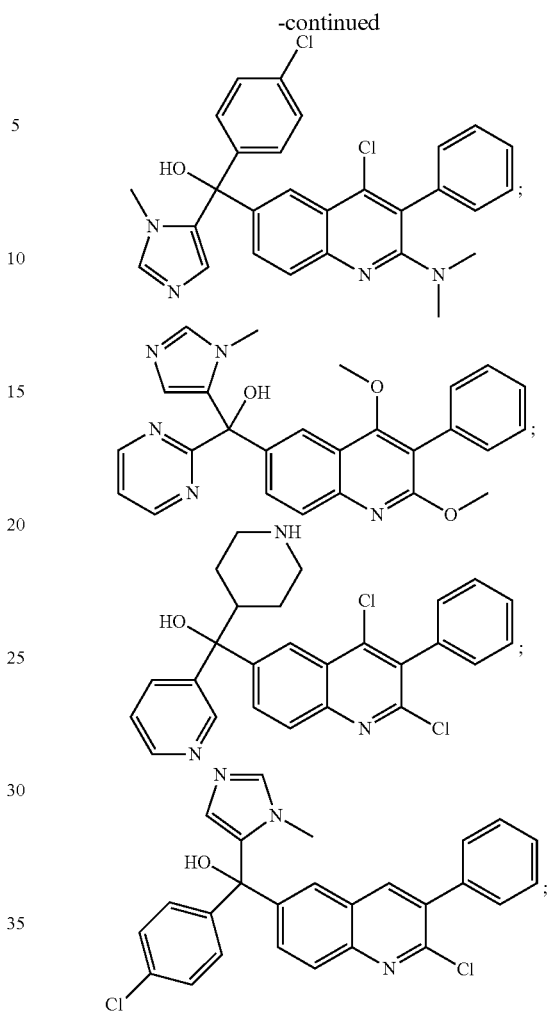

and pharmaceutically acceptable salts thereof.

Another embodiment of the invention comprises a compound of Formula I and a pharmaceutically acceptable carrier.

The present invention also provides a method for treating or ameliorating an RORγt mediated inflammatory syndrome, disorder or disease comprising administering to a subject in need thereof an effective amount of a compound of Formula I or a form, composition or medicament thereof.

The present invention provides a method of preventing, treating or ameliorating a syndrome, disorder or disease, wherein said syndrome, disorder or disease is selected from the group consisting of: ophthalmic disorders, uveitis, atherosclerosis, rheumatoid arthritis, psoriasis, psoriatic arthritis, atopic dermatitis, multiple sclerosis, Crohn's Disease, ulcerative colitis, ankylosing spondylitis, nephritis, organ allograft rejection, fibroid lung, systic fibrosis, renal insufficiency, diabetes and diabetic complications, diabetic nephropathy, diabetic retinopathy, diabetic retinitis, diabetic microangiopathy, tuberculosis, chronic obstructive pulmonary disease, sarcoidosis, invasive *staphylococcia*, inflammation after cataract surgery, allergic rhinitis, allergic conjunctivitis, chronic urticaria, systemic lupus erythematosus, asthma, allergic asthma, steroid resistant asthma, neutrophilic asthma, periodontal diseases, periodontis, gingivitis, gum disease, diastolic cardiomyopathies, cardiac infarction, myocarditis, chronic heart failure, angiostenosis, restenosis, reperfusion disorders, glomerulonephritis, solid tumors and cancers, chronic lymphocytic leukemia, chronic myelocytic leukemia, multiple myeloma, malignant myeloma, Hodgkin's disease, and carcinomas of the bladder, breast, cervix, colon, lung, prostate, or stomach comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, psoriasis, chronic obstructive pulmonary disorder, psoriatic arthritis, ankylosing spondylitis, Crohn's disease, neutrophilic asthma, steroid resistant asthma, multiple sclerosis, systemic lupus erythematosus, and ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is selected from the group consisting of: rheumatoid arthritis, and psoriasis comprising administering to a subject in need thereof an effective amount of a compound of Formula I or a form, composition or medicament thereof.

The present invention provides a method of treating or ameliorating a syndrome, disorder or disease, in a subject in need thereof comprising administering to the subject an effective amount of the compound of Formula I or composition or medicament thereof in a combination therapy with one or more anti-inflammatory agents, or immunosuppressive agents, wherein said syndrome, disorder or disease is selected from the group consisting of: rheumatoid arthritis, and psoriasis.

The present invention provides a method of treating or ameliorating a syndrome, disorder or disease, wherein said syndrome, disorder or disease is rheumatoid arthritis, comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriasis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is chronic obstructive pulmonary disorder comprising administering to a subject in need thereof an effective amount of a compound of Formula I or a form, composition or medicament thereof.

The present invention provides a method of treating or ameliorating a syndrome, disorder or disease, wherein said syndrome, disorder or disease is psoriatic arthritis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ankylosing spondylitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is Crohn's disease comprising administering to a subject in need thereof an effective amount of a compound of Formula I or a form, composition or medicament thereof.

The present invention provides a method of treating or ameliorating a syndrome, disorder or disease, wherein said syndrome, disorder or disease is ulcerative colitis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is neutrophilic asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is steroid resistant asthma comprising administering to a subject in need thereof an effective amount of a compound of Formula I or a form, composition or medicament thereof.

The present invention provides a method of treating or ameliorating a syndrome, disorder or disease, wherein said syndrome, disorder or disease is multiple sclerosis comprising administering to a subject in need thereof an effective amount of a compound of Formula I or a form, composition or medicament thereof.

The present invention provides a method of treating or ameliorating a syndrome, disorder or disease, wherein said syndrome, disorder or disease is systemic lupus erythematosus comprising administering to a subject in need thereof an effective amount of a compound of Formula I or a form, composition or medicament thereof.

The invention also relates to methods of modulating RORγt activity in a mammal by administration of an effective amount of at least one compound of Formula I.

The present invention provides a method of treating or ameliorating a syndrome, disorder or disease, wherein said syndrome, disorder or disease is selected from the group consisting of: inflammatory bowel diseases, rheumatoid arthritis, psoriasis, chronic obstructive pulmonary disorder, psoriatic arthritis, ankylosing spondylitis, neutrophilic asthma, steroid resistant asthma, multiple sclerosis, and systemic lupus erythematosus comprising administering to a subject in need thereof an effective amount of a compound of Formula I or a form, composition or medicament thereof.

The present invention provides a method of treating or ameliorating an inflammatory bowel disease, wherein said inflammatory bowel disease is Crohn's disease comprising administering to a subject in need thereof an effective amount of a compound of Formula I or a form, composition or medicament thereof.

The present invention provides a method of treating or ameliorating an inflammatory bowel diseases, wherein said inflammatory bowel disease is ulcerative colitis comprising administering to a subject in need thereof an effective amount of a compound of Formula I or a form, composition or medicament thereof.

Definitions

The term "administering" with respect to the methods of the invention, means a method for therapeutically or prophylactically preventing, treating or ameliorating a syndrome, disorder or disease as described herein by using a compound of Formula I or a form, composition or medicament thereof. Such methods include administering an effective amount of said compound, compound form, composition or medicament at different times during the course of a therapy or concurrently in a combination form. The methods of the invention are to be understood as embracing all known therapeutic treatment regimens.

The term "subject" refers to a patient, which may be an animal, typically a mammal, typically a human, which has been the object of treatment, observation or experiment and is at risk of (or susceptible to) developing a syndrome, disorder or disease that is associated with aberrant RORγt expression or RORγt overexpression, or a patient with an inflammatory condition that accompanies syndromes, disorders or diseases associated with aberrant RORγt expression or RORγt overexpression.

The term "effective amount" means that amount of active compound or pharmaceutical agent that elicits the biological or medicinal response in a tissue system, animal or human, that is being sought by a researcher, veterinarian, medical doctor, or other clinician, which includes preventing, treating or ameliorating the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl. Any alkyl group may be optionally substituted with one $OCH_3$, one OH, or up to two fluorine atoms.

The term "$C_{(a-b)}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{(1-4)}$ denotes a radical containing 1, 2, 3 or 4 carbon atoms.

The term "cycloalkyl" refers to a saturated or partially unsaturated monocyclic or bicyclic hydrocarbon ring radical derived by the removal of one hydrogen atom from a single ring carbon atom. Typical cycloalkyl radicals include cyclopropyl, cyclobutyl, cyclopentyl, cyclopentenyl, cyclohexyl, cyclohexenyl, cycloheptyl and cyclooctyl. Additional examples include $C_{(3-6)}$ocycloalkyl, $C_{(5-8)}$cycloalkyl, decahydronaphthalenyl, and 2,3,4,5,6,7-hexahydro-1H-indenyl. Any cycloalkyl group may be optionally substituted with one $OCH_3$, one OH, or up to two fluorine atoms.

As used herein, the term "thiophenyl" is intended to describe the radical formed by removing a hydrogen atom from the molecule with the structure:

Pharmaceutically Acceptable Salts

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, $NH_3$, $NH_4OH$, N-methyl-D-glucamine, piperidine, potassium, potassium-t-butoxide, potassium hydroxide (aqueous), procaine, quinine, sodium, sodium carbonate, sodium-2-ethylhexanoate, sodium hydroxide, triethanolamine or zinc.

Methods of Use

The present invention is directed to a method for preventing, treating or ameliorating a RORγt mediated inflammatory syndrome, disorder or disease comprising administering to a subject in need thereof an effective amount of a compound of Formula I or a form, composition or medicament thereof.

Since RORγt is an N-terminal isoform of RORγ, it is recognized that compounds of the present invention which are modulators of RORγt are likely to be modulators of RORγ as well. Therefore the mechanistic description "RORγt modulators" is intended to encompass RORγ modulators as well.

When employed as RORγt modulators, the compounds of the invention may be administered in an effective amount within the dosage range of about 0.5 mg to about 10 g, preferably between about 0.5 mg to about 5 g, in single or divided daily doses. The dosage administered will be affected by factors such as the route of administration, the health, weight and age of the recipient, the frequency of the treatment and the presence of concurrent and unrelated treatments.

It is also apparent to one skilled in the art that the therapeutically effective dose for compounds of the present invention or a pharmaceutical composition thereof will vary according to the desired effect. Therefore, optimal dosages to be administered may be readily determined by one skilled in the art and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this invention.

The compounds of Formula I may be formulated into pharmaceutical compositions comprising any known pharmaceutically acceptable carriers. Exemplary carriers include, but are not limited to, any suitable solvents, dispersion media, coatings, antibacterial and antifungal agents and isotonic agents. Exemplary excipients that may also be components of the formulation include fillers, binders, disintegrating agents and lubricants.

The pharmaceutically-acceptable salts of the compounds of Formula I include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Alternatively or concurrently, administration may be by the oral route. Suitable formulations for parenteral administration include aqueous solutions of the active compounds in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the compounds of the present invention. Additionally, the present invention includes pharmaceutical compositions made by mixing a pharmaceutically acceptable carrier with any of the compounds of the present invention.

Polymorphs and Solvates

Furthermore, the compounds of the present invention may have one or more polymorph or amorphous crystalline forms and as such are intended to be included in the scope of the invention. In addition, the compounds may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the compounds of the present invention. Thus, in the methods of treatment of the present invention, the term "administering" shall encompass the means for treating, ameliorating or preventing a syndrome, disorder or disease described herein with the compounds of the present invention or a polymorph or solvate thereof, which would obviously be included within the scope of the invention albeit not specifically disclosed.

In another embodiment, the invention relates to a compound as described in Formula I for use as a medicament.

In another embodiment, the invention relates to the use of a compound as described in Formula I for the preparation of a medicament for the treatment of a disease associated with an elevated or aberrant RORγt activity.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to a compound of Formula I, shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of Formula I may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Some compounds of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the compounds according to this invention have at least one stereocenter, they may accordingly exist as enantiomers or diastereomers. It is to be understood that all such isomers and mixtures thereof are encompassed within the scope of the present invention.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Abbreviations

Herein and throughout the application, the following abbreviations may be used.

Å angstrom
Ac acetyl
Ac$_2$O acetic anhydride
Boc tert-butyloxy carbonyl
BHT butylated hydroxytoluene
br broad
Bu butyl
n-BuLi n-butyl lithium
t-BuOH tert-butanol
d doublet
dba dibenzylideneacetone
DCE dichloroethane
DCM dichloromethane
Dess-Martin periodinane 1,1,1-tris(acetyloxy)-1,1-dihydro-1,2-benziodoxol-3-(1H)-one
DIEA N,N-diisopropylethylamine
DMA dimethylacetamide
DME dimethoxyethane
DMF N,N-dimethylformamide
DMSO dimethyl sulfoxide
dppf (diphenylphosphino)ferrocene
Eaton's Reagent 7.7 wt % phosphorus pentoxide solution in methanesulfonic acid
EDCI N-(3-dimethylaminopropyl)-N'-ethylcarbodiimide hydrochloride
ESI electrospray ionization
Et ethyl
Et$_2$O diethyl ether
EtOAc ethyl acetate
EtOH ethyl alcohol
FCC flash column chromatography
HATU O-(7-azabenzotriazol-1-yl)-N,N,N',N'-tetramethyluronium hexafluorophosphate
HPLC high pressure liquid chromatography
Hunig's base N,N-diisopropylethylamine
Hz hertz
i-PrOH isopropyl alcohol
KHMDS potassium bis(trimethylsilyl)amide
LCMS liquid chromatography-mass spectrometry
LDA lithium diisopropylamide
m multiplet
M molar (moles/liter)
mCPBA 3-chloroperbenzoic acid
Me methyl
Meldrum's acid 2,2-dimethyl-1,3-dioxane-4,6-dione
MeOH methanol
MeONa sodium methoxide
MHz megahertz
min minutes
mL milliliters
MS mass spectrometry
MTBE methyl tertiary butyl ether
m/z mass to charge ratio
nm nanometers
NaOiPr sodium isopropoxide
NBS N-bromosuccinimide
NMP 1-methyl-2-pyrrolidinone
NMR nuclear magnetic resonance
Ph phenyl
PPA polyphosphoric acid
ppm parts per million
Pr propyl
q quartet
RP-HPLC reverse phase high pressure liquid chromatography
s singlet
t triplet
TBAF tetrabutylammonium fluoride
TEA triethylamine
TEMPO (2,2,6,6-tetramethylpiperidin-1-yl)oxidanyl
TFA trifluoroacetic acid
THF tetrahydrofuran
TLC thin layer chromatography
UV ultra-violet
X-Phos 2-dicyclohexylphosphino-2',4',6'-triisopropylbiphenyl General Schemes:

Compounds of Formula I in the present invention can be synthesized in accordance with the general synthetic methods known to those who are skilled in the art. The following reaction schemes are only meant to represent examples of the invention and are in no way meant to be a limit of the invention.

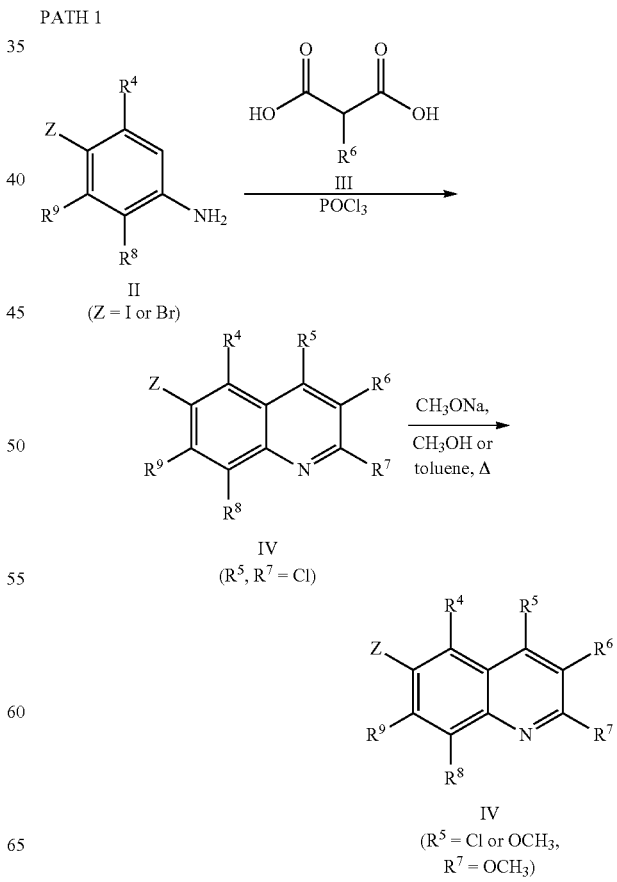

Scheme 1

PATH 2

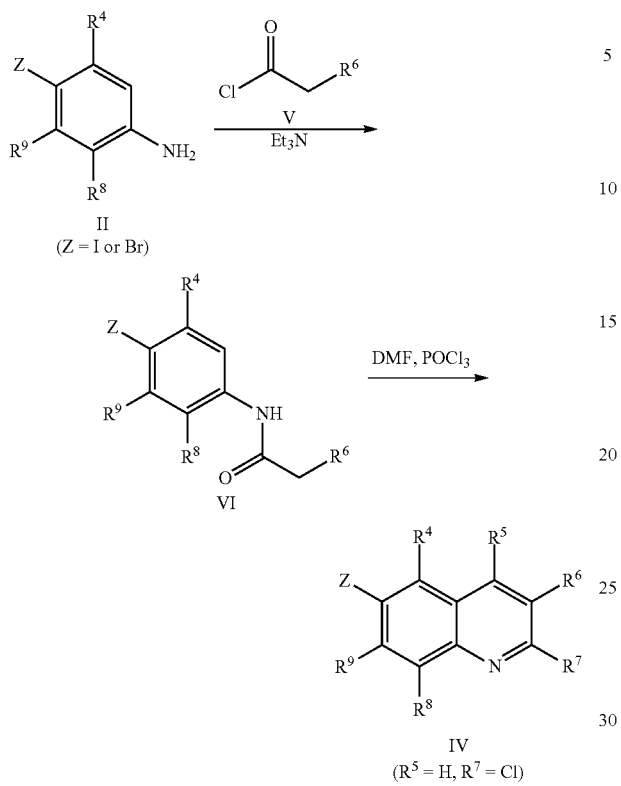

PATH 3

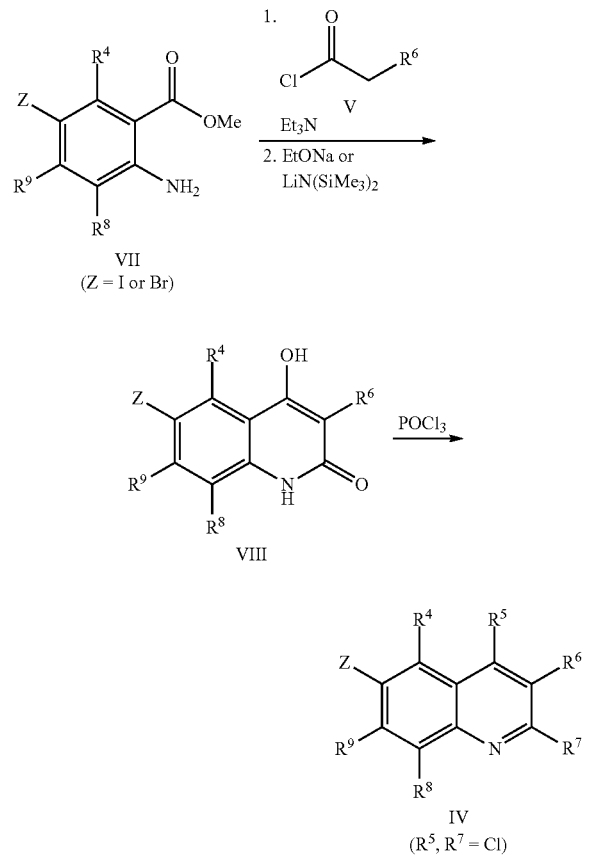

PATH 4

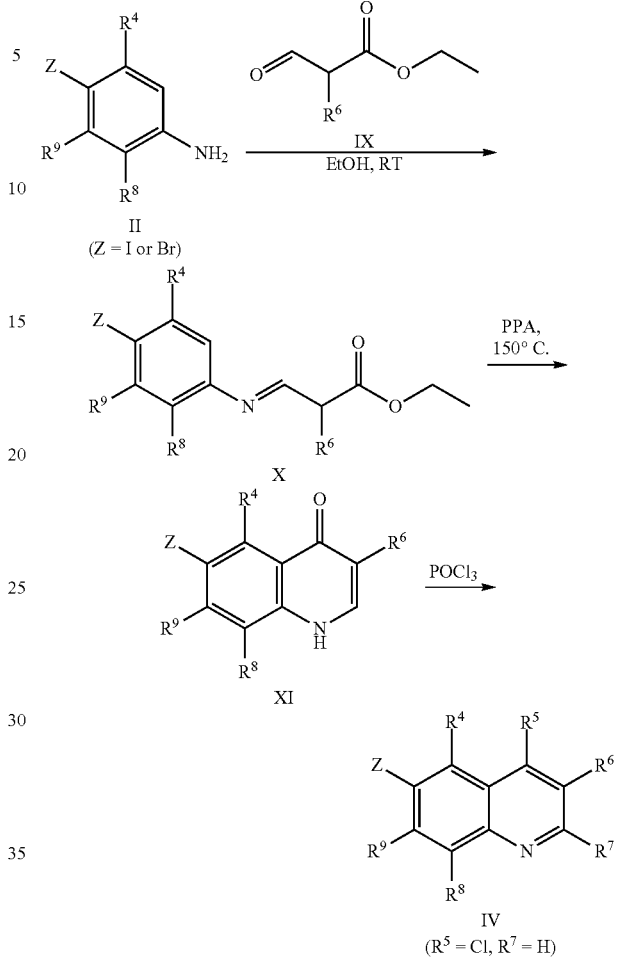

Scheme 1 describes the preparation of 6-bromo or 6-iodo-quinolines of Formula IV by various methods (path 1 to 4). In path 1, cyclization of 4-haloanilines II with commercially available 2-substituted malonic acids III can be done in refluxing phosphorus oxychloride to provide 6-haloquinolines IV, wherein $R^5$ and $R^7$ are Cl. Nucleophilic displacement of 2-chloro substitution with sodium methoxide in hot MeOH or toluene (Alan Osborne et. al. *J. Chem. Soc. Perkin Trans.* 1 (1993) 181-184 and *J. Chem. Research* (S), 2002, 4) gives 6-halo-2-methoxyquinolines IV. Path 2 illustrates the cyclization of amides VI, derived from acylation of 4-haloanilines II with substituted acid chlorides V (acid chlorides V are either commercially available or prepared from the corresponding carboxylic acid precursors by procedures known to those skilled in the art), in the presence of DMF in hot phosphorus oxychloride to generate 6-haloquinolines IV, wherein $R^5$ is H and $R^7$ is Cl. In path 3, methyl 2-aminobenzoates VII can undergo acylation with acid chlorides V to form an amide intermediate, which can be further treated with a base, such as sodium ethoxide or lithium bis(trimethylsilyl)amide, to afford 6-halo-4-hydroxyquinolin-2(1H)-ones VIII. Conversion of hydroxyquinolin-2(1H)-ones VIII to 2,4-dichloro-quinolines IV can be carried out in refluxing phosphorus oxychloride. Path 4 describes the condensation of anilines II and aldehydes IX in ethanol to form compound X which can be further cyclized in polyphosphoric acid at high temperatures to give quinolinones XI. Conversion to the 4-chloroquinolines IV wherein $R^7$ is H can be accomplished in phosphorus oxychloride as previously described.

Scheme 2

PATH 1

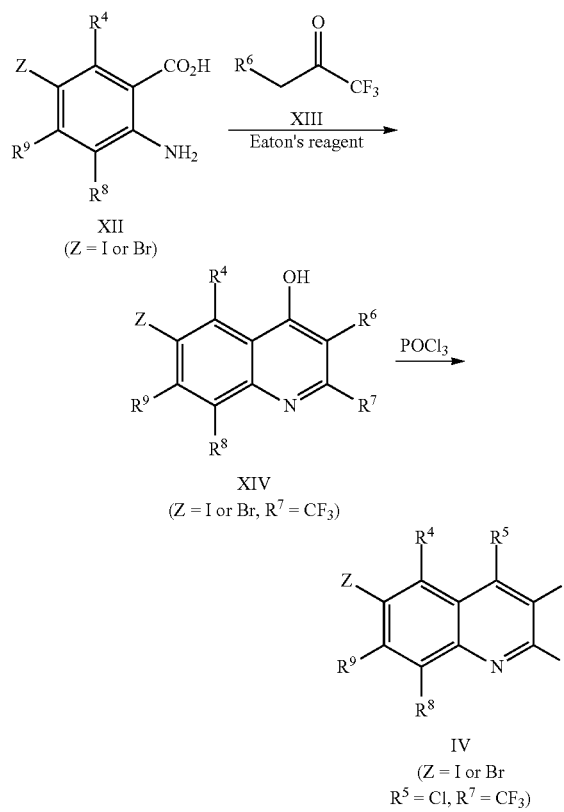

PATH 2

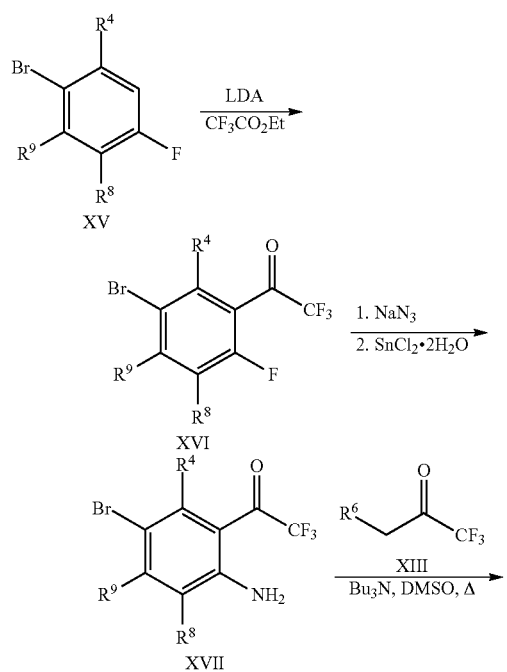

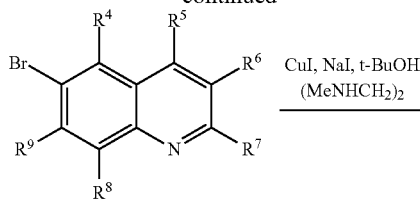

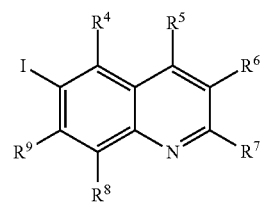

Scheme 2 illustrates the synthesis leading to 6-bromo or 6-iodoquinolines of Formula IV wherein $R^5$ is Cl and $R^7$ is $CF_3$ (path 1), and 6-iodoquinolines of Formula IV where $R^5$ and $R^7$ are $CF_3$ (path 2). In path 1, cyclization of 2-aminobenzoic acids XII with 1,1,1-trifluoropropan-2-ones XIII in Eaton's reagent at elevated temperatures yields 4-hydroxy-2-trifluoromethylquinolines XIV, which upon heating in phosphorus oxychloride at temperatures between 100-120° C. gives 6-bromo or 6-iodoquinolines IV, wherein $R^5$ is Cl and $R^7$ is $CF_3$. 6-Iodo-2,4-bis(trifluoromethyl)quinolines IV can be formed by the reaction sequence illustrated in path 2. Treatment of 1-bromo-4-fluorobenzenes XV with lithium diisopropylamide at −78° C. followed by addition of ethyl trifluoroacetate provides 2-fluorophenyl-2,2,2-trifluoroethanones XVI. Anilines XVII can be prepared by displacing 2-fluoro in XVI with sodium azide followed by reduction with tin (II) chloride dihydrate. Cyclization of XVII with 1,1,1-trifluoropropan-2-ones XIII in the presence of tributylamine in a polar solvent, such as DMF or DMSO, at high temperatures can provide 6-bromo-2,4-bis(trifluoromethyl) quinolines IV. The 6-iodo-2,4-bis(trifluoromethyl)quinolines IV can then be subsequently obtained by conversion of 6-bromoquinoline IV, where $R^5$ and $R^7$ are $CF_3$, with NaI, CuI, and N,N'-dimethylethylenediamine in t-BuOH at high temperatures under microwave conditions.

Scheme 3

PATH 1

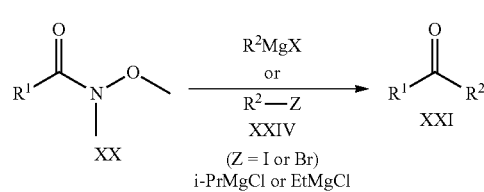

PATH 2

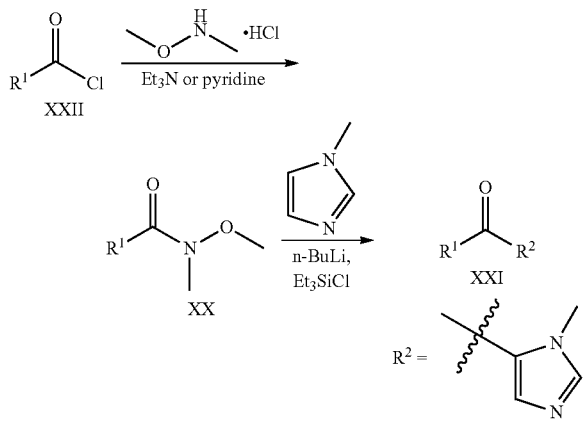

PATH 3

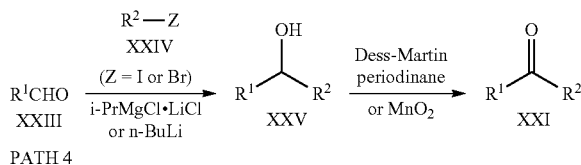

PATH 4

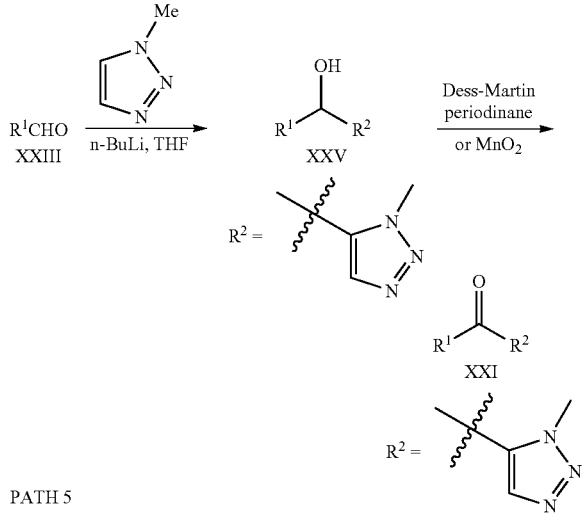

PATH 5

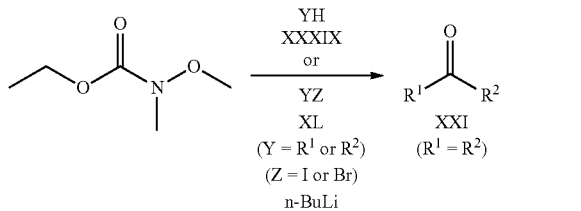

PATH 6

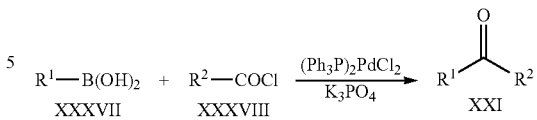

Scheme 3 illustrates synthetic routes (path 1 to 6) to ketones of Formula XXI wherein $R^1$ and $R^2$ are as described in the detailed description of the invention. In path 1, Weinreb amide XX can be prepared from acids XIX by reacting with N, O-dimethylhydroxylamine hydrochloride and 1,1-carbonyldiimidazole or with N, O-dimethylhydroxylamine hydrochloride in the presence of a base such as triethylamine or Hunig's base and a coupling reagent such as EDCI. The amides XX can be further treated with Grignard reagents such as $R^2MgX$ (X is Br or Cl) that can be obtained commercially or preformed by treatment of $R^2Z$ with organometallic reagents such as i-PrMgCl or EtMgCl in THF. Alternatively, Weinreb amides XX can be obtained from acyl chlorides XXII and N,O-dimethylhydroxylamine hydrochloride by using triethylamine or pyridine as a base. 1-Methyl-1H-imidazole can be treated with one equivalent of n-BuLi and one equivalent of chlorotriethylsilane at −78° C. followed by an additional equivalent of n-BuLi, to which the Weinreb amides XX can be added to yield ketones XXI wherein $R^2$ is imidazolyl (path 2).

In path 3, halogen and metal exchange of bromides or iodides XXIV with i-PrMgCl.LiCl or n-BuLi, followed by addition of aldehydes XXIII affords alcohols XXV. Oxidation of XXV with Dess-Martin periodinane or $MnO_2$ can provide ketones XXI. In path 4, ketones XXI, where $R^2$ is triazolyl, can be prepared by treatment of 1-methyl-1H-1,2,3-triazole with n-BuLi followed by reaction with aldehydes XXIII to yield alcohols XXV, which could undergo oxidation with Dess-Martin periodinane or $MnO_2$. Path 5 exemplifies the preparation of symmetrical ketones XXI, wherein $R^1$ and $R^2$ are the same. As illustrated, an aryl or heteroaryl group containing an acidic proton XXXIX (Y=$R^1$ or $R^2$) can be deprotonated in the presence of a strong base such as n-butyllithium once solubilized in a preferred solvent such as tetrahydrofuran at temperatures between 0 and −78° C. then added in excess to ethyl methoxy(methyl)carbamate to provide ketones XXI wherein $R^1$ and $R^2$ are the same. Aryl or heteroaryl bromide or iodide XL can also be lithiated through a lithium/halogen exchange with n-butyllithium before adding in excess to ethyl methoxy(methyl)carbamate as previously described to provide symmetrical ketones XXI. Path 6, which employs palladium catalyzed cross-coupling of aryl-boronic acids XXXVII with acid chlorides XXXVIII using $K_3PO_4$ as a base and $(Ph_3P)_2PdCl_2$ as a catalyst in a high boiling non-polar solvent such as toluene, can also be used to generate ketones XXI.

Scheme 4

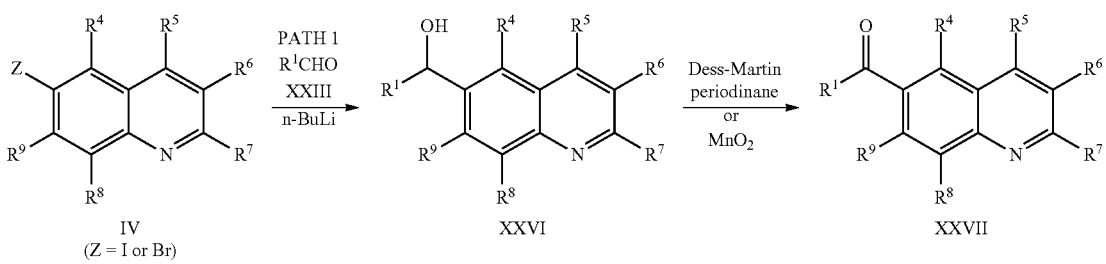

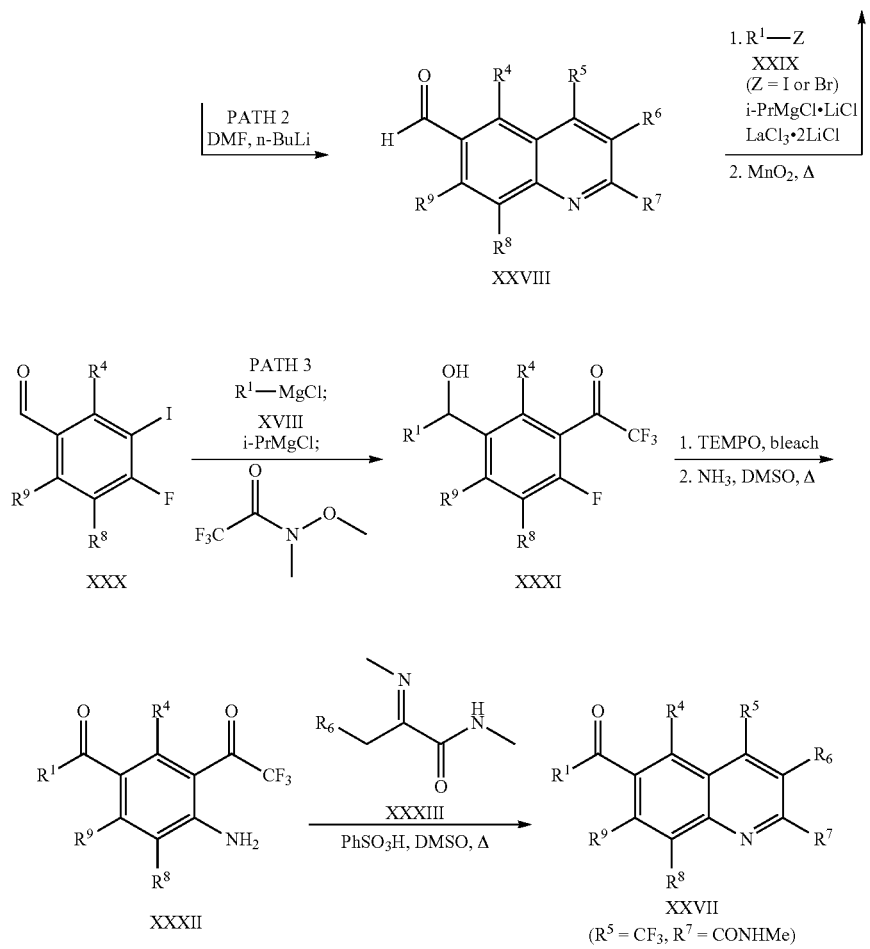

Synthesis leading to intermediate ketones XXVII may also be achieved via chemical routes shown in Scheme 4. In path 1, treatment of 6-bromo or 6-iodoquinolines IV with n-BuLi at −78° C. followed by addition of aldehydes XXIII provides secondary alcohol quinolines XXVI, which can be oxidized to ketones XXVII with Dess-Martin periodinane or $MnO_2$. Alternatively, ketones XXVII may also be prepared by treatment of 6-haloquinolines IV with n-BuLi at −78° C. followed by quenching with DMF affording carboxaldehydes XXVIII. Ketones XXVII can be obtained in a two-step process by addition of aldehyde XXVIII to a reaction mixture of aryl iodides or bromides XXIX and i-PrMgCl.LiCl followed by oxidation with $MnO_2$ (path 2).

As illustrated in path 3, a one-pot reaction of aldehydes XXX and Grignard reagents such as $R^1$—MgCl XVIII followed by treatment with i-PrMgCl and addition of 2,2,2-trifluoro-N-methoxy-N-methylacetamide yields hydroxyl compounds XXXI. The hydroxyl group can be oxidized using bleach and TEMPO. Fluoro displacement can then be achieved with ammonia in hot DMSO to provide anilines XXXII. In the presence of benzenesulfonic acid, condensation of anilines XXXII and 2-(methylimino)butanamides XXXIII in hot DMSO furnishes ketoquinolines XXVII wherein $R^5$ is $CF_3$ and $R^7$ is CONHMe.

Scheme 5

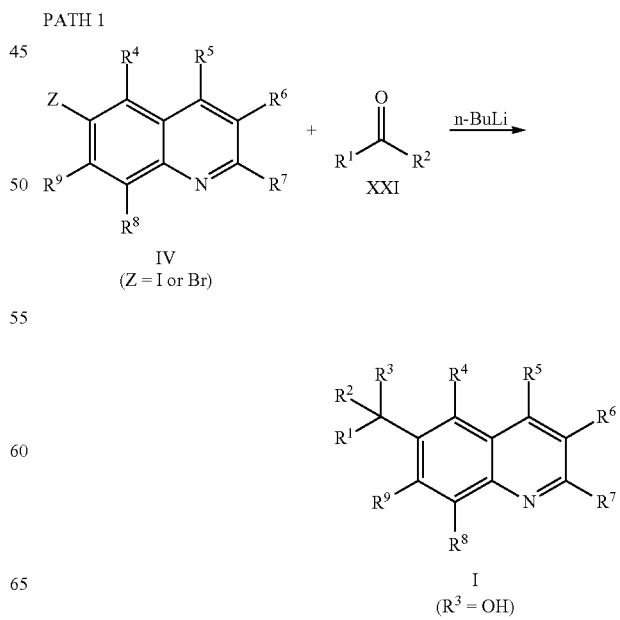

PATH 2

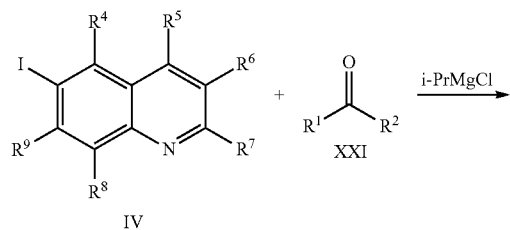

PATH 3

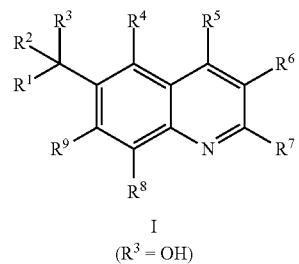

Scheme 5 illustrates synthetic routes leading to compounds of Formula I (path 1 to 3). As illustrated in path 1, a mixture of the 6-bromo or 6-iodoquinolines IV in an appropriate solvent such as THF can be either premixed with the ketones XXI at −78° C. followed by addition of n-BuLi or can be pretreated with n-BuLi at −78° C. prior to the addition of the ketones XXI to afford the tertiary alcohols of Formula I, wherein $R^3$ is OH. In path 2, 6-iodoquinolines IV can be treated with i-PrMgCl followed by addition of ketone XXI to yield compounds of Formula I wherein $R^3$ is OH. As shown in path 3, halogen-metal exchange of aryl halides (iodide or bromide) XXIV with an organometallic reagent, such as n-BuLi, i-PrMgCl.LiCl, or EtMgCl, at an appropriate temperature, such as −78° C. or 0° C., followed by reaction with ketones XXVII may afford tertiary alcohol quinolines of Formula I. Compounds of Formula I wherein $R^2$ is N-Boc piperdinyl can be deprotected under acidic conditions using standard procedures known in the art then further functionalized on nitrogen by treatment with an anhydride or acylating agent such as acetylchloride to provide compounds of Formula I wherein $R^2$ is N-acetyl piperidin-4-yl.

Scheme 6

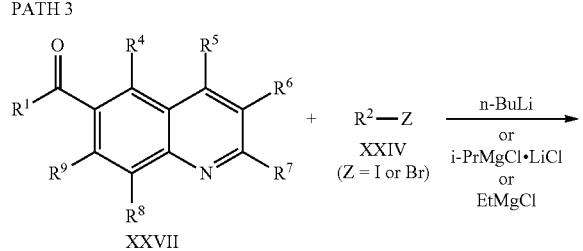

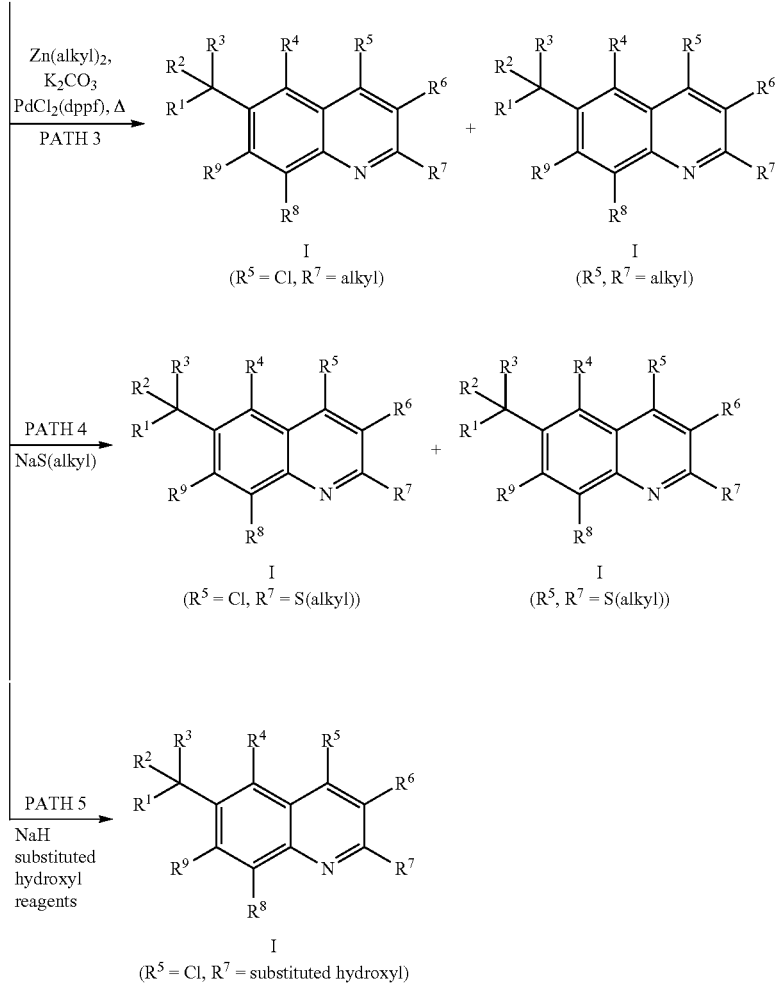

Scheme 6 illustrates methods used to synthesize compounds of Formula I wherein either the chlorine at $R^7$ or at both $R^5$ and $R^7$ positions are replaced with nitrogen, oxygen, sulfur or alkyl groups. In path 1, 4 and 5, nucleophilic displacement of 2,4-dichloroquinolines I ($R^5$ and $R^7$ are Cl) with NaO(alkyl), NaS(alkyl), such as NaOMe, NaSMe, NaOEt, or NaO$^i$Pr, in an appropriate solvent, such as MeOH, EtOH, i-PrOH or DMF at elevated temperatures or with substituted hydroxy reagents such as 2-methoxyethanol, 2,2,2-trifluoroethanol or amine substituted hydroxyl reagents in the presence of a base like sodium hydride in a non-polar solvent such as toluene provides compounds of Formula I wherein $R^5$ is Cl and $R^7$ is O(alkyl), S(alkyl), O(CH$_2$)$_2$OCH$_3$, OCH$_2$CF$_3$, or O(CH$_2$)$_2$NA$^1$A$^2$ wherein A$^1$ and A$^2$ are defined in the detailed description of the invention and compounds of Formula I wherein $R^5$ and $R^7$ are O(alkyl) or S(alkyl). Likewise, nucleophilic displacement of 2,4-dichloroquinolines I ($R^5$ and $R^7$ are Cl) with primary or secondary alkyl amines, heterocycle amines, or N,O-dimethylhydroxylamine in polar solvents such as MeOH, EtOH, or Et$_2$NCHO, or DMF provides quinolines of Formula I (path 2) wherein $R^5$ is NH(alkyl), N(alkyl)$_2$, N(CH$_3$)OCH$_3$, or Cl, and $R^7$ is NH(alkyl), N(alkyl)$_2$, N(CH$_3$)OCH$_3$, NA$^1$A$^2$, NHC$_{(2-3)}$alkylNA$^1$A$^2$ or N(CH$_3$)C$_{(2-4)}$)alkylNA$^1$A$^2$, wherein A$^1$ and A$^2$ are as defined above. Replacement of chlorine at positions 2 and 4 of quinolines I ($R^5$ and $R^7$ are Cl) with alkyl groups could be carried out using Zn(alkyl)$_2$ in the presence of K$_2$CO$_3$ and a palladium catalyst, such as PdCl$_2$(dppf), to afford 2-alkyl and 2,4-dialkylquinolines I (path 3).

Scheme 7

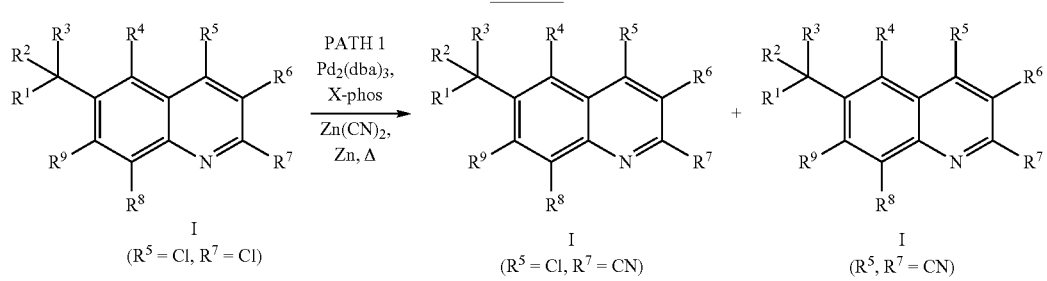

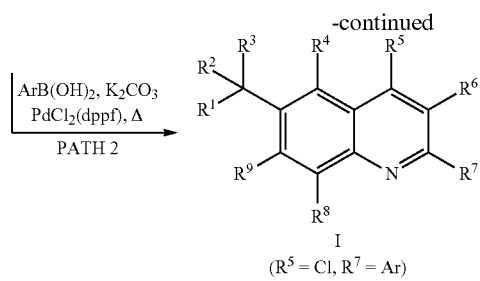

Synthetic routes to compounds of Formula I, wherein $R^5$ is Cl or CN, and $R^7$ is CN or aryl, are illustrated in Scheme 7. In path 1, cyanation of the 2,4-dichloroquinolines I with $Zn(CN)_2$ in the presence of Zn, a palladium catalyst, such as $Pd_2(dba)_3$, and a ligand, such as dppf or X-phos, at high temperatures can provide 2-CN and 2,4-diCN quinolines I. The 2,4-dichloroquinolines I can also undergo a Suzuki reactions with $ArB(OH)_2$ or $ArB(OR)_2$ and a palladium catalyst, such as $PdCl_2(dppf)$, yielding compounds of Formula I wherein $R^7$ is phenyl, substituted phenyl and five or six-membered heteroaryls such as furan, pyridine, pyridazine, pyrazine, pyrimidine, pyrrol, pyrazole or imidazole (path 2).

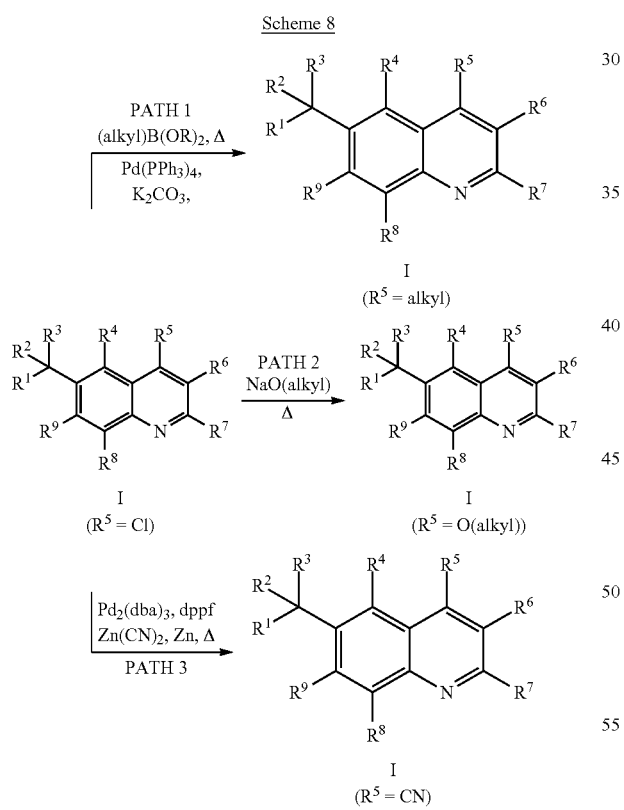

As illustrated in Scheme 8, compounds of Formula I wherein $R^5$ is a chlorine can be further substituted by treatment with alkylboronic acids or esters under Suzuki reaction conditions (path 1), with sodium alkoxides (path 2), or with zinc cyanide (path 3) using conditions previously described to provide compounds of Formula I wherein $R^5$ is alkyl, O(alkyl) or CN and $R^7$ is as described above.

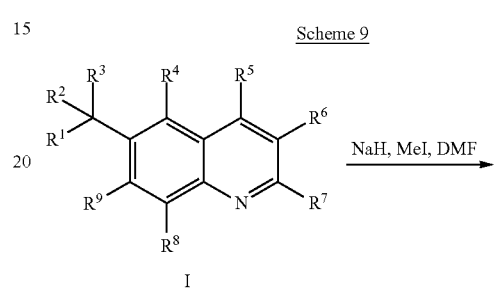

In Scheme 9, tertiary alcohols I can be treated with base, such as NaH, and alkylated with MeI in DMF to provide compounds of Formula I wherein $R^3$ is OMe.

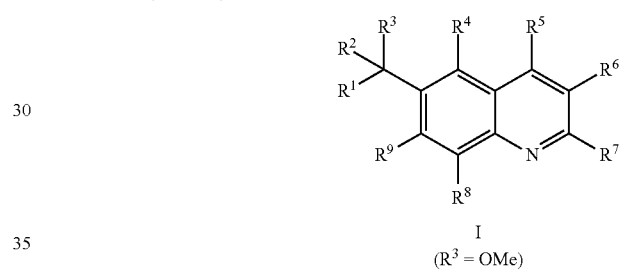

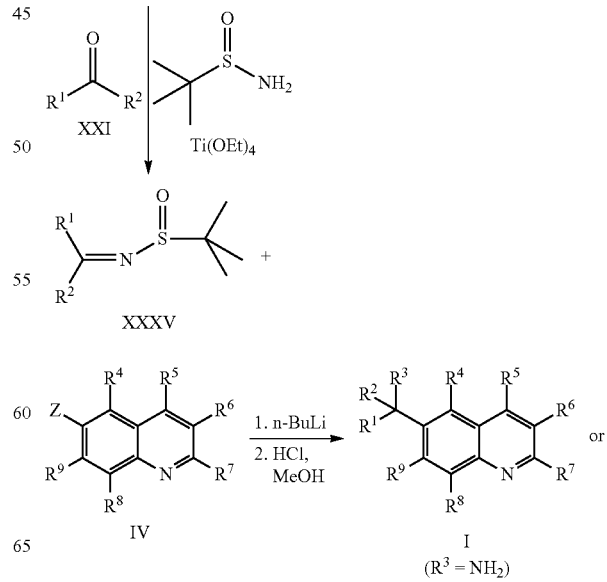

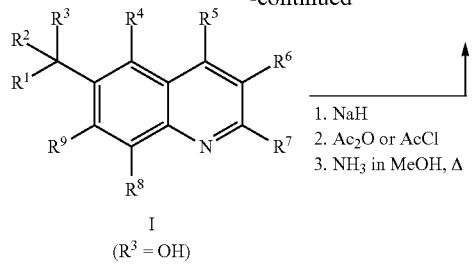

I
($R^3$ = OH)

1. NaH
2. $Ac_2O$ or AcCl
3. $NH_3$ in MeOH, Δ

Synthetic routes to compounds of Formula I, wherein $R^3$ is $NH_2$, are illustrated in Scheme 10. Ketimines XXXV may be prepared by $Ti(OEt)_4$ mediated condensation of ketones XXI with 2-methylpropane-2-sulfinamide in refluxing THF. Addition of n-BuLi to the reaction mixture of ketimines XXXV and 6-bromo or 6-iodoquinolines IV at −78° C. followed by cleavage of tert-butanesulfinyl group with HCl in MeOH liberates amines I. Alternatively, compounds of Formula I, wherein $R^3$ is OH, can be treated with sodium hydride followed by addition of acetic anhydride or acetyl chloride and stirred at room temperature over a 24 to 72 hour period to provide the intermediate acetate wherein $R^3$ is OAc. The acetate can then be combined with a solution of ammonia in methanol and heated at temperatures between 60 and 85° C. to provide compounds of Formula I, wherein $R^3$ is $NH_2$.

Scheme 11

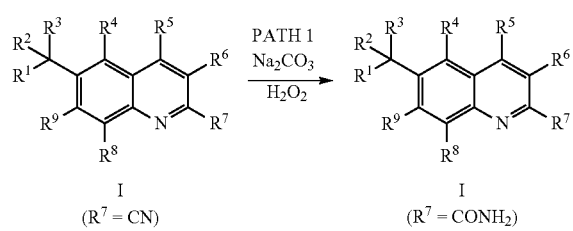

I
($R^7$ = CN)

PATH 1
$Na_2CO_3$
$H_2O_2$

I
($R^7$ = $CONH_2$)

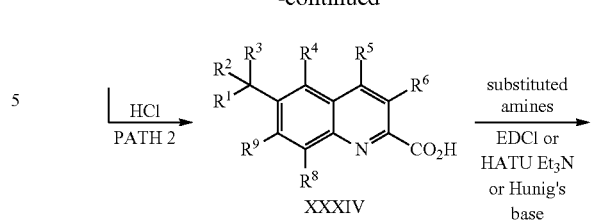

XXXIV

HCl
PATH 2 substituted amines
EDCI or
HATU $Et_3N$
or Hunig's base

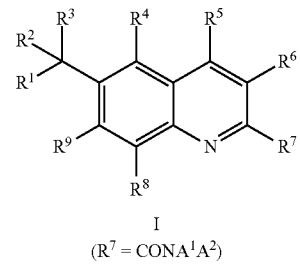

I
($R^7$ = $CONA^1A^2$)

As shown in Scheme 11, the quinolines of Formula I wherein $R^7$ is CN can be hydrolyzed as described in US20080188521 by treatment with sodium carbonate and hydrogen peroxide to provide compounds of Formula I wherein $R^7$ is $CONH_2$ (path 1) or can be treated with a strong acid like HCl to convert CN to a carboxylic acid XXXIV (path 2). Once formed the acid can be further coupled to substituted amines using appropriated coupling reagents such as EDCI or HATU in the presence of a base such as triethylamine or Hunig's base to provide compounds of Formula I wherein $R^7$ is $CONA^1A^2$.

Scheme 12

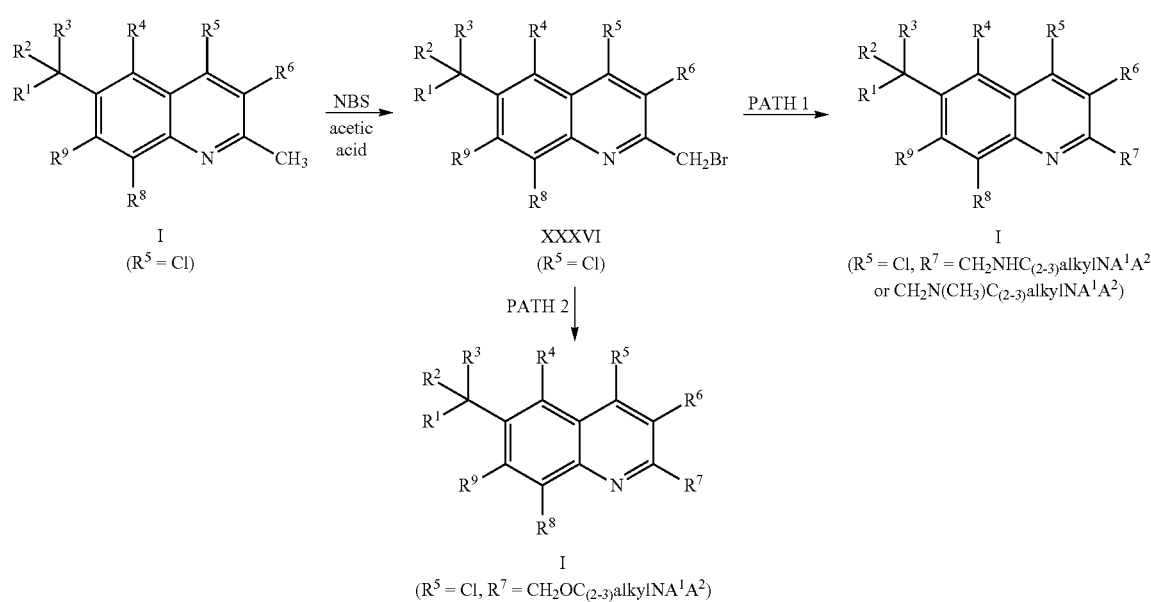

I
($R^5$ = Cl)

NBS
acetic acid

XXXVI
($R^5$ = Cl)

PATH 1

I
($R^5$ = Cl, $R^7$ = $CH_2NHC_{(2-3)}alkylNA^1A^2$
or $CH_2N(CH_3)C_{(2-3)}alkylNA^1A^2$)

PATH 2

I
($R^5$ = Cl, $R^7$ = $CH_2OC_{(2-3)}alkylNA^1A^2$)

Synthesis of compounds of Formula I, wherein $R^7$ is an aminoalkylaminomethylene or an aminoalkoxymethylene can be prepared from 2-methylquinolines as shown in Scheme 12. Bromination of 2-methylquinolines of Formula I can be accomplished with N-bromosuccinimide in acetic acid at elevated temperatures as described in WO2010151740, to provide the methylbromide intermediate XXXVI. Nucleophilic displacement of the bromide under basic conditions using procedures known in the art could afford compounds of Formula I wherein $R^7$ is $-CH_2NHC_{(2-3)}alkylNA^1A^2$ or $CH_2N(CH_3)C_{(2-3)}alkylNA^1A^2$ (path 1) or $CH_2OC_{(2-3)}alkylNA^1A^2$ (path 2) and $A^1$ and $A^2$ are defined above.

Compounds of Formula I wherein $R^1$, $R^2$ or $R^6$ are pyridyl can be treated with m-chloroperbenzoic acid in a chlorinated solvent at ambient to 40° C. to form the pyridyl-N-oxides of Formula I.

As shown in Scheme 13, compounds of the Formula I wherein $R^3$ is H can be prepared by treating compounds of Formula I wherein $R^3$ is OH with a hydride source such as triethylsilane and an acid such as trifluoroacetic acid in a solvent such as dichloromethane at room temperature or with heating (WO2009091735).

Scheme 14 outlines alternative synthetic methods to compounds of Formula I. Acylation of methyl 2-aminobenzoates VII (path 1) or 2-trifluoroketoanilines XVII (path 2) with benzyloxyacetyl chloride in the presence of a base such as triethylamine in a solvent such as dichloromethane can afford amides XLI and XLV respectively. Amides XLI and XLV can undergo an intramolecular cyclization reaction with a base such as potassium bis(trimethylsilyl)amide in a solvent such as tetrahydrofuran to provide the intermediate 6-haloquinolin-2(1H)-ones which can be converted with phosphorus oxychloride, as previously described, to compounds of Formula IV wherein $R^5$ and $R^7$ is Cl (resulting from path 1) and $R^5$ is $CF_3$ and $R^7$ is Cl (resulting from path 2). The coupling of 6-haloquinolines IV and ketones of Formula XXI to introduce $R^1$ and $R^2$ followed by displacement of the 2 or 4-chloro using procedures previously described provides quinolines of Formula XLII wherein R', $R^2$, $R^5$ and $R^7$ are defined in the detailed description of the invention. Palladium-catalyzed hydrogenation of compounds of Formula XLII that are substituted with a benzyloxy at C-3 can provide intermediate quinolin-3-ols XLIII. The quinolin-3-ols XLIII can be converted into the corresponding triflates XLIV with trifluoromethanesulfonic acid in the presence of a base, such as pyridine, in a solvent such as dichloromethane. The triflates XLIV can be converted into compounds of Formula I, wherein $R^6$ is aryl or heteroaryl as defined above, by a palladium-catalyzed cross coupling with organoboron reagents of the formula $R^6B(OR)_2$ in the presence of a base, such as potassium carbonate, in a solvent mixture such as 1,4-dioxane/water.

Scheme 13

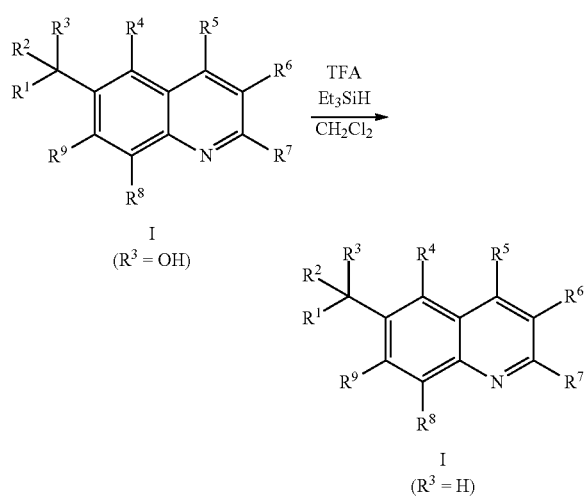

Scheme 14

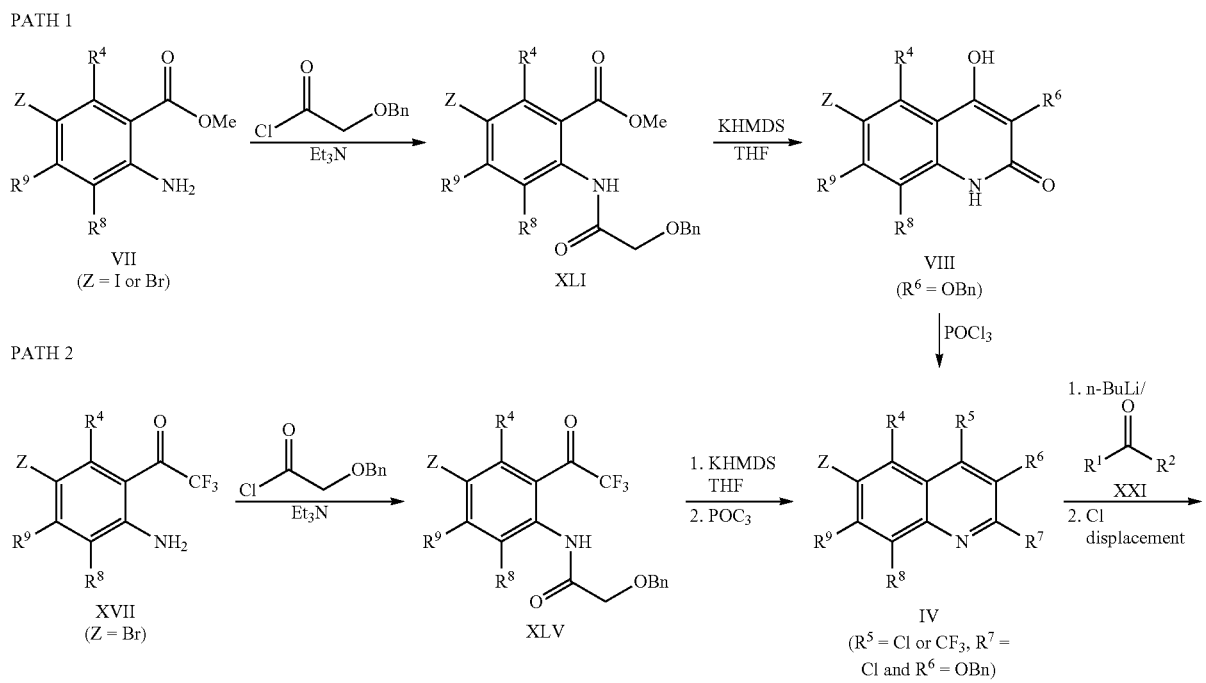

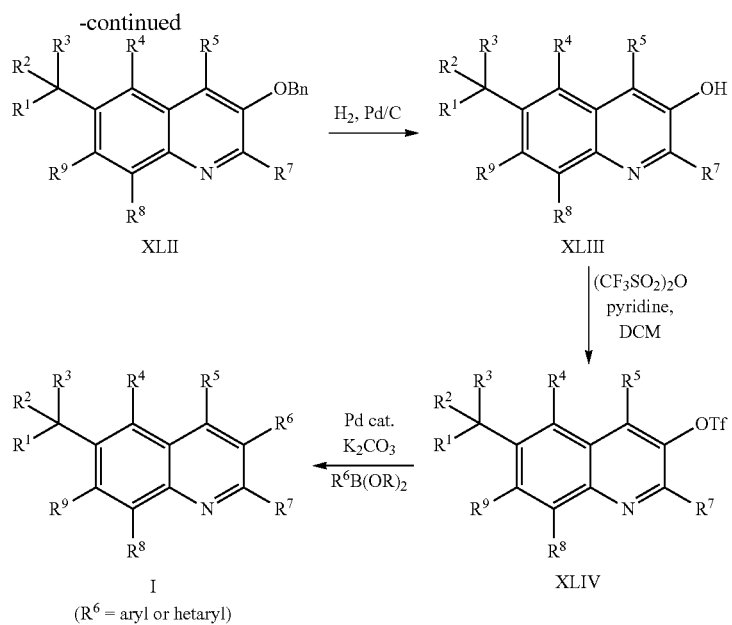

EXAMPLES

Compounds of the present invention can be prepared by methods known to those who are skilled in the art. The following examples are only meant to represent examples of the invention and are in no way meant to be a limit of the invention.

Intermediate 1: Step a tert-Butyl 4-(hydroxy(1-methyl-1H-imidazol-5-yl)methyl)piperidine-1-carboxylate

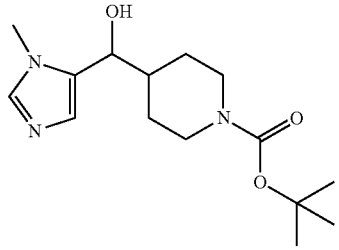 [SMILES: Cn1cncc1C(O)C1CCN(C(=O)OC(C)(C)C)CC1]

A solution of 5-bromo-1-methyl-1H-imidazole (25.0 g, 155 mmol; dried over 3 Å molecular sieves, then filtered) in DCM (310 mL) was stirred in an ice bath while iPrMgCl (72 mL, 2.01 M solution in THF, 145 mmol) was added rapidly dropwise under argon via pressure-equalizing addition funnel. Residual iPrMgCl was rinsed down with 50 mL THF, and the ice bath was removed and the reaction stirred for 25 minutes. A solution of tert-butyl 4-formylpiperidine-1-carboxylate (27.6 g, 130 mmol) in THF (65 mL) was added dropwise over ~5 minutes via pressure-equalizing addition funnel at room temperature. After stirring 1 hour at room temperature, the yellow mixture was quenched with 5 M aqueous NH$_4$Cl (250 mL) in one portion. The organic layer was dried (Na$_2$SO$_4$), filtered, and concentrated to provide the crude title compound as a clear light amber oil.

Intermediate 1: Step b tert-Butyl 4-(1-methyl-1H-imidazole-5-carbonyl)piperidine-1-carboxylate

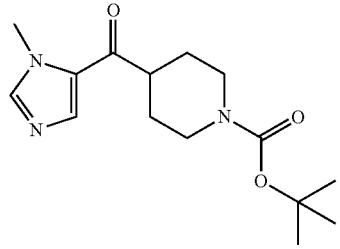 [SMILES: Cn1cncc1C(=O)C1CCN(C(=O)OC(C)(C)C)CC1]

A homogeneous solution of tert-butyl 4-(hydroxy(1-methyl-1H-imidazol-5-yl)methyl)piperidine-1-carboxylate (32.2 g, 109 mmol, Intermediate 1: step a) in 1,4-dioxane (436 mL) was treated with MnO$_2$ (47.6 g, 547 mmol) and stirred at 100° C. open to the air overnight (17 hours). Since the reaction was only ~50% complete by NMR, the reaction was cooled to room temperature and additional MnO$_2$ was added (48.0 g, 552 mmol) and the reaction stirred open to the air at 100° C. for 6.5 hours, then at room temperature for 18 days, then filtered through a pad of Celite® and the black filter cake washed with EtOAc. The crude filtrate was treated with a third portion of MnO$_2$ (28.5 g, 327 mmol) and stirred at room temperature overnight. The reaction was then filtered as above and concentrated to provide the crude title compound as a clear dark yellow oil. This oil was purified by FCC with an EtOAc to 50% acetone/EtOAc gradient to provide the title compound as a clear dark yellow oil.

Intermediate 1: Step c 1-(4-(1-Methyl-1H-imidazole-5-carbonyl)piperidin-1-yl)ethanone

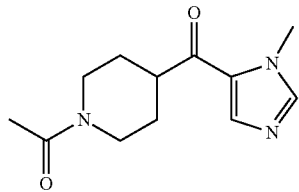 [SMILES: CC(=O)N1CCC(C(=O)c2cncn2C)CC1]

A homogeneous yellow solution of tert-butyl 4-(1-methyl-1H-imidazole-5-carbonyl)piperidine-1-carboxylate (10.1 g, 34.4 mmol, Intermediate 1: step b) in DCM (172 mL) was treated with TFA (26.4 mL, 344 mmol) and stirred at room temperature for 2.5 hours. The reaction was concentrated from toluene (2×100 mL), and the resulting clear light amber residue was taken up in DCM (344 mL) and TEA (23.9 mL, 172 mmol). Acetic anhydride (3.91 mL, 41.3 mmol) was added dropwise and the reaction stirred at room temperature for 1 hour. The reaction was concentrated under high vacuum and the residue was purified by FCC using 95:5 DCM/MeOH with 2% TEA as eluent. The combined fractions were concentrated, dissolved in DCM (200 mL), and washed with water (2×200 mL) to remove TEA. The organic layer was dried (Na$_2$SO$_4$), filtered, and concentrated. The residue was triturated with MTBE (75 mL) at reflux for 15 minutes and then allowed to cool to room temperature. The mixture was filtered and the off-white filter cake was washed with MTBE (2×3 mL) to provide, after air drying at 100° C., the title compound as an off-white fine powder.

Intermediate 2: Step a 6-(Trifluoromethyl)nicotinoyl chloride

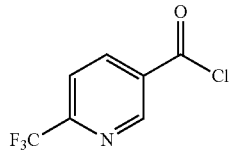 [SMILES: O=C(Cl)c1ccc(C(F)(F)F)nc1]

To a 1 L 3-neck flask equipped with an overhead stirrer, Claisen adaptor, nitrogen bubbler, 60 mL addition funnel, and thermocouple was added 6-(trifluoromethyl)nicotinic acid (45 g, 235.5 mmol), dichloromethane (540 mL) and DMF (0.910 mL, 11.77 mmol) via syringe. To this solution was added oxalyl chloride (24.51 mL, 282.56 mmol) and the reaction was allowed to stir at ambient temperature overnight. The reaction was then filtered and the clear filtrate was concentrated in vacuo to afford the title compound as a brownish semisolid.

Intermediate 2: Step b

N-Methoxy-N-methyl-6-(trifluoromethyl)nicotinamide

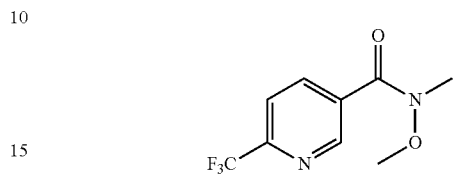

To a 1 L 3-neck flask equipped with an overhead stirrer, Claisen adaptor, nitrogen bubbler, 125 mL addition funnel, and thermocouple was added 6-(trifluoromethyl)nicotinoyl chloride (49.3 g, 235.2 mmol, Intermediate 2: step a), dichloromethane (493 mL), and N,O-dimethylhydroxylamine hydrochloride (25.63 g, 258.8 mmol). After the mixture was cooled to 7° C., diisopropylethylamine (90.26 mL, 517.6 mmol) was added such that the addition temperature did not exceed 16° C. After the addition, the reaction was allowed to warm to room temperature. The reaction was then transferred to a separatory funnel and the organic layer was washed with saturated aqueous NaHCO$_3$ (2×100 mL) followed by water (100 mL) and then dried over sodium sulfate, and filtered. The solvent was then removed in vacuo to afford the title compound as a brownish oil.

Intermediate 2: Step c (1-Methyl-1H-imidazol-5-yl)(6-(trifluoromethyl)pyridin-3-yl)methanone

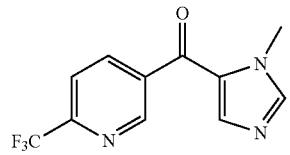 [SMILES: Cn1cncc1C(=O)c1ccc(C(F)(F)F)nc1]

To a 3 L 4-neck flask equipped with an overhead stirrer, nitrogen bubbler, and thermocouple was added 5-bromo-1-methyl-1H-imidazole (47.96 g, 297.9 mmol), followed by THF (537 mL). To this room temperature solution was added isopropylmagnesium chloride/lithium chloride complex [1.3 M in THF] (246.8 mL, 320.8 mmol) (addition temperature maintained between 16.6 and 25° C.) to afford a milky suspension and the reaction was stirred for 60 minutes and then cooled to 5.3° C. in an ice bath. To this mixture was added a solution of N-methoxy-N-methyl-6-(trifluoromethyl)nicotinamide (53.66 g, 229.14 mmol, Intermediate 2: step b) in THF (268.3 mL) (addition temperature between 5.3 and 5.6° C.) to afford an orange mixture. After addition, the reaction was warmed to room temperature over 2 hours. After stirring at room temperature for 18 hours, THF (200 mL) was added and the reaction was stirred for 2 hours. The reaction was then cooled to 4° C. with an ice bath and carefully quenched with 2 N aqueous HCl to pH=7, quenching temperature reached 12° C. The mixture was diluted with ethyl acetate (500 mL), phases split and the organic layer was washed with brine (2×200 mL), dried over sodium sulfate, filtered, and the solvent was removed. Hot ether was added and suspension was filtered to provide the title compound as a solid.

Intermediate 3

6-Bromo-2,4-dichloro-8-methyl-3-phenylquinoline

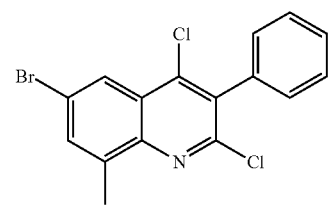 [SMILES: Cc1cc(Br)cc2c(Cl)c(-c3ccccc3)c(Cl)nc12]

A mixture of 2-phenylmalonic acid (7.62 g, 42.3 mmol) and POCl₃ (32.8 mL, 352 mmol) was stirred at reflux (130° C.) for 10 minutes, and the resulting homogeneous yellow solution was cooled in an ice bath. 4-Bromo-2-methylaniline (6.56 g, 35.2 mmol) was added in one portion and the mixture was refluxed for 2 hours. The dark solution was allowed to cool to room temperature and was diluted with DCM (70 mL) and ice (100 mL), and stirred at room temperature for ~5-10 minutes at which point exothermic POCl₃ hydrolysis commenced (ice bath cooling), and was then stirred at room temperature for another 30 minutes. The light yellow aqueous layer was extracted with DCM (1×30 mL), and the combined dark homogeneous organic layers were dried (Na₂SO₄), filtered, and concentrated with silica gel. The silica-adsorbed residue was dry load flash chromatographed with a 20% DCM/heptane to 100% DCM gradient to provide the title compound as an off-white solid.

Intermediate 4

1-(4-Benzoylpiperidin-1-yl)ethanone

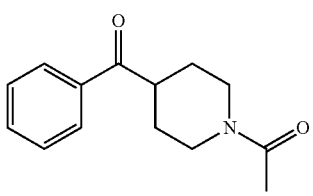 [SMILES: CC(=O)N1CCC(C(=O)c2ccccc2)CC1]

A mixture of phenyl(piperidin-4-yl)methanone hydrochloride (743 mg, 3.29 mmol) in dichloromethane (13.2 mL) and triethylamine (1.10 mL, 7.90 mmol) was treated with Ac₂O (0.373 mL, 3.95 mmol) dropwise over 1 minute in an ice bath under argon, and the resulting translucent mixture was immediately removed from the ice bath and stirred at room temperature overnight. The reaction was then extracted with 1 M aqueous HCl (1×8 mL) and 1 M aqueous NaOH (1×8 mL), and the organic layer was dried (Na₂SO₄), filtered, and concentrated to provide the title compound as a translucent beige oil that crystallized upon standing.

Intermediate 5: Step a 2-(3-(Trifluoromethyl)phenyl)acetyl chloride

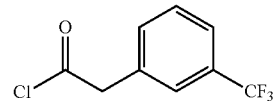

To a solution of 2-(3-(trifluoromethyl)phenyl)acetic acid (4.78 g, 23.4 mmol) in DCM (46 mL) was added oxalyl chloride (12.9 mL, 25.8 mmol). One drop of DMF was then added and the mixture was stirred for 1.5 hours at room temperature. The mixture was concentrated to afford the title compound.

Intermediate 5: Step b

Methyl 5-bromo-2-(2-(3-(trifluoromethyl)phenyl)acetamido)benzoate

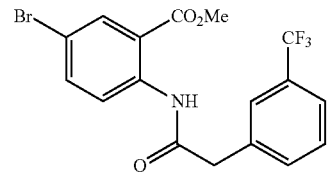 [SMILES: COC(=O)c1cc(Br)ccc1NC(=O)Cc1cccc(C(F)(F)F)c1]

To a solution of 2-(3-(trifluoromethyl)phenyl)acetyl chloride (23.4 mmol assuming quantitative yield in previous step, Intermediate 5: step a) in DCM (50 mL) in an ice bath was added methyl 2-amino-5-bromobenzoate (4.90 g, 21.3 mmol) followed by triethylamine (6.51 mL, 46.8 mmol). The mixture was stirred at room temperature overnight. The reaction mixture was washed with saturated aqueous NH₄Cl then water. The organic phase was dried (Na₂SO₄), filtered, and concentrated and the residue was purified by flash column chromatography (50-70% DCM-heptanes). Some of the title compound was obtained in pure form from the column, along with mixed fractions containing the title compound and the starting aniline. The mixed fractions were left to stand in DCM:heptanes (1:1) overnight, forming crystalline needles of the title compound, which were collected by vacuum filtration and combined with clean fractions from the column.

Intermediate 5: Step c

6-Bromo-4-hydroxy-3-(3-(trifluoromethyl)phenyl)quinolin-2(1H)-one

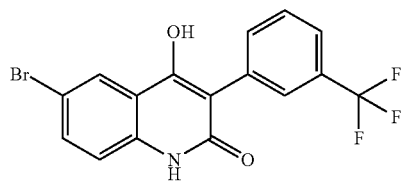 [SMILES: O=c1[nH]c2ccc(Br)cc2c(O)c1-c1cccc(C(F)(F)F)c1]

To a solution of methyl 5-bromo-2-(2-(3-(trifluoromethyl)phenyl)acetamido)benzoate (3.86 g, 9.28 mmol, Intermediate 5: step b) in THF (100 mL) at −78° C. was added KHMDS (0.5 M in toluene, 55.6 mL, 27.8 mmol) over 8 minutes. The resulting light yellow solution was stirred at −78° C. for 5 minutes, then was transferred to an ice bath and stirred for 1 hour 15 minutes. The mixture was diluted with water and extracted once with EtOAc. The aqueous phase was acidified to pH 2 by addition of 1 N aqueous HCl solution. A white precipitate formed upon acidification and was collected by vacuum filtration and air dried to afford the title compound as a white powder.

Intermediate 5: Step d

6-Bromo-2,4-dichloro-3-(3-(trifluoromethyl)phenyl)quinoline

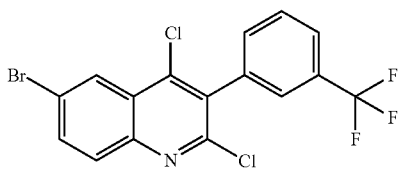 [SMILES: FC(F)(F)c1cccc(-c2c(Cl)nc3ccc(Br)cc3c2Cl)c1]

To a suspension of 6-bromo-4-hydroxy-3-(3-(trifluoromethyl)phenyl)quinolin-2(1H)-one (3.17 g, 8.25 mmol, Intermediate 5: step c) in acetonitrile (35 mL) was added POCl$_3$ (2.31 mL, 24.8 mmol). The resulting white suspension was heated at reflux under a drying tube for 2.5 hours. The mixture was allowed to cool to room temperature and stand for 2 hours. Precipitated solid was collected by vacuum filtration to afford the title compound as a white solid.

Intermediate 5: Step e

6-Bromo-4-chloro-2-methoxy-3-(3-(trifluoromethyl)phenyl)quinoline

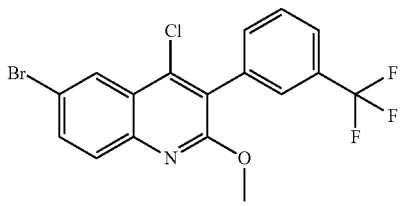 [SMILES: COc1nc2ccc(Br)cc2c(Cl)c1-c1cccc(C(F)(F)F)c1]

To a suspension of 6-bromo-2,4-dichloro-3-(3-(trifluoromethyl)phenyl)quinoline (1.48 g, 3.52 mmol, Intermediate 5: step d) in toluene (15 mL) in a sealed tube was added sodium methoxide (1.90 g, 35.2 mmol) in one portion. The resulting white suspension was heated in a 100° C. oil bath for 24 hours. An aqueous NaHCO$_3$ solution (10 wt. %, 27 mL) was added and the mixture was stirred for a few minutes, and the phases were separated. The aqueous phase was extracted twice with EtOAc. The organic extracts were washed with saturated aqueous NaCl. The organic phase was dried (Na$_2$SO$_4$), filtered, and concentrated. The crude product was purified by flash column chromatography (silica gel, 15-30% DCM-heptanes) to afford the title compound as a white powder.

Intermediate 6: Step a (1-Methyl-1H-1,2,3-triazol-5-yl)(1-methyl-1H-imidazol-5-yl)methanol

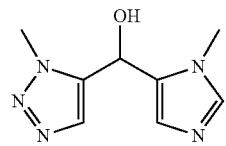

A solution of 1-methyl-1H-1,2,3-triazole (1.47 g, 17.7 mmol, PCT Int. Appl. 2008098104) in 20 mL THF was cooled to −40° C. in a dry-ice/acetonitrile bath. n-Butyllithium (1.6 M in hexane, 10.2 mL, 16.3 mmol) was added dropwise via syringe and the mixture was stirred at −40° C. for 30 minutes. A solution of 1-methyl-1H-imidazole-5-carbaldehyde (1.50 g, 13.6 mmol) in 10 mL THF was then added and the mixture was stirred for 5 minutes, then was transferred to an ice/water bath. After 1 hour, the mixture was quenched by addition of saturated aqueous NH$_4$Cl, diluted with water, and extracted twice with EtOAc. The aqueous phase, which contained the title compound, was then concentrated. The residue was purified by flash column chromatography (silica gel, gradient 3-10% MeOH-DCM) to afford the title compound as a light yellow foam.

Intermediate 6: Step b (1-Methyl-1H-1,2,3-triazol-5-yl)(1-methyl-1H-imidazol-5-yl)methanone

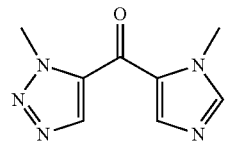

A mixture of (1-methyl-1H-1,2,3-triazol-5-yl)(1-methyl-1H-imidazol-5-yl)methanol (1.90 g, 9.83 mmol, Intermediate 6: step a) and manganese dioxide (5.04 g, 49.3 mmol) in 1,4-dioxane (100 mL) was stirred in a 100° C. oil bath under argon for 2 hours. The mixture was allowed to cool to room temperature, then was filtered through a pad of Celite®, rinsing with DCM. The filtrate was concentrated, yielding the title compound as a brown powder.

Intermediate 7: Step a

Methyl 5-bromo-2-(2-phenylacetamido)benzoate

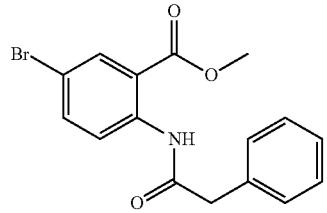 [SMILES: COC(=O)c1cc(Br)ccc1NC(=O)Cc1ccccc1]

To a mixture of methyl 2-amino-5-bromobenzoate (9.00 g, 39.1 mmol) and Et$_3$N (7.6 mL, 54.8 mmol) in CH$_2$Cl$_2$ (90 mL) at 4° C. was added 2-phenylacetyl chloride (7.26 g, 46.9 mmol) dropwise. After completion of the addition, the cooling bath was removed and the mixture was stirred for 27 hours. TLC showed that some of the starting material methyl 2-amino-5-bromobenzoate still remained. More 2-phenylacetyl chloride (1.88 g, 12.2 mmol) and Et₃N (2.2 mL, 15.9 mmol) were added, and the mixture was stirred overnight. K₂CO₃ (aqueous) was added, the organic layer was separated, and the aqueous layer was extracted with CH₂Cl₂. The combined organic layers were washed with water, dried (Na₂SO₄), filtered, and concentrated in vacuo. CH₃CN (100 mL) was added, and the precipitated solid was filtered, washed with Et₂O, and dried to afford the title compound. The filtrate was concentrated in vacuo, and the solid was filtered, washed with Et₂O, and dried to provide additional title compound.

Intermediate 7: Step b

6-Bromo-4-hydroxy-3-phenylquinolin-2(1H)-one

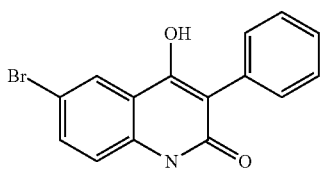 [SMILES: O=c1[nH]c2ccc(Br)cc2c(O)c1-c1ccccc1]

To a solution of methyl 5-bromo-2-(2-phenylacetamido)benzoate (7.71 g, 22.1 mmol, Intermediate 7: step a) in THF (50 mL) at −78° C. was added 1.0 M lithium bis(trimethylsilyl)amide in hexane (48.7 mL, 48.7 mmol) slowly, and the color changed from colorless to clear red. The mixture, at −78° C., was warmed to room temperature over 4 hours, during which time the color changed to cloudy yellow. The reaction was quenched with water, and acidified with 37% HCl until pH~5. The precipitated solid was filtered, washed with water and Et₂O, and air dried to provide the title compound. Another crop precipitated from the filtrate after standing overnight. The solid was collected by filtration, washing with water and Et₂O, and air drying to afford additional title compound.

Intermediate 7: Step c

6-Bromo-2,4-dichloro-3-phenylquinoline

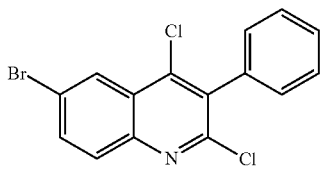 [SMILES: Clc1nc2ccc(Br)cc2c(Cl)c1-c1ccccc1]

A solution of 6-bromo-4-hydroxy-3-phenylquinolin-2(1H)-one (8.50 g, 26.9 mmol, Intermediate 7: step b) in phosphoryl trichloride (51 mL, 547 mmol) was heated at 107° C. for 3.5 hours, and then cooled to room temperature. After evaporation of POCl₃ in vacuo, concentrated NH₄OH (aqueous) was added dropwise at 4° C. until pH 9. The precipitated solid was filtered, washed with water, and dried at 50° C. under vacuum overnight to provide the title compound.

Intermediate 8: Step a

4-Chloro-N-methoxy-N-methylbenzamide

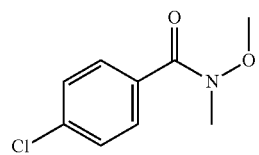

Pyridine (27.6 mL, 343 mmol) was added to N,O-dimethylhydroxylamine hydrochloride (16.7 g, 172 mmol) in DCM (400 mL). 4-Chlorobenzoyl chloride (20 mL, 156 mmol) was then added and the mixture was stirred at room temperature for 3 days. Solids were removed by vacuum filtration, washing with DCM. The filtrate was washed with 1 N aqueous HCl followed by water. The organic phase was dried (Na₂SO₄), filtered, and concentrated, affording the crude title compound as a colorless liquid which was used without purification.

Intermediate 8: Step b (4-Chlorophenyl)(1-methyl-1H-imidazol-5-yl)methanone

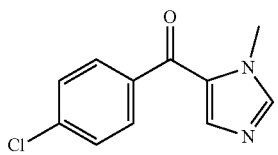

Ethyl magnesium bromide (3.0 M in diethyl ether, 21.5 mL, 64.4 mmol) was added via syringe over a few minutes to a clear colorless solution of 5-bromo-1-methyl-1H-imidazole (10.4 g, 64.4 mmol) in THF (100 mL) under a nitrogen atmosphere in an ice bath. A white precipitate formed during the addition. The mixture was removed from the ice bath and was stirred for 20 minutes, then was again cooled in an ice bath before addition of 4-chloro-N-methoxy-N-methylbenzamide (10.7 g, 53.6 mmol, Intermediate 8: step a). The resulting white suspension was stirred overnight at room temperature. The reaction was quenched by addition of saturated aqueous NH₄Cl and diluted with water. The mixture was partially concentrated to remove THF and was diluted with DCM. The mixture was acidified to pH 1 with 1 N aqueous HCl, then neutralized with saturated aqueous NaHCO₃. The phases were separated and the aqueous phase was further extracted with DCM. The organic extracts were washed with water, then were dried (Na₂SO₄), filtered, and concentrated, affording a white solid. The crude product was triturated with a mixture of EtOAc:heptanes (1:1, 150 mL). The precipitated

Intermediate 9: Step a

Methyl 5-bromo-2-(2-(pyridin-2-yl)acetamido)benzoate

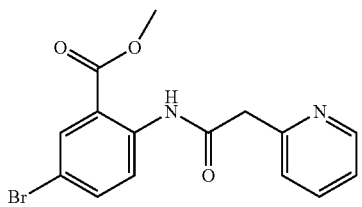 [SMILES: COC(=O)c1cc(Br)ccc1NC(=O)Cc1ccccn1]

Into a 250-mL round-bottom flask was placed a solution of methyl 2-amino-5-bromobenzoate (5 g, 21.73 mmol), 2-(pyridin-2-yl)acetic acid hydrochloride (4.5 g, 25.92 mmol), HATU (10 g, 26.30 mmol) and DIEA (8.5 g, 65.77 mmol) in N,N-dimethylformamide (100 mL). The resulting solution was stirred overnight at 20° C. The reaction was then quenched by the addition of 100 mL of water. The resulting solution was extracted with 3×100 mL of dichloromethane and the organic layers combined and dried over anhydrous sodium sulfate, filtered and concentrated under vacuum. The residue was applied onto a silica gel column with dichloromethane/methanol (1:50) to afford the title compound as a red solid.

Intermediate 9: Step b

6-Bromo-3-(pyridin-2-yl)quinoline-2,4(1H, 3H)-dione

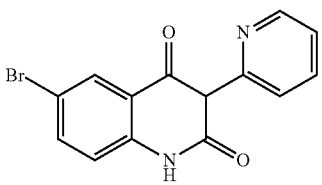 [SMILES: O=C1Nc2ccc(Br)cc2C(=O)C1c1ccccn1]

Into a 250-mL round-bottom flask was placed a solution of methyl 5-bromo-2-[2-(pyridin-2-yl)acetamido]benzoate (3 g, 7.73 mmol, Intermediate 9: step a) and MeONa (11.7 mL, 31 mmol, 2.64 M in MeOH) in tetrahydrofuran (30 mL). The resulting solution was stirred overnight at 20° C. Then, the solvents were removed by a rotary evaporator and 50 mL water was added to the residue. The pH of the resulting mixture was adjusted to 7 with 1 M aqueous HCl. The solid was collected by filtration and dried under vacuum to afford the title compound as a white solid which was used in the next step without further purification.

Intermediate 9: Step c

6-Bromo-2,4-dichloro-3-(pyridin-2-yl)quinoline

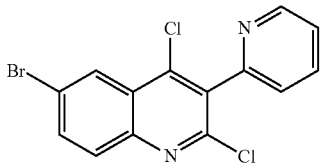 [SMILES: Clc1nc2ccc(Br)cc2c(Cl)c1-c1ccccn1]

Into a 100-mL round-bottom flask was placed a solution of 6-bromo-3-(pyridin-2-yl)quinoline-2,4(1H, 3H)-dione (2.54 g, 7.21 mmol, Intermediate 9: step b) in POCl$_3$ (50 mL). The resulting solution was stirred for 3 hours at 120° C. The reaction was then quenched by the addition of 50 mL of water. The resulting solution was extracted with 3×50 mL of ethyl acetate and the organic layers combined and dried over anhydrous sodium sulfate, filtered and concentrated to afford the title compound as a white solid.

Intermediate 10: Step a

Methyl 5-bromo-2-(2-(pyridin-3-yl)acetamido)benzoate

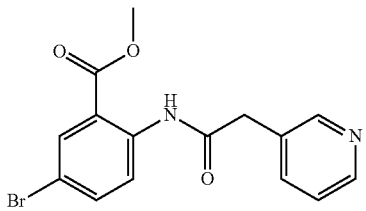 [SMILES: COC(=O)c1cc(Br)ccc1NC(=O)Cc1cccnc1]

Into a 250-mL round-bottom flask was placed a solution of methyl 2-amino-5-bromobenzoate (5 g, 21.73 mmol, 100%), 2-(pyridin-3-yl)acetic acid hydrochloride (4.5 g, 25.92 mmol), HATU (10 g, 26.30 mmol 100%) and DIEA (8.5 g, 65.77 mmol, 100%) in N,N-dimethylformamide (100 mL). The resulting solution was stirred overnight at 20° C. The reaction was then quenched by the addition of 100 mL of water. The resulting solution was extracted with 3×100 mL of dichloromethane and the organic layers combined and dried over anhydrous sodium sulfate and concentrated under vacuum. The residue was applied onto a silica gel column with ethyl acetate/petroleum ether (1:2-1:1) to provide the title compound as a yellow solid.

Intermediate 10: Step b

6-Bromo-3-(pyridin-3-yl)quinoline-2,4(1H, 3H)-dione

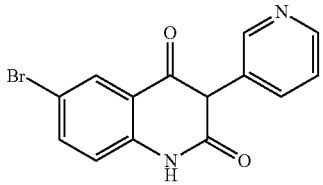 [SMILES: O=C1Nc2ccc(Br)cc2C(=O)C1c1cccnc1]

Into a 100-mL round-bottom flask, was placed a solution of methyl 5-bromo-2-[2-(pyridin-3-yl)acetamido]benzoate (3 g, 7.73 mmol, Intermediate 10: step a) and MeONa (11.7 mL, 31 mmol, 2.64 M in MeOH) in tetrahydrofuran (30 mL). The resulting solution was stirred overnight at 20° C. The solids were collected by filtration and washed with water (3×5 mL). The solids were dried under vacuum to provide the title compound as a white solid.

Intermediate 10: Step c

6-Bromo-2,4-dichloro-3-(pyridin-3-yl)quinoline

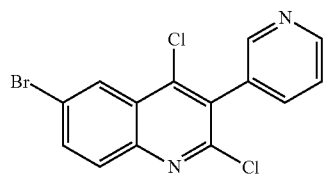 [SMILES: Clc1nc2ccc(Br)cc2c(Cl)c1-c1cccnc1]

Into a 100-mL round-bottom flask, was placed a solution of 6-bromo-3-(pyridin-3-yl)quinoline-2,4(1H, 3H)-dione (700 mg, 1.99 mmol, Intermediate 10: step b) in phosphorus trichloride (20 mL). The resulting solution was stirred for 3 hours at 120° C. The resulting mixture was concentrated under vacuum. The reaction was then quenched by the addition of 20 mL of water. The resulting solution was extracted with 3×20 mL of ethyl acetate and the organic layers combined and dried over anhydrous sodium sulfate, filtered and concentrated to afford the crude title compound as a white solid.

Intermediate 11: Step a

Methyl 2-(2-(benzyloxy)acetamido)-5-bromobenzoate

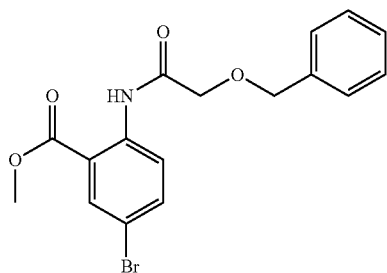 [SMILES: COC(=O)c1cc(Br)ccc1NC(=O)COCc1ccccc1]

To a solution of methyl-2-amino-5-bromobenzoate (15 g, 62.6 mmol) in DCM (241 mL) at 0° C. was added benzyloxyacetyl chloride (12.5 mL, 75.1 mmol) followed by Et$_3$N (20 mL, 144 mmol) dropwise. The resulting white suspension was stirred at room temperature for 3 hours. The mixture was then washed with saturated aqueous NH$_4$Cl (200 mL) followed by water (200 mL). The organics were dried (Na$_2$SO$_4$), filtered and concentrated to dryness. The crude solid was triturated with MeOH (90 mL) and dried under vacuum to afford the title compound as a white solid.

Intermediate 11: Step b 3-(Benzyloxy)-6-bromo-4-hydroxyquinolin-2(1H)-one

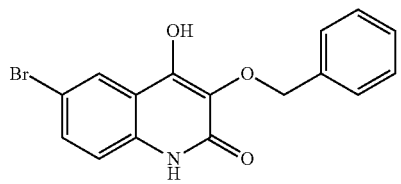 [SMILES: O=c1[nH]c2ccc(Br)cc2c(O)c1OCc1ccccc1]

To a solution of methyl 2-(2-(benzyloxy)acetamido)-5-bromobenzoate (15 g, 39.7 mmol, Intermediate 11: step a) in THF (198 mL) was added KHMDS (1 M in THF, 119 mL, 119 mmol). The resulting solution was stirred at room temperature for 40 minutes and then additional KHMDS (19.8 mL, 19.8 mmol) was added and stirring continued at room temperature for 2 hours. The mixture was quenched with water (225 mL) and the layers were separated. The aqueous layer was acidified with 1 N aqueous HCl to pH 2-3. Some of the title compound precipitated out of solution and was collected by filtration. The aqueous was then extracted with EtOAc (3×200 mL). The organics were combined with the solid collected previously and sonicated. The solution was dried (Na$_2$SO$_4$), filtered and concentrated to dryness to provide the title compound as a yellow solid.

Intermediate 11: Step c 3-(Benzyloxy)-6-bromo-2,4-dichloroquinoline

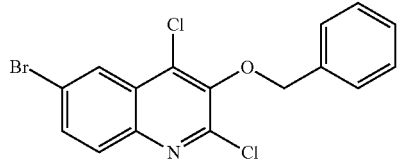 [SMILES: Clc1nc2ccc(Br)cc2c(Cl)c1OCc1ccccc1]

To a suspension of 3-(benzyloxy)-6-bromo-4-hydroxyquinolin-2(1H)-one (12.4 g, 35.8 mmol, Intermediate 11: step b) in acetonitrile (119 mL) was added POCl$_3$ (10 mL, 107.5 mmol) followed by 2,6-lutidine (6.26 mL, 53.7 mmol) dropwise. The suspension was heated to 100° C. for 4 hours, then the reaction was allowed to cool to room temperature. The solids were filtered, rinsed with MeOH and dried under vacuum to afford the title compound as a tan solid.

Intermediate 11: Step d (3-(Benzyloxy)-2,4-dichloroquinolin-6-yl)(1-methyl-1H-imidazol-5-yl)(6-(trifluoromethyl)pyridin-3-yl)methanol

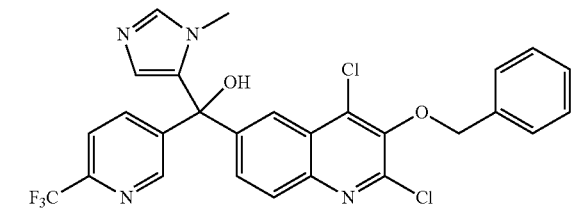 [SMILES: Cn1cncc1C(O)(c1ccc(C(F)(F)F)nc1)c1ccc2nc(Cl)c(OCc3ccccc3)c(Cl)c2c1]

A solution of 3-(benzyloxy)-6-bromo-2,4-dichloroquinoline (2.57 g, 6.71 mmol, Intermediate 11: step c) in THF (100 mL) was cooled to −78° C., during which it became a white suspension. Then, nBuLi (1.6 M in hexanes, 5.87 mL, 9.39 mmol) was added dropwise and the resulting dark red solution was stirred for 10 minutes at −78° C. To this mixture was added a solution of (1-methyl-1H-imidazol-5-yl)(6-(trifluoromethyl)pyridin-3-yl)methanone (2.23 g, 8.72 mmol, Intermediate 2: step c) in THF (30 mL) over 4 minutes and the resulting mixture stirred at −78° C. for 2 minutes. The dry-ice/acetone bath was then replaced with an ice bath and the mixture was stirred for an additional 45 minutes. The reaction was then quenched with water and extracted with EtOAc. The organics were combined, dried (MgSO$_4$), filtered and concentrated to dryness to afford the crude product which was purified by FCC (4% MeOH/DCM) to provide the title compound.

Intermediate 11: Step e (3-(Benzyloxy)-4-chloro-2-methoxyquinolin-6-yl)(1-methyl-1H-imidazol-5-yl)(6-(trifluoromethyl)pyridin-3-yl)methanol

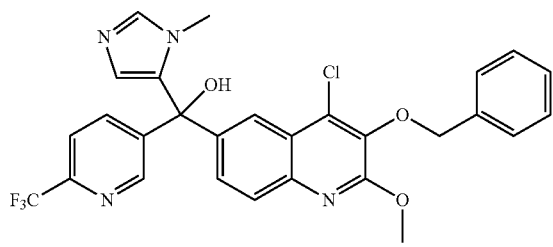 [SMILES: COc1nc2ccc(C(O)(c3ccc(C(F)(F)F)nc3)c3cncn3C)cc2c(Cl)c1OCc1ccccc1]

To a mixture of (3-(benzyloxy)-2,4-dichloroquinolin-6-yl)(1-methyl-1H-imidazol-5-yl)(6-(trifluoromethyl)pyridin-3-yl)methanol (2.46 g, 4.4 mmol, Intermediate 11: step d) in methanol (24.6 mL) was added NaOMe (0.5 M in MeOH, 8.8 mL, 4.4 mmol) and the resulting suspension heated to 65° C. for 8 hours. The mixture was then cooled to room temperature and concentrated to dryness. Water was added and the mixture acidified with 2 N aqueous HCl to ~pH 2. The aqueous was then extracted with EtOAc. The organics were combined and washed with water, saturated aqueous NaHCO$_3$ and brine. The organics were then dried (MgSO$_4$), filtered and concentrated to dryness to afford the title compound which was used without further purification.

Intermediate 11: Step f

4-Chloro-6-(hydroxy(1-methyl-1H-imidazol-5-yl)(6-(trifluoromethyl)pyridin-3-yl)methyl)-2-methoxyquinolin-3-ol

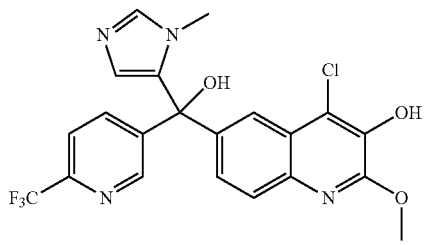 [SMILES: COc1nc2ccc(C(O)(c3ccc(C(F)(F)F)nc3)c3cncn3C)cc2c(Cl)c1O]

To a solution of (3-(benzyloxy)-4-chloro-2-methoxyquinolin-6-yl)(1-methyl-1H-imidazol-5-yl)(6-(trifluoromethyl)pyridin-3-yl)methanol (2.56 g, 4.61 mmol, Intermediate 11: step e) in MeOH (97 mL) was added 10% Pd/C (246 mg, 0.23 mmol). The reaction vessel was evacuated and then placed under an atmosphere of hydrogen for 1.5 hours. The mixture was then flushed with N$_2$ and filtered through a pad of Celite®. The filtrate was concentrated to dryness, then DCM was added and the solution concentrated to dryness. The resulting solid was dried in the oven. The solid was then purified by FCC (15% MeOH/DCM) to provide the title compound.

Intermediate 11: Step g

4-Chloro-6-(hydroxy(1-methyl-1H-imidazol-5-yl)(6-(trifluoromethyl)pyridin-3-yl)methyl)-2-methoxyquinolin-3-yl trifluoromethanesulfonate

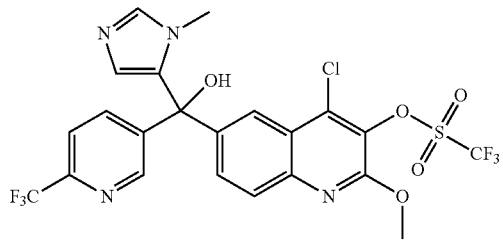 [SMILES: COc1nc2ccc(C(O)(c3ccc(C(F)(F)F)nc3)c3cncn3C)cc2c(Cl)c1OS(=O)(=O)C(F)(F)F]

To a suspension of 4-chloro-6-(hydroxy(1-methyl-1H-imidazol-5-yl)(6-(trifluoromethyl)pyridin-3-yl)methyl)-2-methoxyquinolin-3-ol (750 mg, 1.61 mmol, Intermediate 11: step f) in CH$_2$Cl$_2$ (15 mL) was added pyridine (390 μL, 4.84 mmol) and the reaction became a solution. The solution was cooled to 0° C. and trifluoromethanesulfonic anhydride (683 mg, 2.42 mmol) was added dropwise. The reaction was stirred at 0° C. for 1 hour, then the ice bath was removed and stirring continued for an additional hour. Trifluoromethanesulfonic anhydride (683 mg, 2.42 mmol) was then added and the mixture stirred at room temperature for 1 hour. The solution was poured into a mixture of 1 N aqueous HCl (20 mL) and ice and then the aqueous was extracted with CH$_2$Cl$_2$. The organics were washed with water followed by saturated aqueous NaHCO$_3$ and brine. The aqueous layers were combined and back-extracted with EtOAc. The EtOAc layers were combined and washed with water followed by saturated aqueous NaHCO$_3$ and brine. The CH$_2$Cl$_2$ and EtOAc layers were combined, dried (MgSO$_4$), filtered and concentrated to dryness. The crude material was purified by FCC (0-5% MeOH/CH$_2$Cl$_2$) to provide the title compound.

Intermediate 12: Step a (1-Methyl-1H-imidazol-5-yl)(pyridin-2-yl)methanol

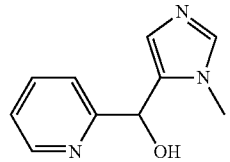

A solution of isopropylmagnesium chloride/lithium chloride complex (1.3 M in THF, 19.5 mL, 25.35 mmol) was added dropwise by syringe to a solution of 5-bromo-1-methyl-1H-imidazole (4.12 g, 25.58 mmol) in dry THF (130 mL) at 0° C. After 15 minutes, the Grignard solution was added via cannulation to a solution of picolinaldehyde (2.0 mL, 20.93 mmol) in dry THF (55 mL) at 0° C. The reaction mixture was stirred for 5 minutes at 0° C., then warmed to room temperature for 1 hour. The reaction mixture was then cooled in an ice bath and quenched with saturated aqueous ammonium chloride. The mixture was partitioned between brine and ethyl acetate. The separated aqueous phase was further extracted with ethyl acetate. The organic phase was dried (Na₂SO₄), filtered, and concentrated. The crude product was purified by flash column chromatography (silica gel, 0-5% MeOH-DCM) to provide the title compound as a white solid.

Intermediate 12: Step b (1-Methyl-1H-imidazol-5-yl)(pyridin-2-yl)methanone

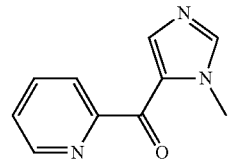

A heterogenous mixture of (1-methyl-1H-imidazol-5-yl)(pyridin-2-yl)methanol (1.41 g, 7.45 mmol, Intermediate 12: step a) and manganese dioxide (3.24 g, 37.27 mmol) in 1,4-dioxane (52 mL) was stirred at 100° C. for 2 hours. The reaction mixture was then cooled to room temperature, filtered through Celite®, washed with DCM, and concentrated to provide the title compound as an off-white solid.

Intermediate 13: Step a

Diethyl 2-(4-(trifluoromethoxy)phenyl)malonate

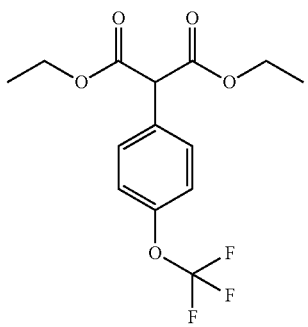 [SMILES: CCOC(=O)C(C(=O)OCC)c1ccc(OC(F)(F)F)cc1]

CuI (0.26 g, 1.378 mmol), 2-picolinic acid (0.24 g, 1.969 mmol) and cesium carbonate (19.24 g, 59.061 mmol) were combined in a reaction vessel and the flask was evacuated and re-filled with argon (3 times). 1,4-Dioxane was then added followed by diethylmalonate (6 mL, 39.374 mmol) and 1-iodo-4-(trifluoromethoxy)benzene (3 mL, 19.687 mmol). The resulting yellow suspension was stirred at room temperature for 48 hours and quenched with saturated NH₄Cl. The mixture was extracted with EtOAc (2×). The combined organic extracts were dried over Na₂SO₄, filtered, and concentrated to provide the title compound.

Intermediate 13: Step b 2-(4-(Trifluoromethoxy)phenyl)malonic acid

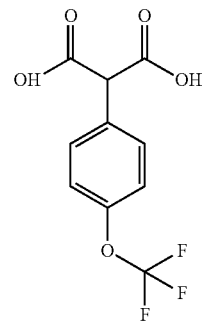 [SMILES: O=C(O)C(C(=O)O)c1ccc(OC(F)(F)F)cc1]

A mixture of diethyl 2-(4-(trifluoromethoxy)phenyl)malonate (5.6 g, 17.486 mmol, Intermediate 13: step a) and an aqueous 3 M NaOH solution was stirred in a 100° C. oil bath for 1 hour, cooled to room temperature, poured into ice water and acidified with 6 N aqueous HCl. The aqueous mixture was extracted with EtOAc. The EtOAc extract was dried over Na₂SO₄, filtered, and evaporated in vacuo to provide the title compound.

Intermediate 13: Step c

6-Bromo-2,4-dichloro-8-methyl-3-(4-(trifluoromethoxy)phenyl)quinoline

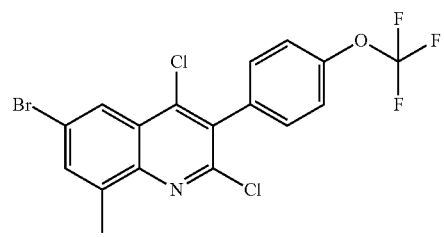 [SMILES: Cc1cc(Br)cc2c(Cl)c(-c3ccc(OC(F)(F)F)cc3)c(Cl)nc12]

A mixture of 2-(4-(trifluoromethoxy)phenyl)malonic acid (3.1 g, 11.74 mmol, Intermediate 13: step b), 4-bromo-2-methylaniline (2.18 g, 11.74 mmol) and POCl₃ (10 mL) was heated at 105° C. for 3 hours, cooled to room temperature, concentrated under reduced pressure then slowly poured into ice water. A NH₄OH solution was added to a basic pH (pH 8-9). The precipitates were collected by filtration, rinsed with H₂O and dried under high vacuum. The resulting tan solids were dissolved in DCM and chromatographed (heptane/DCM) to provide the title compound.

Intermediate 13: Step d

6-Bromo-4-chloro-2-methoxy-8-methyl-3-(4-(trifluoromethoxy)phenyl)quinoline

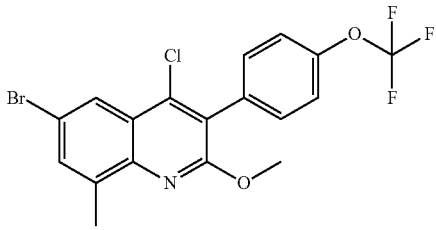 [SMILES: COc1nc2c(C)cc(Br)cc2c(Cl)c1-c1ccc(OC(F)(F)F)cc1]

A mixture of 6-bromo-2,4-dichloro-8-methyl-3-(4-(trifluoromethoxy)phenyl)quinoline (1.97 g, 4.37 mmol, Intermediate 13: step c) and sodium methoxide (1.18 g, 21.84 mmol) in toluene (20 mL) was heated in a sealed tube at 110° C. for 24 hours, cooled to room temperature, diluted with DCM, stirred at room temperature for 30 minutes and filtered through Celite® rinsing several times with DCM. The solvents were removed under reduced pressure and the off-white solid product precipitated from MeOH, filtered and dried to provide the title compound.

Intermediate 14: Step a tert-Butyl 4-(hydroxy(6-(trifluoromethyl)pyridin-3-yl)methyl)piperidine-1-carboxylate

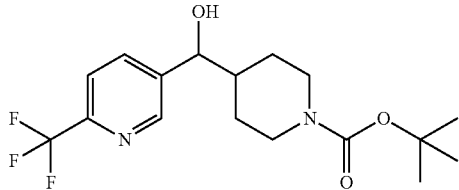 [SMILES: CC(C)(C)OC(=O)N1CCC(C(O)c2ccc(C(F)(F)F)nc2)CC1]

A solution of isopropylmagnesium chloride (2.0 M in THF, 40.3 mL, 80.6 mmol) was added dropwise by syringe to a solution of 5-bromo-2-(trifluoromethyl)pyridine (19.5 g, 86.3 mmol) in dry THF (12 mL) at 2° C. After 30 minutes, tert-butyl 4-formylpiperidine-1-carboxylate (12.3 g, 57.3 mmol) was added to the Grignard solution at 2° C. as a solid. The reaction mixture was warmed to 10° C. over 1.5 hours after which it was quenched with saturated aqueous ammonium chloride solution. The mixture was partitioned between water and ethyl acetate. The separated aqueous phase was further extracted with ethyl acetate and washed with saturated aqueous NaCl solution. The organic phase was dried (MgSO₄), filtered, and concentrated and used crude in the next step.

Intermediate 14: Step b tert-Butyl 4-(6-(trifluoromethyl)nicotinoyl)piperidine-1-carboxylate

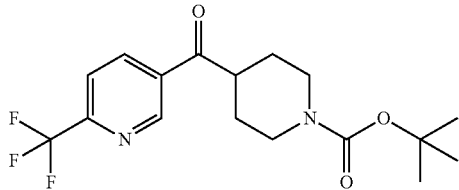 [SMILES: CC(C)(C)OC(=O)N1CCC(C(=O)c2ccc(C(F)(F)F)nc2)CC1]

Dess-Martin periodinane reagent (30.0 g, 70.8 mmol) was added to a solution of tert-butyl 4-(hydroxy(6-(trifluoromethyl)pyridin-3-yl)methyl)piperidine-1-carboxylate (Intermediate 14: step a, 17.8 g, 49.5 mmol) in DCM at room temperature and the mixture was stirred for 2 hours. The reaction mixture was diluted with DCM and washed with saturated aqueous solution of NaHCO₃. The organic phase was dried (MgSO₄), filtered, and concentrated. The crude product was purified by flash column chromatography (silica gel, 0-60% EtOAc-hexanes) to provide the title compound that was 90% pure by NMR and was carried on to the next step.

Intermediate 14: Step c

Piperidin-4-yl(6-(trifluoromethyl)pyridin-3-yl)methanone

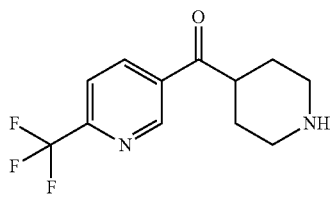 [SMILES: O=C(c1ccc(C(F)(F)F)nc1)C1CCNCC1]

TFA (34.4 mL, 449.3 mmol) was added to a solution of tert-butyl 4-(6-(trifluoromethyl)nicotinoyl)piperidine-1-carboxylate (Intermediate 14: step b, 16.1 g, 44.9 mmol) in DCM (450 mL) and the resulting solution was stirred at room temperature for 3 hours. The mixture was concentrated to remove most of the TFA on the rotary evaporator and a mixture of EtOAc/hexanes was added. The white solid that precipitated was filtered and dried and used in the next step.

Intermediate 14: Step d 1-(4-(6-(Trifluoromethyl)nicotinoyl)piperidin-1-yl)ethanone

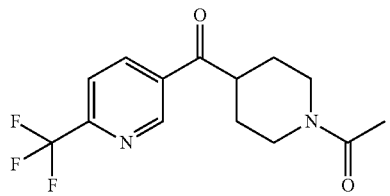 [SMILES: CC(=O)N1CCC(C(=O)c2ccc(C(F)(F)F)nc2)CC1]

TEA (32.1 mL, 230.9 mmol) was added to a solution of piperidin-4-yl(6-(trifluoromethyl)pyridin-3-yl)methanone (Intermediate 14: step c, 14.3 g, 38.5 mmol) in DCM (427 mL) followed by acetic anhydride (5.28 mL, 55.8 mmol). The mixture was stirred for 2 hours and transferred to a reparatory funnel and washed with 100 mL of aqueous 2 M NaH₂PO₄ solution. The organic layer was dried (MgSO₄), filtered and concentrated. The crude product was purified by flash column chromatography (silica gel, 0-3% MeOH-DCM) to provide the title compound.

Intermediate 15: Step a

N-Methoxy-N-methylpyrimidine-2-carboxamide

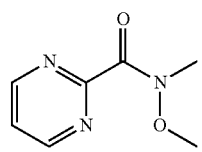

Sodium pyrimidine-2-carboxylate (4.00 g, 27.4 mmol), imidazole hydrochloride (3.15 g, 30.1 mmol), and 1-carbonyldiimidazole (5.26 g, 31.5 mmol) were slurried in acetonitrile (30 mL) at room temperature under an $N_2$ atmosphere. The mixture was then warmed to 52° C. over 30 minutes. Evolution of carbon dioxide was seen when reaction mixture reached approximately 50° C. The mixture was then stirred at 52° C. for approximately 2 hours. The reaction was then cooled to room temperature, then N,O-dimethylhydroxylamine hydrochloride (3.54 g, 35.6 mmol) was then added slowly, portion wise over approximately 15 minutes and a mild exotherm was seen after each addition. The contents were stirred at room temperature overnight. To the reaction mixture was then added deionized water (25 mL) and dichloromethane (25 mL). 6 M Aqueous hydrochloric acid was added dropwise to acidify the aqueous layer to approximately pH 1. The organic phase was then separated and the aqueous phase was extracted twice with dichloromethane. The combined organics were washed with 2 M aqueous hydrochloric acid, separated, then the acidic layer was extracted twice with dichloromethane. The combined organic phases were washed with a saturated, aqueous $NaHCO_3$ solution, then dried over $MgSO_4$, filtered and the solvent was removed by distillation under reduced pressure to provide the title compound.

Intermediate 15: Step b (1-Methyl-1H-imidazol-5-yl)(pyrimidin-2-yl)methanone

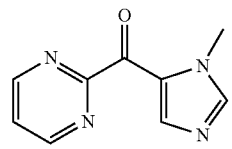

5-Bromo-1-methyl-1H-imidazole (6.66 g, 41.4 mmol) was added to a round bottom flask followed by tetrahydrofuran (150 mL) under an $N_2$ atmosphere. The contents were cooled to 0° C. in an ice water bath. EtMgBr (3.0 M solution in THF, 13.3 mL, 39.8 mmol) was added slowly via syringe over approximately 5 minutes, then the ice bath was removed and contents allowed to warm and stirred at room temperature for approximately 30 minutes. The vessel was then re-cooled to 0° C. and a solution of N-methoxy-N-methylpyrimidine-2-carboxamide (3.09 g, 15.9 mmol, Intermediate 15: step a) in THF (20 mL) was cannulated into the reaction vessel. The contents were allowed to stir at 0° C., then slowly warmed to room temperature, then heated to 40° C. in an oil bath and heated with stirring at that temperature for approximately 36 hours. The contents were then cooled to 0° C., quenched with a saturated aqueous $NH_4Cl$ solution, diluted with ethyl acetate and transferred to a reparatory funnel. The aqueous layer was separated, extracted twice with EtOAc, then the combined organic phases were dried over $MgSO_4$, filtered, then distilled under reduced pressure to afford an amber oil. The crude product was purified by flash column chromatography (silica gel, 0-10% DCM/(10% of a 2 M $NH_3$ MeOH in DCM)) to provide the title compound.

Intermediate 16: Step a (2,4-Dimethylthiazol-5-yl)(1-methyl-1H-1,2,3-triazol-5-yl)methanol

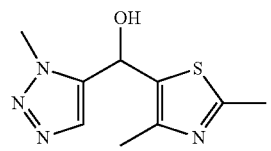

1-Methyl-1H-1,2,3-triazole was prepared according to the literature reference WO2008/98104. To a 2 L flask containing 1-methyl-1H-1,2,3-triazole (9 g, 108.3 mmol) was added THF (1500 mL) and the solution was cooled to −40° C. To this colorless homogeneous solution was added n-butyllithium (2.5 M in hexanes, 45 mL, 112.5 mmol) dropwise which immediately afforded a dark brown viscous mixture. The mixture was kept between −10 to −20° C. for 60 minutes, then a THF solution of 2,4-dimethylthiazole-5-carbaldehyde (17.2 g, 121.8 mmol in 200 mL THF) was introduced via cannula. Once the aldehyde was added the reaction was allowed to warm to room temperature. After 3 hours, the reaction was quenched by pouring it into a saturated solution of aqueous $NH_4Cl$. The aqueous portion was extracted with EtOAc in portions, 7×400 mL. The combined organics were washed with brine, dried over $MgSO_4$, filtered and concentrated to afford a brown oil. Chromatography on silica gel (10% acetone-DCM increasing to 50% acetone and increasing to 10% MeOH-DCM) provided the title compound as an amber solid.

Intermediate 16: Step b (2,4-Dimethylthiazol-5-yl)(1-methyl-1H-1,2,3-triazol-5-yl)methanone

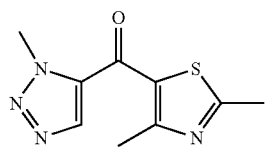

To a 500 mL flask containing (2,4-dimethylthiazol-5-yl)(1-methyl-1H-1,2,3-triazol-5-yl)methanol (10.5 g, 46.8 mmol, Intermediate 16: step a) was added 1,4-dioxane (400 mL) and the contents were warmed to form a homogeneous solution. Activated $MnO_2$ (18 g, 207 mmol) was added and the dark brownish mixture was heated to reflux in an aluminum heating mantle under an atmosphere of N₂. After 1.5 hours, the contents were filtered while still hot through Celite® and rinsed with warm THF. The resulting light orange solution was concentrated and passed through a silica gel column (25% acetone-DCM) to provide the title compound as a light orange solid.

Intermediate 17: Step a

N-Methoxy-N,2,4-trimethylthiazole-5-carboxamide

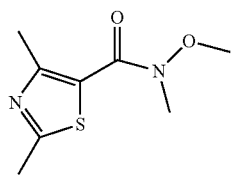

To a flask containing 2,4-dimethylthiazole-5-carboxylic acid (2.5 g, 15.9 mmol) was added DCM (75 mL) to give a suspension. DMF (3 mL) was added which resulted in a homogeneous solution. Then, carbonyldiimidazole (2.84 g, 17.5 mmol) was introduced and the mixture was stirred at room temperature for 2 hours. N,O-dimethylhydroxylamine HCl (1.9 g, 19.9 mmol) was then added and the mixture was stirred at room temperature for 18 hours, at which time the reaction mixture was diluted with water and 1 N aqueous NaOH and the aqueous portion was extracted with DCM (4×50 mL). The combined organics were washed with brine, dried over Na₂SO₄, filtered and concentrated. Chromatography on silica gel (10% EtOAc-DCM increasing to 40% EtOAc) provided the title compound as a colorless oil.

Intermediate 17: Step b (2,4-Dimethylthiazol-5-yl)(1-methyl-1H-imidazol-5-yl)methanone

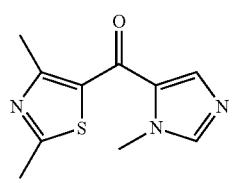

To a flask containing 5-bromo-1-methyl-1H-imidazole (390 mg, 2.42 mmol) was added THF (8 mL) and the solution was cooled to 0° C. To this solution was added isopropylmagnesium chloride-LiCl complex (1.3 M in THF, 2.5 mL, 3.25 mmol) which resulted in a white suspension. The reaction mixture was stirred in a 0° C. bath for 30 minutes, then a THF (2 mL) solution of N-methoxy-N,2,4-trimethylthiazole-5-carboxamide (550 mg, 2.75 mmol, Intermediate 17: step a) was introduced. The reaction mixture was stirred at 50° C. for 18 hours, cooled to room temperature and quenched with aqueous NH₄Cl solution. The aqueous portion was extracted with DCM (4×50 mL) and the combined organics were washed with brine, dried over Na₂SO₄, filtered and concentrated. Chromatography on silica gel (25% EtOAc-DCM increasing to 5% MeOH-DCM) afforded the title compound as an amber solid.

Intermediate 18: Step a (2,4-Dichloro-3-phenylquinolin-6-yl)(1,2-dimethyl-1H-imidazol-5-yl)methanol

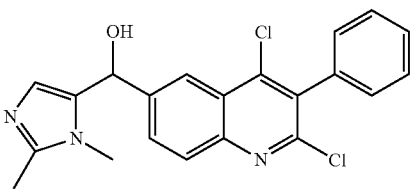 [SMILES: Cc1ncc(C(O)c2ccc3nc(Cl)c(-c4ccccc4)c(Cl)c3c2)n1C]

To a flask containing 6-bromo-2,4-dichloro-3-phenylquinoline (4 g, 11.33 mmol, Intermediate 7: step c) was added THF (200 mL) to give a homogeneous clear solution. The solution was cooled in a dry-ice bath and n-BuLi (2.5 M in hexanes, 4.25 mL, 10.63 mmol) was added which resulted in an immediate reddish-brownish mixture. After 2 minutes, a THF solution of 1,2-dimethyl-1H-imidazole-5-carbaldehyde (1.75 g, 14.1 mmol in 10 mL THF) was added and the reaction mixture became a light yellow color. The −78° C. bath was replaced with a 0° C. ice-bath and after 40 minutes, the reaction mixture was quenched with aqueous NH₄Cl solution and the aqueous portion was extracted with EtOAc (4×100 mL). The combined organics were washed with brine, dried over MgSO₄, filtered and concentrated. The resulting solid was triturated with Et₂O to provide the title compound as an off white powder.

Intermediate 18: Step b (2,4-Dichloro-3-phenylquinolin-6-yl)(1,2-dimethyl-1H-imidazol-5-yl)methanone

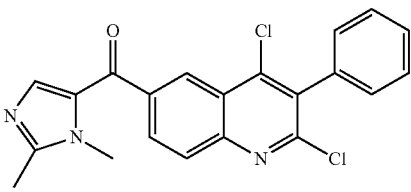 [SMILES: Cc1ncc(C(=O)c2ccc3nc(Cl)c(-c4ccccc4)c(Cl)c3c2)n1C]

To a flask containing (2,4-dichloro-3-phenylquinolin-6-yl)(1,2-dimethyl-1H-imidazol-5-yl)methanol (520 mg, 1.31 mmol, Intermediate 18: step a) was added 1,4-dioxane (12 mL) followed by manganese dioxide (475 mg, 5.46 mmol). The mixture was heated to reflux for 3.25 hours and then the contents were filtered through a Celite® pad, while still warm, and the Celite® pad was rinsed with warm THF. The

Intermediate 19: Step a

6-Bromo-3-phenyl-2-(trifluoromethyl)quinolin-4-ol

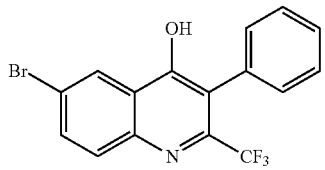 [SMILES: Oc1c(-c2ccccc2)c(C(F)(F)F)nc2ccc(Br)cc12]

A mixture of 2-amino-5-bromobenzoic acid (3.01 g, 13.9 mmol), 1,1,1-trifluoro-3-phenylpropan-2-one (3.11 g, 16.5 mmol), and Eaton's reagent (9.3 mL) in a sealed tube was heated at 100° C. for 4 hours. The reaction mixture was then allowed to cool to room temperature, water was added slowly, and the mixture was stirred vigorously for about 15 minutes. The precipitated solid was collected by filtration, washed with water, and dried to provide the title compound.

Intermediate 19: Step b

6-Bromo-4-chloro-3-phenyl-2-(trifluoromethyl)quinoline

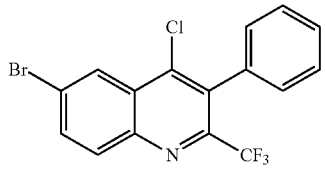 [SMILES: FC(F)(F)c1nc2ccc(Br)cc2c(Cl)c1-c1ccccc1]

A solution of 6-bromo-3-phenyl-2-(trifluoromethyl)quinolin-4-ol (8.29 g, 22.5 mmol, Intermediate 19: step a) in phosphoryl trichloride (25 mL, 269 mmol) was heated at 110° C. for 2 hours, and concentrated in vacuo. Dichloromethane and ice-water were added, and the mixture was basified at 4° C. with concentrated $NH_4OH$ until pH~10. The organic layer was separated and the aqueous layer was extracted with $CH_2Cl_2$. The combined organic phases were dried ($Na_2SO_4$), concentrated, and purified by flash column chromatography (120 g silica gel column, 2-9% EtOAc in heptanes) to afford the title compound as a light yellow solid.

Intermediate 20: Step a

6-Iodo-3-phenyl-2-(trifluoromethyl)quinolin-4-ol

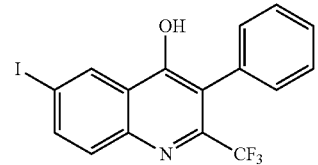 [SMILES: Oc1c(-c2ccccc2)c(C(F)(F)F)nc2ccc(I)cc12]

A mixture of 2-amino-5-iodobenzoic acid (5.20 g, 19.8 mmol), 1,1,1-trifluoro-3-phenylpropan-2-one (3.95 g, 21.0 mmol), and Eaton's reagent (12 mL) in a sealed tube was heated at 100° C. for 2 hours. More 1,1,1-trifluoro-3-phenylpropan-2-one (1.60 g, 8.50 mmol) was added and the mixture was heated for another 2 hours. The reaction was then cooled to room temperature, ice water was added, and the mixture was stirred vigorously for about 20 minutes. 50% Aqueous NaOH and concentrated $NH_4OH$ solutions were added until pH 9. The resulting dark brown gummy material that formed was diluted with DCM which resulted in a solid precipitate that was collected by filtration. The solids were washed with water and $Et_2O$ and air dried to provide the title compound.

Intermediate 20: Step b

4-Chloro-6-iodo-3-phenyl-2-(trifluoromethyl)quinoline

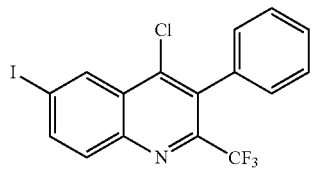

A solution of 6-iodo-3-phenyl-2-(trifluoromethyl)quinolin-4-ol (1.54 g, 3.71 mmol, Intermediate 20: step a) in phosphoryl trichloride (5 mL, 53.8 mmol) was heated at 110° C. for 1 hour 45 minutes, and then cooled to room temperature. Ice-water was added, and the mixture was basified at 4° C. with 50% aqueous NaOH and concentrated $NH_4OH$ until pH 9. The precipitated solid was filtered, washed with water and $Et_2O$, and dried to provide the title compound. The filtrate was separated and the aqueous layer was extracted with $CH_2Cl_2$. The combined organic phases were dried ($Na_2SO_4$), concentrated, and purified by flash column chromatography (80 g silica gel column, 0-5% EtOAc in heptanes), affording a mixture of the title compound and des-iodo by-product, 4-chloro-3-phenyl-2-(trifluoromethyl)quinoline, in about 8:1 ratio as a thick oil, which solidified over night.

Intermediate 21 tert-Butyl 4-nicotinoylpiperidine-1-carboxylate

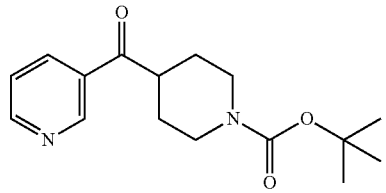 [SMILES: CC(C)(C)OC(=O)N1CCC(C(=O)c2cccnc2)CC1]

A mixture of piperidin-4-yl(pyridin-3-yl)methanone hydrochloride (397 mg, 1.75 mmol), di-tert-butyl dicarbonate (710 mg, 3.25 mmol), N,N-dimethylpyridin-4-amine (28 mg, 0.23 mmol) and $Et_3N$ (1.2 mL, 8.6 mmol) in THF (15 mL) and $CH_2Cl_2$ (5 mL) was stirred for 3 days and then concentrated. The residue was purified by flash column chromatography (40 g silica gel column, 50-70% EtOAc in heptane) to provide the title compound as a clear oil.

Intermediate 22: Step a (3-Chlorophenyl)(6-(trifluoromethyl)pyridin-3-yl)methanone

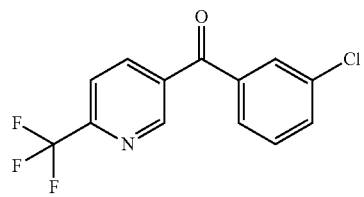 [SMILES: O=C(c1ccc(C(F)(F)F)nc1)c1cccc(Cl)c1]

To a solution of N-methoxy-N-methyl-6-(trifluoromethyl)nicotinamide (1.23 g, 5.25 mmol, Intermediate 2: step b) in THF (12 mL) at 4° C. was added 0.5 M (3-chlorophenyl)magnesium bromide in THF (12.7 mL, 6.35 mmol). The mixture was stirred at 4° C. to room temperature overnight, and quenched with NH$_4$Cl (aqueous). The organic layer was separated, and the aqueous layer was extracted with CH$_2$Cl$_2$. The combined organic phases were dried (Na$_2$SO$_4$), filtered, concentrated, and purified by flash column chromatography (40 g silica gel column, 0-70% EtOAc in heptanes) to provide the title compound as an oil, which solidified upon standing.

Intermediate 22: Step b (3-Chlorophenyl)(2,4-dichloro-3-phenylquinolin-6-yl)(6-(trifluoromethyl)pyridin-3-yl)methanol

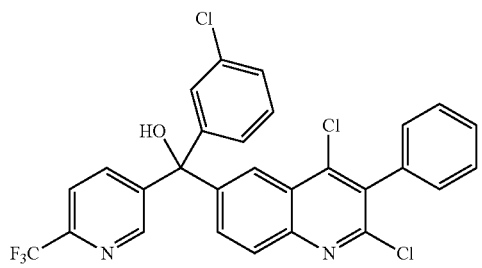 [SMILES: OC(c1ccc(C(F)(F)F)nc1)(c1cccc(Cl)c1)c1ccc2nc(Cl)c(-c3ccccc3)c(Cl)c2c1]

To a solution of 6-bromo-2,4-dichloro-3-phenylquinoline (422 mg, 1.20 mmol, Intermediate 7: step c) and (3-chlorophenyl)(6-(trifluoromethyl)pyridin-3-yl)methanone (340 mg, 1.19 mmol, Intermediate 22: step a) in THF (8 mL) at −78° C. was added 1.6 M n-BuLi in hexane (1.14 mL, 1.82 mmol). The mixture was stirred at −78° C. to 10° C. for 2 hours and then quenched with NH$_4$Cl (aqueous). The organic layer was separated, and the aqueous layer was extracted with CH$_2$Cl$_2$. The combined organic phases were dried (Na$_2$SO$_4$), filtered, concentrated, and purified by flash column chromatography (24 g silica gel column, 30-40% EtOAc in heptane) to provide the title compound as a white solid.

Intermediate 23: Step a

N-Methoxy-N-methyl-2-(trifluoromethyl)isonicotinamide

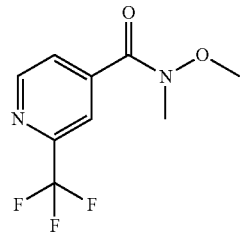 [SMILES: CON(C)C(=O)c1ccnc(C(F)(F)F)c1]

To a suspension of 2-(trifluoromethyl)isonicotinic acid (1.03 g, 5.39 mmol), N,O-dimethylhydroxylamine hydrochloride (0.800 g, 8.20 mmol) and N'(ethylcarbonimidoyl)-N,N-dimethyl-1,3-propanediamine hydrochloride (EDCI, 1.35 g, 7.04 mmol) in CH$_2$Cl$_2$ (30 mL) was added Et$_3$N (1.90 mL, 13.7 mmol), and the mixture immediately turned clear. After stirring at room temperature overnight, NH$_4$Cl (aqueous) was added. The mixture was stirred vigorously for a while, and white solid was then filtered off. The organic layer was separated, and the aqueous layer was extracted with CH$_2$Cl$_2$. The combined organic phases were washed with brine, and the aqueous layer was back extracted with CH$_2$Cl$_2$. The organic phases were combined, dried (Na$_2$SO$_4$), filtered, concentrated, and purified by flash column chromatography (40 g silica gel column, 40-70% EtOAc in heptanes) to afford the title compound as a clear oil.

Intermediate 23: Step b (3-Chlorophenyl)(2-(trifluoromethyl)pyridin-4-yl)methanone

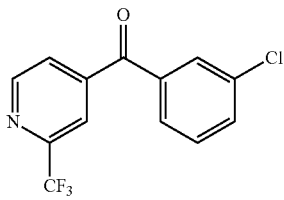 [SMILES: O=C(c1cccc(Cl)c1)c1ccnc(C(F)(F)F)c1]

The title compound was prepared using N-methoxy-N-methyl-2-(trifluoromethyl)isonicotinamide (Intermediate 23: step a) in place of N-methoxy-N-methyl-6-(trifluoromethyl)nicotinamide (Intermediate 2: step b) according to the procedure described in Intermediate 22: step a.

Intermediate 24

(3-Chlorophenyl)(2,4-dichloro-3-phenylquinolin-6-yl)(pyridin-3-yl)methanol

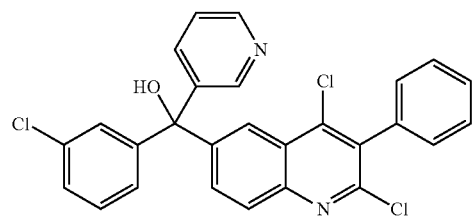 [SMILES: OC(c1cccnc1)(c1cccc(Cl)c1)c1ccc2nc(Cl)c(-c3ccccc3)c(Cl)c2c1]

The title compound was prepared using (3-chlorophenyl)(pyridin-3-yl)methanone in place of (3-chlorophenyl)(6-(trifluoromethyl)pyridin-3-yl)methanone (Intermediate 22: step a) according to the procedure described in Intermediate 22: step b.

Intermediate 25: Step a

N-Methoxy-N-methylisonicotinamide

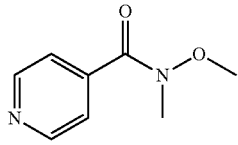

A suspension of 4-picolinic acid (3.00 g, 24.4 mmol) and 1,1-carbonyldiimidazole (4.74 g, 29.2 mmol) in CH$_2$Cl$_2$ (35 mL) was stirred for ~40 minutes, at which time it became a clear solution. After the addition of N,O-dimethylhydroxylamine hydrochloride (2.85 g, 29.2 mmol), the mixture was stirred at room temperature for 22 hours. Water was added, the organic layer was separated, and the aqueous layer was extracted with CH$_2$Cl$_2$. The combined organic layers were washed with water once, and the aqueous layer was back extracted with CH$_2$Cl$_2$. The organic phases were combined, dried (Na$_2$SO$_4$), filtered, concentrated, and purified by flash column chromatography (80 g silica gel column, 100% EtOAc) to provide the title compound as a clear oil.

Intermediate 25: Step b (1-Methyl-1H-imidazol-5-yl)(pyridin-4-yl)methanone

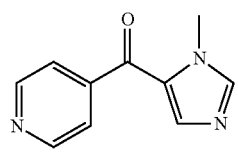

To a heat-gun dried flask containing 1-methyl-1H-imidazole (2.2 mL, 27.7 mmol) and THF (13 mL) at −78° C. was added 1.6 M n-BuLi in hexane (18.5 mL, 29.6 mmol). After stirring at −78° C. for 40 minutes, neat chlorotriethylsilane (4.9 mL, 29.2 mmol) was introduced slowly. The mixture was stirred at −78° C. for 1 hour. 1.6 M n-BuLi in hexane (18 mL, 28.8 mmol) was added, and stirring became very difficult. The cooling bath was removed, and stirring was continued for a while before the temperature reached around 10° C. The mixture was re-cooled to −78° C., a solution of N-methoxy-N-methylisonicotinamide (3.82 g, 23.0 mmol, Intermediate 25: step a) in THF (28 mL) was added via cannula, and stirring stopped. The cooling bath was removed, and the stirring was continued for 40 minutes before room temperature was reached. The reaction was quenched with a few drops of MeOH. Brine was added, the organic layer was separated, and the aqueous layer was extracted with CH$_2$Cl$_2$. The combined organic phases were dried (Na$_2$SO$_4$), filtered, concentrated, and purified by flash column chromatography (silica gel, 50-100% EtOAc in heptane, then 5-10% MeOH in CH$_2$Cl$_2$) to afford the title compound as an off-white solid.

Intermediate 25: Step c (2,4-Dichloro-3-phenylquinolin-6-yl)(1-methyl-1H-imidazol-5-yl)(pyridin-4-yl)methanol.TFA

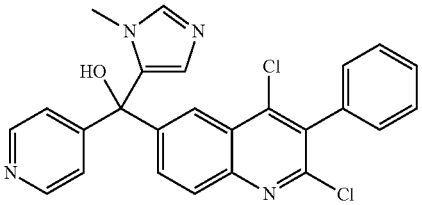 [SMILES: Cn1cncc1C(O)(c1ccncc1)c1ccc2nc(Cl)c(-c3ccccc3)c(Cl)c2c1]

To a solution of 6-bromo-2,4-dichloro-3-phenylquinoline (1.46 g, 4.14 mmol, Intermediate 7: step c) and (1-methyl-1H-imidazol-5-yl)(pyridin-4-yl)methanone (778 mg, 4.16 mmol, Intermediate 25: step b) in THF (65 mL) at −78° C. was added 1.6 M n-BuLi in hexane (3.90 mL, 6.24 mmol). After stirring at −78° C. to room temperature overnight, the mixture was quenched with NH$_4$Cl (aqueous). The organic layer was separated, and the aqueous layer was extracted with CH$_2$Cl$_2$. The combined organic phases were dried (Na$_2$SO$_4$), filtered, concentrated, and purified by flash column chromatography (80 g silica gel column, 100% EtOAc, then 5-10% MeOH in CH$_2$Cl$_2$) and then reverse phase HPLC (water/acetonitrile/0.1% TFA) to afford the title compound.

Intermediate 26

(4-Butyl-2-chloro-3-phenylquinolin-6-yl)(1-methyl-1H-imidazol-5-yl)(pyridin-4-yl)methanol.TFA

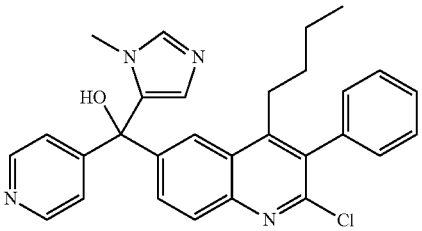 [SMILES: CCCCc1c(-c2ccccc2)c(Cl)nc2ccc(C(O)(c3ccncc3)c3cncn3C)cc12]

The title compound was isolated as a by-product from the reaction that formed (2,4-dichloro-3-phenylquinolin-6-yl)(1-methyl-1H-imidazol-5-yl)(pyridin-4-yl)methanol (Intermediate 25: step c).

Intermediate 27

(2,4-Dichloro-3-phenylquinolin-6-yl)(pyridin-2-yl)(pyridin-4-yl)methanol.TFA

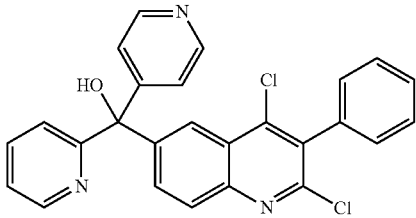 [SMILES: OC(c1ccncc1)(c1ccc2nc(Cl)c(-c3ccccc3)c(Cl)c2c1)c1ccccn1]

The title compound was prepared using pyridin-2-yl(pyridin-4-yl)methanone in place of (1-methyl-1H-imidazol-5-yl)

(pyridin-4-yl)methanone (Intermediate 25: step b) according to the procedure described in Intermediate 25: step c.

Intermediate 28: Step a

2-Fluoro-N-methoxy-N-methylisonicotinamide

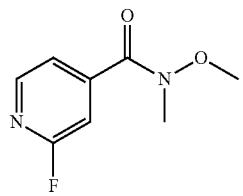

The title compound was prepared using 2-fluoroisonicotinic acid in place of 4-picolinic acid according to the procedure described in Intermediate 25: step a.

Intermediate 28: Step b (2-Fluoropyridin-4-yl)(1-methyl-1H-imidazol-2-yl)methanone

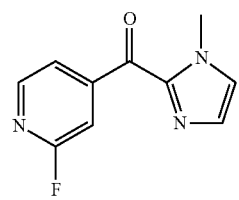

The title compound was prepared using 2-fluoro-N-methoxy-N-methylisonicotinamide (Intermediate 28: step a) in place of N-methoxy-N-methylisonicotinamide (Intermediate 25: step a) according to the procedure described in Intermediate 25: step b.

Intermediate 29 tert-Butyl 4-((2,4-dichloro-3-phenylquinolin-6-yl)(hydroxy)(pyridin-3-yl)methyl)piperidine-1-carboxylate

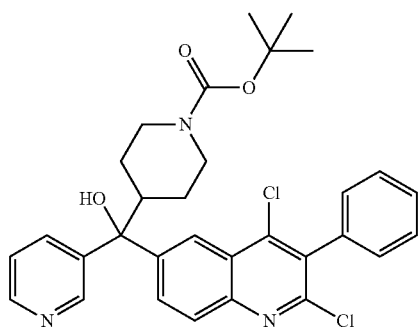 [SMILES: CC(C)(C)OC(=O)N1CCC(C(O)(c2cccnc2)c2ccc3nc(Cl)c(-c4ccccc4)c(Cl)c3c2)CC1]

To a solution of 6-bromo-2,4-dichloro-3-phenylquinoline (174 mg, 0.490 mmol, Intermediate 7: step c) and tert-butyl 4-nicotinoylpiperidine-1-carboxylate (143 mg, 0.490 mmol, Intermediate 21) in THF (5 mL) at −78° C. was added 1.6 M n-BuLi in hexane (0.47 mL, 0.75 mmol). The mixture was stirred at −78° C. to 0° C. for 3 hours and quenched with NH$_4$Cl (aqueous). The organic layer was separated, and the aqueous layer was extracted with CH$_2$Cl$_2$. The combined organic phases were dried (Na$_2$SO$_4$), filtered, concentrated, and purified by flash column chromatography (40 g silica gel column, 50-70% EtOAc in heptane) to provide the title compound as a solid.

Intermediate 30

(4-Chlorophenyl)(2,4-dimethylthiazol-5-yl)methanone

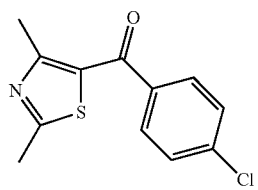 [SMILES: Cc1nc(C)c(C(=O)c2ccc(Cl)cc2)s1]

To a flask containing N-methoxy-N,2,4-trimethylthiazole-5-carboxamide (510 mg, 2.55 mmol, Intermediate 17: step a) was added THF (18 mL) and the solution was cooled to 0° C. To this solution was added (4-chlorophenyl)magnesium chloride (1 M in diethylether, 3.3 mL, 3.3 mmol). A homogeneous yellow mixture resulted and was allowed to warm to room temperature over 15 minutes. After 2 hours, the reaction mixture was quenched with aqueous NH$_4$Cl solution and the aqueous portion was extracted with EtOAc (4×50 mL). The combined organics were washed with brine, dried over MgSO$_4$, filtered and concentrated to dryness. Chromatography on silica gel (100% DCM increasing to 10% EtOAc-DCM) provided the title compound as a white solid.

Intermediate 31: Step a

N-(4-Bromophenyl)-2-phenylacetamide

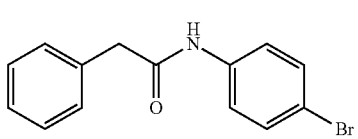 [SMILES: O=C(Cc1ccccc1)Nc1ccc(Br)cc1]

Into a 250-mL round-bottom flask were placed a solution of 4-bromoaniline (17.1 g, 99.42 mmol) and triethylamine (30 g, 297 mmol) in dichloromethane (100 mL). Then, 2-phenylacetyl chloride (18.6 g, 120 mmol) was added dropwise with stirring, and the resulting solution was stirred at room temperature for 6 hours. The solids were filtered out, and the filtrate was concentrated under vacuum. The crude product was purified by re-crystallization from ethyl acetate to provide the title compound as a white solid.

Intermediate 31: Step b

6-Bromo-2-chloro-3-phenylquinoline

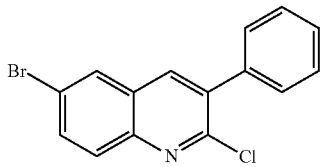 [SMILES: Clc1nc2ccc(Br)cc2cc1-c1ccccc1]

Into a 50-mL round-bottom flask were placed N,N-dimethylformamide (2.15 g, 29.45 mmol) and phosphoryl trichloride (20.3 g, 132.7 mmol) and the mixture was cooled to 0° C. Then, N-(4-bromophenyl)-2-phenylacetamide (5.7 g, 17.87 mmol, Intermediate 23: step a) was added in portions. The resulting solution was heated at 80° C. for 5 hours, then concentrated under vacuum, followed by dilution with 50 mL of $H_2O$, and then extraction with 3×50 mL of ethyl acetate. The combined organic layers were dried over anhydrous sodium sulfate, filtered and concentrated in vacuo. The residue was purified by FCC (1:10 EtOAc/petroleum ether) to afford the title compound as a yellow solid.

Intermediate 32: Step a

Methyl 5-bromo-2-(2-(2-chlorophenyl)acetamido)benzoate

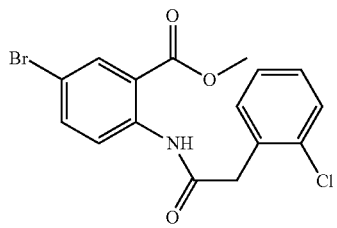 [SMILES: COC(=O)c1cc(Br)ccc1NC(=O)Cc1ccccc1Cl]

The title compound was prepared using 2-chlorophenylacetyl chloride in place of 2-phenylacetyl chloride using the procedure described for Intermediate 7: step a.

Intermediate 32: Step b

6-Bromo-3-(2-chlorophenyl)-4-hydroxyquinolin-2(1H)-one

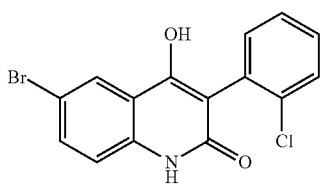 [SMILES: O=c1[nH]c2ccc(Br)cc2c(O)c1-c1ccccc1Cl]

The title compound was prepared using methyl 5-bromo-2-(2-(2-chlorophenyl)acetamido) benzoate (Intermediate 32: step a) in place of 5-bromo-2-(2-phenylacetamido) benzoate using the procedure described for Intermediate 7: step b.

Intermediate 32: Step c

6-Bromo-2,4-dichloro-3-(2-chlorophenyl)quinoline

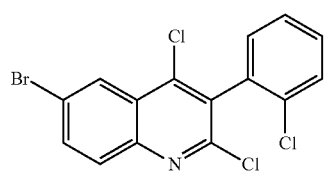 [SMILES: Clc1ccccc1-c1c(Cl)nc2ccc(Br)cc2c1Cl]

The title compound was prepared using 6-bromo-3-(2-chlorophenyl)-4-hydroxyquinolin-2(1H)-one (Intermediate 32: step b) in place of 6-bromo-4-hydroxy-3-phenylquinolin-2(1H)-one using the procedure described for Intermediate 7: step c.

Example 1a 1-(4-((4-Chloro-2-methoxy-3-(3-(trifluoromethyl) phenyl)quinolin-6-yl)(hydroxy)(1-methyl-1H-imidazol-5-yl)methyl)piperidin-1-yl)ethanone

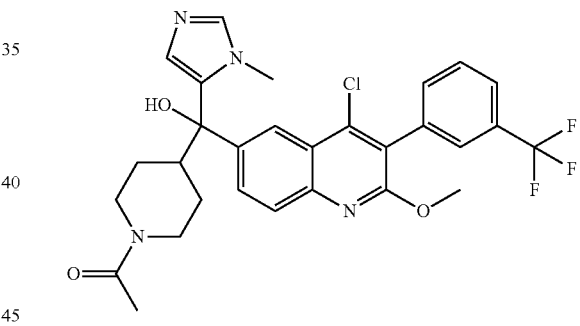

n-Butyllithium (1.6 M in hexane, 0.585 mL, 0.937 mmol) was added over 1 minute to a solution of 6-bromo-4-chloro-2-methoxy-3-(3-(trifluoromethyl)phenyl)quinoline (409.8 mg, 0.984 mmol, Intermediate 5: step e) in THF (3 mL) at −78° C. After 1 minute, a solution of 1-(4-(1-methyl-1H-imidazole-5-carbonyl)piperidin-1-yl)ethanone (231.4 mg, 0.984 mmol, Intermediate 1: step c) in THF (5 mL) was added via cannula. The mixture was stirred at −78° C. for 10 minutes, then was transferred to an ice bath and stirred for 45 minutes. The reaction mixture was quenched by addition of saturated aqueous $NH_4Cl$, diluted with water, and extracted with EtOAc (3×). The organic phase was dried ($Na_2SO_4$), filtered, and concentrated to dryness. The residue was purified by flash column chromatography (silica gel, 0-8% MeOH-DCM) to afford the target compound as a white solid. MS m/e 573.3 $[M+H]^+$.

1-(4-((4-Chloro-2-methoxy-3-(3-(trifluoromethyl)phenyl)quinolin-6-yl)(hydroxy)(1-methyl-1H-imidazol-5-yl) methyl)piperidin-1-yl)ethanone was purified by chiral HPLC (Chiralcel OD-H, EtOH) to give 2 enantiomers. Example 1b: (first enantiomer to elute off chiral column) $^1$H NMR (400

MHz, CDCl₃, 1.2:1 mixture of rotamers, minor rotamer peaks marked *) δ 8.21 (s, 1H), 8.16* (br. s., 1H), 7.85* (d, J=2.53 Hz, 1H), 7.83 (d, J=2.53 Hz, 1H), 7.72* (s, 1H), 7.70 (s, 1H), 7.59-7.66 (m, 4H), 7.54-7.58 (m, 2H), 7.41-7.51 (m, 2H), 7.34 (s, 2H), 7.23 (s, 2H), 4.78 (d, J=12.63 Hz, 1H), 4.61* (d, J=12.63 Hz, 1H), 4.01 (s, 6H), 3.95 (d, J=13.14 Hz, 1H), 3.76* (d, J=11.12 Hz, 1H), 3.28 (s, 3H), 3.27* (s, 3H), 3.11-3.24* (m, 1H), 2.94-3.04 (m, 1H), 2.56-2.70 (m, 3H), 2.40-2.56 (m, 3H), 2.25-2.38 (m, 2H), 2.05 (s, 3H)*, 2.03 (s, 3H), 1.13-1.44 (m, 6H); MS m/e 573.2 [M+H]⁺ and Example 1c: (second enantiomer to elute off chiral column) ¹H NMR (400 MHz, CDCl₃, 1.2:1 mixture of rotamers, minor rotamer peaks marked *) δ 8.21 (s, 1H), 8.16* (br. s., 1H), 7.84* (d, J=3.03 Hz, 1H), 7.82 (d, J=2.53 Hz, 1H), 7.71* (s, 1H), 7.69 (s, 1H), 7.58-7.65 (m, 4H), 7.52-7.58 (m, 2H), 7.40-7.51 (m, 2H), 7.29-7.35 (m, 2H), 7.22 (s, 2H), 4.77 (d, J=13.1 Hz, 1H), 4.60 (d, J=13.6 Hz, 1H), 4.00 (s, 6H), 3.93 (d, J=12.63 Hz, 1H), 3.74* (d, J=13.14 Hz, 1H), 3.27 (s, 3H), 3.26* (s, 3H), 3.12-3.22 (m, 1H), 2.92-3.05 (m, 1H), 2.80 (s, 1H), 2.57-2.74 (m, 2H), 2.39-2.55 (m, 3H), 2.22-2.39 (m, 2H), 2.04* (s, 3H), 2.02 (s, 3H), 1.12-1.46 (m, 6H); MS m/e 573.2 [M+H]⁺.

Example 2a 6-((1-Acetylpiperidin-4-yl)(hydroxy)(1-methyl-1H-imidazol-5-yl)methyl)-2-methoxy-3-(3-(trifluoromethyl)phenyl)quinoline-4-carbonitrile

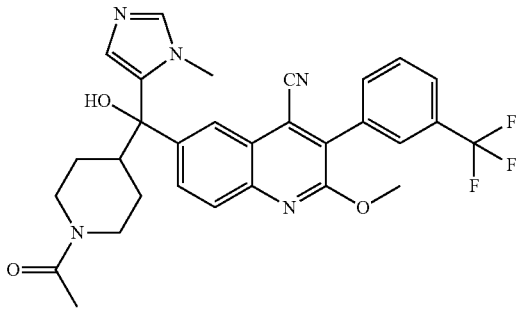 [SMILES: COc1nc2ccc(C(O)(c3cncn3C)C3CCN(C(C)=O)CC3)cc2c(C#N)c1-c1cccc(C(F)(F)F)c1]

A round bottom flask was charged with 1-(4-((4-chloro-2-methoxy-3-(3-(trifluoromethyl)phenyl)quinolin-6-yl)(hydroxy)(1-methyl-1H-imidazol-5-yl)methyl)piperidin-1-yl)ethanone (158 mg, 0.276 mmol, Example 1a), Zn(CN)₂ (58.3 mg, 0.496 mmol), Pd₂(dba)₃ (37.9 mg, 0.041 mmol), zinc nanopowder (5.4 mg, 0.083 mmol), and dicyclohexyl(2',4',6'-triisopropyl-[1,1'-biphenyl]-2-yl)phosphine (X-Phos, 27.1 mg, 0.055 mmol). The flask was evacuated and re-filled with argon (three cycles). Dimethylacetamide (1.4 mL, sparged with argon for 30 minutes) was then added and the mixture was heated at 120° C. for 4 hours. The mixture was cooled to room temperature and was filtered through Celite®, washing with EtOAc. The filtrate was washed sequentially with 2 M aqueous NH₄OH, water, and saturated aqueous NaCl. The organic phase was dried (Na₂SO₄), filtered, and concentrated to dryness. The residue was purified by flash column chromatography (silica gel, 1-8% MeOH-DCM) to afford the title compound. MS m/e 564.3 [M+H]⁺.

6-((1-Acetylpiperidin-4-yl)(hydroxy)(1-methyl-1H-imidazol-5-yl)methyl)-2-methoxy-3-(3-(trifluoromethyl)phenyl)quinoline-4-carbonitrile was purified by chiral HPLC (Chiralcel OD-H, EtOH) to give 2 enantiomers. Example 2b: (first enantiomer to elute off chiral column) ¹H NMR (400 MHz, CDCl₃, 1.1:1 mixture of rotamers, minor rotamer peaks marked *) δ 8.28 (s, 1H), 8.24* (s, 1H), 7.84-7.91 (m, 2H), 7.71-7.84 (m, 6H), 7.63-7.71 (m, 2H), 7.43-7.50 (m, 2H), 7.29-7.33 (m, 2H), 7.21 (s, 2H), 4.76 (d, J=14.65 Hz, 1H), 4.59* (d, J=11.12 Hz, 1H), 4.06* (s, 6H), 3.94 (d, J=12.63 Hz, 1H), 3.68-3.80 (m, 1H), 3.29 (s, 3H), 3.27* (s, 3H), 3.22 (s, 1H), 3.13-3.22* (m, 1H), 3.10* (s, 1H), 2.93-3.04 (m, 1H), 2.58-2.71 (m, 1H), 2.23-2.57 (m, 5H), 2.04 (s, 3H), 2.03 (s, 3H), 1.12-1.47 (m, 6H); MS m/e 564.2 [M+H]⁺ and Example 2c: (second enantiomer to elute off chiral column) ¹H NMR (400 MHz, CDCl₃, 1.1:1 mixture of rotamers, minor rotamer peaks marked *) δ 8.28 (s, 1H), 8.24* (s, 1H), 7.88-7.90* (m, 1H), 7.85-7.87 (m, 1H), 7.71-7.83 (m, 6H), 7.64-7.71 (m, 2H), 7.42-7.50 (m, 2H), 7.31-7.34 (m, 2H), 7.22 (s, 2H), 4.77 (d, J=13.14 Hz, 1H), 4.60* (d, J=14.15 Hz, 1H), 4.07 (s, 6H), 3.94* (d, J=14.15 Hz, 1H), 3.68-3.80 (m, 1H), 3.28 (s, 3H), 3.27* (s, 3H), 3.13-3.23 (m, 1H), 2.96-3.05* (m, 1H), 2.95 (s, 1H), 2.84* (s, 1H), 2.58-2.70 (m, 1H), 2.22-2.57 (m, 5H), 2.05* (s, 3H), 2.03 (s, 3H), 1.17-1.45 (m, 6H); MS m/e 564.2 [M+H]⁺.

Example 3a (4-Chloro-2-methoxy-3-(3-(trifluoromethyl)phenyl)quinolin-6-yl)(1-methyl-1H-1,2,3-triazol-5-yl)(1-methyl-1H-imidazol-5-yl)methanol

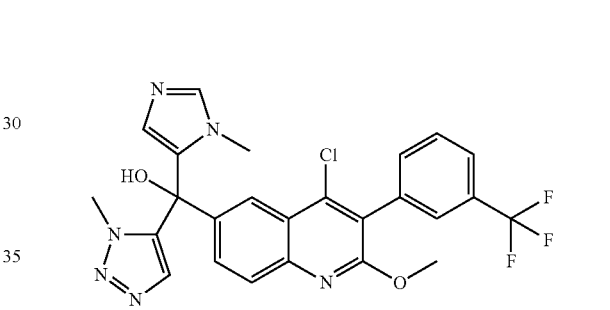

n-Butyllithium (1.6 M in hexane, 0.547 mL, 0.876 mmol) was added over 1 minute to a solution of 6-bromo-4-chloro-2-methoxy-3-(3-(trifluoromethyl)phenyl)quinoline (383 mg, 0.919 mmol, Intermediate 5: step e) in THF (3 mL) at −78° C. After 5 minutes, a solution of (1-methyl-1H-1,2,3-triazol-5-yl)(1-methyl-1H-imidazol-5-yl)methanone (176 mg, 0.919 mmol, Intermediate 6, step b) in THF (15 mL) was added via cannula. The mixture was stirred at −78° C. for 5 minutes, then was transferred to an ice bath and stirred for 30 minutes. The reaction mixture was quenched by addition of saturated aqueous NH₄Cl, diluted with water, and extracted with EtOAc (3×). The organic phase was washed twice with water. The organic phase was dried (Na₂SO₄), filtered, and concentrated. The residue was purified by flash column chromatography (silica gel, 1-7% MeOH-DCM) to afford the target compound as a white solid. MS m/e 529.2 [M+H]⁺.

(4-Chloro-2-methoxy-3-(3-(trifluoromethyl)phenyl)quinolin-6-yl)(1-methyl-1H-1,2,3-triazol-5-yl)(1-methyl-1H-imidazol-5-yl)methanol was purified by chiral SFC (Chiralpack IC, 75% CO₂, 25% (0.2% isopropylamine-2-propanol)) to give 2 enantiomers. The enantiomers were then further purified individually on plug silica gel columns (0-5% MeOH-DCM). Example 3b: first enantiomer to elute off chiral column) ¹H NMR (400 MHz, CDCl₃) δ 8.30 (br. s., 1H), 7.82-8.09 (br. s., 1H), 7.78 (d, J=9.1 Hz, 1H), 7.70-7.75 (m, 1H), 7.61-7.68 (m, 2H), 7.36 (br. s., 1H), 7.26-7.32 (m, 1H), 7.13 (br. s., 1H), 6.19 (br. s., 1H), 3.98 (s, 3H), 3.91 (s, 3H), 3.52 (s, 3H); MS m/e 529.2 [M+H]⁺ and Example 3c: second enantiomer to elute off chiral column) ¹H NMR (400

MHz, CDCl$_3$) δ 8.31 (br. s., 1H), 7.79-8.05 (br. s., 1H), 7.78 (d, J=8.6 Hz, 1H), 7.71-7.75 (m, 1H), 7.61-7.69 (m, 2H), 7.36 (br. s., 1H), 7.26-7.32 (m, 1H), 7.12 (br. s., 1H), 6.19 (br. s., 1H), 3.98 (s, 3H), 3.91 (s, 3H), 3.52 (s, 3H); MS m/e 529.2 [M+H]$^+$.

Example 4a 6-(Hydroxy(1-methyl-1H-1,2,3-triazol-5-yl)(1-methyl-1H-imidazol-5-yl)methyl)-2-methoxy-3-(3-(trifluoromethyl)phenyl)quinoline-4-carbonitrile

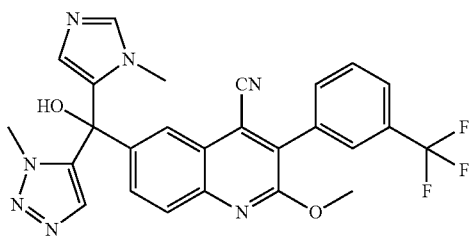 [SMILES: COc1nc2ccc(C(O)(c3cncn3C)c3cnnn3C)cc2c(C#N)c1-c1cccc(C(F)(F)F)c1]

A round bottom flask was charged with (4-chloro-2-methoxy-3-(3-(trifluoromethyl)phenyl)quinolin-6-yl)(1-methyl-1H-1,2,3-triazol-5-yl)(1-methyl-1H-imidazol-5-yl)methanol (96.6 mg, 0.183 mmol, Example 3a), Zn(CN)$_2$ (38.6 mg, 0.329 mmol), Pd$_2$(dba)$_3$ (25.1 mg, 0.027 mmol), zinc nanopowder (3.6 mg, 0.055 mmol), and dicyclohexyl(2',4',6'-triisopropyl-[1,1'-biphenyl]-2-yl)phosphine (X-Phos, 18.0 mg, 0.037 mmol). The flask was evacuated and re-filled with argon (three cycles). Dimethylacetamide (1.8 mL, sparged with argon for 30 minutes) was then added and the mixture was heated at 120° C. for 9 hours. The mixture was cooled to room temperature and was filtered through Celite®, washing with EtOAc. The filtrate was washed sequentially with 2 M aqueous NH$_4$OH, water, and saturated aqueous NaCl. The organic phase was dried (Na$_2$SO$_4$), filtered, and concentrated. To improve conversion, the crude product was resubjected to the reaction conditions as described above for an additional 4.5 hours, then was worked up as described above. The residue was partially purified by flash column chromatography (silica gel, 2-8% MeOH-DCM) then was further purified by RP-HPLC (10-90% CH$_3$CN—H$_2$O, 0.1% TFA). HPLC fractions were basified (saturated aqueous NaHCO$_3$), partially concentrated, and extracted with DCM (3×). The organic extract was dried over Na$_2$SO$_4$, filtered, and concentrated to afford the title compound. MS m/e 519.9 [M+H]$^+$.

6-(Hydroxy(1-methyl-1H-1,2,3-triazol-5-yl)(1-methyl-1H-imidazol-5-yl)methyl)-2-methoxy-3-(3-(trifluoromethyl)phenyl)quinoline-4-carbonitrile was purified by chiral SFC (Chiralpack IC, 90% CO$_2$, 10% (0.2% isopropylamine-EtOH)) to give 2 enantiomers. The enantiomers were then further purified on plug silica gel columns (0-5% MeOH-DCM). Example 4b: (first enantiomer to elute off chiral column) $^1$H NMR (400 MHz, CDCl$_3$) δ 8.27-8.31 (m, 1H), 7.88 (d, J=8.6 Hz, 1H), 7.84 (s, 1H), 7.77-7.82 (m, 1H), 7.73-7.77 (m, 1H), 7.66-7.73 (m, 1H), 7.35 (dd, J=8.6, 1.5 Hz, 1H), 7.16 (s, 1H), 6.33 (br. s., 1H), 6.25 (br. s., 1H), 4.07 (s, 3H), 3.93 (s, 3H), 3.53 (s, 3H); MS m/e 520.2 [M+H]$^+$ and Example 4c: (second enantiomer to elute off chiral column) $^1$H NMR (400 MHz, CDCl$_3$) δ 8.29 (d, J=2.0 Hz, 1H), 7.90 (d, J=8.6 Hz, 1H), 7.84 (s, 1H), 7.77-7.81 (m, 1H), 7.73-7.77 (m, 1H), 7.66-7.73 (m, 1H), 7.37 (dd, J=9.1, 2.0 Hz, 1H), 7.33 (s, 1H), 7.19 (s, 1H), 6.30 (br. s., 1H), 5.54 (br. s., 1H), 4.08 (s, 3H), 3.95 (s, 3H), 3.55 (s, 3H); MS m/e 520.0 [M+H]$^+$.

Example 5

(4-Chlorophenyl)(2,4-dichloro-3-(pyridin-2-yl)quinolin-6-yl)(1-methyl-1H-imidazol-5-yl)methanol.TFA

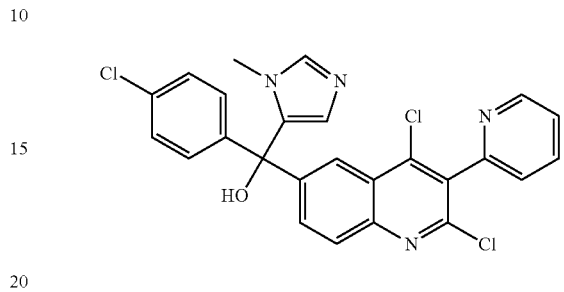

Into a 100-mL round-bottom flask was placed a solution of 6-bromo-2,4-dichloro-3-(pyridin-2-yl)quinoline (380 mg, 1.07 mmol, Intermediate 9: step c) in tetrahydrofuran (10 mL). This was followed by the addition of n-BuLi (0.43 mL, 1.28 mmol, 3.0 M in hexanes) dropwise with stirring at –78° C. The resulting solution was stirred for 30 minutes at –78° C. To this was added a solution of 5-[(4-chlorophenyl)carbonyl]-1-methyl-1H-imidazole (199 mg, 0.90 mmol, Intermediate 8: step b) in tetrahydrofuran (10 mL) dropwise with stirring at –78° C. The resulting solution was allowed to react, with stirring, for an additional 2 hours at room temperature. The reaction was then quenched by the addition of 10 mL of saturated aqueous NH$_4$Cl. The resulting mixture was concentrated under vacuum. The crude product was purified by Prep-HPLC [(1#waters-2767-1): Column, Sunfire prep C18, 5 µm, 19×100 mm; mobile phase, 0.05% TFA in water and MeOH (45% MeOH up to 65% in 10 minutes); Detector, UV 254 nm] to afford the title compound trifluoroacetic acid salt as a white solid. MS (ES, m/z) 495 [M+H]$^+$; $^1$H NMR (300 MHz, CDCl$_3$+D$_2$O) δ 8.86-8.69 (m, 1H), 8.50 (br. s., 1H), 8.40 (br. s., 0.5H), 8.25 (br. s., 0.5H), 8.07 (d, J=8.6 Hz, 1H), 7.97 (t, J=7.5 Hz, 1H), 7.85-7.69 (m, 1H), 7.60-7.43 (m, 2H), 7.43-7.30 (m, 4H), 6.70 (br. s., 0.5H), 6.65 (br. s., 0.5H), 3.59 (br. s., 3H).

Example 6

(4-Chlorophenyl)(2,4-dichloro-3-(pyridin-3-yl)quinolin-6-yl)(1-methyl-1H-imidazol-5-yl)methanol.TFA

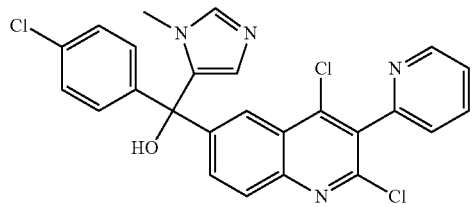 [SMILES: Cn1cncc1C(O)(c1ccc(Cl)cc1)c1ccc2nc(Cl)c(-c3ccccn3)c(Cl)c2c1]

Into a 100-mL round-bottom flask purged and maintained with an inert atmosphere of nitrogen, was placed a solution of 6-bromo-2,4-dichloro-3-(pyridin-3-yl)quinoline (160 mg, 0.45 mmol, Intermediate 10: step c) in tetrahydrofuran (10 mL). This was followed by the addition of t-BuLi (0.85 mL, 1.35 mmol, 1.6 M in pentane) dropwise with stirring at −78° C. The resulting solution was stirred for 30 minutes at −78° C. To this was added a solution of 5-[(4-chlorophenyl)carbonyl]-1-methyl-1H-imidazole (121 mg, 0.55 mmol, Intermediate 8, step b) in tetrahydrofuran (10 mL) dropwise with stirring at −78° C. The resulting solution was stirred for 30 minutes at −78° C. The resulting solution was allowed to react, with stirring, for an additional 30 minutes at −40° C. The resulting solution was allowed to react, with stirring overnight at room temperature. The reaction was then quenched by the addition of 10 mL of saturated aqueous $NH_4Cl$. The resulting solution was extracted with 3×10 mL of ethyl acetate and the organic layers combined and dried over anhydrous sodium sulfate, filtered and concentrated under vacuum. The crude product was purified by Flash-Prep-HPLC [(IntelFlash-1): Column, silica gel; mobile phase, 0.05% TFA in water and $CH_3CN$ (22% $CH_3CN$ up to 44% within 10 minutes; Detector, UV 254 nm] to afford the title compound trifluoroacetic acid salt as an off-white solid. MS (ES, m/z) 495 [M+H]$^+$ and 517 [M+Na]$^+$; $^1$H NMR (400 MHz, CD$_3$OD) δ 9.03 (s, 1H), 8.78-8.62 (m, 2H), 8.39-8.36 (m, 1H), 8.15-8.07 (m, 2H), 7.97-7.94 (m, 1H), 7.80-7.76 (m, 1H), 7.54-7.45 (m, 4H), 7.00 (br. s., 1H), 3.74 (d, J=11.2 Hz, 3H).

Example 7a

{4-Chloro-2-methoxy-3-[4-(methylsulfonyl)phenyl] quinolin-6-yl}(1-methyl-1H-imidazol-5-yl)[6-(trifluoromethyl)pyridin-3-yl]methanol

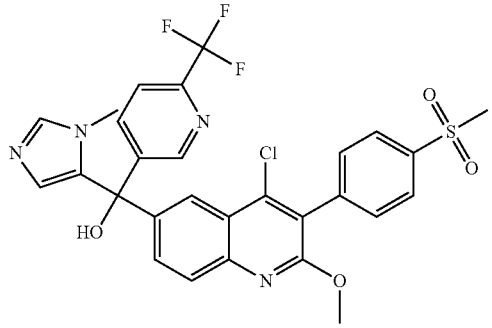 [SMILES: COc1nc2ccc(C(O)(c3ccc(C(F)(F)F)nc3)c3cncn3C)cc2c(Cl)c1-c1ccc(S(C)(=O)=O)cc1]

A mixture of 4-chloro-6-(hydroxy(1-methyl-1H-imidazol-5-yl)(6-(trifluoromethyl)pyridin-3-yl)methyl)-2-methoxyquinolin-3-yl trifluoromethanesulfonate (70 mg, 0.12 mmol, Intermediate 11: step g), (4-(methylsulfonyl)phenyl)boronic acid (35 mg, 0.18 mmol), PdCl$_2$(dppf) (9 mg, 0.012 mmol) and K$_2$CO$_3$ (16 mg, 0.12 mmol) was sparged with nitrogen three times. To this mixture was added 1,4-dioxane (2 mL) and water (0.3 mL) and the suspension purged with nitrogen. The resulting solution was heated to 65° C. for 15 hours. The reaction was allowed to cool to room temperature and concentrated to dryness. The residue was dissolved in DMSO, filtered and purified by reverse-phase HPLC (acetonitrile/water+TFA). The acidic fractions were neutralized by diluting with EtOAc and washing with saturated aqueous NaHCO$_3$ followed by water. The organics were dried (MgSO$_4$), filtered and concentrated to dryness to provide the title compound. $^1$H NMR (400 MHz, CD$_3$OD) δ 8.79-8.76 (m, 1H), 8.24-8.20 (m, 1H), 8.08-8.05 (m, 2H), 8.05-8.01 (m, 1H), 7.96-7.93 (m, 1H), 7.84 (d, J=8.3 Hz, 1H), 7.76-7.72 (m, 2H), 7.65-7.62 (m, 2H), 6.35 (s, 1H), 4.00 (s, 3H), 3.49 (s, 3H), 3.20 (s, 3H); MS (ESI): mass calcd. for C$_{28}$H$_{22}$ClF$_3$N$_4$O$_4$S, 602.1; m/z found, 603.2 [M+H]$^+$.

{4-Chloro-2-methoxy-3-[4-(methylsulfonyl)phenyl] quinolin-6-yl}(1-methyl-1H-imidazol-5-yl)[6-(trifluoromethyl)pyridin-3-yl]methanol was purified by HPLC (Kromasil C18 100 Å, 5 μM column, Mobile phase: 35-100% acetonitrile/water+0.25% ammonium bicarbonate) followed by FCC (0-5% MeOH/DCM) to give 2 enantiomers. The first eluting enantiomer was Example 7b: $^1$H NMR (400 MHz, CD$_3$OD) δ 8.81-8.77 (m, 1H), 8.23 (d, J=2.0 Hz, 1H), 8.09-8.06 (m, 2H), 8.06-8.02 (m, 1H), 7.97-7.93 (m, 1H), 7.85 (d, J=8.2 Hz, 1H), 7.78-7.72 (m, 2H), 7.66-7.62 (m, 2H), 6.37 (s, 1H), 4.01 (s, 3H), 3.50 (s, 3H), 3.21 (s, 3H); MS (ESI): mass calcd. for C$_{28}$H$_{22}$ClF$_3$N$_4$O$_4$S, 602.1; m/z found, 603.2 [M+H]$^+$ and the second eluting enantiomer was Example 7c: $^1$H NMR (400 MHz, CD$_3$OD) δ 8.80-8.77 (m, 1H), 8.22 (d, J=2.1 Hz, 1H), 8.09-8.05 (m, 2H), 8.05-8.01 (m, 1H), 7.96-7.92 (m, 1H), 7.85 (d, J=8.2 Hz, 1H), 7.77-7.71 (m, 2H), 7.66-7.61 (m, 2H), 6.36 (s, 1H), 4.00 (s, 3H), 3.49 (s, 3H), 3.21 (s, 3H); MS (ESI): mass calcd. for C$_{28}$H$_{22}$ClF$_3$N$_4$O$_4$S, 602.1; m/z found, 603.2 [M+H]$^+$.

Example 8

[4-Chloro-2-methoxy-3-(1-methyl-1H-pyrazol-4-yl) quinolin-6-yl](1-methyl-1H-imidazol-5-yl)[6-(trifluoromethyl)pyridin-3-yl]methanol.TFA

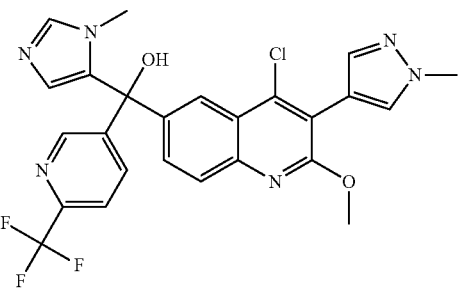 [SMILES: COc1nc2ccc(C(O)(c3ccc(C(F)(F)F)nc3)c3cncn3C)cc2c(Cl)c1-c1cnn(C)c1]

The title compound was prepared using 1-methyl-4-(4,4,5,5-tetramethyl-1,3,2-dioxaborolan-2-yl)-1H-pyrazole in place of (4-(methylsulfonyl)phenyl)boronic acid using the procedure described for Example 7a. $^1$H NMR (400 MHz, CD$_3$OD) δ 9.03 (s, 1H), 8.82 (d, J=2.3 Hz, 1H), 8.25 (d, J=2.1 Hz, 1H), 8.10-8.06 (m, 1H), 8.03 (s, 1H), 7.93 (d, J=8.7 Hz, 1H), 7.90 (d, J=8.3 Hz, 1H), 7.85 (s, 1H), 7.66 (dd, J=8.7, 2.1 Hz, 1H), 7.08-7.06 (m, 1H), 4.09 (s, 3H), 3.98 (s, 3H), 3.71 (s, 3H); MS (ESI): mass calcd. for C$_{25}$H$_{20}$ClF$_3$N$_6$O$_2$, 528.1; m/z found, 529.2 [M+H]$^+$.

Example 9a 5-(4-Chloro-6-{hydroxy(1-methyl-1H-imidazol-5-yl)[6-(trifluoromethyl)pyridin-3-yl]methyl}-2-methoxyquinolin-3-yl)pyrimidine-2-carbonitrile.TFA

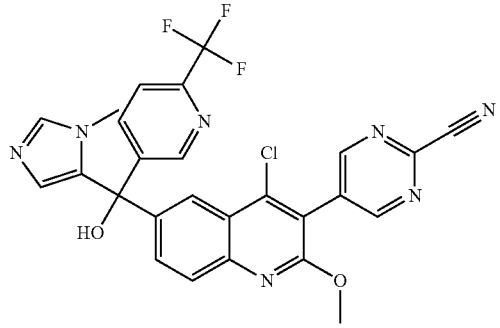 [SMILES: COc1nc2ccc(C(O)(c3ccc(C(F)(F)F)nc3)c3cncn3C)cc2c(Cl)c1-c1cnc(C#N)nc1]

The title compound was prepared using 5-(4,4,5,5-tetramethyl-1,3,2-dioxaborolan-2-yl)pyrimidine-2-carbonitrile in place of (4-(methylsulfonyl)phenyl)boronic acid using the procedure described for Example 7a. $^1$H NMR (400 MHz, CD$_3$OD) δ 9.06-9.02 (m, 3H), 8.84-8.79 (m, 1H), 8.33-8.29 (m, 1H), 8.12-8.08 (m, 1H), 8.02 (d, J=8.9 Hz, 1H), 7.90 (d, J=8.2 Hz, 1H), 7.82-7.77 (m, 1H), 7.10 (s, 1H), 4.06 (s, 3H), 3.71 (s, 3H); MS (ESI): mass calcd. for C$_{26}$H$_{17}$ClF$_3$N$_7$O$_2$, 551.1; m/z found, 552.2 [M+H]$^+$.

5-(4-Chloro-6-{hydroxy(1-methyl-1H-imidazol-5-yl) [6-(trifluoromethyl)pyridin-3-yl]methyl}-2-methoxyquinolin-3-yl)pyrimidine-2-carbonitrile was purified by HPLC (CHIRACEL OD 20 μM Daicel column, Mobile phase: 100% EtOH) followed by FCC (0-10% MeOH/DCM) to give 2 enantiomers. The first eluting enantiomer was Example 9b: $^1$H NMR (400 MHz, CD$_3$OD) δ 9.05 (s, 2H), 8.77 (m, 1H), 8.25 (d, J=2.1 Hz, 1H), 8.04 (dd, J=8.2, 2.2 Hz, 1H), 7.98-7.94 (m, 1H), 7.85 (d, J=8.2 Hz, 1H), 7.79 (dd, J=8.9, 2.1 Hz, 1H), 7.76-7.72 (m, 1H), 6.36 (s, 1H), 4.05 (s, 3H), 3.48 (s, 3H); MS (ESI): mass calcd. for C$_{26}$H$_{17}$ClF$_3$N$_7$O$_2$, 551.1; m/z found, 552.2 [M+H]$^+$ and the second eluting enantiomer was Example 9c: $^1$H NMR (400 MHz, CD$_3$OD) δ 9.05 (s, 2H), 8.80-8.76 (m, 1H), 8.26 (d, J=2.1 Hz, 1H), 8.06-8.02 (m, 1H), 7.97 (d, J=8.8 Hz, 1H), 7.85 (d, J=8.3 Hz, 1H), 7.79 (dd, J=8.9, 2.1 Hz, 1H), 7.75 (s, 1H), 6.36 (s, 1H), 4.06 (s, 3H), 3.49 (s, 3H); MS (ESI): mass calcd. for C$_{26}$H$_{17}$ClF$_3$N$_7$O$_2$, 551.1; m/z found, 552.2 [M+H]$^+$.

Example 10

(4-Chloro-2-methoxy-3-pyrimidin-5-ylquinolin-6-yl) (1-methyl-1H-imidazol-5-yl)[6-(trifluoromethyl) pyridin-3-yl]methanol.TFA The title compound was prepared using pyrimidin-5-ylboronic acid in place of (4-(methylsulfonyl)phenyl)boronic acid using the procedure described for Example 7a. $^1$H NMR (400 MHz, CD$_3$OD) δ 9.23 (s, 1H), 9.04 (s, 1H), 8.88 (s, 2H), 8.84-8.81 (m, 1H), 8.32-8.28 (m, 1H), 8.12-8.08 (m, 1H), 8.03-8.00 (m, 1H), 7.92-7.88 (m, 1H), 7.80-7.76 (m, 1H), 7.11-7.09 (m, 1H), 4.05 (s, 3H), 3.72 (s, 3H); MS (ESI): mass calcd. for C$_{25}$H$_{18}$ClF$_3$N$_6$O$_2$, 526.1; m/z found, 527.1 [M+H]$^+$.

Example 11

{4-Chloro-2-methoxy-3-[3-(methylsulfonyl)phenyl] quinolin-6-yl}(1-methyl-1H-imidazol-5-yl)[6-(trifluoromethyl)pyridin-3-yl]methanol.TFA

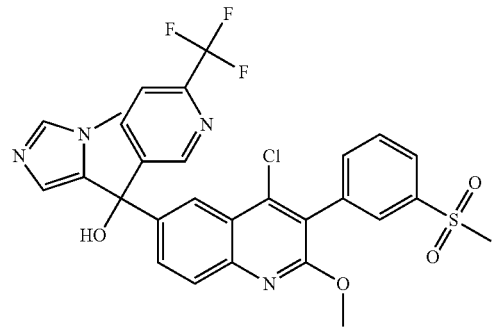 [SMILES: COc1nc2ccc(C(O)(c3ccc(C(F)(F)F)nc3)c3cncn3C)cc2c(Cl)c1-c1cccc(S(C)(=O)=O)c1]

The title compound was prepared using (3-(methylsulfonyl)phenyl)boronic acid in place of (4-(methylsulfonyl)phenyl)boronic acid using the procedure described for Example 7a. $^1$H NMR (400 MHz, CD$_3$OD) δ 9.02 (s, 1H), 8.84-8.81 (m, 1H), 8.30-8.27 (m, 1H), 8.12-8.07 (m, 1H), 8.06-8.03 (m, 1H), 8.00 (d, J=8.8 Hz, 1H), 7.97-7.95 (m, 1H), 7.90 (d, J=8.2 Hz, 1H), 7.79-7.71 (m, 3H), 7.10-7.07 (m, 1H), 4.02 (s, 3H), 3.72 (s, 3H), 3.18 (s, 3H); MS (ESI): mass calcd. for C$_{28}$H$_{22}$ClF$_3$N$_4$O$_4$S, 602.1; m/z found, 603.2 [M+H]$^+$.

Example 12

N-[3-(4-Chloro-6-{hydroxy(1-methyl-1H-imidazol-5-yl)[6-(trifluoromethyl)pyridin-3-yl]methyl}-2-methoxyquinolin-3-yl)phenyl]methanesulfonamide.TFA

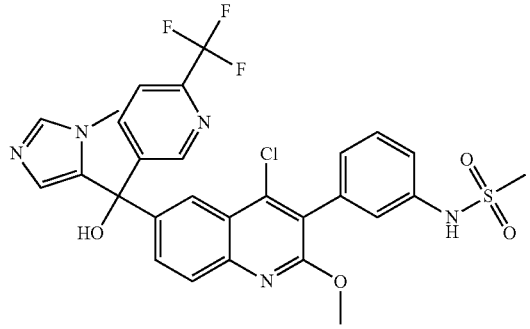 [SMILES: COc1nc2ccc(C(O)(c3ccc(C(F)(F)F)nc3)c3cncn3C)cc2c(Cl)c1-c1cccc(NS(C)(=O)=O)c1]

The title compound was prepared using (3-(methylsulfonamido)phenyl)boronic acid in place of (4-(methylsulfonyl) phenyl)boronic acid using the procedure described for Example 7a. $^1$H NMR (400 MHz, CD$_3$OD) δ 9.03 (s, 1H), 8.85-8.81 (m, 1H), 8.27-8.24 (m, 1H), 8.11-8.06 (m, 1H), 7.99 (d, J=8.7 Hz, 1H), 7.90 (d, J=8.3 Hz, 1H), 7.75-7.70 (m, 1H), 7.48-7.42 (m, 1H), 7.31-7.27 (m, 1H), 7.26-7.23 (m, 1H), 7.14-7.10 (m, 1H), 7.09-7.07 (m, 1H), 4.01 (s, 3H), 3.72

(s, 3H), 2.99 (s, 3H); MS (ESI): mass calcd. for $C_{28}H_{23}ClF_3N_5O_4S$, 617.1; m/z found, 618.0 [M+H]$^+$.

Example 13

{4-Chloro-2-methoxy-3-[5-(methylsulfonyl)pyridin-3-yl]quinolin-6-yl}(1-methyl-1H-imidazol-5-yl)[6-(trifluoromethyl)pyridin-3-yl]methanol.TFA

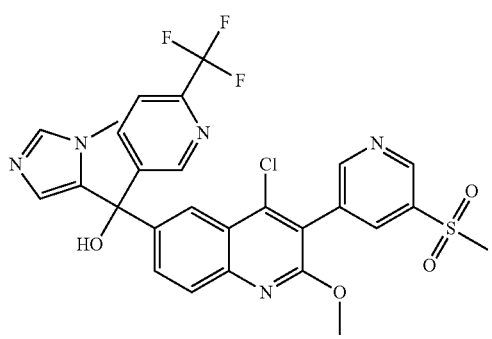 [SMILES: COc1nc2ccc(C(O)(c3ccc(C(F)(F)F)nc3)c3cncn3C)cc2c(Cl)c1-c1cncc(S(C)(=O)=O)c1]

The title compound was prepared using (5-(methylsulfonyl)pyridin-3-yl)boronic acid in place of (4-(methylsulfonyl)phenyl)boronic acid using the procedure described for Example 7a. $^1$H NMR (400 MHz, CD$_3$OD) δ 9.19-9.15 (m, 1H), 9.04 (s, 1H), 8.91-8.87 (m, 1H), 8.82 (d, J=2.2 Hz, 1H), 8.46-8.43 (m, 1H), 8.31 (d, J=2.1 Hz, 1H), 8.13-8.08 (m, 1H), 8.02 (d, J=8.8 Hz, 1H), 7.90 (d, J=8.3 Hz, 1H), 7.80-7.76 (m, 1H), 7.12-7.09 (m, 1H), 4.05 (s, 3H), 3.72 (s, 3H), 3.28 (s, 3H); MS (ESI): mass calcd. for $C_2H_{21}ClF_3N_5O_4S$, 603.1; m/z found, 604.0 [M+H]$^+$.

Example 14a

[4-Chloro-3-(5-chlorothiophen-2-yl)-2-methoxyquinolin-6-yl](1-methyl-1H-imidazol-5-yl)[6-(trifluoromethyl)pyridin-3-yl]methanol.TFA

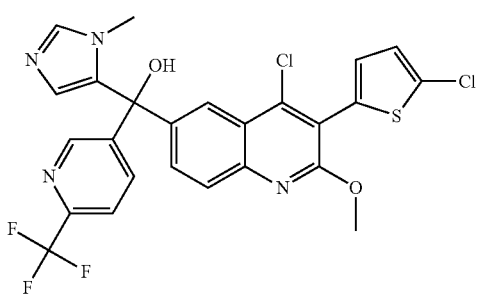 [SMILES: COc1nc2ccc(C(O)(c3ccc(C(F)(F)F)nc3)c3cncn3C)cc2c(Cl)c1-c1ccc(Cl)s1]

A mixture of 4-chloro-6-(hydroxy(1-methyl-1H-imidazol-5-yl)(6-(trifluoromethyl)pyridin-3-yl)methyl)-2-methoxyquinolin-3-yl trifluoromethanesulfonate (40 mg, 0.067 mmol, Intermediate 11: step g), (5-chlorothiophen-2-yl)boronic acid (16 mg, 0.1 mmol), PdCl$_2$(dppf) (5 mg, 0.007 mmol) and K$_2$CO$_3$ (9 mg, 0.067 mmol) was sparged with nitrogen three times. To this mixture was added 1,4-dioxane (1.2 mL) and water (0.17 mL) and the suspension purged with nitrogen. The resulting solution was heated to 65° C. for 15 hours. The mixture was then heated to 75° C. for 6 hours after which it was allowed to cool to room temperature. The solution was diluted with EtOAc, washed with water, dried (MgSO$_4$), filtered and concentrated to dryness. The crude material was purified by reverse-phase HPLC (acetonitrile/water+TFA) to provide the title compound. $^1$H NMR (400 MHz, CD$_3$OD) δ 9.03 (s, 1H), 8.84-8.81 (m, 1H), 8.26 (d, J=2.2 Hz, 1H), 8.11-8.06 (m, 1H), 7.96 (d, J=8.7 Hz, 1H), 7.90 (d, J=8.2 Hz, 1H), 7.74-7.71 (m, 1H), 7.09-7.04 (m, 3H), 4.06 (s, 3H), 3.71 (s, 3H); MS (ESI): mass calcd. for $C_{25}H_{17}Cl_2F_3N_4O_2S$, 564.0; m/z found, 565.0 [M+H]$^+$.

[4-Chloro-3-(5-chlorothiophen-2-yl)-2-methoxyquinolin-6-yl](1-methyl-1H-imidazol-5-yl)[6-(trifluoromethyl)pyridin-3-yl]methanol was purified by HPLC (Kromasil C18 100 Å, 5 μM column, Mobile phase: 35-100% acetonitrile/water+ 0.25% ammonium bicarbonate) to give 2 enantiomers. The first eluting enantiomer was Example 14b: $^1$H NMR (400 MHz, CD$_3$OD) δ 8.79-8.77 (m, 1H), 8.21 (d, J=2.0 Hz, 1H), 8.04-8.00 (m, 1H), 7.90 (d, J=8.8 Hz, 1H), 7.84 (d, J=8.2 Hz, 1H), 7.74 (s, 1H), 7.72 (dd, J=8.8, 2.1 Hz, 1H), 7.08-7.06 (m, 1H), 7.05-7.02 (m, 1H), 6.36-6.34 (m, 1H), 4.05 (s, 3H), 3.48 (s, 3H); MS (ESI): mass calcd. for $C_{25}H_{17}Cl_2F_3N_4O_2S$, 564.0; m/z found, 565.0 [M+H]$^+$ and the second eluting enantiomer was Example 14c: $^1$H NMR (400 MHz, CD$_3$OD) δ 8.80-8.76 (m, 1H), 8.21 (d, J=2.1 Hz, 1H), 8.05-8.00 (m, 1H), 7.91 (d, J=8.8 Hz, 1H), 7.84 (d, J=8.2 Hz, 1H), 7.75 (s, 1H), 7.74-7.70 (m, 1H), 7.08-7.06 (m, 1H), 7.06-7.03 (m, 1H), 6.37-6.34 (m, 1H), 4.05 (s, 3H), 3.48 (s, 3H); MS (ESI): mass calcd. for $C_{25}H_{17}Cl_2F_3N_4O_2S$, 564.0; m/z found, 565.0 [M+H]$^+$.

Example 15

[4-Chloro-2-methoxy-3-(2-methoxypyrimidin-5-yl)quinolin-6-yl](1-methyl-1H-imidazol-5-yl)[6-(trifluoromethyl)pyridin-3-yl]methanol.TFA

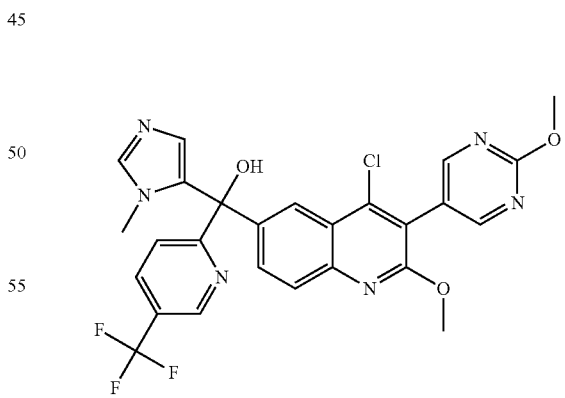

The title compound was prepared using (2-methoxypyrimidin-5-yl)boronic acid in place of (5-chlorothiophen-2-yl) boronic acid using the procedure described for Example 14a. $^1$H NMR (400 MHz, CD$_3$OD) δ 9.05-9.02 (m, 1H), 8.84-8.80 (m, 1H), 8.63 (s, 2H), 8.28 (d, J=2.2 Hz, 1H), 8.12-8.08 (m, 1H), 8.00 (d, J=8.7 Hz, 1H), 7.90 (d, J=8.3 Hz, 1H), 7.78-7.73

(m, 1H), 7.11-7.08 (m, 1H), 4.09 (s, 3H), 4.05 (s, 3H), 3.72 (s, 3H); MS (ESI): mass calcd. for $C_{26}H_{20}ClF_3N_6O_3$, 556.1; m/z found, 557.1 [M+H]$^+$.

Example 16

4-(4-Chloro-6-{hydroxy(1-methyl-1H-imidazol-5-yl)[6-(trifluoromethyl)pyridin-3-yl]methyl}-2-methoxyquinolin-3-yl)benzonitrile.TFA

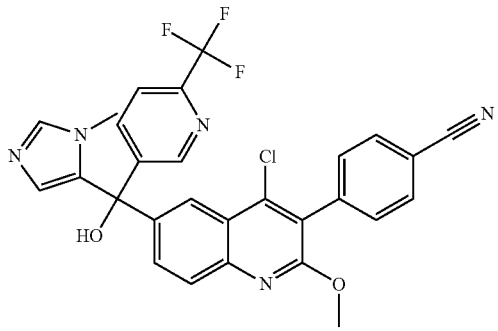 [SMILES: COc1nc2ccc(C(O)(c3ccc(C(F)(F)F)nc3)c3cncn3C)cc2c(Cl)c1-c1ccc(C#N)cc1]

The title compound was prepared using (4-cyanophenyl)boronic acid in place of (5-chlorothiophen-2-yl)boronic acid using the procedure described for Example 14a. $^1$H NMR (400 MHz, CD$_3$OD) δ 9.05-9.03 (m, 1H), 8.84-8.80 (m, 1H), 8.27 (d, J=2.3 Hz, 1H), 8.11-8.07 (m, 1H), 8.00 (d, J=8.7 Hz, 1H), 7.90 (d, J=8.3 Hz, 1H), 7.87-7.83 (m, 2H), 7.74 (dd, J=8.8, 2.2 Hz, 1H), 7.57-7.53 (m, 2H), 7.10-7.07 (m, 1H), 4.00 (s, 3H), 3.72 (s, 3H); MS (ESI): mass calcd. for $C_{28}H_{19}ClF_3N_5O_2$, 549.1; m/z found, 550.2 [M+H]$^+$.

Example 17

N-[4-(4-Chloro-6-{hydroxy(1-methyl-1H-imidazol-5-yl)[6-(trifluoromethyl)pyridin-3-yl]methyl}-2-methoxyquinolin-3-yl)phenyl]methanesulfonamide-.TFA

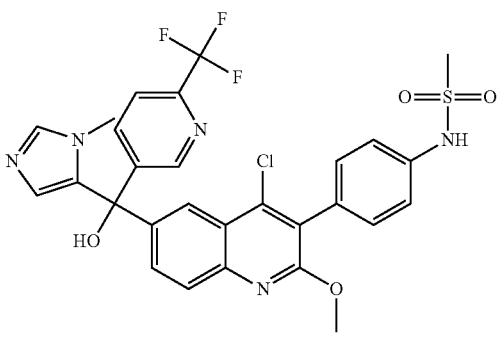 [SMILES: COc1nc2ccc(C(O)(c3ccc(C(F)(F)F)nc3)c3cncn3C)cc2c(Cl)c1-c1ccc(NS(C)(=O)=O)cc1]

The title compound was prepared using (4-(methylsulfonamido)phenyl)boronic acid in place of (5-chlorothiophen-2-yl)boronic acid using the procedure described for Example 14a. $^1$H NMR (400 MHz, CD$_3$OD) δ 9.05-9.03 (m, 1H), 8.84-8.81 (m, 1H), 8.25 (d, J=2.1 Hz, 1H), 8.11-8.06 (m, 1H), 7.97 (d, J=8.6 Hz, 1H), 7.90 (d, J=8.3 Hz, 1H), 7.73-7.69 (m, 1H), 7.37-7.30 (m, 4H), 7.09-7.06 (m, 1H), 4.00 (s, 3H), 3.72 (s, 3H), 3.04 (s, 3H); MS (ESI): mass calcd. for $C_{28}H_{23}ClF_3N_5O_4S$, 617.1; m/z found, 618.2 [M+H]$^+$.

Example 18a 6-(Hydroxy(1-methyl-1H-imidazol-5-yl)(pyridin-2-yl)methyl)-3-phenylquinoline-2,4-dicarbonitrile

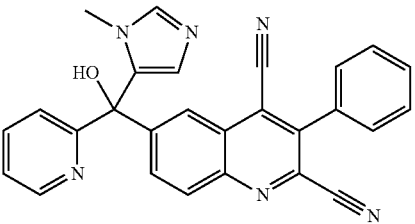 [SMILES: Cn1cncc1C(O)(c1ccc2nc(C#N)c(-c3ccccc3)c(C#N)c2c1)c1ccccn1]

(2,4-Dichloro-3-phenylquinolin-6-yl)(1-methyl-1H-imidazol-5-yl)(pyridin-2-yl)methanol (227.8 mg, 0.494 mmol, Example 64), zinc cyanide (73.8 mg, 0.628 mmol), zinc dust (8.8 mg, 0.135 mmol), dppf (27.7 mg, 0.05 mmol), and Pd$_2$(dba)$_3$ (22.6 mg, 0.0247 mmol) were charged to an oven-dried microwave vial. The vial was evacuated and back-filled with nitrogen. Dimethylacetamide (3 mL) was added to the mixture via syringe. Nitrogen was bubbled through the reaction mixture for 5 minutes and the mixture was stirred and heated at 120° C. for 1 hour, followed by 100° C. for 3 hours under a positive pressure of nitrogen. The mixture was allowed to cool to ambient temperature, filtered through Celite®, and rinsed with ethyl acetate. The filtrate was basified with 5 M aqueous ammonium hydroxide, the layers were separated and the aqueous layer was extracted with excess ethyl acetate. The combined organic layers were dried (Na$_2$SO$_4$), filtered, and concentrated to dryness. Due to an incomplete reaction as shown by LCMS (starting material and mono-cynated product present), the crude material was subjected to additional reaction conditions. In an oven-dried microwave vial, the dry crude material was mixed with zinc cyanide (80.1 mg, 0.682 mmol), zinc dust (8.7 mg, 0.133 mmol), X-Phos (32.7 mg, 0.0665 mmol), and Pd$_2$(dba)$_3$ (62.2 mg, 0.0679 mmol). The vial was evacuated and back-filled with nitrogen. Dimethylacetamide (3.4 mL) was added to the mixture via syringe. Nitrogen was bubbled through the reaction mixture for 5 minutes and the mixture was stirred and heated at 120° C. for 1.25 hours under a positive pressure of nitrogen. The mixture was allowed to cool to ambient temperature, filtered through Celite®, and rinsed with ethyl acetate. The filtrate was basified with 5 M aqueous ammonium hydroxide, the layers were separated and the aqueous layer was extracted with excess ethyl acetate. The combined organic layers were dried (Na$_2$SO$_4$), filtered, and concentrated to dryness. The crude product was purified by flash column chromatography (silica gel, 0-5% MeOH-DCM) followed by reverse phase chromatography (acetonitrile/H$_2$O+0.05% TFA). Product fractions were basified with saturated aqueous sodium bicarbonate and extracted with DCM, before being dried (Na$_2$SO$_4$), filtered, and concentrated to provide the title compound. $^1$H NMR (500 MHz, CDCl$_3$) δ 8.66 (d, J=4.5 Hz, 1H), 8.41 (d, J=1.8 Hz, 1H), 8.27 (d, J=8.9 Hz, 1H), 8.06 (dd, J=8.9, 1.9 Hz, 1H), 7.78 (td, J=7.7, 1.7 Hz, 1H), 7.64-7.58 (m, 5H), 7.48 (s, 1H), 7.38-7.35 (m, 1H), 7.30 (d, J=7.9 Hz, 1H), 6.84 (s, 1H), 6.40 (s, 1H), 3.41 (s, 3H); MS m/e 443.2 [M+H]$^+$.

6-(Hydroxy(1-methyl-1H-imidazol-5-yl)(pyridin-2-yl)methyl)-3-phenylquinoline-2,4-dicarbonitrile was purified by chiral SFC (ChiralPak AD, 100% ethanol) to provide two pure enantiomers. The first eluting enantiomer was Example 18b: $^1$H NMR (500 MHz, CDCl$_3$) δ 8.66 (d, J=4.3 Hz, 1H), 8.41 (d, J=1.7 Hz, 1H), 8.28 (d, J=8.9 Hz, 1H), 8.06 (dd, J=8.9, 1.9 Hz, 1H), 7.78 (td, J=7.7, 1.7 Hz, 1H), 7.66-7.57 (m, 5H), 7.51 (s, 1H), 7.37 (ddd, J=7.5, 4.9, 0.8 Hz, 1H), 7.30 (d, J=7.9 Hz, 1H), 6.82 (s, 1H), 6.41 (s, 1H), 3.42 (s, 3H); MS m/e 443.2 [M+H]$^+$. The second eluting enantiomer was Example 18c: $^1$H NMR (500 MHz, CDCl$_3$) δ 8.66 (d, J=4.8 Hz, 1H), 8.41 (d, J=1.8 Hz, 1H), 8.28 (d, J=8.9 Hz, 1H), 8.06 (dd, J=8.9, 1.9 Hz, 1H), 7.78 (td, J=7.7, 1.6 Hz, 1H), 7.66-7.58 (m, 5H), 7.48 (s, 1H), 7.37 (dd, J=7.1, 5.2 Hz, 1H), 7.29 (d, J=7.9 Hz, 1H), 6.79 (s, 1H), 6.40 (s, 1H), 3.41 (s, 3H); MS m/e 443.2 [M+H]$^+$.

Example 19a 6-(Hydroxy(1-methyl-1H-imidazol-5-yl)(6-(trifluoromethyl)pyridin-3-yl)methyl)-2-methoxy-8-methyl-3-(4-(trifluoromethoxy)phenyl)quinoline-4-carbonitrile

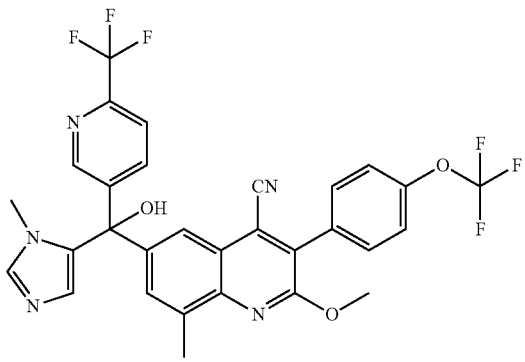 [SMILES: COc1nc2c(C)cc(C(O)(c3ccc(C(F)(F)F)nc3)c3cncn3C)cc2c(C#N)c1-c1ccc(OC(F)(F)F)cc1]

To a round bottom flask containing (4-chloro-2-methoxy-8-methyl-3-(4-(trifluoromethoxy)phenyl)quinolin-6-yl)(1-methyl-1H-imidazol-5-yl)(6-(trifluoromethyl)pyridin-3-yl) methanol (0.19 g, 0.305 mmol, Example 63) was added Zn(CN)$_2$ (64.47 mg, 0.596 mmol), Pd$_2$(dba)$_3$ (41.9 mg, 0.046 mmol), zinc nanopowder (5.9 mg, 0.092 mmol), and dicyclohexyl(2',4',6'-triisopropyl-[1,1'-biphenyl]-2-yl)phosphine (X-Phos, 29.9 mg, 0.061 mmol). The flask was evacuated and re-filled with argon (3×). Dimethylacetamide (1.5 mL, degassed) was then added and the mixture was heated at 120° C. for 4 hours. The mixture was cooled to room temperature, diluted with EtOAc and filtered through Celite® rinsing with EtOAc. The filtrate was diluted with saturated aqueous NH$_4$Cl and H$_2$O and layers were separated. The aqueous layer was again extracted with EtOAc. The combined EtOAc extract was washed with brine, dried over Na$_2$SO$_4$, filtered and evaporated in vacuo to provide an oil. LC/MS showed product plus a significant amount of starting material. The mixture was re-subjected to the conditions above and heated in a 120° C. oil bath for an additional 4 hours. After work-up (same as above) the crude product was purified by chromatography (10% MeOH in DCM on a gradient) to provide the title compound.

6-(Hydroxy(1-methyl-1H-imidazol-5-yl)(6-(trifluoromethyl)pyridin-3-yl)methyl)-2-methoxy-8-methyl-3-(4-(trifluoromethoxy)phenyl)quinoline-4-carbonitrile was purified by chiral HPLC (Chiralpak (IC); solvent A=CO$_2$; solvent B=methanol+0.2% IPA; flow rate 50 mL/min; wavelength 254 nM; temperature 40 degrees) to give 2 enantiomers. The first eluting enantiomer was Example 19b: $^1$H NMR (400 MHz, CDCl$_3$) δ 8.74-8.87 (m, 1H), 8.06-8.16 (m, 1H), 7.91-8.02 (m, 1H), 7.65-7.74 (m, 1H), 7.54-7.65 (m, 2H), 7.42-7.52 (m, 2H), 7.32-7.41 (m, 2H), 6.44-6.60 (m, 1H), 4.09 (s, 3H), 3.28-3.51 (s, 3H), 2.67 (s, 3H); MS (ESI) 614 (M+H)$^+$. The second eluting enantiomer was Example 19c: $^1$H NMR (400 MHz, CDCl$_3$) δ 8.75-8.86 (m, 1H), 8.05-8.16 (m, 1H), 7.89-8.02 (m, 1H), 7.65-7.77 (m, 1H), 7.54-7.63 (m, 2H), 7.42-7.50 (m, 2H), 7.32-7.42 (m, 2H), 6.40-6.60 (m, 1H), 4.08 (s, 3H), 3.35-3.56 (broad s, 3H), 2.68 (s, 3H); MS (ESI) 614 (M+H)$^+$.

Example 20

1-(4-((2,4-Dichloro-8-methyl-3-phenylquinolin-6-yl)(hydroxy)(phenyl)methyl)piperidin-1-yl)ethanone

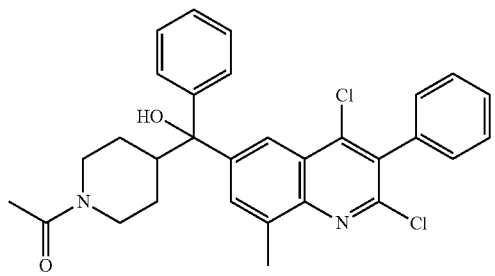 [SMILES: CC(=O)N1CCC(C(O)(c2ccccc2)c2cc(C)c3nc(Cl)c(-c4ccccc4)c(Cl)c3c2)CC1]

A solution of n-butyllithium (1.6 M in hexanes, 0.5 mL, 0.8 mmol) was added dropwise by syringe to a solution of 6-bromo-2,4-dichloro-8-methyl-3-phenylquinoline (0.32 g, 0.88 mmol, Intermediate 3) in dry deoxygenated THF (10 mL) at −78° C. After 2 minutes, a solution of 1-(4-benzoylpiperidin-1-yl)ethanone (0.203 g, 0.88 mmol, Intermediate 4) in dry THF (4 mL) was added dropwise by syringe. An additional 2 mL of THF was used to complete the quantitative addition. After 10 minutes, the flask was removed from the dry-ice bath and placed into an ice-water bath. After 1 hour, the reaction was quenched with saturated aqueous ammonium chloride solution and the mixture was partitioned between water and EtOAc. The layers were separated and the aqueous phase was further extracted with EtOAc and washed with saturated aqueous NaCl solution. The organic phase was dried (MgSO$_4$), filtered, and concentrated to dryness. The crude product was purified by flash column chromatography (silica gel, 0-100% EtOAc-DCM) to provide the title compound. MS m/e 519.1 (M+H)$^+$.

Example 21a 6-((1-Acetylpiperidin-4-yl)(hydroxy)(phenyl)methyl)-8-methyl-3-phenylquinoline-2,4-dicarbonitrile

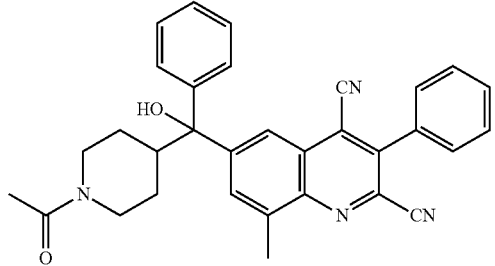 [SMILES: CC(=O)N1CCC(C(O)(c2ccccc2)c2cc(C)c3nc(C#N)c(-c4ccccc4)c(C#N)c3c2)CC1]

A microwave vial was charged with 1-(4-((2,4-dichloro-8-methyl-3-phenylquinolin-6-yl)(hydroxy)(phenyl)methyl)piperidin-1-yl)ethanone (240 mg, 0.46 mmol, Example 20), Zn(CN)$_2$ (55.7 mg, 0.480 mmol), Pd$_2$(dba)$_3$ (43.3 mg, 0.047 mmol), zinc dust (6.05 mg, 0.0926 mmol), and dicyclohexyl(2',4',6'-triisopropyl-[1,1'-biphenyl]-2-yl)phosphine (X-Phos, 22.1 mg, 0.046 mmol). Dimethylacetamide (2.4 mL) was then added and the mixture was sparged with nitrogen for 10 minutes and placed in a pre-heated aluminum block at 120° C. for 2 hours. The mixture was cooled to room temperature and was filtered through Celite®, and washed with EtOAc. The filtrate was washed sequentially with 2 M aqueous NH$_4$OH and aqueous NaCl solution. The organic phase was dried (MgSO$_4$), filtered, and concentrated. The residue was purified by flash column chromatography (silica gel, 0 to 100% EtOAc-DCM). MS (ESI) 501.3 (M+H)$^+$.

6-((1-Acetylpiperidin-4-yl)(hydroxy)(phenyl)methyl)-8-methyl-3-phenylquinoline-2,4-dicarbonitrile was purified by chiral HPLC (Chiralcel OD, 80% heptane/20% ethanol) to give 2 enantiomers. The 2 enantiomers were further purified by reverse-phase HPLC (5-85% CH$_3$CN—H$_2$O, 0.05% TFA). The product was converted to the free base (neutralized with saturated aqueous NaHCO$_3$ and extracted with EtOAc) and the organic fractions were concentrated to afford the title compound. The first eluting enantiomer was Example 21b: $^1$H NMR (600 MHz, CDCl$_3$, mixture of rotamers) δ ppm 8.35-8.32 (m, 1H), 7.84-7.81 (m, 1H), 7.66-7.59 (m, 5H), 7.58-7.55 (m, 2H), 7.41-7.37 (m, 2H), 7.31-7.24 (m, 1H), 4.75 (d, J=13.4 Hz, 0.5H), 4.69 (d, J=13.5 Hz, 0.5H), 3.89 (d, J=13.7 Hz, 0.5H), 3.82 (d, J=13.7 Hz, 0.5H), 3.16 (t, J=12.2 Hz, 0.5H), 3.12-3.03 (m, 0.5H), 2.89-2.83 (m, 1H), 2.82 (s, 1.5H), 2.80 (s, 1.5H), 2.67-2.53 (m, 1H), 2.38 (s, 0.5H), 2.36 (s, 0.5H), 2.07 (s, 1.5H), 2.06 (s, 1.5H), 1.46-1.21 (m, 4H); MS m/e 501.2 [M+H]$^+$ and the second eluting enantiomer was Example 21c: $^1$H NMR (600 MHz, CDCl$_3$, mixture of rotamers) δ ppm 8.35-8.32 (m, 1H), 7.84-7.81 (m, 1H), 7.65-7.59 (m, 5H), 7.58-7.55 (m, 2H), 7.41-7.37 (m, 2H), 7.31-7.24 (m, 1H), 4.75 (d, J=13.5 Hz, 0.5H), 4.69 (d, J=13.5 Hz, 0.5H), 3.89 (d, J=13.7 Hz, 0.5H), 3.82 (d, J=13.6 Hz, 0.5H), 3.18-3.14 (m, 0.5H), 3.11-3.07 (m, 0.5H), 2.86-2.83 (m, 1H), 2.82 (s, 1.5H), 2.80 (s, 1.5H), 2.68-2.54 (m, 1H), 2.37 (s, 0.5H), 2.35 (s, 0.5H), 2.07 (s, 1.5H), 2.06 (s, 1.5H), 1.47-1.21 (m, 4H); MS m/e 501.2 [M+H]$^+$.

Example 22

(4-Chlorophenyl)(2,4-dichloro-8-methyl-3-phenylquinolin-6-yl)(1-methyl-1H-imidazol-5-yl)methanol

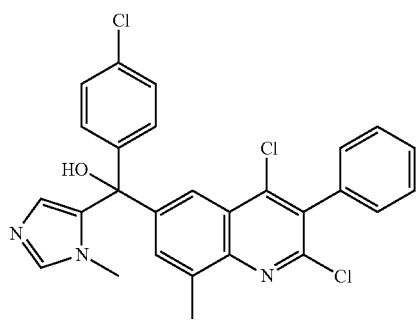 [SMILES: Cc1cc(C(O)(c2ccc(Cl)cc2)c2cncn2C)cc2c(Cl)c(-c3ccccc3)c(Cl)nc12]

The title compound was prepared analogously to the method described in Example 20 using (4-chlorophenyl)(1-methyl-1H-imidazol-5-yl)methanone (Intermediate 8: step b) in place of 1-(4-benzoylpiperidin-1-yl)ethanone (Intermediate 4). MS m/e 508.1 (M+H)$^+$.

Example 23a 6-((4-Chlorophenyl)(hydroxy)(1-methyl-1H-imidazol-5-yl)methyl)-8-methyl-3-phenylquinoline-2,4-dicarbonitrile

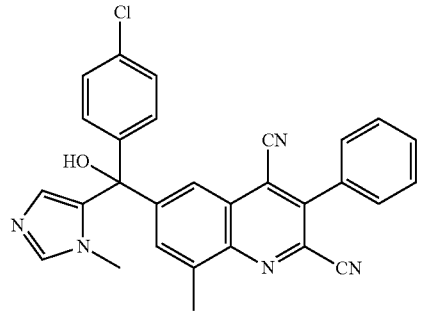 [SMILES: Cc1cc(C(O)(c2ccc(Cl)cc2)c2cncn2C)cc2c(C#N)c(-c3ccccc3)c(C#N)nc12]

The title compound was prepared analogously to the method described in Example 21a using (4-chlorophenyl)(2,4-dichloro-8-methyl-3-phenylquinolin-6-yl)(1-methyl-1H-imidazol-5-yl)methanol (Example 22) in place of 1-(4-((2,4-dichloro-8-methyl-3-phenylquinolin-6-yl)(hydroxy)(phenyl)methyl)piperidin-1-yl)ethanone (Example 20). MS m/e 490.2 (M+H)$^+$.

6-((4-Chlorophenyl)(hydroxy)(1-methyl-1H-imidazol-5-yl)methyl)-8-methyl-3-phenylquinoline-2,4-dicarbonitrile was purified by chiral HPLC (Chiralcel OD, 50% heptane/20% ethanol) to give 2 enantiomers. The 2 enantiomers were further purified by reverse-phase HPLC (5-85% CH$_3$CN—H$_2$O, 0.05% TFA). The product was converted to the free base (neutralized with saturated aqueous NaHCO$_3$ and extracted with EtOAc) and the organic fractions were concentrated to afford the title compound. The first eluting enantiomer was Example 23b: $^1$H NMR (600 MHz, CDCl$_3$) δ ppm 8.21 (s, 1H), 7.62-7.49 (m, 6H), 7.24 (s, 5H), 6.29 (s, 1H), 3.32 (s, 3H), 2.70 (s, 3H); MS m/e 490.2 [M+H]$^+$ and the second eluting enantiomer was Example 23c: $^1$H NMR (600 MHz, CDCl$_3$) δ ppm 8.29 (d, J=1.5 Hz, 1H), 7.67-7.56 (m, 6H), 7.35-7.28 (m, 4H), 7.14 (s, 1H), 6.27 (s, 1H), 3.35 (s, 3H), 2.75 (s, 3H); MS m/e 490.2 [M+H]$^+$.

Example 24

(2,4-Dichloro-8-methyl-3-phenylquinolin-6-yl)(1-methyl-1H-imidazol-5-yl)(6-(trifluoromethyl)pyridin-3-yl)methanol

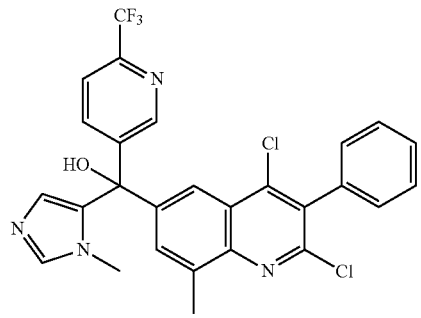 [SMILES: Cc1cc(C(O)(c2ccc(C(F)(F)F)nc2)c2cncn2C)cc2c(Cl)c(-c3ccccc3)c(Cl)nc12]

The title compound was prepared analogously to the method described in Example 20 using (1-methyl-1H-imidazol-5-yl)(6-(trifluoromethyl)pyridin-3-yl)methanone (Intermediate 2: step c) in place of 1-(4-benzoylpiperidin-1-yl)ethanone (Intermediate 4). MS m/e 543.1 (M+H)+.

Example 25a 6-(Hydroxy(1-methyl-1H-imidazol-5-yl)(6-(trifluoromethyl)pyridin-3-yl)methyl)-8-methyl-3-phenylquinoline-2,4-dicarbonitrile

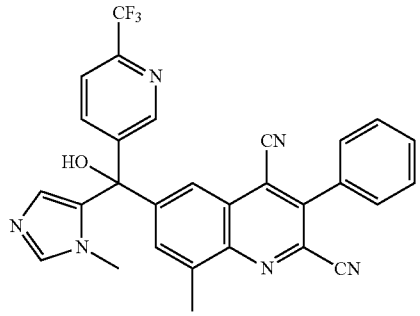 [SMILES: Cc1cc(C(O)(c2ccc(C(F)(F)F)nc2)c2cncn2C)cc2c(C#N)c(-c3ccccc3)c(C#N)nc12]

The title compound was prepared analogously to the method described in Example 21a using (2,4-dichloro-8-methyl-3-phenylquinolin-6-yl)(1-methyl-1H-imidazol-5-yl)(6-(trifluoromethyl)pyridin-3-yl)methanol (Example 24) in place of 1-(4-((2,4-dichloro-8-methyl-3-phenylquinolin-6-yl)(hydroxy)(phenyl)methyl)piperidin-1-yl)ethanone (Example 20). MS m/e 525.2 (M+H)+.

6-(Hydroxy(1-methyl-1H-imidazol-5-yl)(6-(trifluoromethyl)pyridin-3-yl)methyl)-8-methyl-3-phenylquinoline-2,4-dicarbonitrile was purified by chiral HPLC (Chiralcel OD, 80% heptane/20% ethanol) to give 2 enantiomers. The first eluting enantiomer was Example 25b: $^1$H NMR (600 MHz, CDCl$_3$) δ ppm 8.81 (d, J=2.1 Hz, 1H), 8.33 (d, J=1.9 Hz, 1H), 7.98 (dd, J=8.3, 2.2 Hz, 1H), 7.71 (d, J=8.2 Hz, 1H), 7.66-7.59 (m, 6H), 7.37 (s, 1H), 6.45 (s, 1H), 5.29 (s, 1H), 3.41 (s, 3H), 2.80 (s, 3H); MS m/e 525.2 (M+H)+ and the second eluting enantiomer was Example 25c: $^1$H NMR (600 MHz, CDCl$_3$) δ ppm 8.80 (d, J=2.1 Hz, 1H), 8.33 (dd, J=2.2, 0.7 Hz, 1H), 7.97 (dd, J=8.3, 2.2 Hz, 1H), 7.70 (dd, J=8.2, 0.8 Hz, 1H), 7.67-7.58 (m, 6H), 7.31 (s, 1H), 6.38 (d, J=1.2 Hz, 1H), 5.94 (s, 1H), 3.39 (s, 3H), 2.79 (s, 3H); MS m/e 525.2 (M+H)+.

Example 26

1-(4-((2,4-Dichloro-8-methyl-3-phenylquinolin-6-yl)(hydroxy)(6-(trifluoromethyl)pyridin-3-yl)methyl)piperidin-1-yl)ethanone

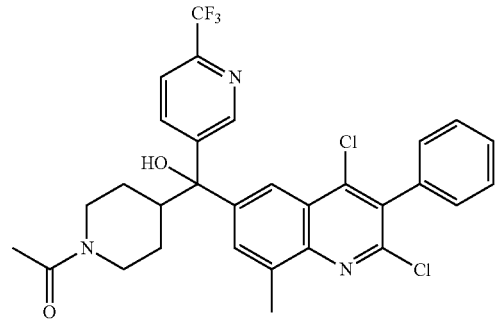 [SMILES: CC(=O)N1CCC(C(O)(c2ccc(C(F)(F)F)nc2)c2cc(C)c3nc(Cl)c(-c4ccccc4)c(Cl)c3c2)CC1]

The title compound was prepared analogously to the method described in Example 20 using 1-(4-(6-(trifluoromethyl)nicotinoyl)piperidin-1-yl)ethanone (Intermediate 14:

step d) in place of 1-(4-benzoylpiperidin-1-yl)ethanone (Intermediate 4). MS m/e 588.2 (M+H)+.

Example 27a 6-((1-Acetylpiperidin-4-yl)(hydroxy)(6-(trifluoromethyl)pyridin-3-yl)methyl)-8-methyl-3-phenylquinoline-2,4-dicarbonitrile

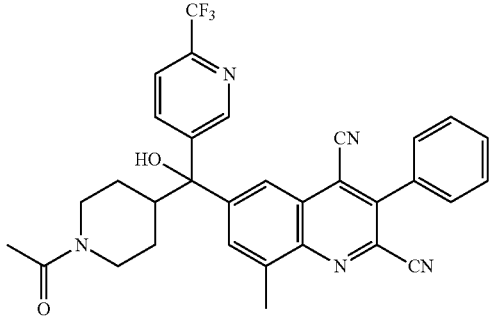 [SMILES: CC(=O)N1CCC(C(O)(c2ccc(C(F)(F)F)nc2)c2cc(C)c3nc(C#N)c(-c4ccccc4)c(C#N)c3c2)CC1]

The title compound was prepared analogously to the method described in Example 21a using 1-(4-((2,4-dichloro-8-methyl-3-phenylquinolin-6-yl)(hydroxy)(6-(trifluoromethyl)pyridin-3-yl)methyl)piperidin-1-yl)ethanone (Example 26). MS m/e 570.3 (M+H)+.

6-((1-Acetylpiperidin-4-yl)(hydroxy)(6-(trifluoromethyl)pyridin-3-yl)methyl)-8-methyl-3-phenylquinoline-2,4-dicarbonitrile was purified by chiral SFC (Chiralpak AD-H, 5 μm, 250×20 mm, mobile phase: 75% CO$_2$, 25% mixture of methanol-isopropanol 50/50 v/v). The first eluting enantiomer was Example 27b: $^1$H NMR (600 MHz, CDCl$_3$, mixture of rotamers) δ ppm 8.98-8.94 (m, 1H), 8.41-8.32 (m, 1H), 8.16-8.13 (m, 1H), 7.87 (s, 0.5H), 7.79 (s, 0.5H), 7.71-7.66 (m, 1H), 7.65-7.56 (m, 5H), 4.74-4.68 (m, 1H), 3.96-3.64 (m, 2H), 3.21-3.08 (m, 1H), 2.93-2.88 (m, 1H), 2.84 (s, 1.5H), 2.83 (s, 1.5H), 2.65-2.60 (m, 1H), 2.03 (s, 1.5H), 2.02 (s, 1.5H), 1.58-1.34 (m, 4H); MS m/e 570.3 (M+H)+ and the second eluting enantiomer was Example 27c: $^1$H NMR (600 MHz, CDCl$_3$, mixture of rotamers) δ ppm 9.01-8.93 (m, 1H), 8.39-8.36 (m, 1H), 8.16-8.13 (m, 1H), 7.87 (s, 0.5H), 7.79 (s, 0.5H), 7.69-7.67 (m, 1H), 7.66-7.58 (m, 5H), 4.74-4.68 (m, 1H), 3.97-3.64 (m, 2H), 3.22-3.06 (m, 1H), 2.93-2.88 (m, 1H), 2.84 (s, 1.5H), 2.83 (s, 1.5H), 2.70-2.53 (m, 1H), 2.03 (s, 1.5H), 2.02 (s, 1.5H) 1.58-1.34 (m, 4H); MS m/e 570.3 (M+H)+.

Example 28

6-((4-Cyanophenyl)(hydroxy)(1-methyl-1H-imidazol-5-yl)methyl)-3-phenyl-2-(trifluoromethyl)quinoline-4-carbonitrile.TFA

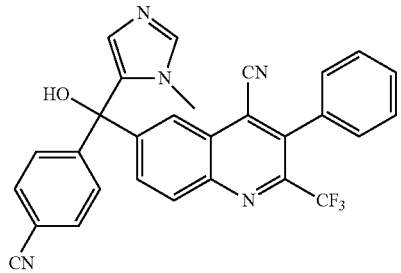 [SMILES: Cn1cncc1C(O)(c1ccc(C#N)cc1)c1ccc2nc(C(F)(F)F)c(-c3ccccc3)c(C#N)c2c1]

The title compound was isolated from the reaction that formed Example 31a. $^1$H NMR (400 MHz, CD$_3$OD) δ 9.04 (s, 1H), 8.40 (d, J=9.09 Hz, 1H), 8.34 (d, J=2.02 Hz, 1H), 8.06 (dd, J=2.27, 8.84 Hz, 1H), 7.84 (d, J=8.59 Hz, 2H), 7.70 (d, J=8.59 Hz, 2H), 7.54-7.60 (m, 3H), 7.43-7.49 (m, 2H), 7.09 (d, J=1.52 Hz, 1H), 3.70 (s, 3H); MS m/e 510.1 [M+H]$^+$.

Example 29

1-(4-((4-Chloro-3-phenyl-2-(trifluoromethyl)quinolin-6-yl)(hydroxy)(pyridin-3-yl)methyl)piperidin-1-yl)ethanone.TFA

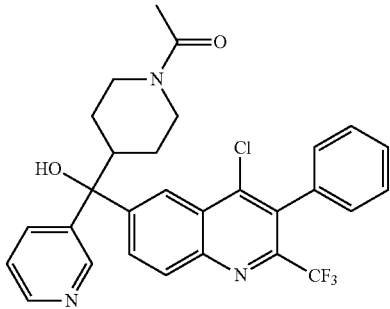 [SMILES: CC(=O)N1CCC(C(O)(c2cccnc2)c2ccc3nc(C(F)(F)F)c(-c4ccccc4)c(Cl)c3c2)CC1]

A mixture of (4-chloro-3-phenyl-2-(trifluoromethyl)quinolin-6-yl)(piperidin-4-yl)(pyridin-3-yl)methanol (198 mg, 0.400 mmol, Example 70), acetyl chloride (0.060 mL, 0.84 mmol), and Et$_3$N (0.16 mL, 1.15 mmol) in CH$_2$Cl$_2$ (4 mL) was stirred at room temperature for 1.5 hours and then concentrated to dryness. The residue was purified by reverse phase HPLC (water/acetonitrile/0.1% TFA) to provide the title compound as a white solid. $^1$H NMR (400 MHz, CD$_3$OD) δ 9.13 (s, 1H), 8.82 (t, J=8.08 Hz, 1H), 8.69-8.75 (m, 2H), 8.27 (d, J=9.09 Hz, 1H), 8.18-8.24 (m, 1H), 7.94-8.02 (m, 1H), 7.49-7.55 (m, 3H), 7.26-7.34 (m, 2H), 4.55-4.65 (m, 1H), 3.91-4.05 (m, 1H), 3.15-3.27 (m, 2H), 2.67-2.77 (m, 1H), 2.08 (d, J=4.04 Hz, 3H), 1.52 (m, 4H); MS m/e 540.3 [M+H]$^+$.

Example 30a 6-((1-Acetylpiperidin-4-yl)(hydroxy)(pyridin-3-yl)methyl)-3-phenyl-2-(trifluoromethyl)quinoline-4-carbonitrile.TFA

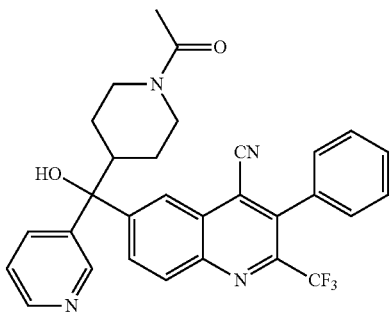 [SMILES: CC(=O)N1CCC(C(O)(c2cccnc2)c2ccc3nc(C(F)(F)F)c(-c4ccccc4)c(C#N)c3c2)CC1]

The title compound was prepared using 1-(4-((4-chloro-3-phenyl-2-(trifluoromethyl)quinolin-6-yl)(hydroxy)(pyridin-3-yl)methyl)piperidin-1-yl)ethanone.TFA (Example 29) in place of (4-chloro-3-phenyl-2-(trifluoromethyl)quinolin-6-yl)(4-chlorophenyl)(1-methyl-1H-imidazol-5-yl)methanol.TFA (Example 62) using the procedure described for Example 31a, with the exception that the reaction mixture was heated at 120° C. for 10 hours. $^1$H NMR (400 MHz, CD$_3$OD) δ 9.17 (s, 1H), 8.87-8.93 (m, 1H), 8.74 (d, J=5.56 Hz, 1H), 8.62 (dd, J=2.02, 5.56 Hz, 1H), 8.37 (d, J=9.09 Hz, 1H), 8.25-8.32 (m, 1H), 8.00-8.07 (m, 1H), 7.53-7.62 (m, 3H), 7.41-7.50 (m, 2H), 4.55-4.66 (m, 1H), 3.92-4.03 (m, 1H), 3.16-3.28 (m, 2H), 2.68-2.77 (m, 1H), 2.08 (d, J=5.05 Hz, 3H), 1.41-1.67 (m, 4H); MS m/e 531.3 [M+H]$^+$.

6-((1-Acetylpiperidin-4-yl)(hydroxy)(pyridin-3-yl)methyl)-3-phenyl-2-(trifluoromethyl)quinoline-4-carbonitrile was neutralized by partitioning between saturated NaHCO$_3$ aqueous solution and DCM (×1) followed by EtOAc (×3). The organic layer was dried (Na$_2$SO$_4$), filtered, concentrated to dryness, and purified by chiral HPLC (Chiralcel OD, CH$_3$CN) to give two pure enantiomers. Example 30b: (first enantiomer to elute off chiral column)$^1$H NMR (400 MHz, CDCl$_3$, ~1:1 mixture of rotamers) δ 8.77-8.94 (m, 1H), 8.54 (dd, J=1.52, 12.13 Hz, 1H), 8.38-8.50 (m, 1H), 8.29 (t, J=9.09 Hz, 1H), 8.07 (dd, J=2.02, 9.09 Hz, 0.5H), 7.99 (dd, J=2.02, 9.09 Hz, 0.5H), 7.95 (d, J=8.08 Hz, 1H), 7.47-7.65 (m, 3H), 7.36-7.42 (m, 2H), 7.19-7.34 (m, 1H), 5.55-5.84 (m, 2H), 5.08-5.18 (m, 1H), 4.56-4.77 (m, 1H), 3.71-3.93 (m, 1H), 3.00-3.21 (m, 1H), 2.78-2.96 (m, 1H), 2.52-2.66 (m, 1H), 1.37-1.75 (m, 3H), 1.22-1.35 (m, 1H); MS m/e 531.3 [M+H]$^+$. Example 30c: Second Enantiomer to Elute Off Chiral Column $^1$H NMR (400 MHz, CDCl$_3$, ~1:1 mixture of rotamers) δ 8.79-8.93 (m, 1H), 8.54 (dd, J=1.52, 11.62 Hz, 1H), 8.40-8.50 (m, 1H), 8.29 (t, J=8.34 Hz, 1H), 8.06 (dd, J=2.02, 9.09 Hz, 0.5H), 7.99 (dd, J=2.02, 9.09 Hz, 0.5H), 7.94 (d, J=8.08 Hz, 1H), 7.51-7.59 (m, 3H), 7.36-7.44 (m, 2H), 7.25-7.34 (m, 1H), 5.62-5.95 (m, 2H), 4.93-5.03 (m, 1H), 4.59-4.76 (m, 1H), 3.76-3.90 (m, 1H), 3.03-3.20 (m, 1H), 2.80-2.93 (m, 1H), 2.52-2.68 (m, 1H), 1.36-1.74 (m, 3H), 1.20-1.36 (m, 1H); MS m/e 531.3 [M+H]$^+$.

Example 31a 6-((4-Chlorophenyl)(hydroxy)(1-methyl-1H-imidazol-5-yl)methyl)-3-phenyl-2-(trifluoromethyl)quinoline-4-carbonitrile.TFA

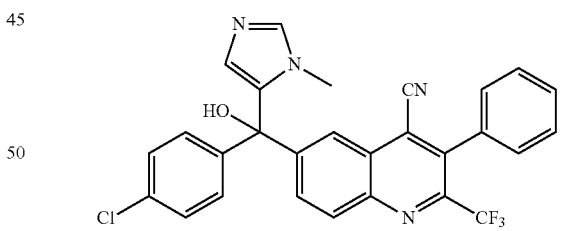

A pressure tube containing (4-chloro-3-phenyl-2-(trifluoromethyl)quinolin-6-yl)(4-chlorophenyl)(1-methyl-1H-imidazol-5-yl)methanol.TFA (145 mg, 0.190 mmol, Example 62), Pd$_2$(dba)$_3$ (18 mg, 0.020 mmol), dicyclohexyl(2',4',6'-triisopropyl-[1,1'-biphenyl]-2-yl)phosphine (X-Phos, 10 mg, 0.021 mmol), zinc cyanide (11.5 mg, 0.098 mmol), and zinc nanopowder (2.5 mg, 0.038 mmol) in N,N-dimethylacetamide (1 mL) was sparged with nitrogen for 8 minutes, and then heated at 120° C. for 2.5 hours. The mixture was allowed to cool to room temperature and filtered through a syringe filter. The filtrate was concentrated in vacuo, EtOAc and saturated NH$_4$Cl aqueous solution were added. The organic layer was separated, and the aqueous layer was extracted with EtOAc. The combined organic layers were dried (Na₂SO₄), filtered, and concentrated to dryness. The residue was purified by reverse phase HPLC (water/acetonitrile/0.1% TFA) to provide the title compound as a white solid. ¹H NMR (400 MHz, CD₃OD) δ 9.02 (s, 1H), 8.39 (d, J=8.59 Hz, 1H), 8.34 (d, J=2.02 Hz, 1H), 8.05 (dd, J=2.27, 8.84 Hz, 1H), 7.52-7.63 (m, 3H), 7.42-7.50 (m, 6H), 7.04 (s, 1H), 3.71 (s, 3H); MS m/e 519.2 [M+H]⁺.

6-((4-Chlorophenyl)(hydroxy)(1-methyl-1H-imidazol-5-yl)methyl)-3-phenyl-2-(trifluoromethyl)quinoline-4-carbonitrile was neutralized by partitioning between saturated NaHCO₃ aqueous solution and DCM. The organic layer was dried (Na₂SO₄), filtered, concentrated to dryness, and purified by chiral HPLC (Chiralcel OD, 90% heptanes/10% EtOH) to give two pure enantiomers. Example 31b: (first enantiomer to elute off chiral column) ¹H NMR (400 MHz, CDCl₃) δ 8.46 (s, 1H), 8.23 (d, J=9.09 Hz, 1H), 7.78 (dd, J=2.02, 9.09 Hz, 1H), 7.52-7.62 (m, 3H), 7.36-7.43 (m, 2H), 7.28-7.36 (m, 4H), 7.18-7.28 (m, 1H), 6.29 (s, 1H), 3.37 (s, 3H); MS m/e 519.2 [M+H]⁺. Example 31c: (second enantiomer to elute off chiral column) ¹H NMR (400 MHz, CDCl₃) δ 8.45 (s, 1H), 8.23 (d, J=9.09 Hz, 1H), 7.78 (d, J=9.09 Hz, 1H), 7.50-7.64 (m, 3H), 7.35-7.43 (m, 2H), 7.27-7.35 (m, 4H), 7.19-7.28 (m, 1H), 6.28 (s, 1H), 3.37 (s, 3H); MS m/e 519.2 [M+H]⁺.

Example 32a (4-Methoxy-3-phenyl-2-(trifluoromethyl)quinolin-6-yl)(1-methyl-1H-imidazol-5-yl)(pyridin-2-yl)methanol.TFA

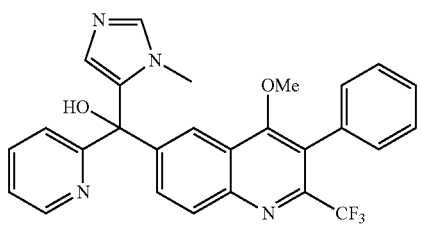 [SMILES: COc1c(-c2ccccc2)c(C(F)(F)F)nc2ccc(C(O)(c3ccccn3)c3cncn3C)cc12]

A mixture of (4-chloro-3-phenyl-2-(trifluoromethyl)quinolin-6-yl)(1-methyl-1H-imidazol-5-yl)(pyridin-2-yl)methanol.TFA (53 mg, 0.073 mmol, Example 61) and 0.5 M NaOMe in MeOH (0.80 mL, 0.40 mmol) in a sealed tube was heated at 70° C. for 2 hours. The solvent was evaporated, and water was added. The mixture was extracted with EtOAc, dried (Na₂SO₄), filtered, and concentrated. The residue was purified by reverse phase HPLC (water/acetonitrile/0.1% TFA) to provide the title compound as a white solid. ¹H NMR (400 MHz, CD₃OD) δ 8.96 (s, 1H), 8.62 (d, J=4.04 Hz, 1H), 8.41 (d, J=2.02 Hz, 1H), 8.19 (d, J=9.09 Hz, 1H), 8.02 (dd, J=2.02, 9.09 Hz, 1H), 7.93 (td, J=2.02, 8.08 Hz, 1H), 7.79 (d, J=8.08 Hz, 1H), 7.47-7.52 (m, 3H), 7.36-7.45 (m, 3H), 7.08 (d, J=1.52 Hz, 1H), 3.63 (s, 3H), 3.55 (s, 3H); MS m/e 491.2 [M+H]⁺.

The racemate was neutralized by partitioning between saturated NaHCO₃ aqueous solution and DCM. The organic layer was dried (Na₂SO₄), filtered, concentrated to dryness, and purified by chiral HPLC (Chiralcel OD, 90% heptanes/ 10% EtOH) to give two enantiomers. The first eluting enantiomer was Example 32b: ¹H NMR (400 MHz, CDCl₃) δ 8.64 (d, J=4.55 Hz, 1H), 8.18-8.24 (m, 2H), 7.88 (dd, J=2.02, 9.09 Hz, 1H), 7.72 (td, J=1.52, 7.58 Hz, 1H), 7.50 (s, 1H), 7.43-7.49 (m, 3H), 7.30-7.40 (m, 3H), 7.23 (d, J=8.08 Hz, 1H), 6.37 (s, 1H), 3.50 (s, 3H), 3.44 (s, 3H); MS m/e 491.2 [M+H]⁺.

Example 33a (4-Chlorophenyl)(4-methoxy-3-phenyl-2-(trifluoromethyl)quinolin-6-yl)(1-methyl-1H-imidazol-5-yl)methanol.TFA

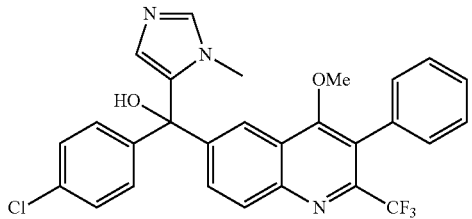 [SMILES: COc1c(-c2ccccc2)c(C(F)(F)F)nc2ccc(C(O)(c3ccc(Cl)cc3)c3cncn3C)cc12]

A mixture of (4-chloro-3-phenyl-2-(trifluoromethyl)quinolin-6-yl)(4-chlorophenyl)(1-methyl-1H-imidazol-5-yl)methanol.TFA (80 mg, 0.11 mmol, Example 62) and 0.5 M NaOMe in MeOH (0.50 mL, 0.25 mmol) in a sealed tube was heated at 70° C. for 7 hours. More 0.5 M NaOMe in MeOH (0.35 mL, 0.18 mmol) was added and the mixture was heated at the same temperature for another hour. The solvent was evaporated, and DMSO was added. After filtering through a syringe filter, the filtrate was purified by reverse phase HPLC (water/acetonitrile/0.1% TFA) to provide the title compound as a white solid. ¹H NMR (400 MHz, CD₃OD) δ 9.00 (s, 1H), 8.25 (d, J=2.02 Hz, 1H), 8.23 (d, J=9.09 Hz, 1H), 7.88 (dd, J=2.02, 9.09 Hz, 1H), 7.47-7.52 (m, 4H), 7.41-7.47 (m, 3H), 7.36-7.41 (m, 2H), 6.97 (s, 1H), 3.71 (s, 3H), 3.53 (s, 3H); MS m/e 524.3 [M+H]⁺.

(4-Chlorophenyl)(4-methoxy-3-phenyl-2-(trifluoromethyl)quinolin-6-yl)(1-methyl-1H-imidazol-5-yl)methanol was neutralized by partitioning between saturated NaHCO₃ aqueous solution and DCM. The organic layer was dried (Na₂SO₄), filtered, concentrated to dryness, and purified by chiral HPLC (Chiralpak OJ, 100% MeOH) to give two enantiomers. The first eluting enantiomer was Example 33b: ¹H NMR (400 MHz, CDCl₃) δ 8.14-8.20 (m, 2H), 7.77 (dd, J=2.27, 8.84 Hz, 1H), 7.44-7.55 (m, 3H), 7.34-7.40 (m, 2H), 7.29-7.34 (m, 4H), 7.24-7.29 (m, 1H), 6.34 (br. s., 1H), 3.48 (s, 3H), 3.36 (s, 3H); MS m/e 524.3 [M+H]⁺ and the second eluting enantiomer was Example 33c: ¹H NMR (400 MHz, CDCl₃) δ 8.14-8.20 (m, 2H), 7.77 (dd, J=2.02, 9.09 Hz, 1H), 7.44-7.50 (m, 3H), 7.36 (d, J=4.04 Hz, 2H), 7.29-7.34 (m, 4H), 7.23-7.29 (m, 1H), 6.32-6.36 (m, 1H), 3.48 (s, 3H), 3.37 (s, 3H); MS m/e 524.1 [M+H]⁺.

Example 34a 1-(4-((4-Chloro-3-phenyl-2-(trifluoromethyl)quinolin-6-yl)(hydroxy)(1-methyl-1H-imidazol-5-yl)methyl)piperidin-1-yl)ethanone

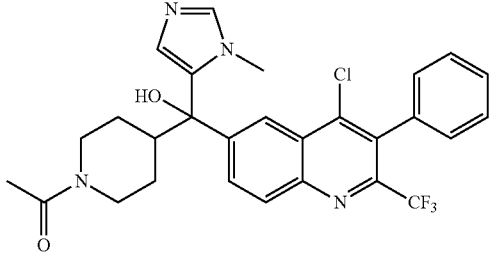 [SMILES: CC(=O)N1CCC(C(O)(c2ccc3nc(C(F)(F)F)c(-c4ccccc4)c(Cl)c3c2)c2cncn2C)CC1]

The racemic title compound was prepared using 1-(4-(1-methyl-1H-imidazole-5-carbonyl)piperidin-1-yl)ethanone (Intermediate 1: step c) in place of (4-chlorophenyl)(1-methyl-1H-imidazol-5-yl)methanone (Intermediate 8: step b) using the procedure described for Example 62, with the exception that the reaction was carried out at −78° C. all the time. $^1$H NMR (400 MHz, CD$_3$OD, ~1:1 mixture of rotamers) δ 8.86 (s, 1H), 8.56 (d, J=4.04 Hz, 1H), 8.27 (d, J=9.09 Hz, 1H), 8.09 (s, 1H), 7.81 (d, J=9.09 Hz, 1H), 7.45-7.58 (m, 3H), 7.31 (d, J=2.53 Hz, 2H), 4.66 (d, J=13.14 Hz, 0.5H), 4.46 (d, J=12.63 Hz, 0.5H), 4.04 (d, J=13.64 Hz, 0.5H), 3.84 (d, J=13.64 Hz, 0.5H), 3.60 (s, 1.5H), 3.58 (s, 1.5H), 3.25-3.30 (overlap with solvent, m, 0.5H), 3.05 (td, J=2.53, 13.14 Hz, 0.5H), 2.67-2.86 (m, 1.5H), 2.55 (td, J=3.03, 12.88 Hz, 0.5H), 2.09-2.28 (m, 1H), 2.08 (s, 1.5H), 2.03 (s, 1.5H), 1.41-1.63 (m, 1H), 1.27-1.41 (m, 1H), 1.05-1.27 (m, 1H); MS m/e 543.2 [M+H]$^+$.

The racemate was neutralized by partitioning between saturated NaHCO$_3$ aqueous solution and DCM. The organic layer was dried (Na$_2$SO$_4$), filtered, concentrated to dryness, and purified by chiral HPLC (Chiralcel OD, 100% EtOH) to give two pure enantiomers. Example 34b: (first enantiomer to elute off chiral column)$^1$H NMR (400 MHz, CDCl$_3$, ~1.5:1 mixture of rotamers) δ 8.45 (d, J=13.64 Hz, 1H), 8.20 (dd, J=4.04, 8.59 Hz, 1H), 7.68 (t, J=10.11 Hz, 1H), 7.48-7.53 (m, 3H), 7.24-7.34 (m, 2H), 7.10-7.24 (m, 2H), 4.65 (d, J=12.63 Hz, 0.6H), 4.56 (d, J=13.14 Hz, 0.4H), 3.91 (d, J=13.14 Hz, 0.4H), 3.66-3.79 (m, 0.6H), 3.31 (s, 1.8H), 3.29 (s, 1.2H), 3.18 (t, J=12.38 Hz, 0.4H), 2.97 (t, J=12.13 Hz, 0.6H), 2.38-2.69 (m, 2H), 2.34 (d, J=13.14 Hz, 0.4H), 2.22 (d, J=12.63 Hz, 0.6H), 2.01 (s, 1.8H), 1.95 (s, 1.2H), 1.13-1.55 (m, 2.4H), 1.09 (d, J=12.63 Hz, 0.6H); MS m/e 543.2 [M+H]$^+$. Example 34c: (second enantiomer to elute off chiral column)$^1$H NMR (400 MHz, CDCl$_3$, ~1.5:1 mixture of rotamers) δ 8.46 (d, J=12.63 Hz, 1H), 8.20 (dd, J=3.79, 8.84 Hz, 1H), 7.68 (t, J=10.11 Hz, 1H), 7.46-7.53 (m, 3H), 7.24-7.35 (m, 2H), 7.10-7.23 (m, 2H), 4.64 (d, J=13.14 Hz, 0.6H), 4.55 (d, J=12.63 Hz, 0.4H), 3.90 (d, J=13.14 Hz, 0.4H), 3.72 (d, J=13.14 Hz, 0.6H), 3.31 (s, 1.8H), 3.29 (s, 1.2H), 3.18 (t, J=12.38 Hz, 0.4H), 2.97 (t, J=12.38 Hz, 0.6H), 2.38-2.68 (m, 2H), 2.34 (d, J=12.63 Hz, 0.4H), 2.21 (d, J=13.14 Hz, 0.6H), 2.01 (s, 1.8H), 1.94 (s, 1.2H), 1.12-1.58 (m, 2.4H), 1.08 (d, J=12.63 Hz, 0.6H); MS m/e 543.2 [M+H]$^+$.

Example 35

(4-Chloro-2-methoxy-3-phenylquinolin-6-yl)(2,4-dimethylthiazol-5-yl)(1-methyl-1H-1,2,3-triazol-5-yl)methanol.TFA

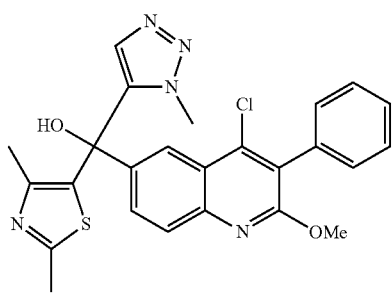 [SMILES: COc1nc2ccc(C(O)(c3sc(C)nc3C)c3cnnn3C)cc2c(Cl)c1-c1ccccc1]

To a flask containing (2,4-dichloro-3-phenylquinolin-6-yl)(2,4-dimethylthiazol-5-yl)(1-methyl-1H-1,2,3-triazol-5-yl)methanol (100 mg, 0.2 mmol, Example 67) was added MeOH (6 mL) followed by solid NaOMe (50 mg, 0.88 mmol, 95% purity) at room temperature. The reaction mixture was heated to reflux for 24 hours, then allowed to cool to room temperature, filtered through Celite® and rinsed with MeOH. The MeOH was removed under reduced pressure and the residue was diluted with water and extracted with EtOAc (3×40 mL). The combined organics were washed with brine, dried over MgSO$_4$, filtered and concentrated to dryness. Purification by RP-HPLC (water/acetonitrile/0.05% TFA) afforded the title compound. $^1$H NMR (500 MHz, CDCl$_3$) δ 8.23 (d, J=2.1 Hz, 1H), 7.88 (d, J=8.8 Hz, 1H), 7.57-7.39 (m, 4H), 7.38-7.30 (m, 2H), 7.17 (s, 1H), 4.75 (s, 1H), 4.02 (s, 3H), 3.92 (s, 3H), 2.56 (s, 3H), 2.12 (s, 3H); MS (ESI): mass calcd. for C$_{25}$H$_{22}$ClN$_5$O$_2$S, 491.1, m/z found 492.0 [M+H]$^+$.

Example 36

(2-Chloro-4-methoxy-3-phenylquinolin-6-yl)(2,4-dimethylthiazol-5-yl)(1-methyl-1H-1,2,3-triazol-5-yl)methanol.TFA

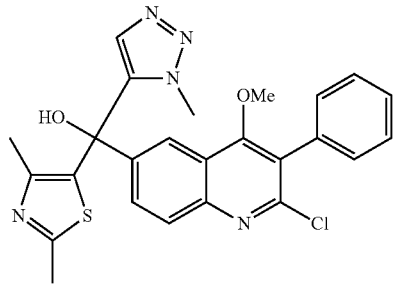 [SMILES: COc1c(-c2ccccc2)c(Cl)nc2ccc(C(O)(c3sc(C)nc3C)c3cnnn3C)cc12]

To a flask containing (2,4-dichloro-3-phenylquinolin-6-yl)(2,4-dimethylthiazol-5-yl)(1-methyl-1H-1,2,3-triazol-5-yl)methanol (100 mg, 0.2 mmol, Example 67) was added MeOH (6 mL) followed by solid NaOMe (50 mg, 0.88 mmol, 95% purity) at room temperature. The reaction mixture was heated to reflux for 24 hours, then allowed to cool to room temperature, filtered through Celite® and rinsed with MeOH. The MeOH was removed under reduced pressure and the residue was diluted with water and extracted with EtOAc (3×40 mL). The combined organics were washed with brine, dried over MgSO$_4$, filtered and concentrated to dryness. Purification by RP-HPLC (water/acetonitrile/0.05% TFA) afforded the title compound. $^1$H NMR (500 MHz, CDCl$_3$) δ 8.13 (d, J=2.1 Hz, 1H), 8.04 (d, J=8.9 Hz, 1H), 7.68 (dd, J=8.9, 2.3 Hz, 1H), 7.54-7.44 (m, 3H), 7.43-7.39 (m, 2H), 7.23 (s, 1H), 3.95 (br.

s, 1H), 3.93 (s, 3H), 3.48 (s, 3H), 2.59 (s, 3H), 2.16 (s, 3H); MS (ESI): mass calcd. for $C_{25}H_{22}ClN_5O_2S$, 491.1, m/z found 492.0 [M+H]$^+$.

Example 37

(4-Chloro-2-methoxy-3-phenylquinolin-6-yl)(2,4-dimethylthiazol-5-yl)(1-methyl-1H-imidazol-5-yl)methanol.TFA

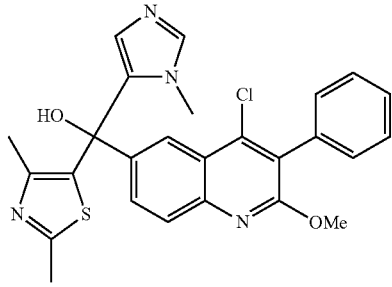 [SMILES: COc1nc2ccc(C(O)(c3sc(C)nc3C)c3cncn3C)cc2c(Cl)c1-c1ccccc1]

To a microwave vial containing (2,4-dichloro-3-phenylquinolin-6-yl)(2,4-dimethylthiazol-5-yl)(1-methyl-1H-imidazol-5-yl)methanol (120 mg, 0.24 mmol, Example 68) was added MeOH (4 mL) followed by solid NaOMe (60 mg, 1.11 mmol, 95% purity) at room temperature. The vial was sealed and evacuated and the mixture was heated to 75° C. for 5.5 hours. The MeOH was removed under reduced pressure and the residue was diluted with water and extracted with EtOAc (4×25 mL). The combined organics were washed with brine, dried over MgSO$_4$, filtered and concentrated to dryness. Purification by RP-HPLC (water/acetonitrile/0.05% TFA) afforded the title compound. $^1$H NMR (500 MHz, CD$_3$OD) δ 9.00 (s, 1H), 8.30 (d, J=2.0 Hz, 1H), 8.01 (d, J=8.9 Hz, 1H), 7.81 (dd, J=8.9, 2.1 Hz, 1H), 7.60-7.37 (m, 5H), 7.26 (s, 1H), 3.75 (s, 3H), 3.55 (s, 3H), 2.62 (s, 3H), 2.25 (s, 3H); MS (ESI): mass calcd. for $C_{26}H_{23}ClN_4O_2S$, 490.1; m/z found 491.1 [M+H]$^+$.

Example 38

(2-Chloro-4-methoxy-3-phenylquinolin-6-yl)(2,4-dimethylthiazol-5-yl)(1-methyl-1H-imidazol-5-yl)methanol.TFA

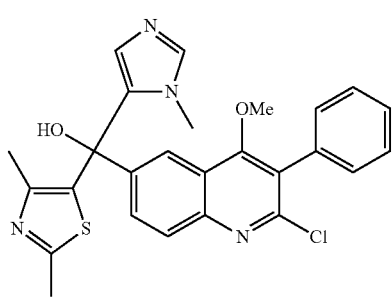 [SMILES: COc1c(-c2ccccc2)c(Cl)nc2ccc(C(O)(c3sc(C)nc3C)c3cncn3C)cc12]

To a microwave vial containing (2,4-dichloro-3-phenylquinolin-6-yl)(2,4-dimethylthiazol-5-yl)(1-methyl-1H-imidazol-5-yl)methanol (120 mg, 0.24 mmol, Example 68) was added MeOH (4 mL) followed by solid NaOMe (60 mg, 1.11 mmol, 95% purity) at room temperature. The vial was sealed and evacuated and the mixture was heated to 75° C. for 5.5 hours. The MeOH was removed under reduced pressure and the residue was diluted with water and extracted with EtOAc (4×25 mL). The combined organics were washed with brine, dried over MgSO$_4$, filtered and concentrated to dryness. Purification by RP-HPLC (water/acetonitrile/0.05% TFA) afforded the title compound. $^1$H NMR (500 MHz, CD$_3$OD) δ 9.00 (s, 1H), 8.28 (d, J=2.1 Hz, 1H), 7.98 (d, J=8.8 Hz, 1H), 7.74 (dd, J=8.8, 2.2 Hz, 1H), 7.51-7.38 (m, 3H), 7.35-7.27 (m, 2H), 7.24 (s, 1H), 4.00 (s, 3H), 3.75 (s, 3H), 2.62 (s, 3H), 2.25 (s, 3H); MS (ESI): mass calcd. for $C_{26}H_{23}ClN_4O_2S$, 490.1; m/z found 491.1 [M+H]$^+$.

Example 39

(2,4-Dichloro-3-phenylquinolin-6-yl)(1,2-dimethyl-1H-imidazol-5-yl)(1-methyl-1H-1,2,3-triazol-5-yl)methanol

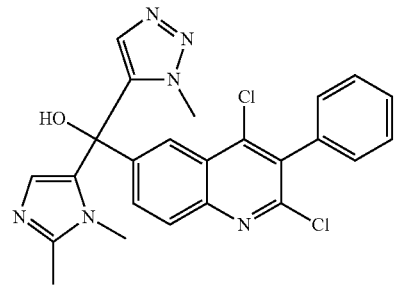 [SMILES: Cc1ncc(C(O)(c2ccc3nc(Cl)c(-c4ccccc4)c(Cl)c3c2)c2cnnn2C)n1C]

To a flask containing 1-methyl-1H-1,2,3-triazole (125 mg, 1.5 mmol) was added THF (10 mL) and the colorless solution was cooled to −45° C. Then, n-BuLi (2.5 M in hexanes, 0.6 mL, 1.5 mmol) was added affording a suspension. The suspension was stirred between −40° C. and −10° C. for 30 minutes, then a THF solution of (2,4-dichloro-3-phenylquinolin-6-yl)(1,2-dimethyl-1H-imidazol-5-yl)methanone (500 mg, 1.26 mmol, Intermediate 18: step b, in 5 mL THF) was introduced and the mixture was allowed to warm up to room temperature. After 1 hour, the reaction mixture was heated to 40° C. for 3 hours and then quenched with aqueous NH$_4$Cl solution. The aqueous portion was extracted with EtOAc (3×50 mL) and then with DCM (3×50 mL). The individual organic portions were washed with brine, dried over MgSO$_4$, filtered, combined and concentrated to dryness. Chromatography on silica gel (5% MeOH-DCM increasing to 10% MeOH) provided material which was re-purified by preparative TLC (5% 2 M-NH$_3$-MeOH-EtOAc) to provide the title compound as light tan solid. $^1$H NMR (500 MHz, CDCl$_3$) δ 8.45-8.36 (m, 1H), 7.94 (d, J=8.8 Hz, 1H), 7.66-7.46 (m, 4H), 7.46-7.30 (m, 2H), 7.01 (s, 1H), 5.94 (s, 1H), 3.91 (s, 3H), 3.34 (s, 3H), 2.17 (s, 3H). MS (ESI): mass calcd. for $C_{24}H_{20}Cl_2N_6O$, 478.1, m/z found 479.1 [M+H]$^+$.

Example 40a (2-Chloro-4-methoxy-3-phenylquinolin-6-yl)(1,2-dimethyl-1H-imidazol-5-yl)(1-methyl-1H-1,2,3-triazol-5-yl)methanol.TFA

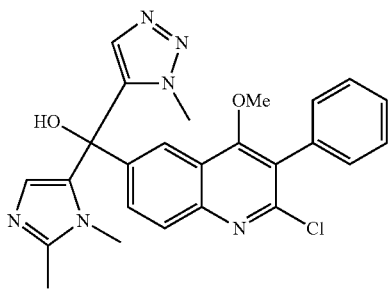 [SMILES: COc1c(-c2ccccc2)c(Cl)nc2ccc(C(O)(c3cnnn3C)c3cnc(C)n3C)cc12]

To a flask containing (2,4-dichloro-3-phenylquinolin-6-yl)(1,2-dimethyl-1H-imidazol-5-yl)(1-methyl-1H-1,2,3-triazol-5-yl)methanol (1.1 g, 2.29 mmol, Example 39) was added MeOH (30 mL) followed by solid NaOMe (505 mg, 9.35 mmol, 95% purity) at room temperature. The mixture was heated to 80° C. for 5 hours, then cooled back to room temperature and the MeOH was removed under reduced pressure. The crude material was passed through a plug of silica gel (5% MeOH-DCM) to afford a light brown solid. This material was further purified by RP-HPLC (water/acetonitrile/0.05% TFA) to afford the title compound. $^1$H NMR (500 MHz, CD$_3$OD) δ 8.34 (d, J=1.8 Hz, 1H), 8.01 (d, J=8.8 Hz, 1H), 7.67 (dd, J=8.8, 2.1 Hz, 1H), 7.58-7.36 (m, 6H), 6.90 (s, 1H), 4.01 (s, 3H), 3.69 (s, 3H), 3.55 (s, 3H), 2.66 (s, 3H); MS (ESI): mass calcd. for $C_{25}H_{23}ClN_6O_2$, 474.2, m/z found 475.1 [M+H]$^+$.

The racemic mixture was separated by chiral chromatography using [Chiralpak AD, 1000A, 20 µM (Diacel), heptane: 2-propanol (80:20 with 0.2% TEA), to give two enantiomers. The first eluting enantiomer was Example 40b and the second eluting enantiomer was Example 40c.

Example 41a (4-Chloro-2-methoxy-3-phenylquinolin-6-yl)(1,2-dimethyl-1H-imidazol-5-yl)(1-methyl-1H-1,2,3-triazol-5-yl)methanol.TFA

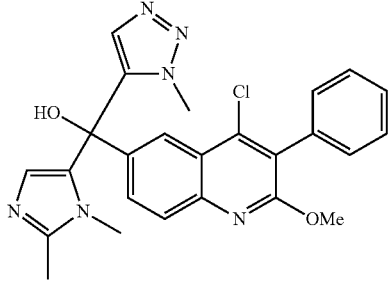 [SMILES: COc1nc2ccc(C(O)(c3cnnn3C)c3cnc(C)n3C)cc2c(Cl)c1-c1ccccc1]

To a flask containing (2,4-dichloro-3-phenylquinolin-6-yl)(1,2-dimethyl-1H-imidazol-5-yl)(1-methyl-1H-1,2,3-triazol-5-yl)methanol (1.1 g, 2.29 mmol, Example 39) was added MeOH (30 mL) followed by solid NaOMe (505 mg, 9.35 mmol, 95% purity) at room temperature. The mixture was heated to 80° C. for 5 hours, then cooled back to room temperature and the MeOH was removed under reduced pressure. The crude material was passed through a plug of silica gel (5% MeOH-DCM) to afford a light brown solid. This material was further purified by RP-HPLC (water/acetonitrile/0.05% TFA) to afford the title compound. $^1$H NMR (500 MHz, CD$_3$OD) δ 8.32 (d, J=2.1 Hz, 1H), 7.98 (d, J=8.8 Hz, 1H), 7.60 (dd, J=8.8, 2.2 Hz, 1H), 7.50-7.37 (m, 4H), 7.34-7.25 (m, 2H), 6.87 (s, 1H), 4.00 (s, 3H), 3.99 (s, 3H), 3.70 (s, 3H), 2.67 (s, 3H); MS (ESI): mass calcd. for $C_{25}H_{23}ClN_6O_2$, 474.2, m/z found 475.1 [M+H]$^+$.

The racemic mixture was separated by chiral chromatography using [Chiralpak AD, 1000A, 20 µM (Diacel), heptane: 2-propanol (75:25 with 0.2% TEA), to give two enantiomers. The first eluting enantiomer was Example 41b and the second eluting enantiomer was Example 41c.

Example 42

(2,4-Bis(methylthio)-3-phenylquinolin-6-yl)(2,4-dimethylthiazol-5-yl)(1-methyl-1H-imidazol-5-yl)methanol.TFA

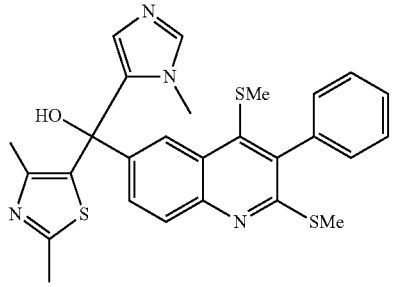 [SMILES: CSc1nc2ccc(C(O)(c3sc(C)nc3C)c3cncn3C)cc2c(SC)c1-c1ccccc1]

To a flask containing (2,4-dichloro-3-phenylquinolin-6-yl)(2,4-dimethylthiazol-5-yl)(1-methyl-1H-imidazol-5-yl)methanol (198 mg, 0.4 mmol, Example 68) was added DMF (67.5 mL) followed by sodium methanethiolate (37 mg, 0.53 mmol) at room temperature. After 15 minutes, the reaction mixture was concentrated and chromatographed directly on silica gel (2% MeOH-DCM increasing to 5% MeOH) which afforded a mixture of two products. This material was re-purified by RP-HPLC (water/acetonitrile/0.05% TFA) to provide the title compound. $^1$H NMR (500 MHz, CDCl$_3$) δ 8.72 (s, 1H), 8.60 (s, 1H), 8.25 (d, J=8.3 Hz, 1H), 7.77 (d, J=8.3 Hz, 1H), 7.59-7.45 (m, 3H), 7.39-7.28 (m, 2H), 7.20 (s, 1H), 3.71 (s, 3H), 2.80 (s, 3H), 2.68 (s, 3H), 2.32 (s, 3H), 1.95 (s, 3H); MS (ESI): mass calcd. for $C_{27}H_{26}N_4OS_3$, 518.1, m/z found 519.1 [M+H]$^+$.

Example 43

(4-Chloro-2-(methylthio)-3-phenylquinolin-6-yl)(2,4-dimethylthiazol-5-yl)(1-methyl-1H-imidazol-5-yl)methanol.TFA

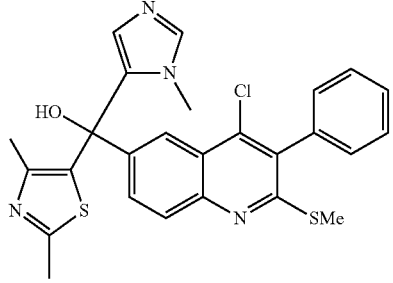 [SMILES: CSc1nc2ccc(C(O)(c3sc(C)nc3C)c3cncn3C)cc2c(Cl)c1-c1ccccc1]

To a flask containing (2,4-dichloro-3-phenylquinolin-6-yl)(2,4-dimethylthiazol-5-yl)(1-methyl-1H-imidazol-5-yl)methanol (198 mg, 0.4 mmol, Example 68) was added DMF (67.5 mL) followed by sodium methanethiolate (37 mg, 0.53 mmol) at room temperature. After 15 minutes, the reaction mixture was concentrated to dryness and chromatographed directly on silica gel (2% MeOH-DCM increasing to 5% MeOH) which afforded a mixture of two products. This material was re-purified by RP-HPLC (water/acetonitrile/0.05% TFA) to provide the title compound. $^1$H NMR (500 MHz, CDCl$_3$) δ 8.70 (s, 1H), 8.63 (s, 1H), 8.12 (d, J=8.9 Hz, 1H), 7.78 (d, J=8.7 Hz, 1H), 7.56-7.43 (m, 3H), 7.34 (d, J=7.1 Hz, 2H), 7.20 (s, 1H), 3.71 (s, 3H), 2.78 (s, 3H), 2.34 (s, 3H), 1.94 (s, 3H); MS (ESI): mass calcd. for C$_{26}$H$_{23}$ClN$_4$OS$_2$, 506.1, m/z found 507.0 [M+H]$^+$.

Example 44

[2-(2-Aziridin-1-ylethoxy)-4-chloro-3-phenylquinolin-6-yl](4-chlorophenyl)(1-methyl-1H-imidazol-5-yl)methanol

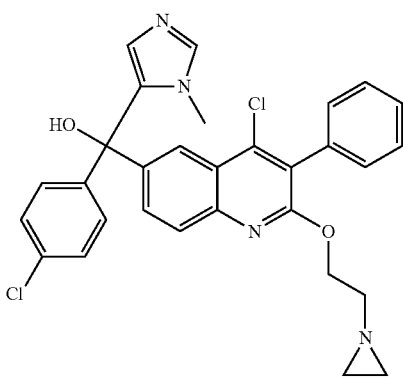 [SMILES: Cn1cncc1C(O)(c1ccc(Cl)cc1)c1ccc2nc(OCCN3CC3)c(-c3ccccc3)c(Cl)c2c1]

(4-Chlorophenyl)(2,4-dichloro-3-phenylquinolin-6-yl)(1-methyl-1H-imidazol-5-yl)methanol (100 mg, 0.202 mmol, Example 65), 2-(aziridin-1-yl)ethanol (16.2 µL, 0.20 mmol), toluene (2 mL), and sodium hydride (60% dispersion in mineral oil, 20.2 mg, 0.51 mmol) were combined in a round bottom flask under an N$_2$ atmosphere. The reaction solution was heated to reflux and refluxed overnight, cooled and stirred at room temperature an additional night before workup. Reaction contents were transferred to a separatory funnel with EtOAc dilution, and extracted with saturated, aqueous NH$_4$Cl then saturated, aqueous NaHCO$_3$ solutions. The organic phase was separated then dried over MgSO$_4$, filtered and concentrated under reduced pressure. The crude product was purified by flash column chromatography (silica gel, 0-10% DCM/MeOH) to afford the title compound. MS (ESI): mass calcd. for C$_{30}$H$_{26}$Cl$_2$N$_4$O$_2$, 544.1; m/z found, 545.1 [M+H]$^+$; $^1$H NMR (600 MHz, CD$_3$OD) δ ppm 8.05 (d, J=2.0 Hz, 1H), 7.74 (d, J=8.7 Hz, 1H), 7.61-7.57 (m, 2H), 7.40-7.35 (m, 2H), 7.35-7.31 (m, 1H), 7.28-7.23 (m, 6H), 6.18 (d, J=1.1 Hz, 1H), 4.51-4.44 (m, 2H), 3.37 (s, 3H), 2.50-2.39 (m, 2H), 1.48-1.37 (m, 2H), 0.97-0.94 (m, 2H).

Example 45

(4-Chlorophenyl)[4-chloro-3-phenyl-2-(2,2,2-trifluoroethoxy)quinolin-6-yl](1-methyl-1H-imidazol-5-yl)methanol.TFA

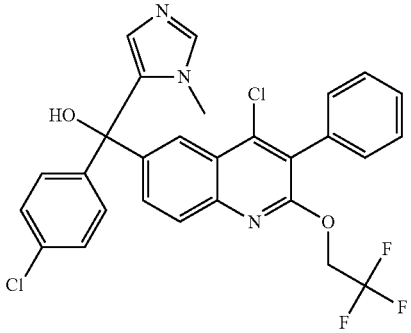 [SMILES: Cn1cncc1C(O)(c1ccc(Cl)cc1)c1ccc2nc(OCC(F)(F)F)c(-c3ccccc3)c(Cl)c2c1]

(4-Chlorophenyl)(2,4-dichloro-3-phenylquinolin-6-yl)(1-methyl-1H-imidazol-5-yl)methanol (100 mg, 0.202 mmol, Example 65), 2,2,2-trifluoroethanol (14.5 µL, 0.202 mmol), toluene (2 mL), and sodium hydride (60% dispersion in mineral oil, 20 mg, 0.51 mmol) were combined in a round bottom flask under an N$_2$ atmosphere. The reaction solution was heated to reflux and refluxed overnight. The reaction solution was cooled to room temperature then transferred to a separatory funnel with EtOAc dilution, and extracted with saturated, aqueous NH$_4$Cl then saturated, aqueous NaHCO$_3$ solutions. The organic phase was separated then dried over MgSO$_4$, filtered and concentrated under reduced pressure. The crude product was purified by flash column chromatography (silica gel, 0-10% DCM/MeOH) then via reverse phase chromatography using acetonitrile with 0.05% trifluoroacetic acid in water as eluent. The fractions from the purification containing the desired product were transferred to a separatory funnel with EtOAc and extracted with a saturated, aqueous NaHCO$_3$ solution. The aqueous layer was separated, extracted with EtOAc, then the combined organic phases were dried over MgSO$_4$, filtered and concentrated under reduced pressure to provide the title compound. MS (ESI): mass calcd. for C$_{28}$H$_{20}$Cl$_2$F$_3$N$_3$O$_2$, 557.1; m/z found, 558.3 [M+H]$^+$; $^1$H NMR (600 MHz, CDCl$_3$) δ ppm 8.38 (s, 1H), 8.17 (d, J=2.0 Hz, 1H), 7.87 (d, J=8.8 Hz, 1H), 7.60 (dd, J=8.8, 2.1 Hz, 1H), 7.52-7.43 (m, 3H), 7.38-7.31 (m, 6H), 6.56 (s, 1H), 4.92 (q, J=8.4 Hz, 2H), 3.62 (s, 3H).

Example 46

2-[{4-Chloro-6-[(4-chlorophenyl)(hydroxy)(1-methyl-1H-imidazol-5-yl)methyl]-3-phenylquinolin-2-yl}(methyl)amino]ethanol.TFA

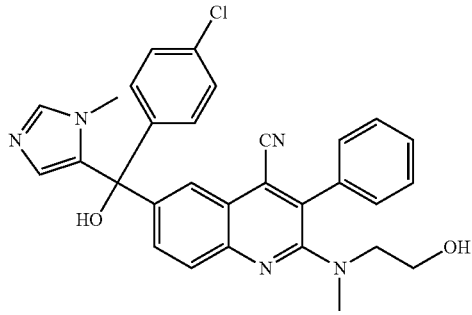 [SMILES: CN(CCO)c1nc2ccc(C(O)(c3ccc(Cl)cc3)c3cncn3C)cc2c(C#N)c1-c1ccccc1]

(4-Chlorophenyl)(2,4-dichloro-3-phenylquinolin-6-yl)(1-methyl-1H-imidazol-5-yl)methanol (100 mg, 0.202 mmol, Example 65), 2-(methylamino)ethanol (16.2 µL, 0.202 mmol), toluene (2 mL), and sodium hydride (60% dispersion in mineral oil, 28.3 mg, 0.707 mmol) were combined in a round bottom flask and heated at reflux for 48 hours under an $N_2$ atmosphere. The reaction solution was then cooled to room temperature, diluted with EtOAc, transferred to a reparatory funnel, extracted with saturated, aqueous $NH_4Cl$ then saturated, aqueous $NaHCO_3$ solutions. The organic phase was separated then dried over $MgSO_4$, filtered and concentrated under reduced pressure. The crude product was purified by flash column chromatography (silica gel, 0-10% DCM/MeOH) then further purified via reverse phase chromatography using acetonitrile with 0.05% trifluoroacetic acid in water as eluent, then lyophilized to afford the title compound as a trifluoroacetate salt. MS (ESI): mass calcd. for $C_{29}H_{26}Cl_2N_4O_2$, 532.1; m/z found, 533.2 [M+H]+; 1H NMR (600 MHz, $CD_3OD$) δ ppm 8.98 (s, 1H), 8.22 (s, 1H), 7.83 (d, J=8.8 Hz, 1H), 7.79 (d, J=8.9 Hz, 1H), 7.55 (t, J=7.4 Hz, 2H), 7.50 (t, J=7.4 Hz, 1H), 7.47-7.39 (m, 6H), 6.93 (d, J=1.4 Hz, 1H), 3.80-3.73 (m, 2H), 3.69 (s, 3H), 3.61-3.57 (m, 2H), 2.75 (s, 3H).

Example 47a 6-((2,4-Dimethylthiazol-5-yl)(hydroxy)(1-methyl-1H-1,2,3-triazol-5-yl)methyl)-3-phenylquinoline-2,4-dicarbonitrile

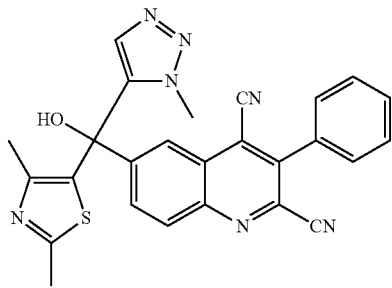 [SMILES: Cc1nc(C)c(C(O)(c2ccc3nc(C#N)c(-c4ccccc4)c(C#N)c3c2)c2cnnn2C)s1]

(2,4-Dichloro-3-phenylquinolin-6-yl)(2,4-dimethylthiazol-5-yl)(1-methyl-1H-1,2,3-triazol-5-yl)methanol (100 mg, 0.2 mmol, Example 67), zinc cyanide (75 mg, 0.64 mmol), X-Phos (25 mg, 0.052 mmol), and $Pd_2(dba)_3$ (60 mg, 0.066 mmol) were all added to a large microwave vial. DMA (3 mL) was added and the vial was sealed and evacuated and the mixture was heated to 120° C. in an oil bath. After 1.5 hours, the reaction mixture was filtered while still warm through Celite® and rinsed with EtOAc. The effluent was concentrated and the DMA was partially removed under high vacuum. The crude material was chromatographed on silica gel (3% MeOH-DCM increasing to 8% MeOH) which provided the title compound as a pale yellow foam. 1H NMR (500 MHz, $CDCl_3$) δ 8.53 (s, 1H), 8.26 (d, J=8.9 Hz, 1H), 7.79 (d, J=9.0 Hz, 1H), 7.71-7.54 (m, 5H), 7.10 (s, 1H), 6.10 (s, 1H), 4.00 (s, 3H), 2.57 (s, 3H), 2.14 (s, 3H); MS (ESI): mass calcd. for $C_{26}H_{19}N_7OS$, 477.1, m/z found 478.1 [M+H]+.

The racemic mixture was separated by chiral chromatography using [Chiralcel OJ, 1000A, 20 µM (Diacel), and 100% MeOH], to give two enantiomers. The first eluting enantiomer was Example 47b and the second eluting enantiomer was Example 47c.

Example 48

[4-Chloro-2-(2-methoxyethoxy)-3-phenylquinolin-6-yl](4-chlorophenyl)(1-methyl-1H-imidazol-5-yl)methanol

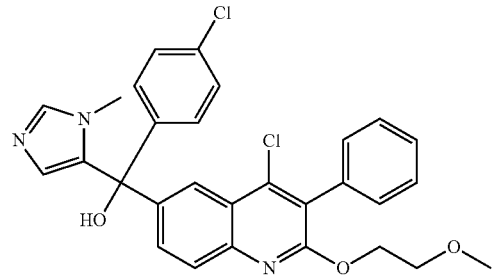 [SMILES: COCCOc1nc2ccc(C(O)(c3ccc(Cl)cc3)c3cncn3C)cc2c(Cl)c1-c1ccccc1]

(4-Chlorophenyl)(2,4-dichloro-3-phenylquinolin-6-yl)(1-methyl-1H-imidazol-5-yl)methanol (100 mg, 0.202 mmol, Example 65), 2-methoxyethanol (16.0 µL, 0.202 mmol), toluene (2 mL), and sodium hydride (60% dispersion in mineral oil, 20.2 mg, 0.505 mmol) were combined in a round bottom flask under an $N_2$ atmosphere. The contents were heated to reflux and refluxed overnight. The reaction solution turned from a heterogeneous white mixture to slightly yellowish with a moderate amount of precipitate. The contents were cooled to room temperature then transferred to a separatory funnel with EtOAc dilution, and extracted with saturated, aqueous $NH_4Cl$ and saturated, aqueous $NaHCO_3$ solutions. The organic phase was separated then dried over $MgSO_4$, filtered and concentrated under reduced pressure. The crude product was purified by flash column chromatography (silica gel, 0-10% DCM/(10% of a 2 M $NH_3$ MeOH in DCM)) then further purified via reverse phase chromatography using acetonitrile with ammonium hydroxide in water as eluent to afford the title compound. MS (ESI): mass calcd. for $C_{29}H_{25}Cl_2N_3O_3$, 533.1; m/z found, 534.2 [M+H]+; 1H NMR (600 MHz, $CD_3OD$) δ ppm 8.96 (d, J=0.9 Hz, 1H), 8.19 (d, J=1.9 Hz, 1H), 7.91 (d, J=8.8 Hz, 1H), 7.70 (dd, J=8.8, 2.2 Hz, 1H), 7.48-7.44 (m, 4H), 7.43-7.39 (m, 3H), 7.36-7.33 (m, 2H), 6.90 (d, J=1.6 Hz, 1H), 4.59-4.54 (m, 2H), 3.70 (s, 3H), 3.68-3.63 (m, 2H), 3.25 (s, 3H).

Example 49a (4-Chloro-2-methoxy-3-phenylquinolin-6-yl)(4-chlorophenyl)(1-methyl-1H-imidazol-5-yl)methanol.TFA

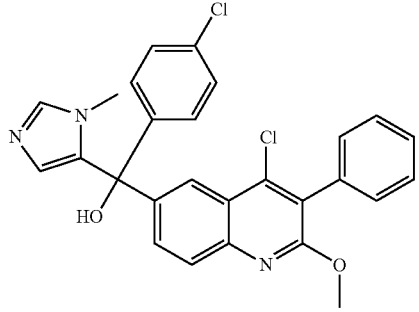 [SMILES: COc1nc2ccc(C(O)(c3ccc(Cl)cc3)c3cncn3C)cc2c(Cl)c1-c1ccccc1]

(4-Chlorophenyl)(2,4-dichloro-3-phenylquinolin-6-yl)(1-methyl-1H-imidazol-5-yl)methanol (100 mg, 0.202 mmol, Example 65), toluene (2 mL), and sodium methoxide (109 mg, 2.02 mmol) were combined in a round bottom flask equipped with a stirbar and condenser under an $N_2$ atmosphere. The reaction solution was heated to reflux and refluxed overnight. Analysis showed an incomplete reaction, so additional sodium methoxide (109 mg, 2.02 mmol) was added and contents were refluxed for an additional day. The reaction was cooled to room temperature and contents were transferred to a separatory funnel with EtOAc dilution, and extracted with saturated, aqueous $NH_4Cl$ then saturated, aqueous $NaHCO_3$ solutions. The organic phase was separated, dried over $MgSO_4$, filtered and concentrated under reduced pressure. The crude material was purified via reverse phase chromatography using acetonitrile with 0.05% trifluoroacetic acid in water as eluent. The fractions from the purification containing the desired product were lyophilized to provide the title compound as a trifluoroacetate salt. MS (ESI): mass calcd. for $C_{27}H_{21}Cl_2N_3O_2$, 489.1; m/z found, 490.1 [M+H]$^+$; $^1$H NMR (600 MHz, $CD_3OD$) δ ppm 8.97 (d, J=0.9 Hz, 1H), 8.18 (d, J=1.9 Hz, 1H), 7.94 (d, J=8.9 Hz, 1H), 7.71 (dd, J=8.8, 2.2 Hz, 1H), 7.48-7.44 (m, 4H), 7.43-7.40 (m, 3H), 7.32-7.28 (m, 2H), 6.90 (d, J=1.6 Hz, 1H), 3.98 (s, 3H), 3.70 (s, 3H).

(4-Chloro-2-methoxy-3-phenylquinolin-6-yl)(4-chlorophenyl)(1-methyl-1H-imidazol-5-yl)methanol.TFA was purified on a chiralcel AD column (8 cm) with ethanol to provide two enantiomers. The first eluting enantiomer was Example 49b: MS (ESI): mass calcd. for $C_{27}H_{21}Cl_2N_3O_2$, 489.1; m/z found, 490.2 [M+H]$^+$; $^1$H NMR (600 MHz, $CD_3OD$) δ ppm 8.14 (d, J=2.0 Hz, 1H), 7.94 (s, 1H), 7.87 (d, J=8.8 Hz, 1H), 7.69 (dd, J=8.8, 2.1 Hz, 1H), 7.45 (dd, J=11.4, 4.4 Hz, 2H), 7.42-7.34 (m, 5H), 7.33-7.27 (m, 2H), 6.40 (s, 1H), 3.97 (s, 3H), 3.51 (s, 3H) and the second eluting enantiomer was Example 49c: MS (ESI): mass calcd. for $C_{27}H_{21}Cl_2N_3O_2$, 489.1; m/z found, 490.1 [M+H]$^+$; $^1$H NMR (600 MHz, $CD_3OD$) δ ppm 8.20-8.14 (m, 2H), 7.88 (d, J=8.8 Hz, 1H), 7.69 (dd, J=8.8, 2.1 Hz, 1H), 7.47-7.42 (m, 2H), 7.42-7.35 (m, 5H), 7.31-7.27 (m, 2H), 6.51 (s, 1H), 3.96 (s, 3H), 3.55 (s, 3H).

Example 50

{4-Chloro-2-[(2-methoxyethyl)(methyl)amino]-3-phenylquinolin-6-yl}(4-chlorophenyl)(1-methyl-1H-imidazol-5-yl)methanol

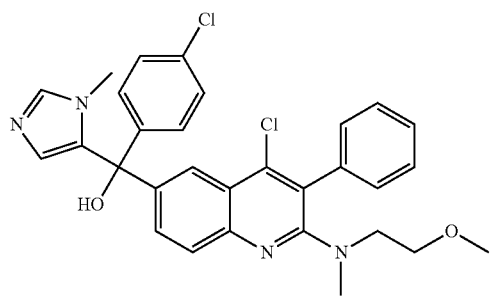 [SMILES: COCCN(C)c1nc2ccc(C(O)(c3ccc(Cl)cc3)c3cncn3C)cc2c(Cl)c1-c1ccccc1]

(4-Chlorophenyl)(2,4-dichloro-3-phenylquinolin-6-yl)(1-methyl-1H-imidazol-5-yl)methanol (100 mg, 0.202 mmol, Example 65), N-(2-methoxymethyl)methylamine (900 μL, 10.1 mmol), and methanol (2 mL) were combined in a reaction tube, which was then sealed and heated to 100° C. for 72 hours. The contents were then cooled to room temperature, transferred to a round bottom flask and the solvent was removed via reduced pressure distillation. The crude residue was then taken up into EtOAc, transferred to a separatory funnel, extracted twice with a saturated, aqueous $NH_4Cl$ solution. The organic phase was separated, dried over $MgSO_4$, filtered and concentrated under reduced pressure. The crude product was purified by flash column chromatography (silica gel, 0-10% DCM/(10% of a 2 M $NH_3$ MeOH in DCM)) then further purified via reverse phase chromatography using acetonitrile with 0.05% trifluoroacetic acid in water as eluent. The fractions from the purification containing the desired product were transferred to a separatory funnel with EtOAc and extracted with a saturated, aqueous $NaHCO_3$ solution. The aqueous layer was separated, extracted with EtOAc, then the combined organic phases were dried over $MgSO_4$, filtered and concentrated under reduced pressure to afford the title compound. MS (ESI): mass calcd. for $C_{30}H_{28}Cl_2N_4O_2$, 546.2; m/z found, 547.3 [M+H]$^+$; $^1$H NMR (600 MHz, $CD_3OD$) δ ppm 8.05 (d, J=2.0 Hz, 1H), 7.97 (s, 1H), 7.75 (d, J=8.8 Hz, 1H), 7.60 (dd, J=8.8, 2.1 Hz, 1H), 7.45 (dd, J=10.3, 4.6 Hz, 2H), 7.38 (ddd, J=8.6, 4.5, 1.2 Hz, 1H), 7.36-7.31 (m, 6H), 6.42 (s, 1H), 3.51 (s, 3H), 3.31-3.28 (m, 2H), 3.24 (dd, J=8.7, 3.0 Hz, 2H), 3.17 (s, 3H), 2.74 (s, 3H).

Example 51

N-[2-({4-Chloro-6-[(4-chlorophenyl)(hydroxy)(1-methyl-1H-imidazol-5-yl)methyl]-3-phenylquinolin-2-yl}oxy)ethyl]propanamide

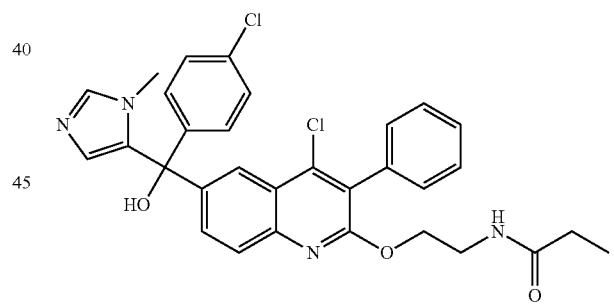

(4-Chlorophenyl)(2,4-dichloro-3-phenylquinolin-6-yl)(1-methyl-1H-imidazol-5-yl)methanol (100 mg, 0.202 mmol, Example 65), N-(2-hydroxylethyl)propanamide (34.2 μL, 0.303 mmol), toluene (2 mL), and sodium hydride (60% dispersion in mineral oil, 32.3 mg, 0.808 mmol) were combined in a round bottom flask under an $N_2$ atmosphere. The reaction solution was heated to reflux and refluxed overnight. The reaction solution was cooled to room temperature then transferred to a separatory funnel with EtOAc dilution, and extracted with saturated, aqueous $NH_4Cl$ then saturated, aqueous $NaHCO_3$ solutions. The organic phase was separated, then dried over $MgSO_4$, filtered and concentrated under reduced pressure. The crude product was purified by flash column chromatography (silica gel, 0-10% DCM/MeOH) then via reverse phase chromatography using acetonitrile with 0.05% trifluoroacetic acid in water as eluent. The fractions from the purification containing the desired product were transferred to a separatory funnel with EtOAc and extracted with a saturated, aqueous NaHCO$_3$ solution. The aqueous layer was separated, extracted with EtOAc, then the combined organic phases were dried over MgSO$_4$, filtered and concentrated under reduced pressure to provide the title compound. MS (ESI): mass calcd. for C$_{31}$H$_{28}$Cl$_2$N$_4$O$_3$, 574.2; m/z found, 575.2 [M+H]$^+$; $^1$H NMR (600 MHz, CD$_3$OD) δ ppm 8.14 (s, 1H), 7.83 (d, J=8.8 Hz, 1H), 7.78 (s, 1H), 7.68 (dd, J=8.8, 1.7 Hz, 1H), 7.47-7.41 (m, 2H), 7.41-7.37 (m, 1H), 7.38-7.34 (m, 4H), 7.34-7.30 (m, 2H), 6.32 (s, 1H), 4.52 (t, J=5.6 Hz, 2H), 3.53-3.44 (m, 5H), 2.11 (q, J=7.6 Hz, 2H), 1.04 (t, J=7.6 Hz, 3H).

Example 52

[2-(2-Aminoethoxy)-4-chloro-3-phenylquinolin-6-yl](4-chlorophenyl)(1-methyl-1H-imidazol-5-yl)methanol

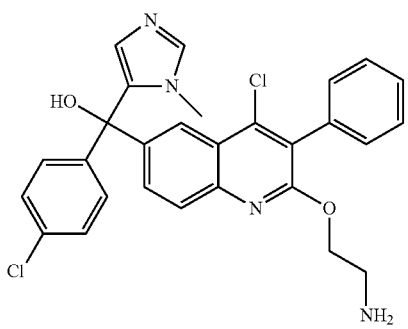 [SMILES: Cn1cncc1C(O)(c1ccc(Cl)cc1)c1ccc2nc(OCCN)c(-c3ccccc3)c(Cl)c2c1]

(4-Chlorophenyl)(2,4-dichloro-3-phenylquinolin-6-yl)(1-methyl-1H-imidazol-5-yl)methanol (100 mg, 0.202 mmol, Example 65), N-(2-hydroxyethyl)-2,2,2-trifluoroacetamide (49 mg, 0.30 mmol), toluene (2 mL), and sodium hydride (60% dispersion in mineral oil, 32.3 mg, 0.808 mmol) were combined in a round bottom flask and heated at reflux for 48 hours under an N$_2$ atmosphere. Analysis after overnight reaction showed only partial conversion, so additional N-(2-hydroxyethyl)-2,2,2-trifluoroacetamide (33 mg, 0.21 mmol) and sodium hydride (60% dispersion in mineral oil, 25 mg, 1.03 mmol) were added and the vessel was resealed and heated at reflux for an additional 48 hours. The reaction solution was then cooled to room temperature, diluted with EtOAc, transferred to a separatory funnel, and extracted with saturated, aqueous NH$_4$Cl then saturated, aqueous NaHCO$_3$ solutions. The organic phase was separated then dried over MgSO$_4$, filtered and concentrated under reduced pressure. The crude product was purified via reverse phase chromatography using acetonitrile with 0.05% trifluoroacetic acid in water as eluent. The fractions from the purification containing the desired product were transferred to a separatory funnel with EtOAc and extracted with a saturated, aqueous NaHCO$_3$ solution. The aqueous layer was separated, extracted with EtOAc, then the combined organic phases were dried over MgSO$_4$, filtered and concentrated under reduced pressure to afford the title compound. MS (ESI): mass calcd. for C$_{28}$H$_{24}$Cl$_2$N$_4$O$_2$, 518.1; m/z found, 519.2 [M+H]$^+$; $^1$H NMR (600 MHz, CD$_3$OD) δ ppm 8.17 (d, J=2.0 Hz, 1H), 7.87 (d, J=8.8 Hz, 1H), 7.72 (dd, J=8.8, 2.1 Hz, 1H), 7.69 (s, 1H), 7.50-7.45 (m, 2H), 7.44-7.40 (m, 1H), 7.39-7.33 (m, 6H), 6.26 (s, 1H), 4.67-4.60 (m, 2H), 3.47 (s, 3H), 3.20 (t, J=5.3 Hz, 2H).

Example 53

{4-Chloro-2-[(2-methoxyethyl)(methyl)amino]-3-phenylquinolin-6-yl}(1-methyl-1H-imidazol-5-yl)[6-(trifluoromethyl)pyridin-3-yl]methanol

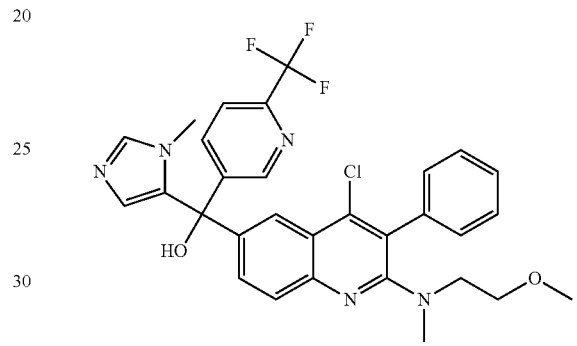

(2,4-Dichloro-3-phenylquinolin-6-yl)(1-methyl-1H-imidazol-5-yl) [6-(trifluoromethyl) pyridin-3-yl]methanol (200 mg, 0.378 mmol, Example 66), N-(2-methoxymethyl)methylamine (842 µL, 9.45 mmol), and methanol (2 mL) were combined in a reaction tube, which was then sealed and heated to 100° C. for 48 hours. The contents were then cooled to room temperature, transferred to a round bottom flask and the solvent was removed via reduced pressure distillation. The crude residue was then taken up into EtOAc, transferred to a separatory funnel and extracted twice with a saturated, aqueous NH$_4$Cl solution. The organic phase was separated, dried over MgSO$_4$, filtered and concentrated under reduced pressure. The crude product was purified via reverse phase chromatography using acetonitrile with 0.05% trifluoroacetic acid in water as eluent. The fractions from the purification containing the desired product were transferred to a separatory funnel with EtOAc and extracted with a saturated, aqueous NaHCO$_3$ solution. The aqueous layer was separated, extracted with EtOAc, then the combined organic phases were dried over MgSO$_4$, filtered and concentrated under reduced pressure to afford the title compound. MS (ESI): mass calcd. for C$_{30}$H$_{27}$ClF$_3$N$_5$O$_2$, 581.2; m/z found, 582.2 [M+H]$^+$; $^1$H NMR (600 MHz, CD$_3$OD) δ ppm 8.77 (d, J=1.8 Hz, 1H), 8.08 (d, J=2.0 Hz, 1H), 8.01 (dd, J=8.2, 1.9 Hz, 1H), 7.92 (s, 1H), 7.84 (d, J=8.2 Hz, 1H), 7.80 (d, J=8.8 Hz, 1H), 7.61 (dd, J=8.8, 2.1 Hz, 1H), 7.49 (t, J=7.5 Hz, 2H), 7.42 (ddd, J=6.7, 2.5, 1.2 Hz, 1H), 7.39-7.35 (m, 2H), 6.44 (s, 1H), 3.52 (s, 3H), 3.35-3.32 (m, 2H), 3.30-3.27 (m, 2H), 3.19 (s, 3H), 2.78 (s, 3H).

Example 54

[4-Chloro-3-phenyl-2-(2,2,2-trifluoroethoxy)quinolin-6-yl](1-methyl-1H-imidazol-5-yl)[6-(trifluoromethyl)pyridin-3-yl]methanol

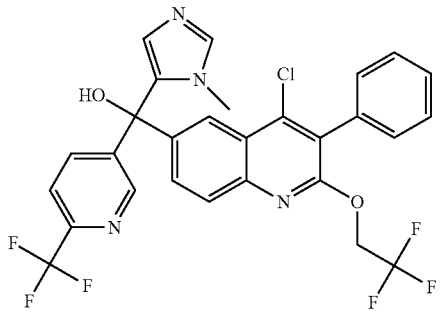 [SMILES: Cn1cncc1C(O)(c1ccc(C(F)(F)F)nc1)c1ccc2nc(OCC(F)(F)F)c(-c3ccccc3)c(Cl)c2c1]

(2,4-Dichloro-3-phenylquinolin-6-yl)(1-methyl-1H-imidazol-5-yl) [6-(trifluoromethyl) pyridin-3-yl]methanol (200 mg, 0.378 mmol, Example 66), 2,2,2-trifluoroethanol (14.0 µL, 0.19 mmol), toluene (2 mL), and sodium hydride (60% dispersion in mineral oil, 19 mg, 0.47 mmol) were combined in a round bottom flask under an $N_2$ atmosphere. The reaction solution was heated to reflux and refluxed overnight. Analysis showed the reaction had only progressed a moderate amount, so additional reagents were added, 2,2,2-trifluoroethanol (14.0 µL, 0.19 mmol) and sodium hydride (60% dispersion in mineral oil, 6 mg, 0.19 mmol) and contents were heated at reflux for an additional 48 hours. The contents were cooled to room temperature then transferred to a separatory funnel with EtOAc dilution, and extracted with saturated, aqueous $NH_4Cl$ then saturated, aqueous $NaHCO_3$ solutions. The organic phase was separated then dried over $MgSO_4$, filtered and concentrated under reduced pressure. The crude material was purified via reverse phase chromatography using acetonitrile with 0.05% trifluoroacetic acid in water as eluent. The fractions from the purification containing the desired product were transferred to a separatory funnel with EtOAc and extracted with a saturated, aqueous $NaHCO_3$ solution. The aqueous layer was separated, extracted with EtOAc, then the combined organic phases were dried over $MgSO_4$, filtered and concentrated under reduced pressure to afford the title compound. MS (ESI): mass calcd. for $C_{28}H_{19}ClF_6N_4O_2$, 592.1; m/z found, 593.2 [M+H]$^+$; $^1$H NMR (600 MHz, $CD_3OD$) δ ppm 8.80 (d, J=2.1 Hz, 1H), 8.28 (d, J=1.9 Hz, 1H), 8.17 (s, 1H), 8.05 (dd, J=8.2, 2.0 Hz, 1H), 7.97 (d, J=8.7 Hz, 1H), 7.86 (dd, J=8.3, 0.4 Hz, 1H), 7.75 (dd, J=8.8, 2.2 Hz, 1H), 7.51-7.42 (m, 3H), 7.37-7.34 (m, 2H), 6.60 (s, 1H), 5.00 (q, J=8.6 Hz, 2H), 3.56 (s, 3H).

Example 55

(2,4-Dichloro-3-phenylquinolin-6-yl)(1-methyl-1H-imidazol-5-yl)pyrimidin-2-ylmethanol

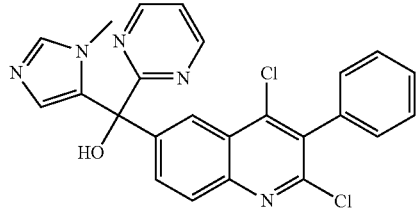 [SMILES: Cn1cncc1C(O)(c1ccc2nc(Cl)c(-c3ccccc3)c(Cl)c2c1)c1ncccn1]

6-Bromo-2,4-dichloro-3-phenylquinoline (0.895 g, 2.54 mmol, Intermediate 7: step c) and (1-methyl-1H-imidazol-5-yl)(pyrimidin-2-yl)methanone (500 mg, 2.66 mmol, Intermediate 15: step b) were dissolved in THF (250 mL) in a dry round bottom flask under an $N_2$ atmosphere, then cooled to −78° C. in dry ice acetone bath. n-BuLi (2.5 M in hexanes, 0.966 mL, 2.42 mmol) was then added dropwise via syringe over approximately 2 minutes. The reaction contents were stirred at −78° C. for approximately 1.5 hours, then the dry ice bath was removed and allowed to warm to room temperature and stir for approximately 1 hour. The reaction was then re-cooled to 0° C. and quenched with a saturated, aqueous $NH_4Cl$ solution, then transferred to a separatory funnel with EtOAc. The organic phase was separated, then the aqueous layer was back extracted with EtOAc, then the combined organic phases were dried over $MgSO_4$, filtered and concentrated under reduced pressure. The crude product was purified by flash column chromatography (silica gel, 0-10% DCM/(10% of a 2M $NH_3$ MeOH in DCM)) then further purified via reverse phase chromatography using acetonitrile with 0.05% trifluoroacetic acid in water as eluent. The fractions from the purification containing the desired product were transferred to a separatory funnel with EtOAc and extracted with a saturated, aqueous $NaHCO_3$ solution. The aqueous layer was separated, extracted with EtOAc, then the combined organic phases were dried over $MgSO_4$, filtered and concentrated under reduced pressure to afford the title compound. MS (ESI): mass calcd. for $C_{24}H_{17}Cl_2N_5O$, 461.1; m/z found, 462.1 [M+H]$^+$; $^1$H NMR (600 MHz, $CD_3OD$) δ ppm 8.88 (d, J=4.9 Hz, 2H), 8.57 (d, J=1.8 Hz, 1H), 8.08 (dd, J=8.9, 2.0 Hz, 1H), 7.99 (d, J=8.9 Hz, 1H), 7.80 (s, 1H), 7.54-7.45 (m, 4H), 7.36-7.32 (m, 2H), 6.49 (d, J=1.0 Hz, 1H), 3.43 (s, 3H).

Example 56

{4-Chloro-2-[methoxy(methyl)amino]-3-phenylquinolin-6-yl}(1-methyl-1H-imidazol-5-yl)[6-(trifluoromethyl)pyridin-3-yl]methanol

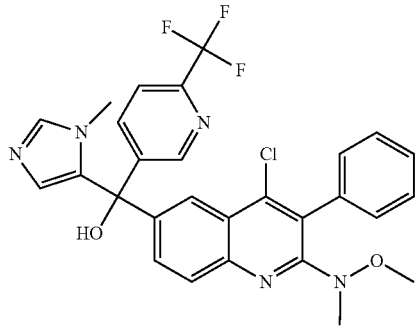 [SMILES: CON(C)c1nc2ccc(C(O)(c3ccc(C(F)(F)F)nc3)c3cncn3C)cc2c(Cl)c1-c1ccccc1]

(2,4-Dichloro-3-phenylquinolin-6-yl)(1-methyl-1H-imidazol-5-yl) [6-(trifluoromethyl)pyridin-3-yl]methanol (200 mg, 0.378 mmol, Example 66), N,O-dimethylhydroxylamine hydrochloride (376 mg, 3.78 mmol), and dimethylformamide (2 mL) were combined in a reaction tube which was then sealed and heated to 100° C. for 48 hours. Analysis shows desired product, but also the presence of starting material. Additional N,O-dimethylhydroxylamine hydrochloride (190 mg, 0.195 mmol) was added and the contents were heated for an additional 24 hours. The contents were then cooled, transferred to a separatory funnel, diluted with EtOAc and extracted with a saturated, aqueous $NH_4Cl$ solution, followed by deionized water (4×). The organic phase was separated, dried over MgSO$_4$, filtered and concentrated under reduced pressure. The crude material was purified via reverse phase chromatography using acetonitrile with ammonium hydroxide in water as eluent to afford the title compound. MS (ESI): mass calcd. for C$_{28}$H$_{23}$ClF$_3$N$_5$O$_2$, 553.1; m/z found, 554.2 [M+H]$^+$; $^1$H NMR (400 MHz, CD$_3$OD) δ ppm 8.79 (d, J=2.1 Hz, 1H), 8.19 (d, J=1.9 Hz, 1H), 8.02 (dd, J=8.2, 1.9 Hz, 1H), 7.96 (d, J=8.8 Hz, 1H), 7.83 (d, J=8.2 Hz, 1H), 7.75-7.68 (m, 2H), 7.48 (t, J=7.4 Hz, 2H), 7.40 (ddd, J=7.4, 3.9, 1.3 Hz, 1H), 7.32-7.24 (m, 2H), 6.35 (s, 1H), 3.48 (s, 3H), 3.07 (s, 3H), 2.77 (s, 3H).

Example 57

{2,4-Bis[methoxy(methyl)amino]-3-phenylquinolin-6-yl}(1-methyl-1H-imidazol-5-yl)[6-(trifluoromethyl)pyridin-3-yl]methanol

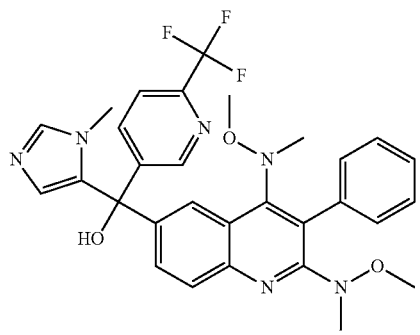 [SMILES: CON(C)c1nc2ccc(C(O)(c3ccc(C(F)(F)F)nc3)c3cncn3C)cc2c(N(C)OC)c1-c1ccccc1]

Purification of the crude product from the synthesis of {4-chloro-2-[methoxy(methyl)amino]-3-phenylquinolin-6-yl}(1-methyl-1H-imidazol-5-yl)[6-(trifluoromethyl)pyridin-3-yl]methanol (Example 56) also provided the title compound. MS (ESI): mass calcd. for C$_{30}$H$_{29}$F$_3$N$_6$O$_3$, 578.2; m/z found, 579.2 [M+H]$^1$; $^1$H NMR (400 MHz, CD$_3$OD) δ ppm 8.75 (d, J=2.0 Hz, 1H), 8.36 (d, J=2.0 Hz, 1H), 8.02 (dd, J=8.3, 1.8 Hz, 1H), 7.97 (d, J=8.9 Hz, 1H), 7.84 (d, J=8.2 Hz, 1H), 7.78-7.70 (m, 2H), 7.44-7.37 (m, 2H), 7.36-7.29 (m, 1H), 7.24 (d, J=7.3 Hz, 2H), 6.33 (s, 1H), 3.50 (s, 3H), 3.26 (s, 3H), 3.02 (s, 3H), 2.86 (s, 3H), 2.78 (s, 3H).

Example 58

{4-Chloro-2-[methoxy(methyl)amino]-3-phenylquinolin-6-yl}(4-chlorophenyl)(1-methyl-1H-imidazol-5-yl)methanol

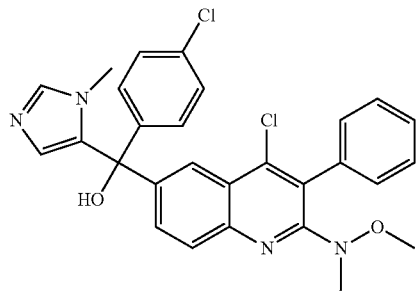 [SMILES: CON(C)c1nc2ccc(C(O)(c3ccc(Cl)cc3)c3cncn3C)cc2c(Cl)c1-c1ccccc1]

(4-Chlorophenyl)(2,4-dichloro-3-phenylquinolin-6-yl)(1-methyl-1H-imidazol-5-yl)methanol (250 mg, 0.505 mmol, Example 65), N,O-dimethylhydroxylamine hydrochloride (1.01 g, 10.1 mmol), and dimethylformamide (2 mL) were combined in a reaction tube, which was then sealed and heated to 100° C. for 48 hours. The contents were then cooled, transferred to a reparatory funnel, diluted with EtOAc and extracted with saturated, aqueous NH$_4$Cl solution, followed by deionized water (4×). The organic phase was separated and dried over MgSO$_4$, filtered and concentrated under reduced pressure. The crude material was purified via reverse phase chromatography using acetonitrile with ammonium hydroxide in water as eluent to afford the title compound. MS (ESI): mass calcd. for C$_{28}$H$_{24}$Cl$_2$N$_4$O$_2$, 518.1; m/z found, 519.2 [M+H]$^+$; $^1$H NMR (400 MHz, CD$_3$OD) δ ppm 8.14 (d, J=1.9 Hz, 1H), 7.91 (d, J=8.8 Hz, 1H), 7.70 (dd, J=8.8, 2.1 Hz, 1H), 7.67 (s, 1H), 7.47 (dd, J=11.4, 4.3 Hz, 2H), 7.39 (dt, J=4.4, 1.8 Hz, 1H), 7.36 (d, J=4.1 Hz, 4H), 7.26 (dd, J=8.2, 1.3 Hz, 2H), 6.28 (s, 1H), 3.46 (s, 3H), 3.05 (s, 3H), 2.76 (s, 3H).

Example 59

{2,4-Bis[methoxy(methyl)amino]-3-phenylquinolin-6-yl}(4-chlorophenyl)(1-methyl-1H-imidazol-5-yl)methanol

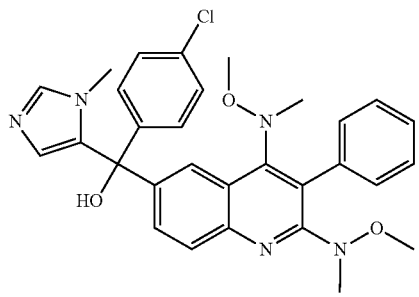 [SMILES: CON(C)c1nc2ccc(C(O)(c3ccc(Cl)cc3)c3cncn3C)cc2c(N(C)OC)c1-c1ccccc1]

Purification of the crude product from the synthesis of {4-chloro-2-[methoxy(methyl)amino]-3-phenylquinolin-6-yl}(4-chlorophenyl)(1-methyl-1H-imidazol-5-yl)methanol (Example 58) also provided the title compound. MS (ESI): mass calcd. for C$_{30}$H$_{30}$ClN$_5$O$_3$, 543.2; m/z found, 544.3 [M+H]$^+$; $^1$H NMR (400 MHz, CD$_3$OD) δ ppm 8.36 (d, J=1.8 Hz, 1H), 7.96-7.89 (m, 1H), 7.71 (dd, J=8.9, 2.2 Hz, 1H), 7.66 (s, 1H), 7.42-7.28 (m, 7H), 7.24 (d, J=6.6 Hz, 2H), 6.28 (d, J=1.0 Hz, 1H), 3.48 (s, 3H), 3.25 (s, 3H), 3.01 (s, 3H), 2.85 (s, 3H), 2.79 (s, 3H).

Example 60a (4-Chloro-2-methoxy-3-phenylquinolin-6-yl)(1-methyl-1H-imidazol-5-yl)pyrimidin-2-ylmethanol

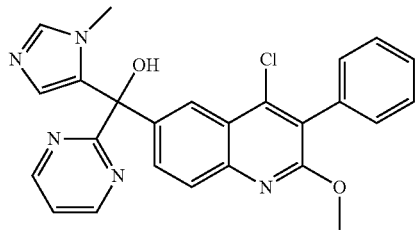 [SMILES: COc1nc2ccc(C(O)(c3ncccn3)c3cncn3C)cc2c(Cl)c1-c1ccccc1]

(2,4-Dichloro-3-phenylquinolin-6-yl)(1-methyl-1H-imidazol-5-yl)pyrimidin-2-ylmethanol (156 mg, 0.337 mmol, Example 55), toluene (2 mL), and sodium methoxide (365 mg, 6.75 mmol) were combined in a round bottom flask equipped with a stirbar and condenser under an N₂ atmosphere. The contents were heated to reflux and refluxed overnight. The reaction was cooled and the contents were transferred to a separatory funnel with EtOAc dilution, and extracted with saturated, aqueous NH₄Cl then saturated, aqueous NaHCO₃ solutions. The organic phase was separated, dried over MgSO₄, filtered and concentrated under reduced pressure. The crude material was purified via reverse phase chromatography using acetonitrile with 0.05% trifluoroacetic acid in water as eluent. The fractions from the purification containing the desired product were transferred to a separatory funnel with EtOAc and extracted with a saturated, aqueous NaHCO₃ solution. The aqueous layer was separated, extracted with EtOAc, then the combined organic phases were dried over MgSO₄, filtered and concentrated under reduced pressure to provide the title compound. MS (ESI): mass calcd. for C₂₅H₂₀ClN₅O₂, 457.1; m/z found, 458.2 [M+H]⁺; ¹H NMR (400 MHz, CDCl₃) δ ppm 8.81 (d, J=4.9 Hz, 2H), 8.48 (d, J=1.8 Hz, 1H), 7.92-7.81 (m, 2H), 7.54-7.39 (m, 4H), 7.36-7.28 (m, 3H), 6.55 (s, 1H), 6.15 (s, 1H), 3.98 (s, 3H), 3.40 (s, 3H).

(4-Chloro-2-methoxy-3-phenylquinolin-6-yl)(1-methyl-1H-imidazol-5-yl)pyrimidin-2-ylmethanol was purified on a chiralcel OD column (20 μm, Diacel) with methanol to provide two enantiomers. The first eluting enantiomer was Example 60b: MS (ESI): mass calcd. for C₂₅H₂₀ClN₅O₂, 457.1; m/z found, 458.2 [M+H]⁺; ¹H NMR (600 MHz, CD₃OD) δ ppm 8.86 (d, J=4.9 Hz, 2H), 8.41 (d, J=2.0 Hz, 1H), 7.90 (dd, J=8.8, 2.0 Hz, 1H), 7.82 (d, J=8.8 Hz, 1H), 7.63 (s, 1H), 7.46-7.41 (m, 3H), 7.41-7.37 (m, 1H), 7.29 (d, J=7.0 Hz, 2H), 6.41 (s, 1H), 3.95 (s, 3H), 3.39 (s, 3H).

Example 61

(4-Chloro-3-phenyl-2-(trifluoromethyl)quinolin-6-yl)(1-methyl-1H-imidazol-5-yl)(pyridin-2-yl)methanol.TFA

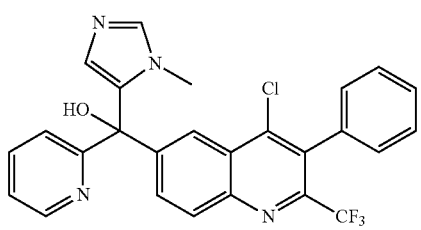 [SMILES: Cn1cncc1C(O)(c1ccc2nc(C(F)(F)F)c(-c3ccccc3)c(Cl)c2c1)c1ccccn1]

The title compound was prepared using (1-methyl-1H-imidazol-5-yl)(pyridin-2-yl)methanone (Intermediate 12: step b) in place of tert-butyl 4-nicotinoylpiperidine-1-carboxylate using the procedure described for Example 69. ¹H NMR (400 MHz, CD₃OD) δ 8.97 (s, 1H), 8.58-8.65 (m, 2H), 8.28 (d, J=9.09 Hz, 1H), 8.11 (dd, J=2.02, 9.09 Hz, 1H), 7.88-7.97 (m, 1H), 7.80 (d, J=7.58 Hz, 1H), 7.48-7.55 (m, 3H), 7.38-7.46 (m, 1H), 7.26-7.34 (m, 2H), 7.11 (s, 1H), 3.63 (s, 3H); MS m/e 495.3 [M+H]⁺.

Example 62

(4-Chloro-3-phenyl-2-(trifluoromethyl)quinolin-6-yl)(4-chlorophenyl)(1-methyl-1H-imidazol-5-yl)methanol.TFA

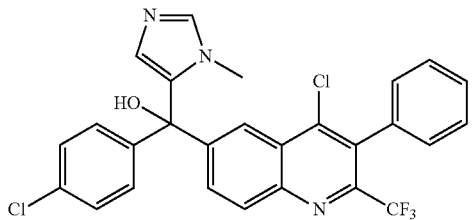

A mixture of 6-bromo-4-chloro-3-phenyl-2-(trifluoromethyl)quinoline (864 mg, 2.23 mmol, Intermediate 19: step b), (4-chlorophenyl)(1-methyl-1H-imidazol-5-yl)methanone (490 mg, 2.22 mmol, Intermediate 8: step b) and 22 mL of THF was purged with N₂ and cooled to −78° C. To the mixture was added n-BuLi (1.6 M in hexanes, 1.8 mL, 2.9 mmol) dropwise and the color changed to orange then almost black. The reaction mixture was stirred at −78° C. to 0° C. for 70 minutes, then allowed to warm up to room temperature overnight. Saturated NH₄Cl (aqueous) was added and the organic layer was separated. The aqueous layer was extracted with dichloromethane. The combined organic phases were dried (Na₂SO₄), filtered, and concentrated. The crude was purified by flash column chromatography (silica gel, 5-10% MeOH in DCM) followed by reverse phase HPLC (water/acetonitrile/0.1% TFA) to provide the title compound as a white solid. ¹H NMR (400 MHz, CD₃OD) δ 9.00 (s, 1H), 8.42 (d, J=2.02 Hz, 1H), 8.31 (d, J=8.59 Hz, 1H), 7.97 (dd, J=2.02, 9.09 Hz, 1H), 7.47-7.54 (m, 4H), 7.41-7.47 (m, 3H), 7.27-7.34 (m, 2H), 6.99 (d, J=1.52 Hz, 1H), 3.71 (s, 3H); MS m/e 528.2 [M+H]⁺.

Example 63

(4-Chloro-2-methoxy-8-methyl-3-(4-(trifluoromethoxy)phenyl)quinolin-6-yl)(1-methyl-1H-imidazol-5-yl)(6-(trifluoromethyl)pyridin-3-yl)methanol

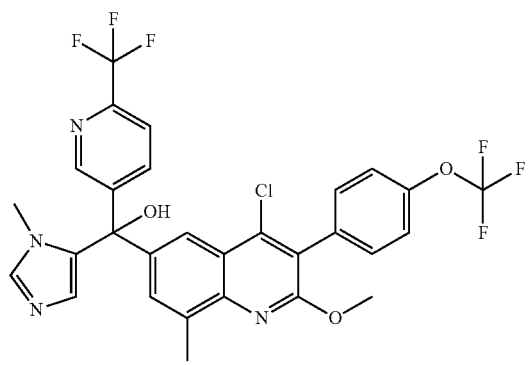 [SMILES: COc1nc2c(C)cc(C(O)(c3ccc(C(F)(F)F)nc3)c3cncn3C)cc2c(Cl)c1-c1ccc(OC(F)(F)F)cc1]

n-Butyllithium (2.0 mL, 3.202 mmol) was added to a −78° C. mixture of 6-bromo-4-chloro-2-methoxy-8-methyl-3-(4-

(trifluoromethoxy)phenyl)quinoline (1.1 g, 2.463 mmol, Intermediate 13: step d) and (1-methyl-1H-imidazol-5-yl)(6-(trifluoromethyl)pyridin-3-yl)methanone (0.691 g, 2.709 mmol, Intermediate 2: step c) in dry THF (25 mL) over a 2 minute period. After complete addition stirring was continued at −78° C. for 10 minutes then the reaction was warmed up to 0° C. and stirred for 1 hour. Saturated aqueous NH₄Cl was added and the reaction mixture slowly warmed to room temperature. Water was added and the layers were separated. The aqueous layer was extracted with EtOAc. The combined organic extracts were dried (Na₂SO₄), filtered, evaporated in vacuo and chromatographed (DCM/10% MeOH in EtOAc) to provide the product. Further purification using reverse phase HPLC (acetonitrile/water+0.1% TFA) provided the title compound. MS (ESI) 623.1 (M+H)⁺.

Example 64

(2,4-Dichloro-3-phenylquinolin-6-yl)(1-methyl-1H-imidazol-5-yl)(pyridin-2-yl)methanol

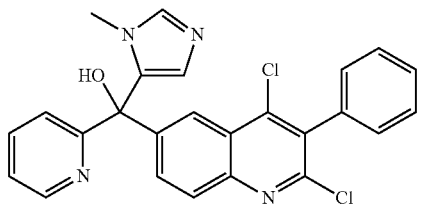 [SMILES: Cn1cncc1C(O)(c1ccc2nc(Cl)c(-c3ccccc3)c(Cl)c2c1)c1ccccn1]

A solution of n-BuLi (2.5 M in hexanes, 0.34 mL, 0.85 mmol) was added dropwise by syringe to a solution of 6-bromo-2,4-dichloro-3-phenylquinoline (305.4 mg, 0.865 mmol, Intermediate 7: step c) in dry THF (4.4 mL) at −78° C. After 1.5 minutes, a solution of (1-methyl-1H-imidazol-5-yl)(pyridin-2-yl)methanone (0.175 g, 0.936 mmol, Intermediate 12: step b) in dry THF (1.8 mL) was added dropwise. The reaction mixture was stirred for 5 minutes at −78° C., then the reaction flask was placed into an ice-water bath. After 10 minutes, the mixture was warmed to room temperature and the reaction was quenched with methanol and water. The mixture was partitioned between water and DCM. The separated aqueous phase was further extracted with DCM. The organic phase was dried (Na₂SO₄), filtered, and concentrated. The crude product was purified by flash column chromatography (silica gel, 0-10% MeOH-DCM) to provide the title compound as a white solid. ¹H NMR (500 MHz, CDCl₃) δ 8.65 (ddd, J=4.9, 1.6, 1.0 Hz, 1H), 8.30 (d, J=1.7 Hz, 1H), 8.06 (d, J=8.8 Hz, 1H), 7.86 (dd, J=8.8, 2.0 Hz, 1H), 7.73 (td, J=7.7, 1.7 Hz, 1H), 7.55-7.47 (m, 4H), 7.36-7.29 (m, 3H), 7.23 (d, J=8.0 Hz, 1H), 6.37 (d, J=1.1 Hz, 1H), 3.44 (s, 3H); MS m/e 461.1 [M+H]⁺.

Example 65

(4-Chlorophenyl)(2,4-dichloro-3-phenylquinolin-6-yl)(1-methyl-M-imidazol-5-yl)methanol

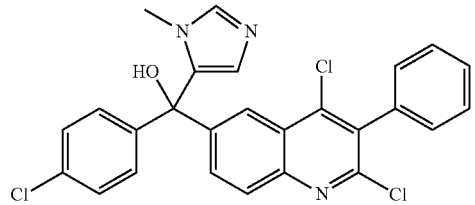 [SMILES: Cn1cncc1C(O)(c1ccc(Cl)cc1)c1ccc2nc(Cl)c(-c3ccccc3)c(Cl)c2c1]

To (4-chlorophenyl)(1-methyl-1H-imidazol-5-yl)methanone (830 mg, 3.76 mmol, Intermediate 8: step b) under an atmosphere of nitrogen was added THF (30 mL) and the mixture was heated until a solution was obtained. To 6-bromo-2,4-dichloro-3-phenylquinoline (1.21 g, 3.42 mmol, Intermediate 7: step c) under an atmosphere of nitrogen was added THF (25 mL). The resulting colorless solution was cooled in a dry ice/acetone bath. n-BuLi (1.6 M in hexane, 2.35 mL, 3.76 mmol) was added dropwise. The mixture was stirred for 5 minutes before addition of the THF solution of (4-chlorophenyl)(1-methyl-1H-imidazol-5-yl)methanone via cannula. The reaction mixture was stirred in the dry ice/acetone bath for 30 minutes, then in an ice bath for 50 minutes and at room temperature for 15 minutes, then was quenched by addition of saturated, aqueous NH₄Cl solution. The mixture was diluted with water and extracted three times with EtOAc. The organic phase was dried (Na₂SO₄), filtered, and concentrated and the residue was purified by flash column chromatography (silica gel, 0-4% MeOH-DCM) to afford the title compound. ¹H NMR (400 MHz, CDCl₃) δ ppm 8.32 (d, J=1.96 Hz, 1H), 8.02 (d, J=8.80 Hz, 1H), 7.72 (dd, J=2.20, 8.80 Hz, 1H), 7.48-7.56 (m, 3H), 7.30-7.38 (m, 7H), 6.40 (d, J=1.22 Hz, 1H), 3.39 (s, 3H); MS m/e 494.1 (M+H)⁺.

Example 66

(2,4-Dichloro-3-phenylquinolin-6-yl)(1-methyl-1H-imidazol-5-yl)[6-(trifluoromethyl)pyridin-3-yl]methanol.TFA

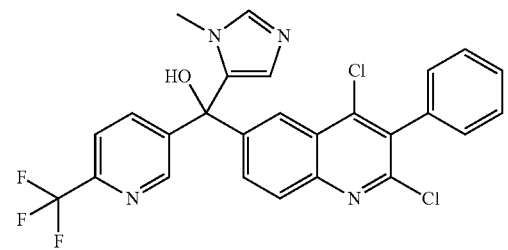 [SMILES: Cn1cncc1C(O)(c1ccc(C(F)(F)F)nc1)c1ccc2nc(Cl)c(-c3ccccc3)c(Cl)c2c1]

(1-Methyl-1H-imidazol-5-yl)(6-(trifluoromethyl)pyridin-3-yl)methanone (3.00 g, 8.50 mmol, Intermediate 2: step c) and 6-bromo-2,4-dichloro-3-phenylquinoline (2.32 g, 9.08 mmol, Intermediate 7: step c) were dissolved in THF (250 mL) under an N₂ atmosphere in a dry round bottom flask, then cooled to −78° C. in dry ice/acetone bath. n-BuLi (2.5 M in hexanes, 3.24 mL, 8.09 mmol) was then added dropwise via syringe over approximately 2 minutes. The contents were stirred at −78° C. for approximately 2.5 hours, then the dry ice bath was removed and the contents were allowed to warm to room temperature. The reaction was then cooled to 0° C. in an ice water bath and quenched with a saturated, aqueous NH₄Cl solution, then transferred to a reparatory funnel with EtOAc dilution. The organic phase was separated, then the aqueous layer was back extracted twice with EtOAc, then the combined organic phases were dried over MgSO₄, filtered and concentrated under reduced pressure. The crude product was purified by RP-HPLC (40-80% CH₃CN—H₂O, 0.1% TFA) to afford the title compound as a yellow solid. MS (ESI): mass calcd. for C₂₆H₁₇Cl₂F₃N₄O, 528.1; m/z found, 529.4 [M+H]⁺; ¹H NMR (600 MHz, CD₃OD) δ ppm 8.80 (d, J=2.1 Hz, 1H), 8.35 (d, J=1.8 Hz, 1H), 8.07-8.03 (m, 2H), 7.88 (dd, J=8.9, 2.1 Hz, 1H), 7.85 (d, J=8.3 Hz, 1H), 7.76 (s, 1H), 7.54-7.50 (m, 3H), 7.37-7.33 (m, 2H), 6.39 (d, J=1.1 Hz, 1H), 3.48 (s, 3H).

Example 67

(2,4-Dichloro-3-phenylquinolin-6-yl)(2,4-dimethylthiazol-5-yl)(1-methyl-1H-1,2,3-triazol-5-yl)methanol

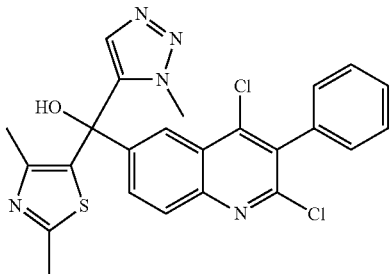 [SMILES: Cc1nc(C)c(C(O)(c2ccc3nc(Cl)c(-c4ccccc4)c(Cl)c3c2)c2cnnn2C)s1]

To a flask containing 6-bromo-2,4-dichloro-3-phenylquinoline (750 mg, 2.12 mmol, Intermediate 7: step c) was added THF (30 mL) to give a homogeneous clear solution. The solution was cooled in a dry ice bath and n-BuLi (2.5 M in hexanes, 0.840 mL, 2.1 mmol) was introduced. After 2 minutes, a solution of (2,4-dimethylthiazol-5-yl)(1-methyl-1H-1,2,3-triazol-5-yl)methanone (600 mg, 2.7 mmol, Intermediate 16: step b) in 18 mL THF was added. The dry-ice bath was replaced with a 0° C. ice-bath and after 45 minutes the reaction mixture was quenched with NH$_4$Cl solution and the aqueous portion was extracted with EtOAc (4×50 mL). The combined organics were washed with brine, dried over MgSO$_4$, filtered and concentrated. The crude material was triturated with Et$_2$O to afford the title compound as a light tan solid. The mother liquors were chromatographed on silica gel (2% MeOH/DCM increasing to 5% MeOH) which provided additional title compound. $^1$H NMR (500 MHz, CDCl$_3$) δ 8.32 (d, J=2.0 Hz, 1H), 8.09 (d, J=8.9 Hz, 1H), 7.73 (dd, J=8.9, 2.2 Hz, 1H), 7.58-7.46 (m, 3H), 7.20-7.33 (m, 2H), 7.20 (s, 1H), 4.38 (s, 1H), 3.94 (s, 3H), 2.58 (s, 3H), 2.16 (s, 3H); MS (ESI); mass calcd. for C$_{24}$H$_{19}$Cl$_2$N$_5$OS, 495.1, m/z found 496.1 [M+H]$^+$.

Example 68

(2,4-Dichloro-3-phenylquinolin-6-yl)(2,4-dimethylthiazol-5-yl)(1-methyl-1H-imidazol-5-yl)methanol

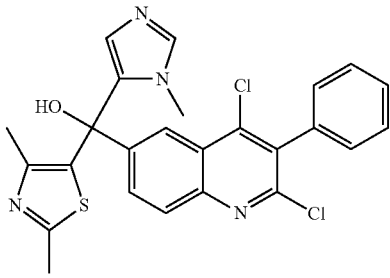 [SMILES: Cc1nc(C)c(C(O)(c2ccc3nc(Cl)c(-c4ccccc4)c(Cl)c3c2)c2cncn2C)s1]

To a flask containing 6-bromo-2,4-dichloro-3-phenylquinoline (450 mg, 1.27 mmol, Intermediate 7: step c) was added THF (15 mL) to give a homogeneous clear solution. The solution was cooled in a dry ice bath and n-BuLi (2.5 M in hexanes, 0.45 mL, 1.13 mmol) was added. After 2 minutes, a solution of (2,4-dimethylthiazol-5-yl)(1-methyl-1H-imidazol-5-yl)methanone (350 mg, 1.58 mmol, Intermediate 17: step b) in 4 mL THF was introduced. The dry-ice bath was replaced with a 0° C. bath and after 35 minutes the reaction mixture was quenched with aqueous NH$_4$Cl solution and the aqueous portion was extracted with EtOAc (4×50 mL). The combined organics were washed with brine, dried over MgSO$_4$, filtered and concentrated. Chromatography on silica gel (20% acetone-DCM increasing to 5% MeOH-DCM) afforded the title compound as a pale yellowish solid. $^1$H NMR (500 MHz, CDCl$_3$) δ 8.35 (d, J=1.9 Hz, 1H), 8.03 (d, J=8.8 Hz, 1H), 7.79 (dd, J=8.8, 2.1 Hz, 1H), 7.59-7.41 (m, 3H), 7.40-7.31 (m, 2H), 7.28 (d, J=6.4 Hz, 1H), 6.44 (s, 1H), 5.46 (s, 1H), 3.48 (s, 3H), 2.56 (s, 3H), 2.13 (s, 3H); MS (ESI): mass calcd. for C$_{25}$H$_{20}$Cl$_2$N$_4$OS, 494.1, m/z found 495.0 [M+H]$^+$.

Example 69 tert-Butyl 4-((4-chloro-3-phenyl-2-(trifluoromethyl)quinolin-6-yl)(hydroxy)(pyridin-3-yl)methyl)piperidine-1-carboxylate

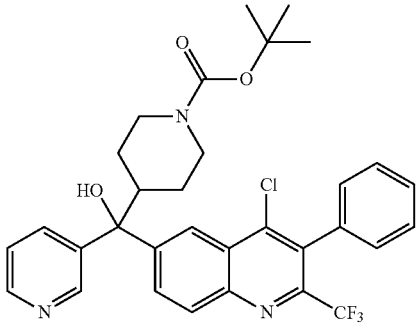 [SMILES: CC(C)(C)OC(=O)N1CCC(C(O)(c2cccnc2)c2ccc3nc(C(F)(F)F)c(-c4ccccc4)c(Cl)c3c2)CC1]

To a solution of 4-chloro-6-iodo-3-phenyl-2-(trifluoromethyl)quinoline (Intermediate 20: step b, containing about 13% molar of 4-chloro-3-phenyl-2-(trifluoromethyl)quinoline as impurity, 340 mg) in THF (4 mL) at −78° C. under N$_2$ was added iPrMgCl (2.0 M in THF, 0.40 mL, 0.8 mmol). After stirring for 8 minutes, the cooling bath was removed, and stirring was continued for 20 minutes, then tert-butyl 4-nicotinoylpiperidine-1-carboxylate (225 mg, 0.770 mmol, Intermediate 21) was added in neat. After stirring at room temperature overnight, the mixture became clear brown and was heated at 50° C. for 1.5 hours. The mixture was quenched with saturated NH$_4$Cl aqueous solution, and extracted with EtOAc. The extracts were dried over Na$_2$SO$_4$, filtered, and concentrated. The crude mixture was purified by flash column chromatography (silica gel, 20-100% EtOAc in heptanes) to provide the title compound. $^1$H NMR (400 MHz, CDCl$_3$) δ 9.17-9.35 (m, 1H), 8.50-8.88 (m, 2H), 8.29 (d, J=7.58 Hz, 1H), 8.24 (d, J=8.59 Hz, 1H), 7.82-8.00 (m, 1H), 7.47-7.57 (m, 4H), 7.21-7.33 (m, 2H), 4.08-4.26 (m, 2H), 2.69-2.99 (m, 3H), 1.82-1.92 (m, 1H), 1.53-1.80 (m, 3H), 1.47 (s, 4.5H), 1.41 (s, 4.5H); MS m/e 598.3 [M+H]⁺.

Example 70

(4-Chloro-3-phenyl-2-(trifluoromethyl)quinolin-6-yl)(piperidin-4-yl)(pyridin-3-yl)methanol

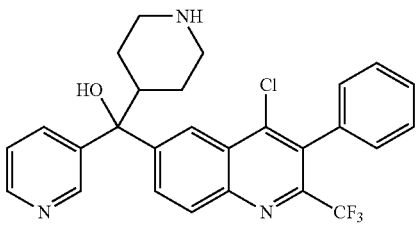 [SMILES: OC(c1cccnc1)(c1ccc2nc(C(F)(F)F)c(-c3ccccc3)c(Cl)c2c1)C1CCNCC1]

A solution of tert-butyl 4-((4-chloro-3-phenyl-2-(trifluoromethyl)quinolin-6-yl)(hydroxy)(pyridin-3-yl)methyl)piperidine-1-carboxylate (313 mg, 0.520 mmol, Example 69) in DCM (6 mL) was treated with 1.8 mL of TFA, stirred for 3 hours, and concentrated. The residue was partitioned between saturated NaHCO₃ aqueous solution and DCM. The organic layer was dried (Na₂SO₄), filtered and concentrated to dryness to provide the title compound as a light brown solid. ¹H NMR (400 MHz, CDCl₃) δ 8.86 (s, 1H), 8.55 (s, 1H), 8.44 (d, J=4.55 Hz, 1H), 8.21 (d, J=9.09 Hz, 1H), 7.89-7.96 (m, 2H), 7.46-7.53 (m, 4H), 7.23-7.32 (m, 2H), 3.23-3.36 (m, 2H), 2.77-2.91 (m, 3H), 1.66-1.86 (m, 4H).

Example 71

4-Chloro-6-((4-chlorophenyl)(1-methyl-1H-imidazol-5-yl)methyl)-N,N-dimethyl-3-phenylquinolin-2-amine

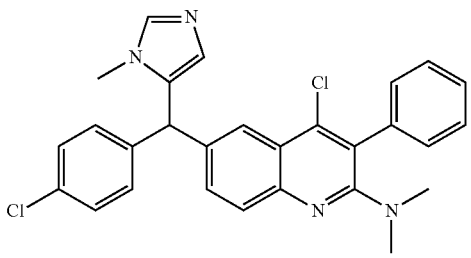 [SMILES: CN(C)c1nc2ccc(C(c3ccc(Cl)cc3)c3cncn3C)cc2c(Cl)c1-c1ccccc1]

To (4-chloro-2-(dimethylamino)-3-phenylquinolin-6-yl)(4-chlorophenyl)(1-methyl-1H-imidazol-5-yl)methanol (83.6 mg, 0.166 mmol, Example 90) in NMP (1.5 mL), was added copper (I) cyanide (16.4 mg, 0.183 mmol). The mixture was heated by microwave irradiation for 10 minutes at 120° C. The mixture was partitioned between MTBE and saturated aqueous NH₄OH. The organic phase was washed with water. The organic phase was dried (Na₂SO₄), filtered, and concentrated in vacuo. The residue was purified by RP-HPLC (10-90% CH₃CN—H₂O, 0.1% TFA) and fractions were converted to the corresponding free base by extraction from saturated aqueous NaHCO₃ with DCM. Further purification by flash column chromatography (silica gel, 10-70% acetone-DCM) afforded the title compound. ¹H NMR (400 MHz, CDCl₃) δ 7.82 (d, J=1.96 Hz, 1H), 7.76 (d, J=8.80 Hz, 1H), 7.55 (br. s., 1H), 7.43-7.50 (m, 2H), 7.34-7.42 (m, 4H), 7.30 (d, J=8.56 Hz, 2H), 7.12 (d, J=8.56 Hz, 2H), 6.48 (br. s., 1H), 5.45 (s, 1H), 3.37 (s, 3H), 2.71 (s, 6H); MS m/e 487.0 (M+H)⁺.

Example 72

4-Chloro-6-((4-chlorophenyl)(1-methyl-1H-imidazol-5-yl)methyl)-3-phenylquinoline-2-carbonitrile.TFA

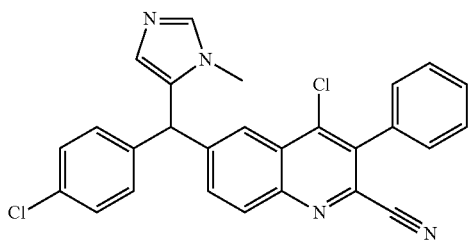 [SMILES: Cn1cncc1C(c1ccc(Cl)cc1)c1ccc2nc(C#N)c(-c3ccccc3)c(Cl)c2c1]

Copper (I) cyanide (44.4 mg, 0.496 mmol) was added to a colorless solution of (4-chlorophenyl)(2,4-dichloro-3-phenylquinolin-6-yl)(1-methyl-1H-imidazol-5-yl)methanol (123 mg, 0.248 mmol, Example 65) in NMP (1 mL). The mixture was stirred until CuCN dissolved, then was heated by microwave irradiation at 145° C. for 40 minutes. The mixture was partitioned between saturated aqueous NH₄OH and MTBE. The aqueous phase was extracted twice with MTBE. The organic phases were combined, dried (Na₂SO₄), filtered, and concentrated in vacuo. The residue was purified by RP-HPLC (10-90% CH₃CN—H₂O, 0.1% TFA) to afford the title compound. ¹H NMR (400 MHz, CDCl₃) δ 8.68 (s, 1H), 8.26 (d, J=8.80 Hz, 1H), 8.05 (d, J=1.96 Hz, 1H), 7.66 (dd, J=1.96, 8.80 Hz, 1H), 7.52-7.62 (m, 3H), 7.37-7.49 (m, 4H), 7.12 (d, J=8.31 Hz, 2H), 6.78 (s, 1H), 5.63 (s, 1H), 3.62 (s, 3H); MS m/e 469.0 (M+H)⁺.

Example 73

(2,4-Dichloro-3-(2-chlorophenyl)quinolin-6-yl)(phenyl)(pyridin-4-yl)methanol

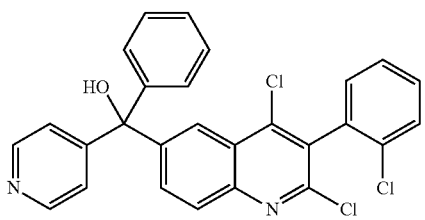 [SMILES: OC(c1ccccc1)(c1ccncc1)c1ccc2nc(Cl)c(-c3ccccc3Cl)c(Cl)c2c1]

To a solution of 6-bromo-2,4-dichloro-3-(2-chlorophenyl)quinoline (387.5 mg, 1 mmol, Intermediate 32: step c) in THF (15 mL) at −78° C. was added nBuLi (2.5 M in hexanes, 0.52 mL, 1.3 mmol) dropwise and the resulting mixture stirred at −78° C. for 15 minutes. Then, phenyl(pyridin-4-yl)methanone (183 mg, 1 mmol) was added, and the resulting mixture stirred at −78° C. for 15 minutes. The dry ice-acetone bath was then removed and the mixture was allowed to warm to room temperature over 2 hours. The reaction was quenched by the addition of water (10 mL) and then extracted with DCM (2×20 mL). The organics were combined, dried (MgSO$_4$), filtered and concentrated to dryness. The residue was purified by FCC (1:20 MeOH/DCM) to provide the title compound. MS (ESI): mass calcd. for C$_{27}$H$_{17}$Cl$_3$N$_2$O, 490.0, m/z found 491.0 [M+H]$^+$. $^1$H NMR (300 MHz, CD$_3$OD) δ 8.54 (dd, J=4.7, 1.7 Hz, 2H), 8.25-8.22 (m, 1H), 8.06-8.02 (m, 1H), 7.93-7.88 (m, 1H), 7.64-7.60 (m, 1H), 7.57-7.52 (m, 1H), 7.52-7.50 (m, 1H), 7.50-7.47 (m, 2H), 7.42-7.33 (m, 6H).

Example 74

(2,4-Dichloro-3-(2-chlorophenyl)quinolin-6-yl)(oxazol-2-yl)(phenyl)methanol

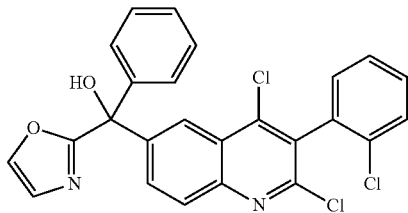 [SMILES: OC(c1ccccc1)(c1ccc2nc(Cl)c(-c3ccccc3Cl)c(Cl)c2c1)c1ncco1]

To a solution of 6-bromo-2,4-dichloro-3-(2-chlorophenyl)quinoline (387.5 mg, 1 mmol, Intermediate 32: step c) in THF (15 mL) at −78° C. was added nBuLi (2.5 M in hexanes, 0.52 mL, 1.3 mmol) dropwise and the resulting mixture stirred at −78° C. for 15 minutes. Then, phenyl(pyridin-4-yl)methanone (183 mg, 1 mmol) was added, and the resulting mixture stirred at −78° C. for 15 minutes. The dry ice-acetone bath was then removed and the mixture was allowed to warm to room temperature over 2 hours. The reaction was quenched by the addition of water (10 mL) and then extracted with DCM (2×20 mL). The organics were combined, dried (MgSO$_4$), filtered and concentrated to dryness. The residue was purified by FCC (1:5 EtOAc/petroleum ether) to provide the title compound. MS (ESI): mass calcd. for C$_{25}$H$_{15}$Cl$_3$N$_2$O$_2$, 480.0, m/z found 481.0 [M+H]$^+$. $^1$H NMR (300 MHz, CD$_3$OD) δ 8.34 (d, J=1.8 Hz, 1H), 8.03-7.89 (m, 3H), 7.64-7.57 (m, 1H), 7.56-7.44 (m, 2H), 7.42-7.29 (m, 6H), 7.23 (s, 1H).

Example 75

6-((3-Chlorophenyl)(hydroxy)(6-(trifluoromethyl)pyridin-3-yl)methyl)-3-phenylquinoline-2-carbonitrile

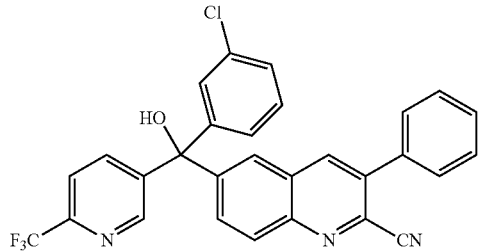 [SMILES: N#Cc1nc2ccc(C(O)(c3ccc(C(F)(F)F)nc3)c3cccc(Cl)c3)cc2cc1-c1ccccc1]

A pressure tube containing (3-chlorophenyl)(2,4-dichloro-3-phenylquinolin-6-yl)(6-(trifluoromethyl)pyridin-3-yl)methanol (94 mg, 0.17 mmol, Intermediate 22: step b), Pd$_2$(dba)$_3$ (8.0 mg, 0.0087 mmol), 1,1'-bis(diphenylphosphino)ferrocene (dppf, 10 mg, 0.018 mmol), zinc cyanide (25 mg, 0.21 mmol), and zinc nanopowder (3.0 mg, 0.046 mmol) in N,N-dimethylacetamide (1 mL) was sparged with nitrogen for 5 minutes, and then heated at 120° C. for 1 hour followed by 100° C. for 3 hours. The mixture was allowed to cool to room temperature and filtered through a syringe filter. The filtrate was concentrated in vacuo, then EtOAc and NH$_4$OH (aqueous) were added. The organic layer was separated, and the aqueous layer was extracted with EtOAc. The combined organic layers were dried (Na$_2$SO$_4$), filtered, and concentrated. The residue was purified by flash column chromatography (silica gel column, 30-50% EtOAc in heptane), and then by reverse phase HPLC (water/acetonitrile/0.1% TFA) to provide the title compound as a by-product. $^1$H NMR (400 MHz, CDCl$_3$) δ 8.76 (d, J=2.02 Hz, 1H), 8.25 (s, 1H), 8.20 (d, J=9.60 Hz, 1H), 7.93 (dd, J=2.02, 8.08 Hz, 1H), 7.75-7.79 (m, 2H), 7.71 (d, J=8.08 Hz 1H), 7.60-7.65 (m, 2H), 7.51-7.58 (m, 3H), 7.32-7.40 (m, 3H), 7.15 (dt, J=1.52, 7.58 Hz, 1H).

Example 76

6-((3-Chlorophenyl)(hydroxy)(2-(trifluoromethyl)pyridin-4-yl)methyl)-3-phenylquinoline-2,4-dicarbonitrile

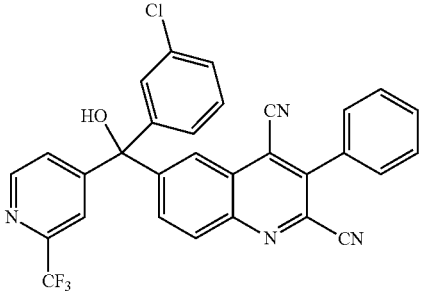 [SMILES: N#Cc1nc2ccc(C(O)(c3cccc(Cl)c3)c3ccnc(C(F)(F)F)c3)cc2c(C#N)c1-c1ccccc1]

The title compound was prepared using (3-chlorophenyl)(2,4-dichloro-3-phenylquinolin-6-yl)(2-(trifluoromethyl)pyridin-4-yl)methanol (Example 77) in place of (3-chlorophenyl)(2,4-dichloro-3-phenylquinolin-6-yl)(6-(trifluoromethyl)pyridin-3-yl)methanol (Intermediate 22: step b) according to the procedure described in Example 75. $^1$H NMR (400 MHz, CDCl$_3$) δ 8.81 (d, J=5.56 Hz, 1H), 8.46 (d, J=1.52 Hz, 1H), 8.31 (d, J=9.09 Hz, 1H), 7.90 (d, J=1.52 Hz, 1H), 7.84 (dd, J=2.02, 8.59 Hz, 1H), 7.60-7.67 (m, 5H), 7.58 (dd, J=1.52, 5.05 Hz, 1H), 7.35-7.46 (m, 2H), 7.23-7.27 (m, 1H), 7.10 (dt, J=1.52, 8.08 Hz, 1H).

Example 77

(3-Chlorophenyl)(2,4-dichloro-3-phenylquinolin-6-yl)(2-(trifluoromethyl)pyridin-4-yl)methanol

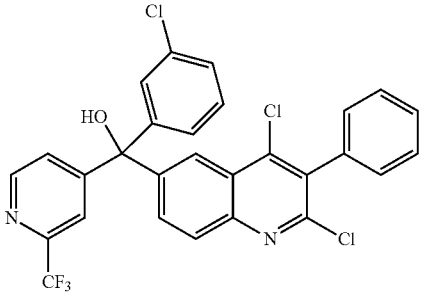

To a solution of 6-bromo-2,4-dichloro-3-phenylquinoline (286 mg, 0.810 mmol, Intermediate 7: step c) and (3-chlorophenyl)(2-(trifluoromethyl)pyridin-4-yl)methanone (231 mg, 0.810 mmol, Intermediate 23: step b) in THF (6 mL) at −78° C. was added 1.6 M n-BuLi in hexane (0.76 mL, 1.22 mmol). The mixture was stirred at −78° C. to 10° C. for 2 hours and then quenched with NH₄Cl (aqueous). The organic layer was separated, and the aqueous layer was extracted with CH₂Cl₂. The combined organic phases were dried (Na₂SO₄), filtered, concentrated, and purified by flash column chromatography (40 g silica gel column, 10-40% EtOAc in heptane) to afford the title compound as a yellow solid. ¹H NMR (400 MHz, CDCl₃) δ 8.74 (d, J=5.56 Hz, 1H), 8.23 (d, J=2.53 Hz, 1H), 8.09 (d, J=9.09 Hz, 1H), 7.84 (d, J=1.52 Hz, 1H), 7.68 (dd, J=2.02, 8.59 Hz, 1H), 7.46-7.56 (m, 4H), 7.30-7.40 (m, 4H), 7.25-7.28 (m, 1H), 7.13 (dt, J=1.52, 7.58 Hz, 1H).

Example 78

(2,4-Dichloro-3-phenylquinolin-6-yl)(1-methylpiperidin-4-yl)(pyridin-3-yl)methanol.TFA

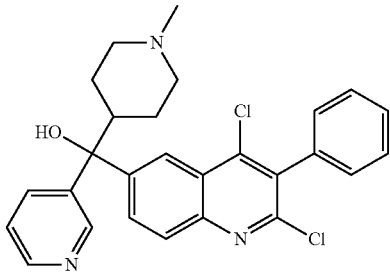 [SMILES: CN1CCC(C(O)(c2cccnc2)c2ccc3nc(Cl)c(-c4ccccc4)c(Cl)c3c2)CC1]

To a mixture of (2,4-dichloro-3-phenylquinolin-6-yl)(piperidin-4-yl)(pyridin-3-yl)methanol.TFA (15 mg, 0.022 mmol, Example 91), formaldehyde (0.010 mL, 0.13 mmol, 37% in water), and MeOH (1 mL) was added NaCNBH₃ (4.0 mg, 0.063 mmol). After stirring at room temperature overnight, the mixture was concentrated and purified by reverse phase HPLC (water/acetonitrile/0.1% TFA) to provide the title compound as a white solid. ¹H NMR (400 MHz, CD₃OD) δ 8.97 (s, 1H), 8.56-8.62 (m, 2H), 8.44 (d, J=8.31 Hz, 1H), 8.03 (s, 2H), 7.70-7.76 (m, 1H), 7.47-7.57 (m, 3H), 7.33 (d, J=6.85 Hz, 2H), 3.50-3.60 (m, 2H), 3.03-3.19 (m, 3H), 2.86 (s, 3H), 1.82-1.98 (m, 2H), 1.64-1.77 (m, 2H); MS m/e 478.0 [M+H]⁺.

Example 79

(3-Chlorophenyl)(2-isopropoxy-3-phenylquinolin-6-yl)(pyridin-3-yl)methanol.TFA

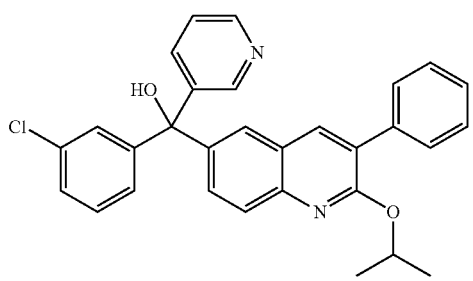 [SMILES: CC(C)Oc1nc2ccc(C(O)(c3cccnc3)c3cccc(Cl)c3)cc2cc1-c1ccccc1]

A mixture of (3-chlorophenyl)(2,4-dichloro-3-phenylquinolin-6-yl)(pyridin-3-yl)methanol (21 mg, 0.043 mmol, Intermediate 24) and NaOiPr (11 mg, 0.13 mmol) in iPrOH (0.4 mL) was heated in a sealed tube at 80° C. for 5 hours. More NaOiPr (15 mg, 0.18 mmol) was added and the mixture was heated at the same temperature for 21 hours. After cooling to room temperature, the mixture was purified by reverse phase HPLC (water/acetonitrile/0.1% TFA) to provide the title compound as a by-product. ¹H NMR (400 MHz, CD₃OD) δ 8.86 (s, 1H), 8.75-8.81 (m, 1H), 8.52 (d, J=8.31 Hz, 1H), 8.03 (s, 1H), 7.97-8.03 (m, 1H), 7.82 (d, J=8.80 Hz, 1H), 7.65 (d, J=2.20 Hz, 1H), 7.56-7.63 (m, 3H), 7.46-7.48 (m, 1H), 7.33-7.45 (m, 5H), 7.25-7.29 (m, 1H), 5.59-5.66 (m, 1H), 1.38 (d, J=6.36 Hz, 6H).

Example 80

(4-Butyl-2-isopropoxy-3-phenylquinolin-6-yl)(1-methyl-1H-imidazol-5-yl)(pyridin-4-yl)methanol.TFA

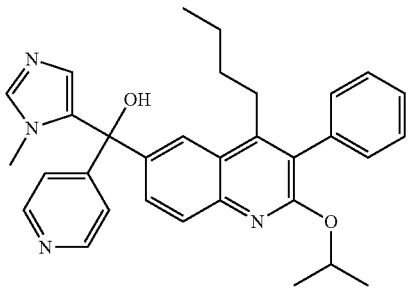 [SMILES: CCCCc1c(-c2ccccc2)c(OC(C)C)nc2ccc(C(O)(c3ccncc3)c3cncn3C)cc12]

A mixture of (4-butyl-2-chloro-3-phenylquinolin-6-yl)(1-methyl-1H-imidazol-5-yl)(pyridin-4-yl)methanol.TFA (16 mg, 0.023 mmol, Intermediate 26) and NaOiPr (19 mg, 0.23 mmol) in iPrOH (0.4 mL) was heated in a sealed tube at 80° C. for 17 hours. More NaOiPr (7.0 mg, 0.085 mmol) was added and the mixture was heated at the same temperature for 64 hours. After cooling to room temperature, the mixture was purified by reverse phase HPLC (water/acetonitrile/0.1% TFA) to provide the title compound. ¹H NMR (400 MHz, CD₃OD) δ 9.06 (s, 1H), 8.78 (d, J=6.57 Hz, 2H), 7.86-7.90 (m, 4H), 7.67 (dd, J=2.02, 9.09 Hz, 1H), 7.36-7.47 (m, 3H), 7.16-7.20 (m, 2H), 7.12 (d, J=1.52 Hz, 1H), 5.44-5.52 (m, 1H), 3.72 (s, 3H), 2.66-2.74 (m, 2H), 1.34-1.44 (m, 2H), 1.22 (d, J=6.06 Hz, 6H), 1.12-1.19 (m, 2H), 0.73 (t, J=7.33 Hz, 3H); MS m/e 507.3 [M+H]⁺.

Example 81

(3-Chlorophenyl)(2,4-diethoxy-3-phenylquinolin-6-yl)(pyridin-3-yl)methanol.TFA

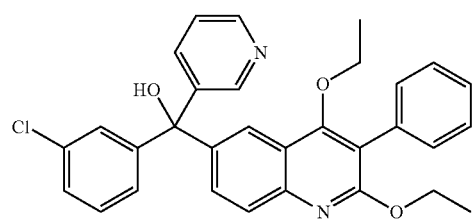 [SMILES: CCOc1nc2ccc(C(O)(c3cccnc3)c3cccc(Cl)c3)cc2c(OCC)c1-c1ccccc1]

A mixture of (3-chlorophenyl)(2,4-dichloro-3-phenylquinolin-6-yl)(pyridin-3-yl)methanol (27 mg, 0.055 mmol, Intermediate 24) and NaOEt (0.30 mL, 3.8 mmol, 21% wt. in EtOH) was heated in a sealed tube at 82° C. for 24 hours. After cooling to room temperature, the mixture was purified by reverse phase HPLC (water/acetonitrile/0.1% TFA) to provide the title compound. $^1$H NMR (400 MHz, CD$_3$OD) δ 8.89 (s, 1H), 8.81 (s, 1H), 8.55 (d, J=8.07 Hz, 1H), 8.05 (br. s., 1H), 7.87 (s, 1H), 7.84 (d, J=8.80 Hz, 1H), 7.61 (d, J=7.09 Hz, 1H), 7.49 (s, 1H), 7.33-7.45 (m, 7H), 7.29 (br. s., 1H), 4.47 (q, J=7.09 Hz, 2H), 3.51-3.63 (m, 2H), 1.30 (t, J=6.97 Hz, 3H), 0.95 (t, J=7.09 Hz, 3H).

Example 82

(4-Chloro-2-(methyl(2-(methylamino)ethyl)amino)-3-phenylquinolin-6-yl)(1-methyl-1H-imidazol-5-yl)(pyridin-4-yl)methanol.TFA

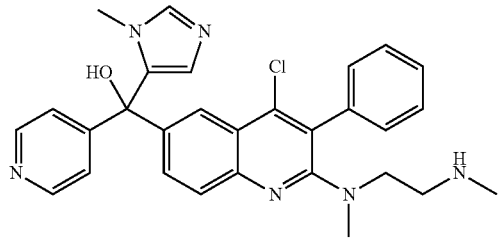 [SMILES: CNCCN(C)c1nc2ccc(C(O)(c3ccncc3)c3cncn3C)cc2c(Cl)c1-c1ccccc1]

A mixture of (2,4-dichloro-3-phenylquinolin-6-yl)(1-methyl-1H-imidazol-5-yl)(pyridin-4-yl)methanol.TFA (18 mg, 0.026 mmol, Intermediate 25: step c) and N$^1$,N$^2$-dimethylethane-1,2-diamine (500 mg, 5.67 mmol) was heated in a sealed tube at 80° C. for 24 hours. After cooling to room temperature, the mixture was purified by reverse phase HPLC (water/acetonitrile/0.1% TFA) to provide the title compound. $^1$H NMR (400 MHz, CD$_3$OD) δ 9.09 (s, 1H), 8.87 (br. s., 2H), 8.25 (d, J=2.02 Hz, 1H), 8.09 (d, J=6.57 Hz, 2H), 7.90 (d, J=9.09 Hz, 1H), 7.72 (dd, J=2.02, 8.59 Hz, 1H), 7.49-7.59 (m, 2H), 7.43-7.49 (m, 1H), 7.35-7.43 (m, 2H), 7.21 (d, J=1.52 Hz, 1H), 3.76-3.88 (m, 2H), 3.70 (s, 3H), 3.22-3.29 (m, 2H), 2.76 (s, 3H), 2.51 (s, 3H); MS m/e 513.0 [M+H]$^+$.

Example 83

2-((4-Chloro-6-(hydroxy(1-methyl-1H-imidazol-5-yl)(pyridin-4-yl)methyl)-3-phenylquinolin-2-yl)(methyl)amino)ethanol.TFA

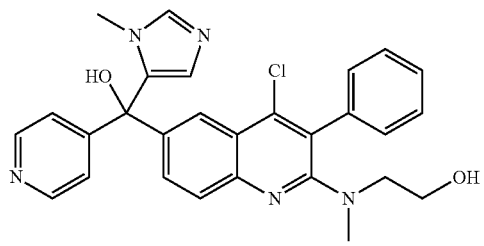 [SMILES: CN(CCO)c1nc2ccc(C(O)(c3ccncc3)c3cncn3C)cc2c(Cl)c1-c1ccccc1]

A mixture of (2,4-dichloro-3-phenylquinolin-6-yl)(1-methyl-1H-imidazol-5-yl)(pyridin-4-yl)methanol.TFA (20 mg, 0.029 mmol, Intermediate 25: step c) and 2-(methylamino) ethanol (408 mg, 5.43 mmol) was heated in a sealed tube at 80° C. for 16 hours. After cooling to room temperature, the mixture was purified by reverse phase HPLC (water/acetonitrile/0.1% TFA) to provide the title compound. $^1$H NMR (400 MHz, CD$_3$OD) δ 9.08 (s, 1H), 8.81 (br. s., 2H), 8.37 (s, 1H), 7.97 (d, J=6.06 Hz, 2H), 7.89 (s, 2H), 7.59-7.64 (m, 1H), 7.52-7.58 (m, 2H), 7.42-7.47 (m, 2H), 7.21 (d, J=1.52 Hz, 1H), 3.81 (t, J=4.55 Hz, 2H), 3.69 (s, 3H), 3.64 (t, J=4.55 Hz, 2H), 2.78 (s, 3H); MS m/e 500.0 [M+H]$^+$.

Example 84

(4-Chloro-2-(dimethylamino)-3-phenylquinolin-6-yl)(pyridin-2-yl)(pyridin-4-yl)methanol.TFA

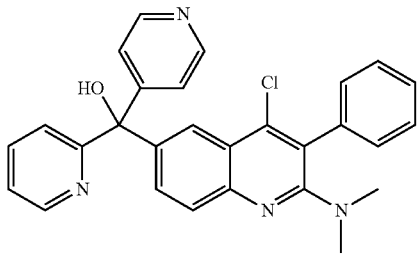 [SMILES: CN(C)c1nc2ccc(C(O)(c3ccncc3)c3ccccn3)cc2c(Cl)c1-c1ccccc1]

A mixture of (2,4-dichloro-3-phenylquinolin-6-yl)(pyridin-2-yl)(pyridin-4-yl)methanol.TFA (35 mg, 0.051 mmol, Intermediate 27) and dimethylamine (0.8 mL, 1.6 mmol, 2.0 M in MeOH) was heated in a sealed tube at 80° C. for 4.5 days. After cooling to room temperature, the mixture was purified by reverse phase HPLC (water/acetonitrile/0.1% TFA) to provide the title compound. $^1$H NMR (400 MHz, CD$_3$OD) δ 8.81 (d, J=7.09 Hz, 2H), 8.57-8.61 (m, 1H), 8.20-8.26 (m, 3H), 8.06 (d, J=8.80 Hz, 1H), 7.92-7.98 (m, 1H), 7.85-7.92 (m, 2H), 7.50-7.61 (m, 3H), 7.37-7.47 (m, 3H), 3.00 (s, 6H).

Example 85

(2-Chloro-4-(dimethylamino)-3-phenylquinolin-6-yl)(1-methyl-1H-imidazol-5-yl)(pyridin-2-yl)methanol.TFA

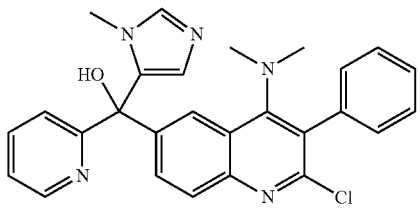 [SMILES: CN(C)c1c(-c2ccccc2)c(Cl)nc2ccc(C(O)(c3ccccn3)c3cncn3C)cc12]

A mixture of (2,4-dichloro-3-phenylquinolin-6-yl)(1-methyl-1H-imidazol-5-yl)(pyridin-2-yl)methanol (28 mg, 0.41 mmol, Example 64) and dimethylamine (0.8 mL, 1.6 mmol, 2.0 M in MeOH) was heated in a sealed tube at 80° C. for 4.5 days. After cooling to room temperature, the mixture was purified by reverse phase HPLC (water/acetonitrile/0.1% TFA) to afford the title compound. $^1$H NMR (400 MHz, CD$_3$OD) δ 8.94 (s, 1H), 8.59-8.64 (m, 1H), 8.18-8.20 (m, 1H), 7.87-7.96 (m, 3H), 7.77 (d, J=8.07 Hz, 1H), 7.41-7.53

(m, 4H), 7.25-7.32 (m, 2H), 7.03 (d, J=1.71 Hz, 1H), 3.64 (s, 3H), 2.69 (s, 6H); MS m/e 470.0 [M+H]+.

Example 86

(2,4-Dichloro-3-phenylquinolin-6-yl)(2-fluoropyridin-4-yl)(1-methyl-1H-imidazol-2-yl)methanol

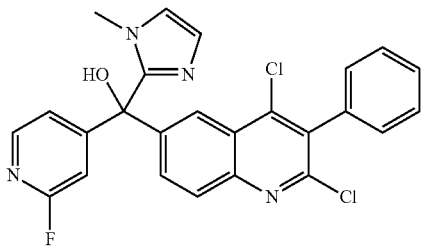 [SMILES: Cn1ccnc1C(O)(c1ccnc(F)c1)c1ccc2nc(Cl)c(-c3ccccc3)c(Cl)c2c1]

The title compound was prepared using (2-fuoropyridin-4-yl)(1-methyl-1H-imidazol-2-yl)methanone (Intermediate 28: step b) in place of (3-chlorophenyl)(2-(trifluoromethyl)pyridin-4-yl)methanone (Intermediate 23: step b) according to the procedure described in Example 77. $^1$H NMR (400 MHz, CDCl$_3$) δ 8.18 (d, J=1.96 Hz, 1H), 8.15 (d, J=5.38 Hz, 1H), 8.05 (d, J=8.80 Hz, 1H), 7.73 (dd, J=2.20, 8.80 Hz, 1H), 7.49-7.53 (m, 3H), 7.27-7.34 (m, 2H), 7.21 (dt, J=1.59, 5.38 Hz, 1H), 6.99 (s, 1H), 6.91 (d, J=1.22 Hz, 1H), 6.88 (d, J=1.22 Hz, 1H), 3.39 (s, 3H); MS m/e 478.8 [M+H]+.

Example 87

(4-Chlorophenyl)(2,4-dichloro-3-phenylquinolin-6-yl)(2,4-dimethylthiazol-5-yl)methanol

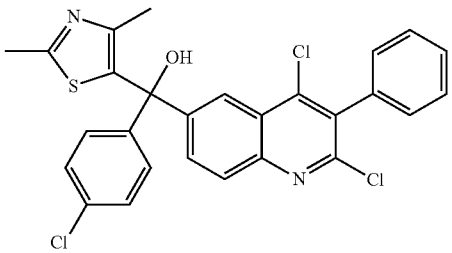 [SMILES: Cc1nc(C)c(C(O)(c2ccc(Cl)cc2)c2ccc3nc(Cl)c(-c4ccccc4)c(Cl)c3c2)s1]

To a flask containing 6-bromo-2,4-dichloro-3-phenylquinoline (255 mg, 0.72 mmol, Intermediate 7: step c) was added THF (8 mL) to give a homogeneous clear solution. The solution was cooled in a −78° C. bath and then n-BuLi (2.5 M in hexanes, 0.26 mL, 0.65 mmol) was added which resulted in an immediate orange homogeneous solution. After approximately 2 minutes, (4-chlorophenyl)(2,4-dimethylthiazol-5-yl)methanone (210 mg, 0.83 mmol, Intermediate 30, in 3 mL THF) was added. The reaction mixture was maintained at −75° C. for 5 minutes then replaced with a 0° C. ice-bath. After 45 minutes, the reaction mixture was quenched with aqueous NH$_4$Cl solution. The aqueous portion was extracted with EtOAc (3×50 mL) and the combined organics were washed with brine, dried over MgSO$_4$, filtered and concentrated to dryness. Chromatography on silica gel (100% DCM increasing to 20% EtOAc-DCM) provided the title compound as a white amorphous solid. $^1$H NMR (500 MHz, CD$_2$Cl$_2$) δ 8.33 (s, 1H), 8.01 (d, J=8.8 Hz, 1H), 7.82 (dd, J=8.9, 2.1 Hz, 1H), 7.59-7.46 (m, 3H), 7.46-7.28 (m, 6H), 2.54 (s, 3H), 2.03 (s, 3H). MS (ESI): mass calcd. for C$_{27}$H$_{19}$Cl$_3$N$_2$OS, 524.0, m/z found 525.0 [M+H]+.

Example 88

(2,4-Dimethoxy-3-phenylquinolin-6-yl)(1-methyl-1H-imidazol-5-yl)(pyrimidin-2-yl)methanol

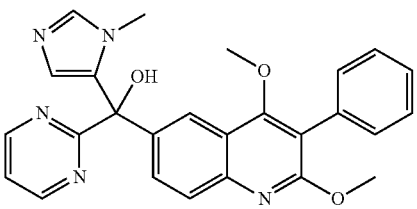 [SMILES: COc1nc2ccc(C(O)(c3ncccn3)c3cncn3C)cc2c(OC)c1-c1ccccc1]

Purification of the crude reaction mixture from the synthesis of (4-chloro-2-methoxy-3-phenylquinolin-6-yl)(1-methyl-1H-imidazol-5-yl)pyrimidin-2-ylmethanol (Example 60a) also afforded the title compound as a regioisomer. MS (ESI): mass calcd. for C$_{26}$H$_{23}$N$_5$O$_3$, 453.2; m/z found, 454.3 [M+H]+. $^1$H NMR (400 MHz, CD$_3$OD) δ 8.86 (d, J=4.9 Hz, 2H), 8.26 (d, J=1.7 Hz, 1H), 7.86-7.75 (m, 3H), 7.47-7.36 (m, 6H), 6.52 (s, 1H), 3.95 (s, 3H), 3.48 (s, 3H), 3.44 (s, 3H).

Example 89

(2-Chloro-3-phenylquinolin-6-yl)(4-chlorophenyl)(1-methyl-1H-imidazol-5-yl)methanol

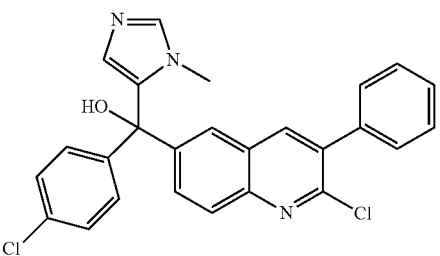 [SMILES: Cn1cncc1C(O)(c1ccc(Cl)cc1)c1ccc2nc(Cl)c(-c3ccccc3)cc2c1]

To a 50-mL round-bottom flask containing a solution of 6-bromo-2-chloro-3-phenylquinoline (210 mg, 0.66 mmol, Intermediate 31: step b) in tetrahydrofuran (10 mL) was added 2.5 M n-BuLi in hexanes (0.29 mL, 0.72 mmol) dropwise with stirring at −78° C. After 45 minutes at −78° C., a solution of (4-chlorophenyl)(1-methyl-1H-imidazol-5-yl)methanone (132 mg, 0.60 mmol, Intermediate 8: step b) in tetrahydrofuran (2 mL) was added dropwise. The resulting solution was stirred at −78° C. for an additional 2 hours, then quenched with 30 mL of aqueous NH$_4$Cl and extracted with ethyl acetate (2×30 mL). The combined organic layers were dried over anhydrous sodium sulfate and concentrated under vacuum. The residue was purified by FCC (20:1 DCM/MeOH) to provide the title compound as a white solid. MS (ES): mass calcd. for C$_{26}$H$_{19}$Cl$_2$N$_3$O, 459.1; m/z found, 460.0 [M+H]+. $^1$H NMR (400 MHz, CD$_3$OD) δ 8.96 (d, J=3.9

Hz, 1H), 8.33 (s, 1H), 8.05 (d, J=6.0 Hz, 1H), 7.94 (s, 1H), 7.88 (d, J=6.6 Hz, 1H), 7.42-7.56 (m, 9H), 6.93 (s, 1H), 3.71 (s, 3H).

Example 90

(4-Chloro-2-(dimethylamino)-3-phenylquinolin-6-yl)(4-chlorophenyl)(1-methyl-1H-imidazol-5-yl)methanol

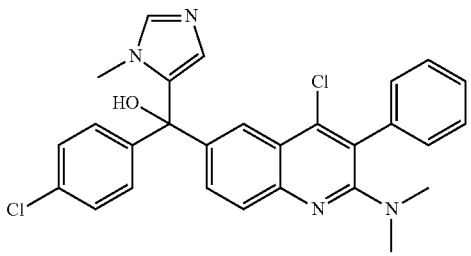 [SMILES: CN(C)c1nc2ccc(C(O)(c3ccc(Cl)cc3)c3cncn3C)cc2c(Cl)c1-c1ccccc1]

(4-Chlorophenyl)(2,4-dichloro-3-phenylquinolin-6-yl)(1-methyl-1H-imidazol-5-yl)methanol (124 mg, 0.251 mmol, Example 65) was treated with dimethylamine (2 M in MeOH, 2 mL, 4 mmol) and the resulting suspension was heated in a sealed tube in an 85° C. oil bath for 2 days. The mixture was concentrated in vacuo and the residue was purified by flash column chromatography (Biotage NH column, 0-1% MeOH-DCM) to provide the title compound as a cream-colored foam. $^1$H NMR (400 MHz, CDCl$_3$) δ 8.10 (d, J=2.20 Hz, 1H), 7.72 (d, J=8.80 Hz, 1H), 7.43-7.52 (m, 3H), 7.34-7.43 (m, 3H), 7.22-7.34 (m, 6H), 6.33 (s, 1H), 3.36 (s, 3H), 2.72 (s, 6H).

Example 91

(2,4-Dichloro-3-phenylquinolin-6-yl)(piperidin-4-yl)(pyridin-3-yl)methanol.TFA

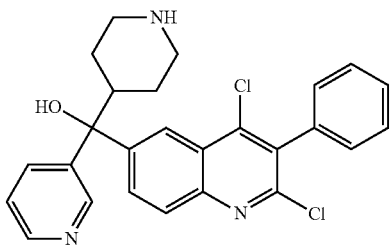 [SMILES: OC(c1cccnc1)(c1ccc2nc(Cl)c(-c3ccccc3)c(Cl)c2c1)C1CCNCC1]

A solution of tert-butyl 4-((2,4-dichloro-3-phenylquinolin-6-yl)(hydroxy)(pyridin-3-yl)methyl)piperidine-1-carboxylate (149 mg, 0.260 mmol, Intermediate 29) and TFA (1 mL) was stirred at room temperature for 1 hour and concentrated to provide the title compound. $^1$H NMR (400 MHz, CD$_3$OD) δ 9.12 (s, 1H), 8.69-8.77 (m, 2H), 8.62 (s, 1H), 8.02-8.11 (m, 2H), 7.97 (dd, J=5.56, 8.08 Hz, 1H), 7.49-7.58 (m, 3H), 7.30-7.36 (m, 2H), 3.40-3.50 (m, 2H), 3.17-3.27 (m, 1H), 3.05-3.17 (m, 2H), 1.75-1.94 (m, 2H), 1.60-1.74 (m, 2H).

In Vitro Biological Data

ThermoFluor® Assay

ThermoFluor® is a fluorescence based assay that estimates ligand binding affinities by measuring the effect of a ligand on protein thermal stability (Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) High-density miniaturized thermal shift assays as a general strategy for drug discovery. *J Biomol Screen* 6, 429-40, and Matulis, D., Kranz, J. K., Salemme, F. R., and Todd, M. J. (2005) Thermodynamic stability of carbonic anhydrase: measurements of binding affinity and stoichiometry using ThermoFluor. *Biochemistry* 44, 5258-66). This approach is applicable to a wide variety of systems, and rigorous in theoretical interpretation through quantitation of equilibrium binding constants ($K_D$).

In a ThermoFluor® experiment where protein stability is monitored as the temperature is steadily increased, an equilibrium binding ligand causes the midpoint of an unfolding transition ($T_m$) to occur at a higher temperature. The shift in the melting point described as a $\Delta T_m$ is proportional to the concentration and affinity of the ligand. The compound potency may be compared as a rank order of either $\Delta T_m$ values at a single compound concentration or in terms of $K_D$ values, estimated from concentration response curves.

RORγt ThermoFluor® Assay Construct

For the RORγt construct used in the ThermoFluor® assay, numbering for the nucleotide sequences was based on the reference sequence for human RORγt, transcript variant 2, NCBI Accession: NM_001001523.1 (SEQ ID NO:1). Nucleotides 850-1635 (SEQ ID NO:2) coding for the wild type human RORγt ligand binding domain (RORγt LBD) were cloned into the pHIS1 vector, a modified pET *E. coli* expression vector (Accelagen, San Diego), containing an in-frame N-terminal His-tag and a TurboTEV protease cleavage site (ENLYFQG, SEQ ID NO:3) upstream of the cloned insert sequence. The amino acid sequence for the RORγt construct used in the Thermofluor assay is shown as SEQ ID NO:4.

ThermoFluor® experiments were carried out using instruments owned by Janssen Research and Discovery, L.L.C. through its acquisition of 3-Dimensional Pharmaceuticals, Inc. 1,8-ANS (Invitrogen) was used as a fluorescent dye. Protein and compound solutions are dispensed into black 384-well polypropylene PCR microplates (Abgene) and overlayed with silicone oil (1 μL, Fluka, type DC 200) to prevent evaporation.

Bar-coded assay plates are robotically loaded onto a thermostatically controlled PCR-type thermal block and then heated at a typical ramp-rate of 1° C./min for all experiments. Fluorescence was measured by continuous illumination with UV light (Hamamatsu LC6) supplied via fiber optic and filtered through a band-pass filter (380-400 nm; >6 OD cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. Images were collected at each temperature, and the sum of the pixel intensity in a given area of the assay plate was recorded versus temperature. Reference wells contained RORγt without compounds, and the assay conditions were as follows:

0.065 mg/mL RORγt
60 μM 1,8-ANS
100 mM Hepes, pH 7.0
10 mM NaCl
2.5 mM GSH
0.002% Tween-20

Project compounds were arranged in a pre-dosed mother plate (Greiner Bio-one) wherein compounds are serially diluted in 100% DMSO by 1:2 from a high concentration of 10 mM over 12 columns within a series (column 12 is a reference well containing DMSO, no compound). The compounds were robotically dispensed directly into assay plates (1×=46 nL) using a Hummingbird capillary liquid handling instrument (Digilab). Following compound dispense, protein and dye in buffer was added to achieve the final assay volume of 3 µL, followed by 1 µL of silicone oil.

The binding affinity was estimated as described previously (Matulis, D., Kranz, J. K., Salemme, F. R., and Todd, M. J. (2005) Thermodynamic stability of carbonic anhydrase: measurements of binding affinity and stoichiometry using ThermoFluor®. Biochemistry 44, 5258-66) using the following thermodynamic parameters of protein unfolding:

Reference RORγt $T_m$: 47.8° C.
$\Delta H_{(Tm)}$=115 kcal/mol
$\Delta C_{p(Tm)}$=3 kcal/mol Cell Based Biological Data
RORγt Reporter Assay A reporter assay was used to test functional activity of RORγt modulatory compounds on transcriptional activation driven by the RORγt LBD. Cells used in the assay were co-transfected with two constructs. The first construct, pBIND-RORγt LBD, contained the wild type human RORγt LBD fused to the DNA binding domain of the GAL4 protein. The second construct, pGL4.31 (Promega Cat no. C935A), contained multiple GAL4 responsive DNA elements upstream of firefly luciferase. To generate a background control, cells were similarly co-transfected with two constructs, but in the first construct the AF2 amino acid motif in the RORγt LBD was changed from LYKELF (SEQ ID NO:5) to LFKELF (SEQ ID NO:6). The AF2 mutation has been shown to prevent co-activator binding to the RORγt LBD, thus preventing transcription of firefly luciferase. The mutant construct was called pBIND-RORγt-AF2.

For the RORγt constructs used in the reporter assay, numbering for the nucleotide sequences was also based on the reference sequence for human RORγt, transcript variant 2, NCBI Accession: NM_001001523.1 (SEQ ID NO:1). For the wild type human RORγt LBD construct, pBIND-RORγt LBD, nucleotides 850-1635 (SEQ ID NO:2) coding for the wild type human RORγt LBD were cloned into EcoRI and NotI sites in the pBIND vector (Promega cat. No E245A). The pBIND vector contains the GAL4 DNA Binding Domain (GAL4 DBD) and the renilla luciferase gene under control of the SV40 promoter. Renilla luciferase expression serves as a control for transfection efficiency and cell viability. For the background control construct, pBIND-RORγt-AF2, the AF2 domain of RORγt LBD was mutated using the Quik Change II Site Directed Mutagenesis System (Stratagene Cat. No. 200519). The nucleotide sequence coding for the RORγt LBD sequence with the mutated AF2 domain is shown as SEQ ID NO:7. The amino acid sequences for the wild type RORγt LBD and RORγt LBD with the mutated AF2 domain are shown as SEQ ID NO:8 and SEQ ID NO:9, respectively.

The reporter assay was performed by transiently transfecting HEK293T cells with 5 ng of pBIND-RORγt LBD or pBIND-RORγt LBD-AF2 and 5 µg pGL4.31 (Promega Cat no. C935A) using Fugene 6 (Invitrogen Cat no. E2691) at a 1:6 ratio of DNA:Fugene 6 in a T-75 flask in which cells were at least 80% confluent. Twenty four hours after bulk transfection, cells were plated into 96-well plates at 50,000 cells/well in phenol-red free DMEM containing 5% Lipid Reduced FCS and Pen/Strep. Six hours after plating, cells were treated with compounds for 24 hours. Media was removed and cells were lysed with 50 µL 1× Glo Lysis Buffer (Promega). Dual Glo Luciferase Reagent (50 µL/well) was then added and firefly luciferase luminescence was read on an Envision after a ten minute incubation. Finally, Stop and Glo reagent (50 µL/well) was added and renilla luciferase luminescence was read on an Envision instrument after a ten minute incubation. To calculate the effect of compounds on RORγt activity, the ratio of firefly to renilla luciferase was determined and plotted against compound concentration. Agonist compounds increase RORγt-driven luciferase expression, and antagonist or inverse agonist compounds decrease luciferase expression.

Human Th17 Assay

The human Th17 assay tests the effect of RORγt modulatory compounds on IL-17 production by CD4 T cells under conditions which favor Th17 differentiation. Total CD4$^+$ T cells were isolated from the peripheral blood mononuclear cells (PBMC) of healthy donors using a CD4$^+$ T cell isolation kit II, following the manufacturer's instructions (Miltenyi Biotec). Cells were resuspended in a medium of RPMI-1640 supplemented with 10% fetal bovine serum, penicillin, streptomycin, glutamate, and β-mercaptoethanol and were added to 96-well plates at 1.5×10$^5$ per 100 µL per well. 50 µL of compound at titrated concentrations in DMSO were added into each well at final DMSO concentration at 0.2%. Cells were incubated for 1 hour, then 50 µL of Th17 cell differentiation medium was added to each well. The final concentrations of antibodies and cytokines (R&D Systems) in differentiation medium were: 3×10$^6$/mL anti-CD3/CD28 beads (prepared using human T cell activation/expansion kit, Miltenyi Biotec), 10 µg/mL anti-IL4, 10 µg/mL anti-IFNγ, 10 ng/mL IL1 β, 10 ng/mL IL23, 50 ng/mL IL6, 3 ng/mL TGFβ and 20 U/mL IL2. Cells were cultured at 37° C. and 5% CO$_2$ for 3 days. Supernatants were collected and the accumulated IL-17 in culture was measured by using MULTI-SPOT® Cytokine Plate following manufacture's instruction (Meso Scale Discovery). The plate was read using Sector Imager 6000, and IL-17 concentration was extrapolated from the standard curve. The IC50s were determined by GraphPad.

TABLE 1

| Example Number | ThermoFluor ® Assay, Kd (µM) | RORγt reporter Assay, IC50 (µM) | RORγt reporter Assay, % inhibition @ 6 µM | Human Th17 Assay, IC$_{50}$ (µM) |
|---|---|---|---|---|
| 1a | ND | ND | ND | ND |
| 1b | 0.13 | 0.16 | 89 | 0.4 |
| 1c | 0.033 | 0.11 | 95 | 0.31 |
| 2a | ND | ND | ND | ND |
| 2b | 0.13 | 0.2 | 91 | 2.9 |
| 2c | 0.14 | 0.17 | 95 | 0.67 |
| 3a | ND | ND | ND | ND |
| 3b | 0.00056 | 0.003 | 96 | 0.013 |
| 3c | 0.0023 | 0.0066 | 98 | 0.043 |
| 4a | ND | ND | ND | ND |
| 4b | 0.0044 | 0.0095 | 98 | 0.061 |
| 4c | 0.0014 | 0.011 | 98 | 0.031 |
| 5 | 0.62 | 1.7 | 87 | ND |
| 6 | 0.94 | 1.9 | 92 | ND |
| 7a | 0.072 | >6 | −60 | ND |
| 7b | 0.037 | >6 | −78 | >6 |
| 7c | 0.77 | >6 | −20 | >6 |
| 8 | 0.27 | 0.89 | 87 | ND |
| 9a | 0.068 | 0.27 | 90 | ~0.9 |
| 9b | 0.7 | 1.2 | 95 | ND |
| 9c | 0.032 | 0.31 | 96 | ND |
| 10 | 0.2 | 0.32 | 89 | 1.5 |
| 11 | 0.64 | >6 | 32 | ND |
| 12 | 0.65 | ~2 | 90 | ND |
| 13 | 2 | >6 | −52 | ND |
| 14a | 0.0067 | 1.1 | 55 | ND |
| 14b | 0.0052 | 0.24 | 53 | 0.079 |
| 14c | 0.14 | 0.51 | 87 | 0.31 |
| 15 | 0.021 | >6 | −29 | ND |
| 16 | 0.027 | 0.2 | 86 | 0.081 |

TABLE 1-continued

| Example Number | ThermoFluor® Assay, Kd (μM) | RORγt reporter Assay, IC50 (μM) | RORγt reporter Assay, % inhibition @ 6 μM | Human Th17 Assay, IC$_{50}$ (μM) |
|---|---|---|---|---|
| 17 | 0.026 | 0.53 | 87 | ND |
| 18a | ND | ND | ND | ND |
| 18b | 14 | >6 | 40 | ND |
| 18c | 0.33 | 0.85 | 95 | ND |
| 19a | ND | ND | ND | ND |
| 19b | 0.36 | 0.3 | 94 | 0.4 |
| 19c | 0.017 | >6 | 35 | ND |
| 20 | ND | ND | ND | ND |
| 21a | ND | ND | ND | ND |
| 21b | 1.3 | 1.6 | 87 | ND |
| 21c | 0.11 | 0.19 | 96 | 0.18 |
| 22 | ND | ND | ND | ND |
| 23a | ND | ND | ND | ND |
| 23b | 15 | ~4 | 60 | ND |
| 23c | 0.15 | 0.23 | 100 | 0.4 |
| 24 | ND | ND | ND | ND |
| 25a | ND | ND | ND | ND |
| 25b | 3.5 | ~2 | 87 | ND |
| 25c | 0.061 | 0.16 | 95 | 0.16 |
| 26 | ND | ND | ND | ND |
| 27a | ND | ND | ND | ND |
| 27b | 15 | ~4 | 80 | ND |
| 27c | 0.82 | 2.1 | 96 | ND |
| 28 | 0.046 | 0.024, ~0.04 | 96 | ND |
| 29 | 0.026 | 0.085 | 97 | ND |
| 30a | 0.023 | 0.11 | 91 | ND |
| 30b | 0.3 | 0.049 | 95 | 0.057 |
| 30c | 0.009 | 0.14 | 93 | ND |
| 31a | ND | 0.15 | 102 | ND |
| 31b | 0.005 | 0.042 | 103 | 0.02 |
| 31c | 3.3 | 1.6 | 85 | ND |
| 32a | ND | ND | ND | ND |
| 32b | 0.77 | 1.2 | 92 | ND |
| 33a | 0.16 | 0.65 | 98 | ND |
| 33b | 13 | ~4 | 64 | ND |
| 33c | 0.077 | 0.13 | 99 | 0.29 |
| 34a | ND | ND | ND | ND |
| 34b | 0.45 | 1 | 90 | ND |
| 34c | 0.1 | 0.27 | 96 | 0.26 |
| 35 | 0.018 | 0.16 | 101 | ND |
| 36 | 0.00089 | 0.011, ~0.04 | 97 | ND |
| 37 | 0.0072 | 0.26 | 90 | ND |
| 38 | 0.00026 | 0.03 | 93 | ND |
| 39 | 0.0052 | 0.034 | 103 | ND |
| 40a | 0.0015 | 0.023 | 104 | ND |
| 40b | 0.15 | 0.68 | 97 | ND |
| 40c | 0.12 | 0.19 | 103 | 0.21 |
| 41a | 0.089 | 0.32 | 98 | ND |
| 41b | 0.0014 | 0.0086 | 102 | 0.007 |
| 41c | 0.0065 | 0.27 | 102 | 0.21 |
| 42 | 0.00051 | 0.017 | 103 | ND |
| 43 | 0.0035 | 0.039 | 98 | ND |
| 44 | 5.4 | >6 | 31 | ND |
| 45 | 0.77 | 0.57 | 93 | ND |
| 46 | 0.23 | 0.83 | 106 | ND |
| 47a | 0.0083 | 0.04 | 98 | ND |
| 47b | 0.93 | ~2 | 80 | ND |
| 47c | 0.0019 | 0.025 | 100 | 0.054 |
| 48 | 0.81 | 0.67 | 103 | ND |
| 49a | 0.1 | 0.22 | 104 | ND |
| 49b | 10 | ~5 | 71 | ND |
| 49c | 0.065 | 0.23 | 100 | 0.28 |
| 50 | 0.09 | 0.031 | 99 | ND |
| 51 | 1.1 | 1.1 | 96 | ND |
| 52 | 3.5 | ~6 | 52 | ND |
| 53 | 0.0072 | ND | ND | ND |
| 54 | 0.38 | 0.44 | 102 | ND |
| 55 | 3.3 | ~3 | 70 | ND |
| 56 | 0.06 | 0.023 | 102 | ND |
| 57 | 0.58 | 0.69 | 100 | ND |
| 58 | 0.22 | 0.15 | 99 | ND |
| 59 | 1.2 | 0.54 | 98 | ND |
| 60a | ND | ND | ND | ND |
| 60b | 0.9 | ~2 | 87 | ND |
| 61 | 0.45 | 0.13 | 105 | 0.48 |
| 62 | 0.057 | 0.12 | 110 | 0.1 |
| 63 | 0.0093 | >6 | 26 | ND |
| 64 | 0.96 | 1 | 93 | ND |
| 65 | 0.16 | 0.26 | 101 | 1.8 |
| 66 | 0.031 | 0.18 | 100 | ND |
| 67 | 0.0035 | 0.02 | 106 | ND |
| 68 | 0.0011 | 0.01 | 104 | 0.02 |
| 69 | ND | ND | ND | ND |
| 70 | ND | ND | ND | ND |
| 71 | 2.2 | 1.4 | 84 | ND |
| 72 | 0.89 | 0.63 | 100 | ND |
| 73 | 20 | 0.7 | 80 | ~6 |
| 74 | 11 | >6 | 60 | ND |
| 75 | 14 | 2.9 | 99 | ND |
| 76 | 18 | ~2 | 80 | ND |
| 77 | 12 | >6 | 48 | ND |
| 78 | 14 | >6 | 33 | ND |
| 79 | 17 | ND | ND | ND |
| 80 | 12 | >6 | 72 | ND |
| 81 | 14 | ND | ND | ND |
| 82 | 11 | >6 | 18 | ND |
| 83 | 15 | 1.9 | 73 | ND |
| 84 | 17 | 3.5 | 93 | ND |
| 85 | 20 | 3.5 | 81 | ND |
| 86 | 20 | >6 | 37 | ND |
| 87 | 12 | >6 | 56 | ND |
| 88 | 20 | >6 | 32 | ND |
| 89 | 10 | >4 | 57 | ND |
| 90 | ND | ND | ND | ND |
| 91 | 21 | >6 | 0 | ND |

All data shown in Table 1 is either the value of one data point or the average of more than one data point. In cases where more than one value is shown in a table cell, values with qualifiers such as ~, > or < shown on the right side of the table cell could not be included in the averaging calculation for the value shown on the left side of the table cell. ND—no data.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

All documents cited herein are incorporated by reference.

What is claimed is:

1. The compounds of Formula I:

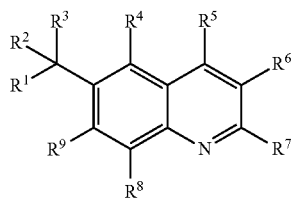

Formula I wherein:

$R^1$ is azetidinyl, pyrrolyl, pyrazolyl, imidazolyl, triazolyl, thiazolyl, pyridyl, pyridyl N-oxide, pyrazinyl, pyrimidinyl, pyridazyl, piperidinyl, tetrahydropyranyl, phenyl, oxazolyl, isoxazolyl, thiophenyl, benzoxazolyl, or quinolinyl; wherein said piperidinyl, pyridyl, pyridyl N-oxide, imidazolyl, phenyl, thiophenyl, benzoxazolyl, and pyrazolyl are optionally substituted with $SO_2CH_3$, $C(O)CH_3$, $C(O)NH_2$, $CH_3$, $CH_2CH_3$, $CF_3$, Cl, F, —CN, $OCH_3$, $N(CH_3)_2$, —$(CH_2)_3OCH_3$, $SCH_3$, OH, $CO_2H$, $CO_2C(CH_3)_3$, or $OCH_2OCH_3$; and optionally substituted with up to two additional substituents independently selected from the group consisting of Cl, $OCH_3$, and $CH_3$; and wherein said triazolyl, oxazolyl, isoxazolyl, and thiazolyl are optionally substituted with one or two $CH_3$ groups; and wherein said azetidinyl is optionally substituted with $CO_2C(CH_3)_3$, $C(O)NH_2$, $CH_3$, $SO_2CH_3$, or $C(O)CH_3$;

$R^2$ is 1-methyl-1,2,3-triazolyl, pyridyl, pyridyl-N-oxide, 1-methyl pyrazol-4-yl, pyrimidin-5-yl, pyridazyl, pyrazin-2-yl, oxazolyl, isoxazolyl, N-acetyl-azetidin-3-yl, N-methylsulfonyl-azetidin-3-yl, N-Boc-azetidin-3-yl, N-methyl-azetidin-3-yl, N-acetamidyl-azetidin-3-yl, N-acetyl piperidinyl, 1-H-piperidinyl, N-Boc-piperidinyl, N-$C_{(1-2)}$alkyl-piperidinyl, thiazol-5-yl, 1-methyl imidazol-2-yl, 1-(3-methoxypropyl)-imidazol-5-yl, or 1-$C_{(1-2)}$alkyl imidazol-5-yl; wherein said 1-$C_{(1-2)}$alkyl imidazol-5-yl is optionally substituted with up to two additional $CH_3$ groups, or one substituent selected from the group consisting of $SCH_3$, and Cl; and said pyridyl, and pyridyl-N-oxide are optionally substituted with up to two substituents independently selected from the group consisting of $C(O)NH_2$, —CN, $OCH_3$, $CF_3$, Cl, and $CH_3$; and said thiazol-5-yl, oxazolyl, and isoxazolyl are optionally substituted with up to two $CH_3$ groups; and said 1-methyl pyrazol-4-yl is optionally substituted with up to two additional $CH_3$ groups;

$R^3$ is H, OH, $OCH_3$, $NHCH_3$, $N(CH_3)_2$, or $NH_2$;

$R^4$ is H, or F;

$R^5$ is H, Cl, —CN, $CF_3$, $SCH_3$, $OC_{(1-3)}$alkyl, OH, $C_{(1-4)}$alkyl, $N(CH_3)OCH_3$, $NH(C_{(1-2)}$alkyl), $N(C_{(1-2)}$alkyl)$_2$, NH-cyclopropyl, $OCHF_2$, 4-hydroxy-piperidinyl, azetidin-1-yl, or fur-2-yl;

$R^6$ is 2-chloro-thiophen-5-yl, 1-methyl-pyrazol-4-yl, phenyl, pyrimidinyl, or pyridyl, wherein said phenyl, pyrimidinyl, and pyridyl are optionally substituted with $SO_2CH_3$, $NHSO_2CH_3$, $CF_3$, F, Cl, —CN, $OCH_3$, or $OCF_3$;

$R^7$ is H, Cl, —CN, $C_{(1-4)}$alkyl, $OCH_2CF_3$, $OCH_2CH_2OCH_3$, $CF_3$, $SCH_3$, $SO_2CH_3$, $OCHF_2$, $NA^1A^2$, $C(O)NHCH_3$, $N(CH_3)CH_2CH_2NA^1A^2$, $OCH_2CH_2NA^1A^2$, $OCH_2CH_2NH_2$, $OC_{(1-3)}$alkyl, $OCH_2$-(1-methyl)-imidazol-2-yl, imidazol-2-yl, fur-2-yl, pyrazol-4-yl, pyrid-3-yl, or pyrimidin-5-yl; thiophen-3-yl, 1-methyl-indazol-5-yl, 1-methyl-indazol-6-yl, phenyl, or

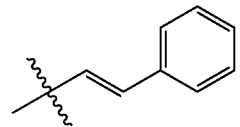 [SMILES: */C=C/c1ccccc1]

wherein said imidazolyl or pyrazolyl can be optionally substituted with a $CH_3$ group;

$A^1$ is H or $C_{(1-4)}$alkyl;

$A^2$ is $C_{(1-4)}$alkyl, cyclopropyl, $C_{(1-4)}$alkyl$OC_{(1-4)}$alkyl, $C_{(1-4)}$alkylOH, $C(O)C_{(1-2)}$alkyl, or $OCH_3$; or $A^1$ and $A^2$ may be taken together with their attached nitrogen to form a ring selected from the group consisting of:

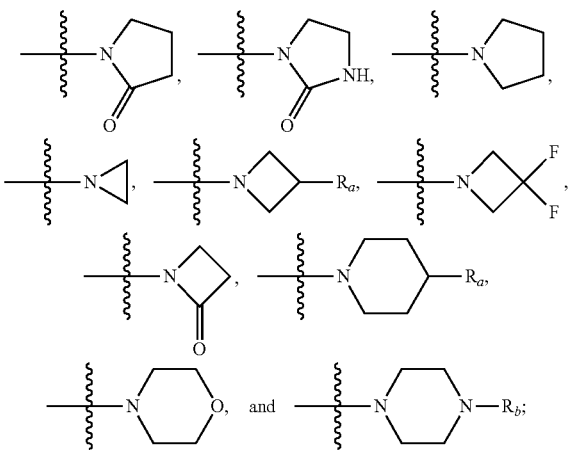

$R_a$ is H, F, $OCH_3$, or OH;
$R_b$ is $CH_3$, or phenyl;
$R^8$ is H, $CH_3$, $OCH_3$, or F;
$R^9$ is H, or F;

and pharmaceutically acceptable salts thereof;

provided that (4-chloro-3-phenylquinolin-6-yl)(1-methyl-1H-imidazol-5-yl)(pyridin-3-yl)methanamine, (4-chlorophenyl)(2,4-dichloro-3-(2-chlorophenyl)quinolin-6-yl)(1-methyl-1H-imidazol-2-yl)methanol, (4-chloro-3-phenylquinolin-6-yl)(1-methyl-1H-imidazol-5-yl)(pyridin-4-yl)methanamine, (4-chlorophenyl)(3-(2,6-dichlorophenyl)quinolin-6-yl)(1-methyl-1H-imidazol-5-yl)methanol, (4-chloro-3-phenylquinolin-6-yl)(2-(dimethylamino)pyridin-4-yl)(1-methyl-1H-imidazol-2-yl)methanol, 4-(2-((4-chloro-6-((4-chlorophenyl)(hydroxy)(1-methyl-1H-imidazol-5-yl)methyl)-3-phenylquinolin-2-yl)oxy)ethyl)thiomorpholine 1,1-dioxide, 1-(2-((4-chloro-6-((4-chlorophenyl)(hydroxy)(1-methyl-1H-imidazol-5-yl)methyl)-3-phenylquinolin-2-yl)oxy)ethyl)pyrrolidin-2-one, (2-chloro-4-(dimethylamino)-3-phenylquinolin-6-yl)(pyridin-2-yl)(pyridin-4-yl)methanol, (4-chloro-3-phenylquinolin-6-yl)(2-fluoropyridin-4-yl)(1-methyl-1H-imidazol-2-yl)methanol, (4-chloro-2-(1-methyl-1H-pyrazol-4-yl)-3-phenylquinolin-6-yl)(4-chlorophenyl)(pyridin-3-yl)methanol, (2,4-dichloro-3-phenylquinolin-6-yl)di(pyridin-2-yl)methanol, 6-((3-chlorophenyl)(hydroxy)(2-(trifluoromethyl)pyridin-4-yl)methyl)-3-phenylquinoline-2-carbonitrile, (2,4-dichloro-8-methyl-3-phenylquinolin-6-yl)(1-methyl-1H-imidazol-4-yl)(6-methylpyridin-3-yl)methanol, (4-chlorophenyl)(2,4-dichloro-3-(2-chlorophenyl)quinolin-6-yl)(1-methyl-1H-imidazol-5-yl)methanol, (2,4-dichloro-3-phenylquinolin-6-yl)phenyl)(pyridin-2-yl)methanol, and (2,4-dichloro-3-phenylquinolin-6-yl)(oxazol-2-yl)(phenyl)methanol are excluded from the claim.

2. The compounds of claim 1, wherein:
$R^1$ is imidazolyl, thiazolyl, pyridyl, pyrimidinyl, or phenyl; wherein said pyridyl and said phenyl are optionally substituted with —CN, $CF_3$, F, or Cl; and wherein said imidazolyl, and thiazolyl are optionally substituted with one or two $CH_3$ groups;
$R^2$ is 1-methyl-1,2,3-triazol-5-yl, N-acetyl piperidin-4-yl, N-Boc-piperidin-4-yl, N-methyl piperidin-4-yl, 1-H-piperidin-4-yl, oxazol-2-yl, 2,4-dimethyl thiazol-5-yl, 1-methyl imidazol-2-yl, 1-methyl-imidazol-5-yl, or pyridyl; wherein said pyridyl is optionally substituted with $CF_3$;
$R^3$ is H or OH;
$R^4$ is H;
$R^5$ is H, Cl, —CN, $C_{(1-4)}$alkyl, $OC_{(1-2)}$alkyl, $SCH_3$, $N(CH_3)_2$, or $N(CH_3)OCH_3$;
$R^6$ is 2-chloro-thiophen-5-yl, 1-methyl-pyrazol-4-yl, phenyl, pyrimidinyl, or pyridyl, wherein said phenyl, pyrimidinyl, and pyridyl are optionally substituted with $SO_2CH_3$, $NHSO_2CH_3$, $CF_3$, Cl, —CN, $OCH_3$, or $OCF_3$;
$R^7$ is Cl, —CN, $CF_3$, $SCH_3$, $OCH_2CF_3$, $NA^1A^2$, $N(CH_3)CH_2CH_2NA^1A^2$, $OC_{(1-3)}$alkyl, $OCH_2CH_2OCH_3$, $OCH_2CH_2NA^1A^2$, or $OCH_2CH_2NH_2$;
$A^1$ is H, or $CH_3$;
$A^2$ is $OCH_3$, $CH_3$, $CH_2CH_2OH$, $C(O)C_{(1-2)}$alkyl, or $CH_2CH_2OCH_3$; or $A^1$ and $A^2$ may be taken together with their attached nitrogen to form a ring selected from the group consisting of:

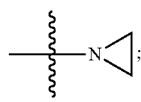 [SMILES: *N1CC1 ; ";"]

$R^8$ is H, or $CH_3$;
$R^9$ is H;
and pharmaceutically acceptable salts thereof;
provided that (4-chlorophenyl)(2,4-dichloro-3-(2-chlorophenyl)quinolin-6-yl)(1-methyl-1H-imidazol-5-yl)methanol, 6-((3-chlorophenyl)(hydroxy)(2-(trifluoromethyl)pyridin-4-yl)methyl)-3-phenylquinoline-2-carbonitrile, (2,4-dichloro-3-phenylquinolin-6-yl)di(pyridin-2-yl)methanol, (2,4-dichloro-3-phenylquinolin-6-yl)(phenyl)(pyridin-2-yl)methanol, (2-chloro-4-(dimethylamino)-3-phenylquinolin-6-yl)(pyridin-2-yl)(pyridin-4-yl)methanol, (4-chlorophenyl)(2,4-dichloro-3-(2-chlorophenyl)quinolin-6-yl)(1-methyl-1H-imidazol-2-yl)methanol, and (2,4-dichloro-3-phenylquinolin-6-yl)(oxazol-2-yl)(phenyl)methanol are excluded from the claim.

3. A compound of claim 1 selected from the group consisting of:

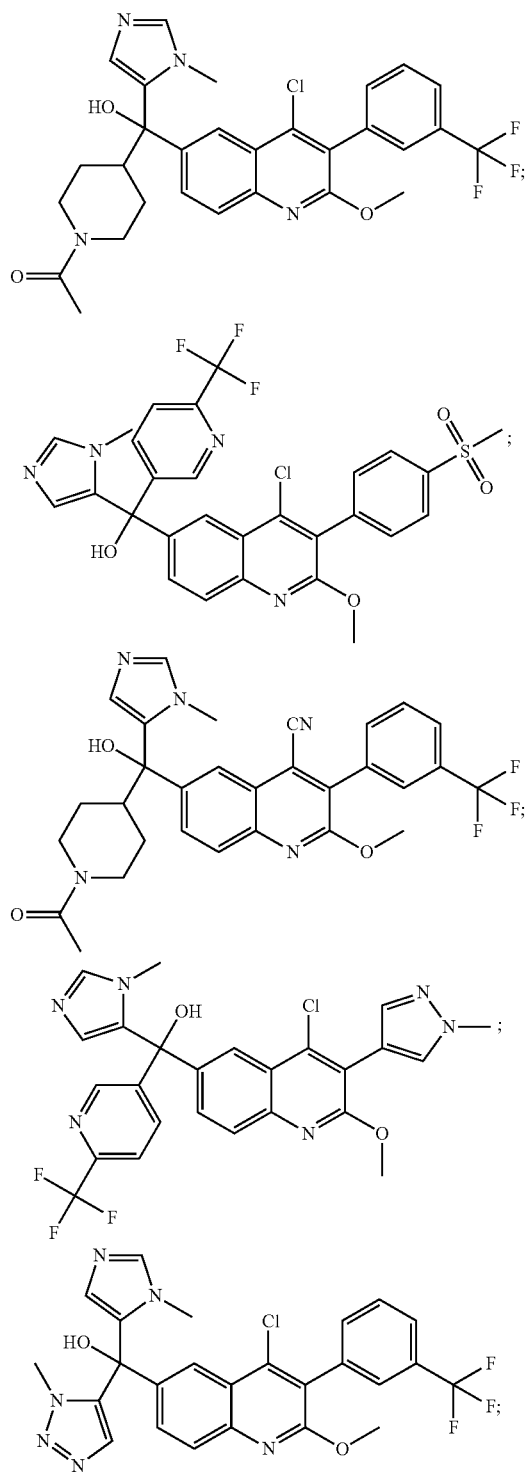

161
-continued
162
-continued
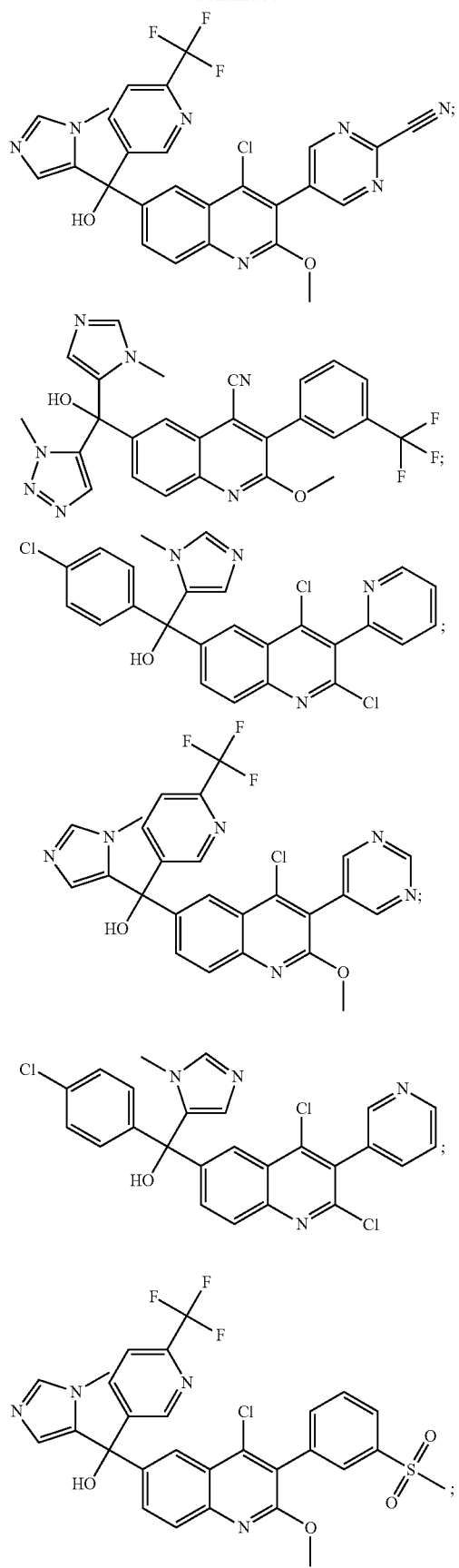
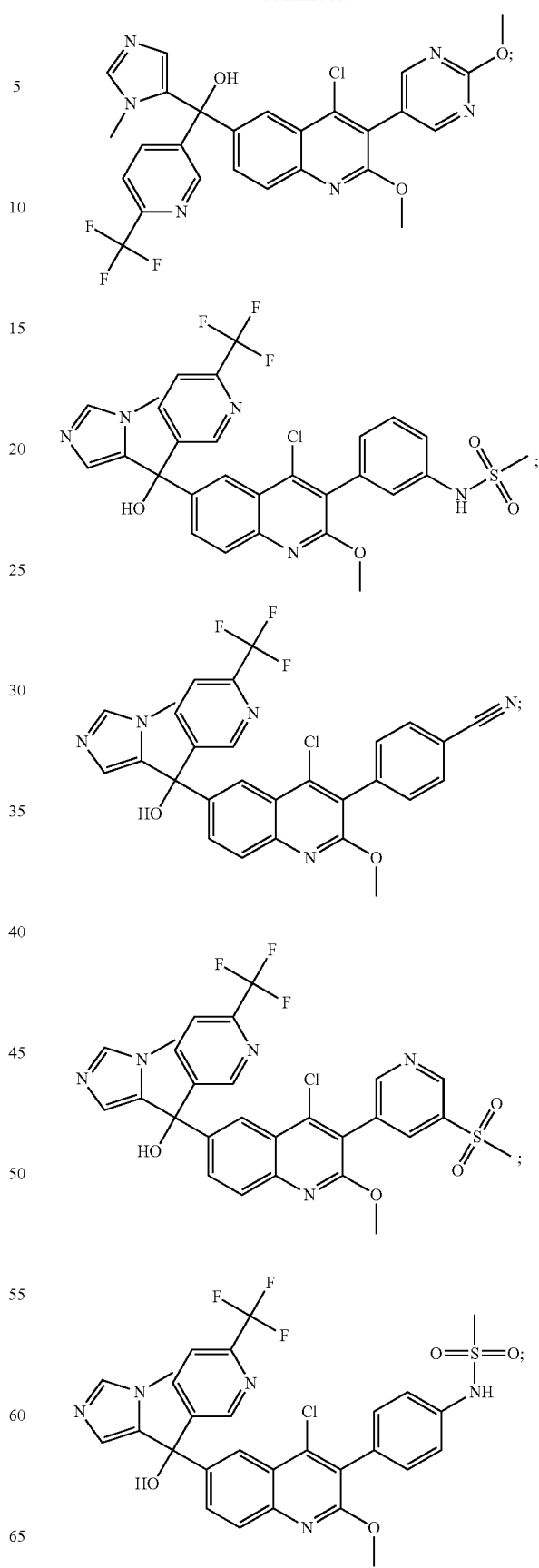

163
-continued
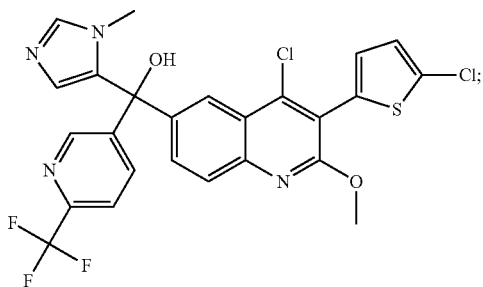
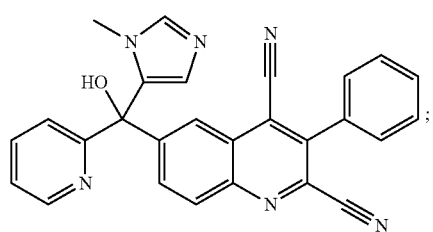
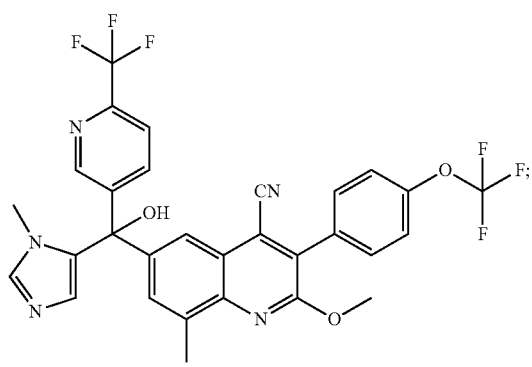
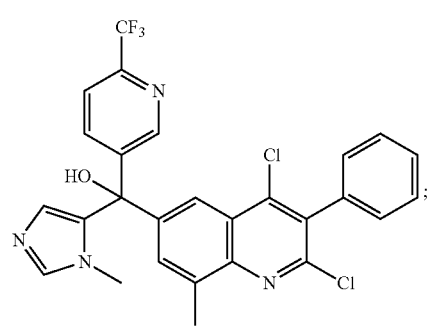
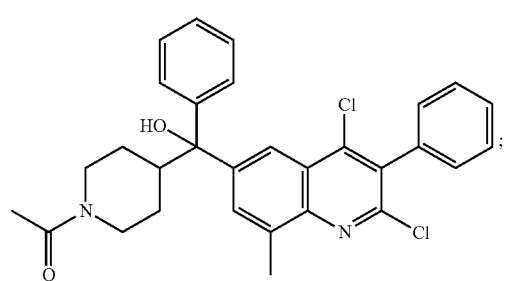
164
-continued
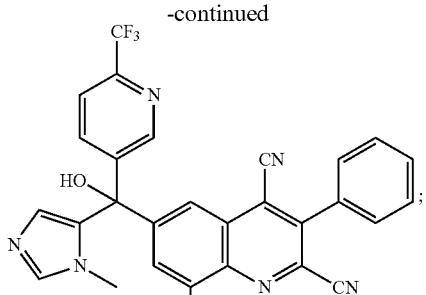
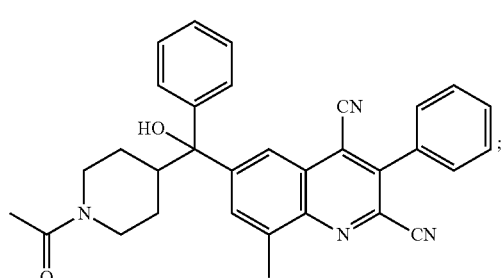
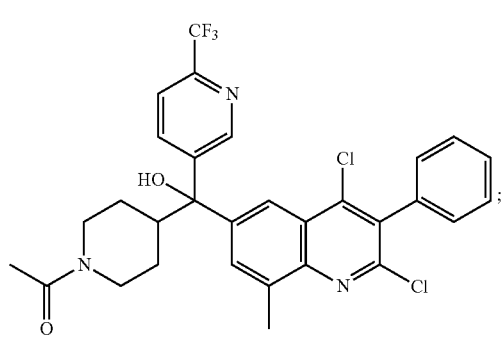
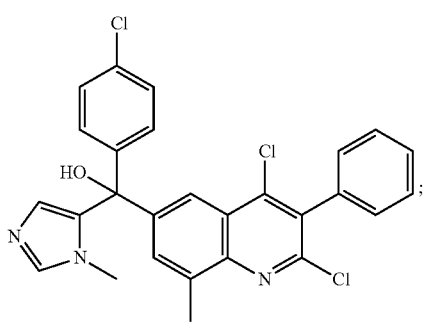
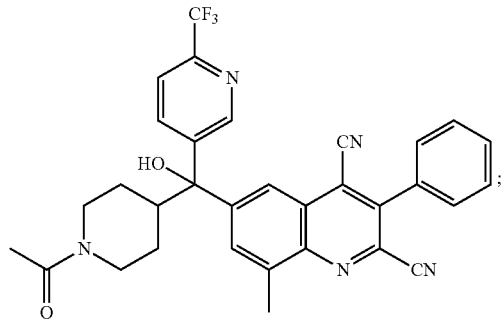

165
-continued
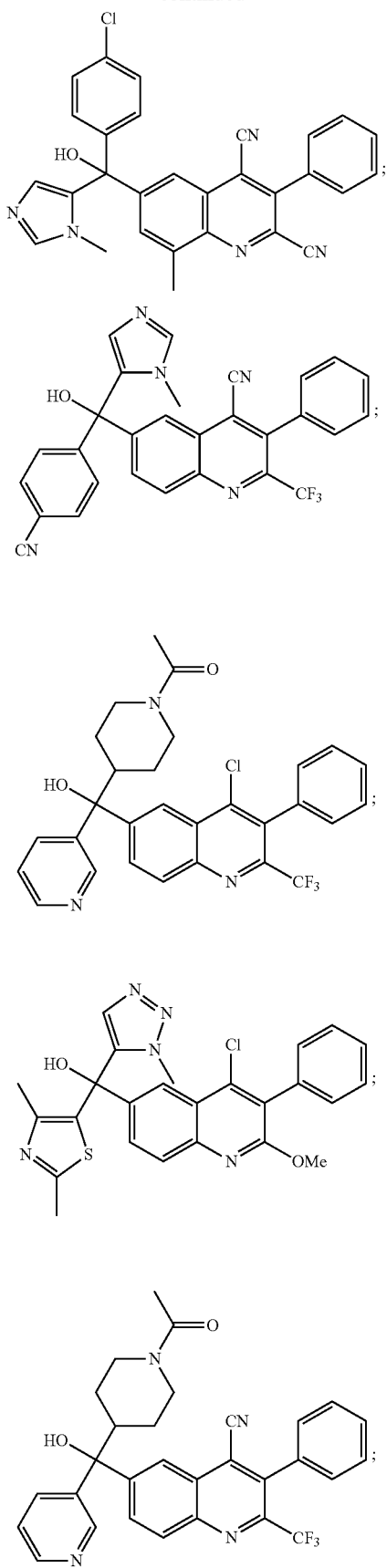
166
-continued
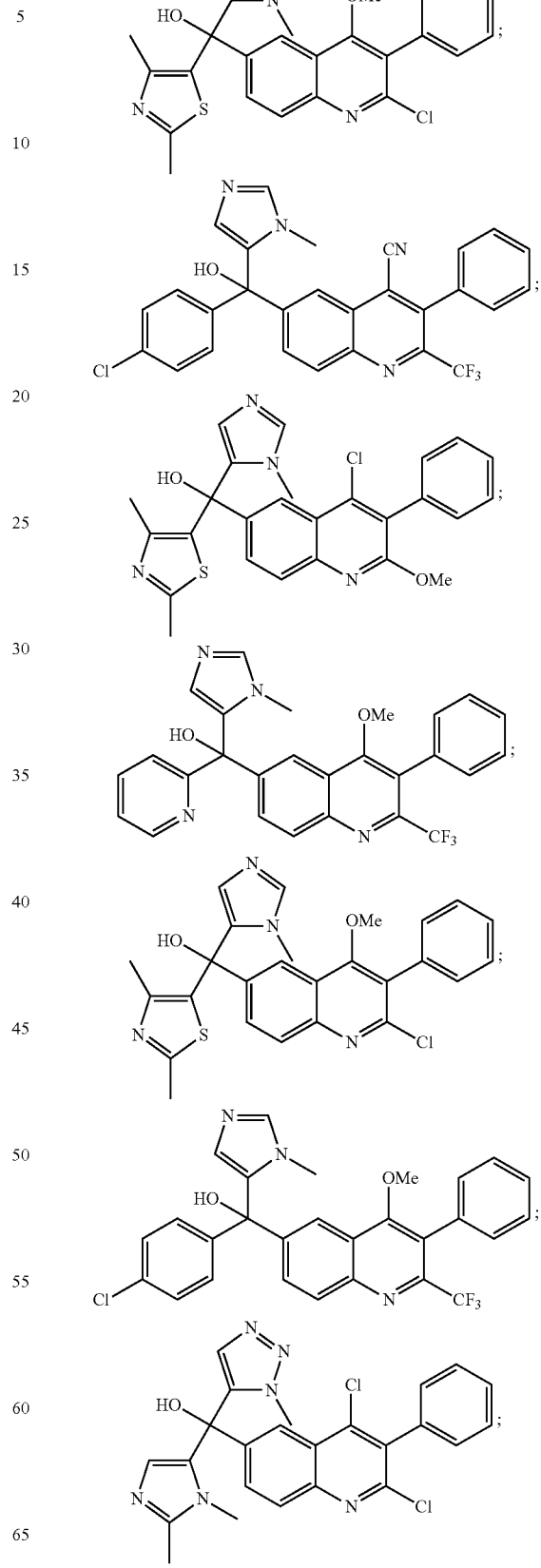

167
-continued
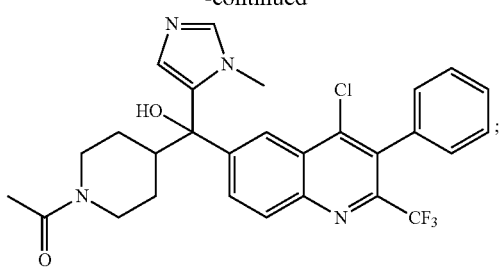
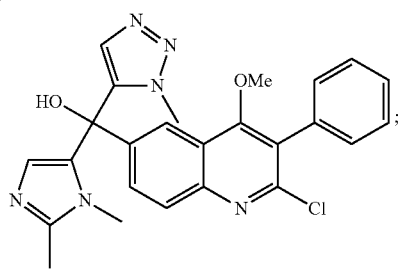
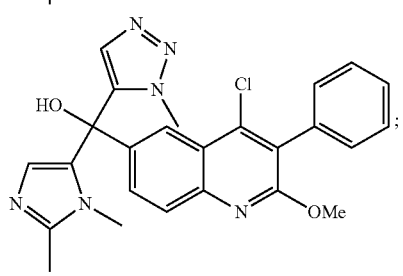
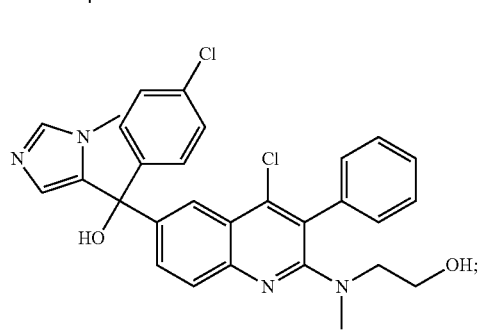
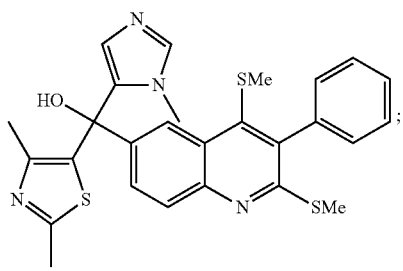
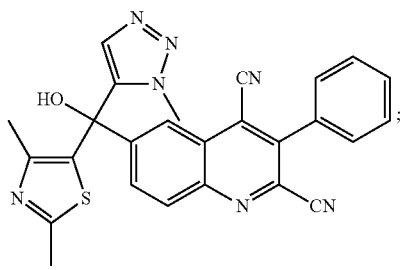
168
-continued
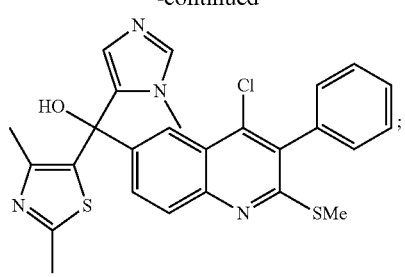

-continued
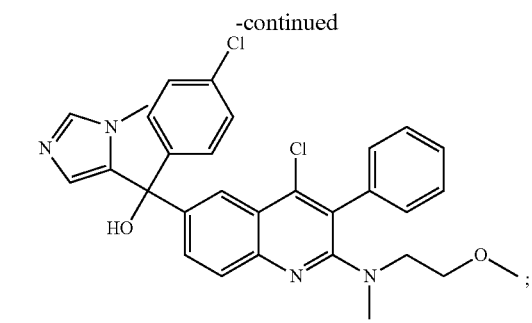
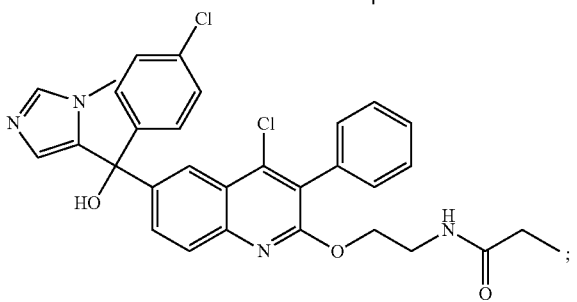
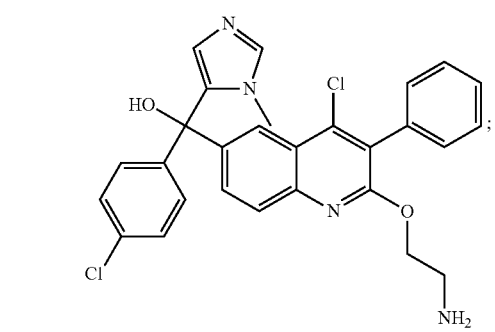
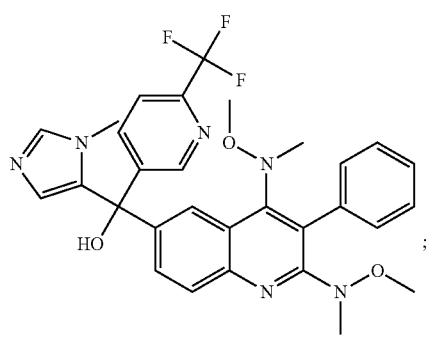
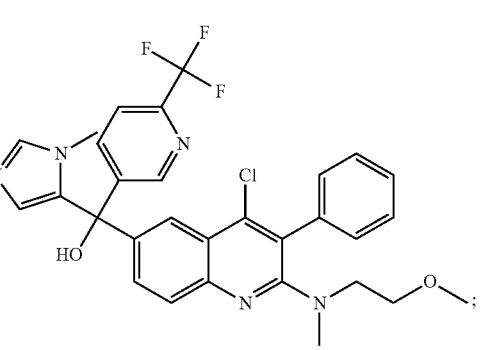
-continued
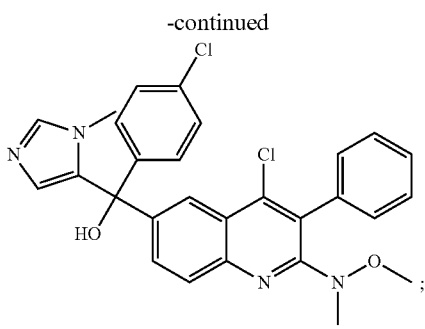
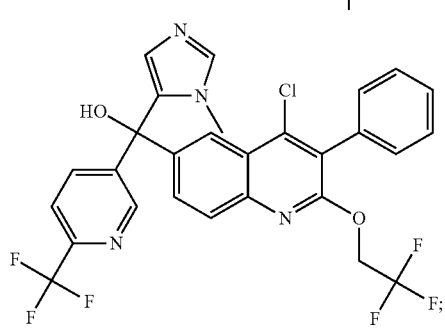
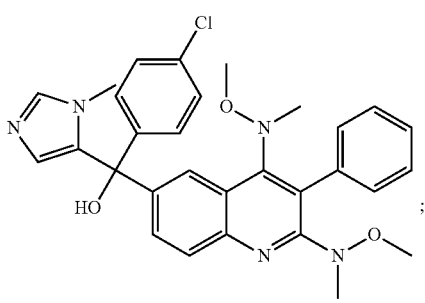
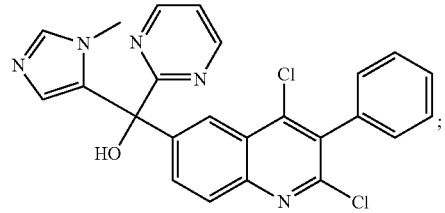
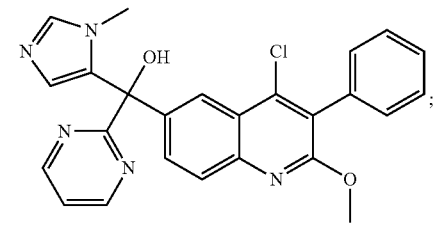
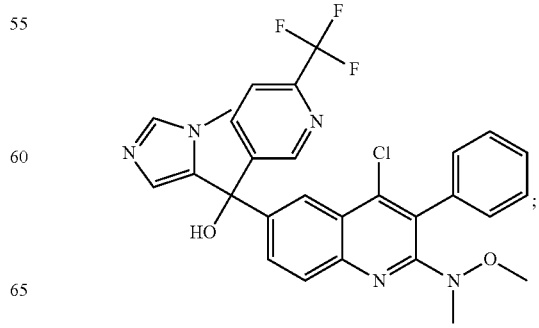

171
-continued
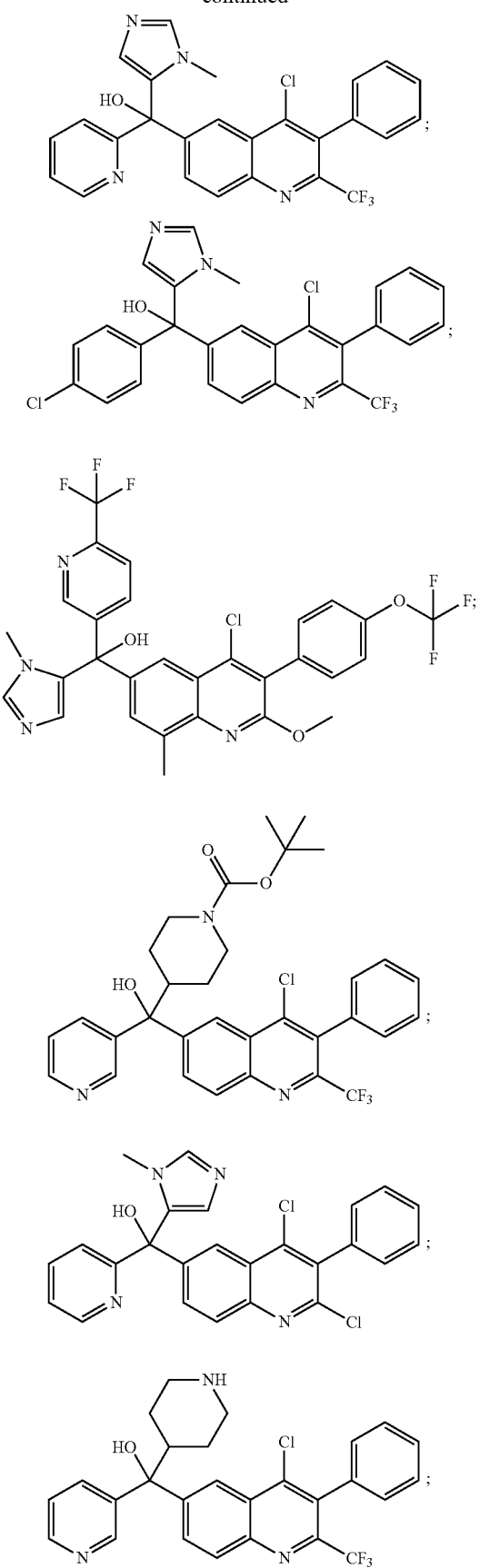
172
-continued
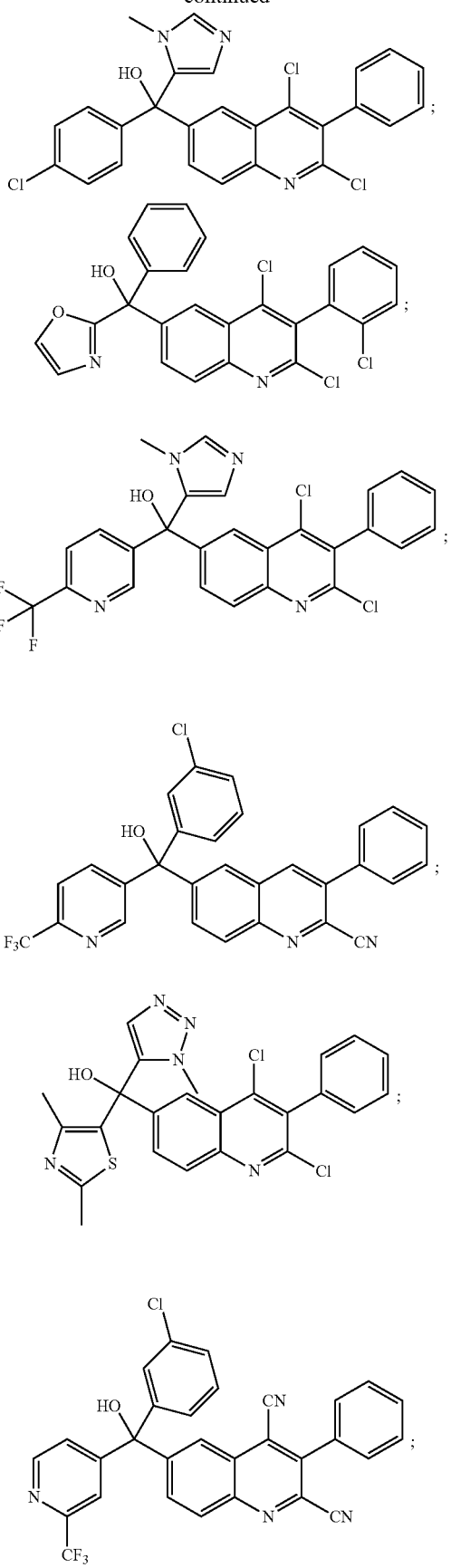

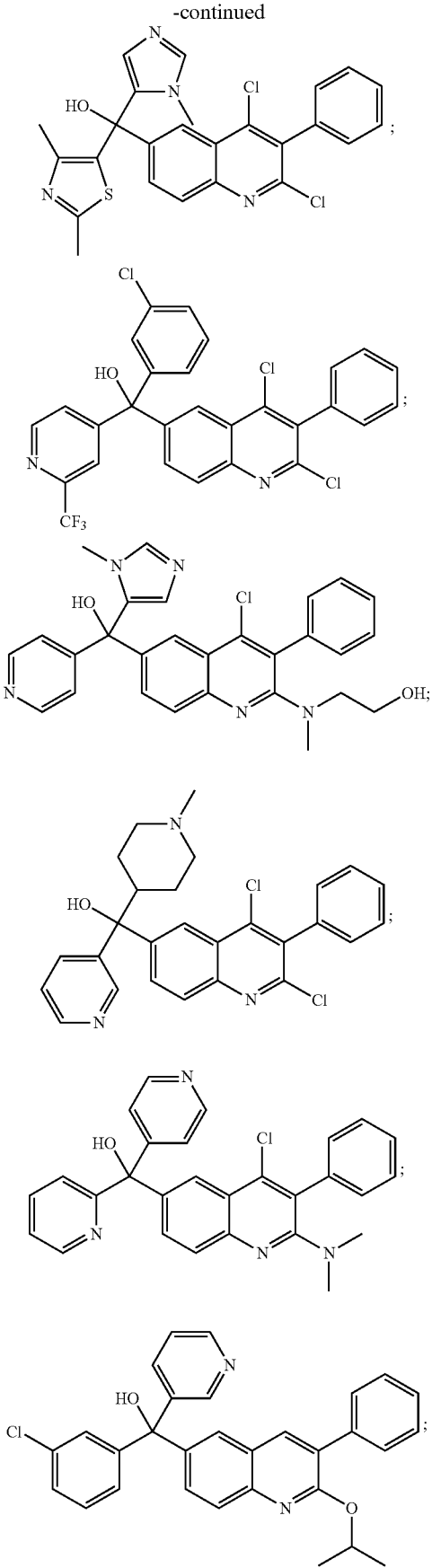
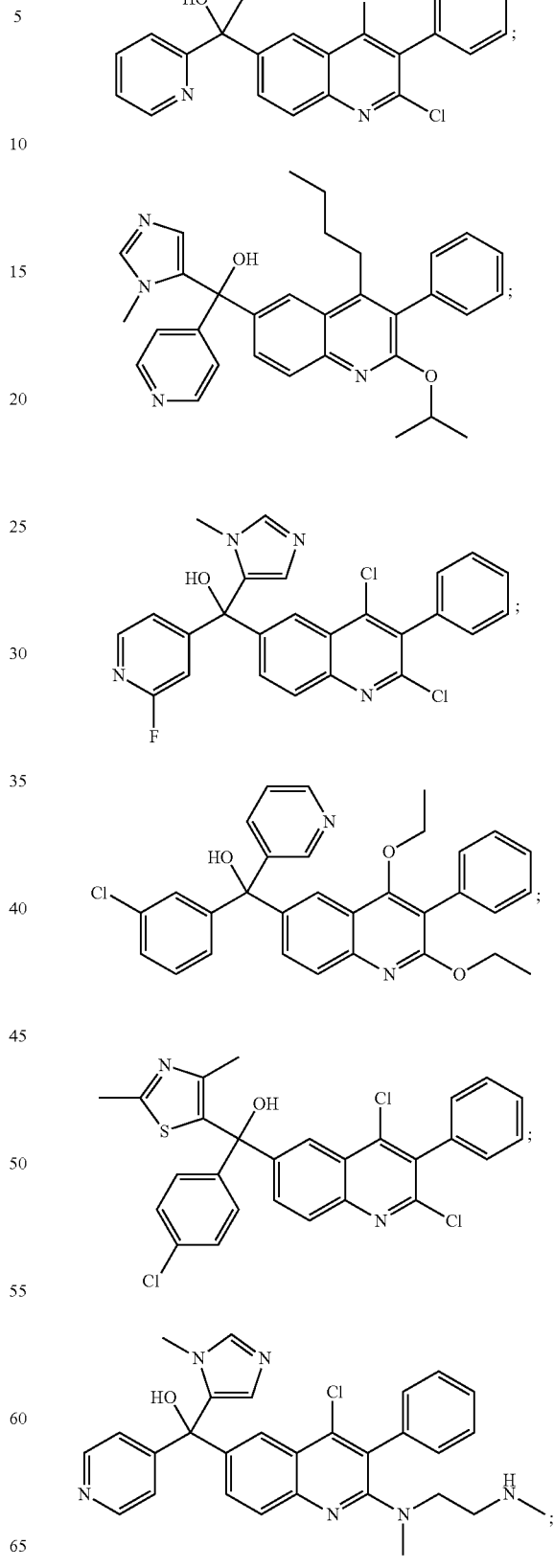

-continued
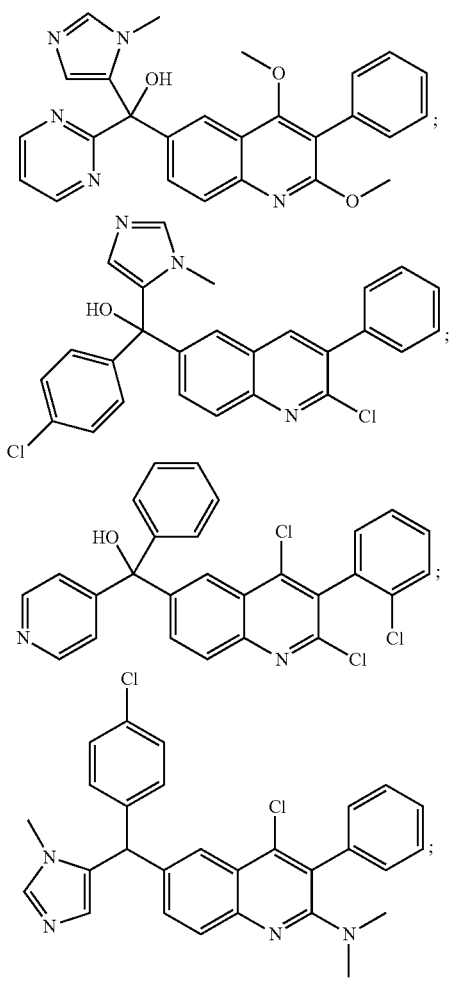
-continued
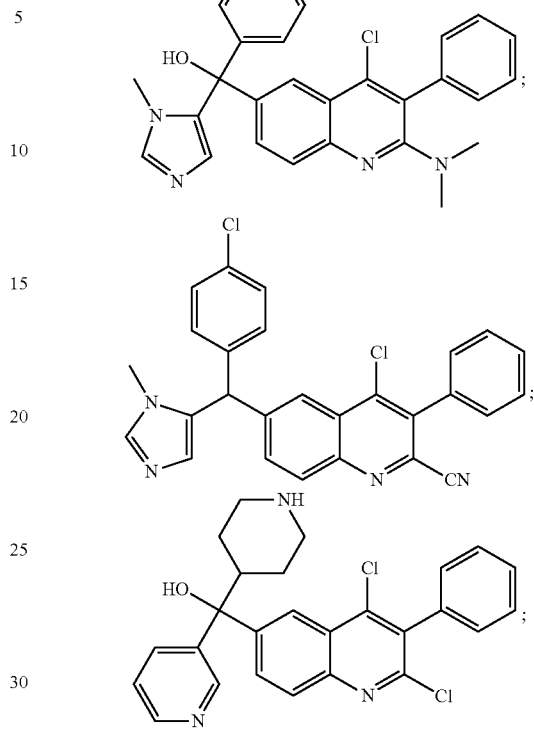
and pharmaceutically acceptable salts thereof.
4. A pharmaceutical composition, comprising a compound of claim 1 and a pharmaceutically acceptable carrier.
5. A pharmaceutical composition made by mixing a compound of claim 1 and a pharmaceutically acceptable carrier.
* * * * *